US008821955B2

(12) United States Patent
Tang

(10) Patent No.: US 8,821,955 B2
(45) Date of Patent: *Sep. 2, 2014

(54) PROTEIN CONCENTRATES AND ISOLATES, AND PROCESSES FOR THE PRODUCTION THEREOF

(75) Inventor: Qingnong Nelson Tang, Saskatoon (CA)

(73) Assignee: Siebte PMI Verwaltungs GmbH, Hamburg (DE)

(*) Notice: Subject to any disclaimer, the term of this patent is extended or adjusted under 35 U.S.C. 154(b) by 825 days.

This patent is subject to a terminal disclaimer.

(21) Appl. No.: 12/927,313

(22) Filed: Nov. 10, 2010

(65) Prior Publication Data

US 2011/0287478 A1 Nov. 24, 2011

Related U.S. Application Data

(63) Continuation-in-part of application No. 12/616,375, filed on Nov. 11, 2009, now Pat. No. 8,623,445, which is a continuation-in-part of application No. 12/467,227, filed on May 15, 2009, now Pat. No. 8,529,981.

(60) Provisional application No. 61/053,858, filed on May 16, 2008, provisional application No. 61/099,783, filed on Sep. 24, 2008.

(51) Int. Cl.
A23J 1/14 (2006.01)
C07K 14/415 (2006.01)

(52) U.S. Cl.
CPC . A23J 1/14 (2013.01); C07K 14/415 (2013.01)
USPC .............................. 426/656; 530/377; 530/422

(58) Field of Classification Search
USPC .......................................... 426/656; 530/377
See application file for complete search history.

(56) References Cited

U.S. PATENT DOCUMENTS

| 3,966,971 A | 6/1976 | Morehouse et al. |
| 4,079,048 A | 3/1978 | Chao |
| 4,889,921 A | 12/1989 | Diosady et al. |
| 5,844,096 A | 12/1998 | Hinrichs et al. |
| 6,005,076 A | 12/1999 | Murray |

(Continued)

FOREIGN PATENT DOCUMENTS

| CA | 2450388 | 5/2004 |
| CA | 2724391 | 11/2009 |

(Continued)

OTHER PUBLICATIONS

Aider, M. and Barbana, C., "Canola proteins; composition, extraction, functional properties, bioactivity, applications as a food ingredient and allergenicity—A practical and critical review," Trends in Food Science & Technology, 22 (2011) 21-39.*

(Continued)

Primary Examiner — Humera Sheikh
Assistant Examiner — Jeffrey Mornhinweg
(74) Attorney, Agent, or Firm — Koppel, Patrick, Heybl & Philpott; Michael J. Ram

(57) ABSTRACT

Protein concentrates and protein isolates, in addition to processes for the production of protein concentrates and protein isolates, are disclosed. In particular, the disclosure relates to the removal of fiber from an oilseed meal using low g-force centrifugation.

43 Claims, 51 Drawing Sheets

(56) References Cited

U.S. PATENT DOCUMENTS

| | | | |
|---|---|---|---|
| 6,132,795 | A | 10/2000 | Holbrook et al. |
| 6,800,308 | B2 | 10/2004 | Maenz et al. |
| 6,905,713 | B2 | 6/2005 | Diosady et al. |
| 6,992,173 | B2 | 1/2006 | Milanova et al. |
| 7,001,990 | B2 | 2/2006 | Hiron et al. |
| 7,087,720 | B2 | 8/2006 | Murray et al. |
| 7,090,887 | B2 | 8/2006 | Newkirk et al. |
| 7,211,286 | B2 | 5/2007 | Hiron |
| 7,211,288 | B2 | 5/2007 | Hiron |
| 7,309,773 | B2 | 12/2007 | Green et al. |
| 8,529,981 | B2 * | 9/2013 | Tang .............................. 426/656 |
| 8,535,907 | B2 * | 9/2013 | Tang ............................. 435/68.1 |
| 2003/0021884 | A1 | 1/2003 | Murray |
| 2003/0109679 | A1 | 6/2003 | Green et al. |
| 2003/0124241 | A1 | 7/2003 | Westdal |
| 2003/0125526 | A1 | 7/2003 | Barker et al. |
| 2004/0005395 | A1 | 1/2004 | Hiron et al. |
| 2004/0034200 | A1 | 2/2004 | Logie et al. |
| 2004/0039174 | A1 | 2/2004 | Barker et al. |
| 2004/0077838 | A1 | 4/2004 | Green et al. |
| 2004/0197378 | A1 | 10/2004 | Murray |
| 2004/0254353 | A1 | 12/2004 | Barker et al. |
| 2005/0031767 | A1 | 2/2005 | Schweizer et al. |
| 2005/0042715 | A1 | 2/2005 | Murray et al. |
| 2005/0064086 | A1 | 3/2005 | Hiron et al. |
| 2005/0107593 | A1 | 5/2005 | Green et al. |
| 2005/0165220 | A1 | 7/2005 | Barker et al. |
| 2005/0181112 | A1 | 8/2005 | Schweizer et al. |
| 2005/0208021 | A1 | 9/2005 | Cabs |
| 2005/0226909 | A1 | 10/2005 | Westdal |
| 2005/0249828 | A1 | 11/2005 | Logie et al. |
| 2005/0249866 | A1 | 11/2005 | Murray |
| 2005/0255226 | A1 | 11/2005 | Schweizer et al. |
| 2005/0283001 | A1 | 12/2005 | Schweizer et al. |
| 2006/0035003 | A1 | 2/2006 | McMindes et al. |
| 2006/0073250 | A1 | 4/2006 | Mozaffar et al. |
| 2006/0121171 | A1 | 6/2006 | Schweizer et al. |
| 2006/0128020 | A1 | 6/2006 | Cabs |
| 2006/0193965 | A1 | 8/2006 | Newkirk et al. |
| 2006/0205929 | A1 | 9/2006 | Milanova et al. |
| 2006/0217318 | A1 | 9/2006 | Wu |
| 2006/0281904 | A1 | 12/2006 | Green |
| 2006/0286281 | A1 | 12/2006 | Hiron et al. |
| 2007/0004908 | A1 | 1/2007 | Gosnell et al. |
| 2007/0015910 | A1 | 1/2007 | Barker et al. |
| 2007/0065567 | A1 | 3/2007 | Segall et al. |
| 2007/0098876 | A1 | 5/2007 | Hiron |
| 2007/0178566 | A1 | 8/2007 | Schweizer et al. |
| 2007/0191593 | A1 | 8/2007 | Green et al. |
| 2007/0237877 | A1 | 10/2007 | Diosady et al. |
| 2007/0244300 | A1 | 10/2007 | Schweizer et al. |
| 2007/0269583 | A1 | 11/2007 | McMindes et al. |
| 2008/0125577 | A1 | 5/2008 | Gosnell et al. |
| 2008/0166469 | A1 | 7/2008 | Schweizer et al. |
| 2008/0299282 | A1 | 12/2008 | Schweizer et al. |
| 2008/0319171 | A1 | 12/2008 | Barker et al. |
| 2009/0036655 | A1 | 2/2009 | Segall et al. |
| 2009/0076252 | A1 | 3/2009 | Barker et al. |
| 2009/0081355 | A1 | 3/2009 | Murray |
| 2009/0175999 | A1 | 7/2009 | Segall et al. |
| 2009/0203880 | A1 | 8/2009 | Gosnell et al. |
| 2009/0286961 | A1 | 11/2009 | Tang |
| 2010/0249378 | A1 * | 9/2010 | Wanasundara et al. ....... 530/377 |

FOREIGN PATENT DOCUMENTS

| | | |
|---|---|---|
| WO | 02/089597 | 11/2002 |
| WO | 03/088760 | 10/2003 |
| WO | 2007/003044 | 1/2007 |
| WO | 2008/024840 | 2/2008 |

OTHER PUBLICATIONS

Folawiyo, Y.L. and Apenten, R.K.O., Effect of pH and Ionic Strength on the Heat Stability of Rapeseed 12S Globulin (Cruciferin) by the ANS Fluorescence Method, Journal of Science Food Agric., 1996, pp. 241-246, vol. 70.

McCurdy, S.M. and March, B.E., "Processing of Canola Meal for Incorporation in Trout and Salmon Diets", Jaocs, 1992, pp. 213-220, vol. 69, No. 3.

Gerbanowski, A., Malabat, C., Rabiller, C., Gueguen, J., "Grafting of Aliphatic and Aromatic Probes on Rapeseed 2S and 12S Proteins: Influence on Their Structural and Physiochemical Properties," J. Agric. Food Chem., 1999, 47:5218-5226.

Vioque et al., "Production and Characterization of an Extensive Rapeseed Protein Hydrolystate". Journal of the American Oil Chemists' Society, 76(7):819-23, 1999.

Chronakis, Ioannis S., Gelatin of Edible Blue-Gree Algae Protein Isolate (*Spirulina platensis* Strain Pacifica): Thermal Transitions, Rheological Properties, and Molecular Forces Involved. J. Agric. Food Chem. 49:888-898, 2001.

Dawczynski, C., Schbert, R., Jahreis, G. Amino Acids, Fatty Acids, and Dietary Fibre in Edible Seaweed Products. Food Chemistry, 103:891-899, 2007.

Morris, H.J., Almarales, A., Carillo, O., Bermudez, R.C. "Utilisation of *Chlorella vulgaris* Cell Biomass for the Production of Enzymatic Protein Hydrolysates". Bioresource Technology. 99:7723-7729, 2008.

* cited by examiner

PROTEIN CONCENTRATES AND ISOLATES, AND PROCESSES FOR THE PRODUCTION THEREOF

PRIORITY INFORMATION

This application is a continuation-in-part of U.S. application Ser. No. 12/467,227 filed Nov. 11, 2009 (now U.S. Pat. No. 8,623,445), which is a continuation-in-part of U.S. application Ser. No. 12/467,227, filed May 15, 2009 (now U.S. Pat. No. 8,529,981), which claims the benefit of U.S. Provisional Application Nos. 61/053,858 and 61/099,783 filed on May 16, 2008 and Sep. 24, 2008, respectively, and entitled Process for the production of protein CONCENTRATES AND PROTEIN ISOLATES, the contents of which of which are expressly incorporated herein by reference.

FIELD OF THE DISCLOSURE

The present disclosure relates to protein concentrates and protein isolates comprising combinations of proteins, peptides and amino acids, as well as processes for their production. In particular, the disclosure relates to a process for removing fiber from an oilseed meal to produce edible protein products.

BACKGROUND

Oilseeds typically contain from about 20 percent oil to about 50 percent oil by weight, with the percentages varying with the type of oilseed. Generally, the seed is pressed, with or without a prior heat treatment step, to obtain a pressed oil and a pressed seedcake. Generally, the pressed seedcake is then solvent extracted to remove or reduce the remaining oil. After removal of the solvent from the pressed seedcake and drying of the seedcake, there generally remains a defatted meal, which contains from about 25% to about 55% of protein on a dry weight basis.

Some defatted meals, depending upon the oilseed, contain a high amount of fiber, as well as other anti-nutritional factors and undesirable compounds, such as glucosinolates, phytic acid or phytates, sinapine and sinigrin. The fiber and antinutritional factors present in the protein render the defatted meal unattractive for commercial uses.

In the case of canola defatted meal, one method of separating the protein from the fiber, antinutritional factors and other undesirable compounds has been to dissolve the canola protein in a high ionic strength (i.e. high salt content) aqueous solution. This results in the canola protein dissolving in the aqueous solution, while the fiber is insoluble. However, the salt is difficult and uneconomical to remove and recover from the resultant canola protein solution.

SUMMARY OF THE DISCLOSURE

Herein, a process for the production of protein concentrates and protein isolates is disclosed. In addition, protein concentrates and protein isolates produced in accordance with the processes of the disclosure are also disclosed. In particular, the disclosure relates to a process for the facile removal of fiber, antinutritional factors and other constituents from an oilseed meal containing such, to produce protein concentrates and protein isolates of high quality.

In an embodiment of processes of the present disclosure, an oilseed is heat treated to a temperature of about 60° C. to about 120° C., optionally about 70° C. to about 100° C., or about 80° C. to about 90° C., or about 80° C.

In another embodiment of the present disclosure, a process for the production of a protein concentrate possessing a protein content of about 70% to about 75% is disclosed.

Accordingly, the disclosure includes a process for the production of a protein concentrate from a defatted or a protein-enriched meal, comprising:

1) removing fiber from the defatted or protein-enriched meal to form a fiber depleted meal, comprising either:
   i) mixing the defatted meal or protein-enriched meal with a mixing solvent to form a first mixture; and
      separating and removing fiber from the first mixture, optionally by using a mesh screen; or
      optionally treating the mixture with phytase at a temperature and a pH suitable for phytase activity; or
   ii) mixing the defatted or protein-enriched meal with water to form a second mixture; and
      optionally adjusting the pH of the second mixture to a pH suitable for enzyme activity, optionally about 3 to about 7, optionally 4 to 6; and
      adding cellulase complex or other enzyme having fiber hydrolysis activity to the second mixture and heating to a temperature suitable for enzyme activity, to hydrolyze the fiber;
      optionally treating the mixture with phytase at a temperature and a pH suitable for phytase activity,
2) washing the fiber depleted meal with an extraction solvent to form an extract and a washed defatted or protein-enriched meal;
3) separating the extract from the washed defatted or protein-enriched meal;
4) optionally repeating steps 2) and 3) at least once; and
5) optionally desolventizing the washed defatted or protein-enriched meal to form a protein concentrate.

In another embodiment, the defatted or protein-enriched meal comprises a canola, rapeseed, mustard seed, broccoli seed, flax seed, cotton seed, hemp seed, safflower seed, sesame seed or soybean meal. In a further embodiment, the protein-enriched meal comprises a canola meal. In an embodiment, the protein-enriched meal comprises a soybean meal. In another embodiment, the protein-enriched meal comprises mustard seed meal. In a further embodiment, the protein-enriched meal comprises flax seed meal.

In another embodiment, the mixing solvent comprises water, methanol, ethanol or isopropanol, and mixtures thereof. In a further embodiment, the solvent is water or ethanol, and mixtures thereof. In an embodiment of the disclosure, the defatted or protein-enriched meal is mixed with a mixing solvent in a ratio of about 3 to about 10 parts solvent to about 1 part of the defatted or protein-enriched meal, optionally about 4 to about 8, or about 4 to about 6, on a weight-to-weight basis.

In another embodiment of the disclosure, the mixture is screened through a mesh screen of typically about 10 to about 200 US mesh size, optionally a mesh screen of about 20 to about 200 US mesh size. In another embodiment, the mesh size is 40 US mesh size.

In an embodiment of the present disclosure, the defatted or protein-enriched meal is mixed thoroughly with water to form the second mixture. In an embodiment, the mixing of water and the defatted or protein-enriched meal comprises using a wet mill or an inline mixer.

In another embodiment of the present disclosure, the cellulase complex is added to the second mixture in an amount of about 1 gram to about 10 grams for about every 1 kg of dry solids of the defatted or protein-enriched meal (about 0.1% to about 1%). In a further embodiment, the cellulase complex is mixed with the second mixture for about 0.5 hours to about 5 hours. In another embodiment, the cellulase complex is mixed with the second mixture for about 1 to about 3 hours.

In another embodiment of the disclosure, the second mixture with the added cellulase complex is heated to a temperature of about 30° C. to about 60° C., suitably about 40° C. to about 60° C.

In an embodiment, the cellulase complex comprises at least one of endocellulase, exocellulase, cellobiohydrolase, cellobiase, endohemicellulase and exohemicellulase.

In an embodiment of the disclosure, the extraction solvent comprises methanol, ethanol or isopropanol, and mixtures thereof. In a further embodiment, the extraction solvent comprises ethanol or water, and mixtures thereof.

In an embodiment of the present disclosure, the first or second mixture is washed at least once with about 5% to about 100%, optionally about 25% to about 85%, or about 50% to about 85%, or about 60% to about 85%, of the extraction solvent (v/v) in water.

In an embodiment of the present disclosure, the ratio of the extraction solvent to the first or second mixture is about 5% to about 95%, optionally about 10% to about 90%, about 20% to about 70%, or about 40% to about 80% (v/v) (extraction solvent to first or second mixture).

In an embodiment of the present disclosure, the first or second mixture is washed with the extraction solvent at a temperature of about 10° C. to about 90° C. In another embodiment, the first or second mixture is washed with the extraction solvent at a temperature of about 20° C. to about 60° C. In a further embodiment, the first or second mixture is washed with the extraction solvent at a temperature of about 20° C. to about 25° C.

In another embodiment of the present disclosure, the extract is separated from the washed defatted or protein-enriched meal by centrifugation, vacuum filtration, pressure filtration, decantation or gravity draining in an extractor.

In another embodiment of the present disclosure, steps 2) and 3) are repeated at least twice.

In another embodiment of the present disclosure, the process further comprises the step of drying the washed defatted or protein-enriched meal to form the protein concentrate. In a further embodiment, the washed defatted or protein-enriched meal is dried in a vacuum dryer, fluidized bed dryer, ring dryer or spray dryer. In another embodiment, the washed defatted or protein-enriched meal is dried to a moisture content of about 0.5% to about 12%, optionally about 1% to about 10%, about 4% to about 8%. In a further embodiment, the washed defatted or protein-enriched meal is dried to a moisture content of about 6%.

In another embodiment of the present disclosure, the extract is desolventized and dried to form a high sugar fraction. In an embodiment, the extract is desolventized by spray drying, drum drying or vacuum drying.

In an embodiment of the present disclosure, a process for the production of a protein concentrate possessing a protein content of about 75% to about 90% is disclosed. In another embodiment, the protein concentrate is hydrolyzed to produce peptides and free amino acids. In another embodiment, the hydrolyzed protein concentrate comprises peptides and/or free amino acids.

The disclosure also includes a process for the production of a protein concentrate from a defatted or protein-enriched meal, comprising:
  removing fiber from the defatted or protein-enriched meal, comprising:
    i) mixing the defatted or protein-enriched meal with a mixing solvent to form a mixture;
    separating fiber from the mixture, optionally by screening the mixture to remove fiber,
    optionally adjusting the pH of the mixture to a pH of about 4.5 to about 8.0, optionally about 6.5 to about 7.5, or optionally about 7;
    optionally treating the mixture with phytase at a temperature and a pH suitable for phytase activity,
    optionally milling the mixture;
    separating fiber, optionally by centrifuging the mixture, to remove fiber,
    thereby forming a protein slurry; and
  ii) separating the protein slurry, optionally by centrifuging the protein slurry, to form a protein precipitate and a soluble protein fraction;
  iii) washing the protein precipitate with an extraction solvent at least once and separating, optionally by centrifuging, to form a purified protein precipitate;
  iv) optionally drying the purified protein precipitate to form the protein concentrate.

In another embodiment, the defatted or protein-enriched meal comprises a canola, rapeseed, mustard seed, broccoli seed, flax seed, cotton seed, hemp seed, safflower seed, sesame seed or soybean meal. In a further embodiment, the protein-enriched meal comprises a canola meal. In an embodiment, the protein-enriched meal comprises a soybean meal. In another embodiment, the protein-enriched meal comprises mustard seed meal. In a further embodiment, the protein-enriched meal comprises flax seed meal.

In another embodiment of the disclosure, the mixing solvent comprises water, methanol, ethanol, or isopropanol, and mixtures thereof. In a further embodiment, the mixing solvent comprises water or ethanol, and mixtures thereof. In another embodiment, the ratio of defatted or protein-enriched meal to the mixing solvent is about 1:3 to about 1:20. In a further embodiment, the ratio is about 1:6 to about 1:10. In an embodiment, the ratio is about 1:6 to about 1:8.

In another embodiment of the disclosure, the mixture is screened through a mesh screen of typically about 10 to about 200 US mesh size, optionally a mesh screen of about 20 to about 200 US mesh size. In another embodiment, the mesh size is 40 US mesh size.

In another embodiment of the present disclosure, the pH of mixture is adjusted with aqueous sodium hydroxide. In an embodiment, the aqueous sodium hydroxide has a concentration of about 1% to about 40% by weight of sodium hydroxide. In a further embodiment, the concentration of sodium hydroxide is about 5% to about 30% sodium hydroxide.

In another embodiment, the optional milling step comprises using a wet mill.

In an embodiment, the mixture is centrifuged using a decanting centrifuge. In an embodiment, the mixture is centrifuged with a decanting centrifuge at a speed of about 500 rpm to about 6000 rpm. In another embodiment, the speed is about 1500 rpm.

In an embodiment of the disclosure, the protein slurry is centrifuged using a decanter or disc stack centrifuge. In a further embodiment, the protein slurry is centrifuged at a speed of about 2500 rpm to about 8500 rpm.

In another embodiment of the disclosure, the extraction solvent is water, methanol, ethanol or isopropanol, and mixtures thereof. In a further embodiment, the extraction solvent is water or ethanol, and mixtures thereof. In an embodiment, the extraction solvent is water. In an embodiment, the protein precipitate is washed at least twice with the extraction solvent.

In an embodiment of the present disclosure, the washed protein precipitate is centrifuged with a disc stack centrifuge at a speed of about 7500 rpm to about 8500 rpm.

In an embodiment of the disclosure, the purified protein precipitate is dried in a vacuum dryer, fluidized bed dryer, ring dryer or spray dryer to form the protein concentrate. In a further embodiment, the protein concentrate is dried to a moisture content of about 1% to about 10%. In another embodiment, the protein concentrate is dried to a moisture content of about 6%.

In another embodiment, the protein concentrate comprises a hydrolyzed protein concentrate. In another embodiment, the protein concentrate is hydrolyzed to produce peptides and free amino acids. In another embodiment, the hydrolyzed protein concentrate comprises peptides and/or free amino acids.

In another embodiment of the present disclosure, a process for the production of a protein isolate possessing a protein content of greater than about 90% is disclosed.

Accordingly, the disclosure includes a process for the production of a protein isolate from a defatted or protein-enriched meal, comprising:
 removing fiber from the defatted or protein-enriched meal, comprising:
  i) mixing the defatted or protein-enriched meal with a mixing solvent to form a mixture;
   separating fiber from the mixture to remove fiber,
   optionally adjusting the pH of the mixture to a pH of about 6.0 to about 8.0, optionally about 6.5 to about 7.5, or optionally about 7;
   optionally milling the mixture;
   optionally treating the mixture with phytase at a temperature and a pH suitable for phytase activity, separating fiber, optionally by centrifuging the mixture, to remove fiber,
  thereby forming a protein slurry;
  ii) separating the protein slurry, optionally by centrifuging the protein slurry, to form a protein precipitate and a soluble protein fraction;
  iii) filtering the soluble protein fraction to separate it from protein precipitate; and
  iv) optionally drying the soluble protein to form the protein isolate.

In another embodiment, the defatted or protein-enriched meal comprises a canola, rapeseed, mustard seed, broccoli seed, flax seed, cotton seed, hemp seed, safflower seed, sesame seed or soybean meal. In a further embodiment, the protein-enriched meal comprises a canola meal. In an embodiment, the protein-enriched meal comprises a soybean meal. In another embodiment, the protein-enriched meal comprises mustard seed meal. In a further embodiment, the protein-enriched meal comprises flax seed meal.

In another embodiment of the disclosure, the mixing solvent comprises water or a salt solution. In an embodiment, the salt solution comprises less than 5%, optionally about 3% to about 4%, or 3.5% by weight of salt in solution. In a further embodiment, the mixing solvent comprises water. In another embodiment, the ratio of defatted or protein-enriched meal to the mixing solvent is about 1:3 to about 1:20. In a further embodiment, the ratio is about 1:6 to about 1:10. In an embodiment, the ratio is about 1:6 to about 1:8.

In another embodiment of the present disclosure, the pH of mixture is adjusted with aqueous sodium hydroxide. In an embodiment, the aqueous sodium hydroxide has a concentration of about 1% to about 40% by weight of sodium hydroxide. In a further embodiment, the concentration of sodium hydroxide is about 5% to about 30% sodium hydroxide.

In another embodiment of the disclosure, the mixture is screened through a mesh screen of about 10 to about 200 US mesh size, optionally a mesh screen of about 20 to about 200 US mesh size. In an embodiment, the mesh size is 40 US mesh size.

In an embodiment, the mixture is centrifuged using a decanting centrifuge. In an embodiment, the mixture is centrifuged with a decanting centrifuge at a speed of about 500 rpm to about 6000 rpm. In another embodiment, the speed is about 1500 rpm.

In another embodiment, the optional milling step comprises using a wet mill.

In an embodiment of the disclosure, the protein slurry is centrifuged using a disc stack centrifuge. In a further embodiment, the protein slurry is centrifuged at a speed of about 6500 rpm to about 8500 rpm.

In another embodiment of the disclosure, the soluble protein fraction is filtered using an ultrafiltration or diafiltration apparatus. In a further embodiment, the ultrafiltration or diafiltration apparatus comprises a membrane to filter proteins of larger than about 1,000 daltons, optionally 10,000 daltons, optionally about 30,000 daltons, or about 100,000 daltons. In another embodiment, the ultrafiltration or diafiltration is performed at a temperature of about 1° C. to about 60° C., optionally about 40° C. to about 55° C.

In another embodiment of the disclosure, the soluble protein is dried in a vacuum dryer, fluidized bed dryer, ring dryer or spray dryer to form the protein isolate. In an embodiment, the protein isolate is dried to a moisture content of about 1% to about 10%. In a further embodiment, the protein isolate is dried to a moisture content of about 6%.

In another embodiment, the protein isolate comprises a hydrolyzed protein isolate. In another embodiment, the protein isolate is hydrolyzed to produce peptides and free amino acids. In another embodiment, the hydrolyzed protein isolate comprises peptides and/or free amino acids.

In another embodiment of the present disclosure, a process for the production of a protein isolate possessing a protein content of greater than about 90% is disclosed.

Accordingly, the disclosure includes a process for the production of a protein isolate from a defatted or protein-enriched meal, comprising:
 removing fiber from the defatted or protein-enriched meal, comprising:
  i) mixing the defatted or protein-enriched meal with a mixing solvent to form a mixture;
   separating fiber from the mixture to remove fiber,
   optionally adjusting the pH of the mixture to a pH of about 6.0 to about 8.0, optionally about 6.5 to about 7.5, or optionally about 7;
   optionally milling the mixture;
   optionally treating the mixture with phytase at a temperature and a pH suitable for phytase activity, separating fiber, optionally by centrifuging the mixture, to remove fiber,
  thereby forming a protein slurry; and
  ii) separating the protein slurry, optionally by centrifuging the protein slurry, to form a protein precipitate and a soluble protein fraction;
  iii) mixing the protein precipitate with water to form a protein precipitate mixture and optionally adjusting the pH to a pH suitable for enzyme activity, optionally about 3 to about 7, optionally about 4 to about 6;
  iv) adding cellulase complex or other enzyme having fiber hydrolysis activity to the protein precipitate mixture to hydrolyze fiber, typically residual fiber;

v) washing the protein precipitate mixture with an extraction solvent at least once and separating, optionally by centrifuging; to form a protein isolate.

In another embodiment, the defatted or protein-enriched meal comprises a canola, rapeseed, mustard seed, broccoli seed, flax seed, cotton seed, hemp seed, safflower seed, sesame seed or soybean meal. In a further embodiment, the protein-enriched meal comprises a canola meal. In an embodiment, the protein-enriched meal comprises a soybean meal. In another embodiment, the protein-enriched meal comprises mustard seed meal. In a further embodiment, the protein-enriched meal comprises flax seed meal.

In another embodiment of the disclosure, the mixing solvent comprises water or a salt solution. In an embodiment, the salt solution comprises less than 5%, optionally about 3% to about 4%, or 3.5% by weight of salt in solution. In a further embodiment, the mixing solvent comprises water. In another embodiment, the ratio of defatted or protein-enriched meal to the mixing solvent is about 1:3 to about 1:20. In a further embodiment, the ratio is about 1:6 to about 1:10. In an embodiment, the ratio is about 1:6 to about 1:8.

In another embodiment of the disclosure, the mixture is screened through a mesh screen of about 10 to about 200 US mesh size, optionally a mesh screen of about 20 to about 200 US mesh size. In another embodiment, the mesh size is 40 US mesh size.

In another embodiment of the present disclosure, the pH of mixture is adjusted with aqueous sodium hydroxide. In an embodiment, the aqueous sodium hydroxide has a concentration of about 1% to about 40% by weight of sodium hydroxide. In a further embodiment, the concentration of sodium hydroxide is about 5% to about 30% sodium hydroxide.

In another embodiment, the optional milling step comprises using a wet mill.

In an embodiment, the mixture is centrifuged using a decanting centrifuge. In an embodiment, the mixture is centrifuged with a decanting centrifuge at a speed of about 500 rpm to about 6000 rpm. In another embodiment, the speed is about 1500 rpm.

In an embodiment of the disclosure, the protein slurry is centrifuged using a disc stack centrifuge. In a further embodiment, the protein slurry is centrifuged at a speed of about 6500 rpm to about 8500 rpm.

In another embodiment of the disclosure, the cellulase complex is added to the protein precipitate mixture in an amount of about 0.1% to about 1% by weight of the protein precipitate mixture. In a further embodiment, the cellulase complex is mixed with the protein precipitate mixture for about 0.5 hours to about 5 hours. In another embodiment, the cellulase complex is mixed with the protein precipitate mixture for about 1 to about 3 hours. In a further embodiment, the cellulase complex comprises at least one of endocellulase, exocellulase, cellobiohydrolase, cellobiase, endohemicellulase and exohemicellulase. In an embodiment, the protein precipitate mixture with cellulase complex is heated to a temperature of about 30° C. to about 60° C. optionally about 40° C. to about 60° C.

In another embodiment of the disclosure, the mixing solvent comprises water. In another embodiment, the ratio of defatted or protein-enriched meal to the mixing solvent is about 1:3 to about 1:20. In another embodiment, the ratio is about 1:6 to about 1:10. In another embodiment, the ratio is about 1:6 to about 1:8.

In another embodiment of the present disclosure, the protein precipitate mixture is centrifuged using a decanter or disc stack centrifuge. In a further embodiment, the protein precipitate mixture is centrifuged at a speed of about 2500 rpm to about 8500 rpm.

In another embodiment of the present disclosure, the protein isolate is subjected to high pressure jet cooking.

In an embodiment of the present disclosure, the protein isolate is hydrolyzed using proteases to form a hydrolyzed protein extract. In a further embodiment, the proteases comprise Alcalase® (serine endopeptidase, typically from *Bacillus subtilis*), or Flavourzyme® (fungal protease/peptidase complex, typically produced from *Aspergillus oryzae* fermentation), both proteases from Novozymes® North America, Inc. In an embodiment, the ratio of Alcalase® to the protein isolate is about 0.1% to about 1%. In another embodiment, the ratio of Alcalase® to the protein isolate is about 0.5%. In a further embodiment, the ratio of Flavourzyme® to the protein isolate is about 0.1% to about 1%. In an embodiment, the ratio of Flavourzyme® to the protein isolate is about 0.5%.

In another embodiment, the protein isolate comprises a hydrolyzed protein isolate. In another embodiment, the protein isolate is hydrolyzed to produce peptides and free amino acids. In another embodiment, the hydrolyzed protein isolate comprises peptides and/or free amino acids.

In another embodiment of the disclosure, there is a provided a process for the production of a protein concentrate from an oilseed meal, comprising:
  i) mixing the partially defatted, fully defatted or protein-enriched meal with a mixing solvent to form a mixture and optionally treating the mixture with phytase at a temperature and a pH suitable for phytase activity,
  ii) optionally adjusting the pH of the mixture to a pH of about 2.0 to about 10.0;
  iii) separating fiber from the mixture to form a protein slurry, wherein the protein slurry comprises a soluble protein fraction and an insoluble protein fraction;
  iv) optionally repeating steps i)-iii) by mixing the protein slurry with additional partially defatted, fully defatted or protein-enriched meal;
  v) mixing the protein slurry with an extraction solvent to form an extract and a washed insoluble protein fraction;
  vi) separating the extract from the washed insoluble protein fraction;
  vii) optionally repeating steps v) and vi) at least once; and
  viii) optionally desolventizing the washed insoluble protein fraction to form a protein concentrate.

In another embodiment of the disclosure, the ratio of partially defatted, fully defatted or protein-enriched meal to mixing solvent is about 1:3 to about 1:30 (w/w). In another embodiment, the ratio of partially defatted, fully defatted or protein-enriched meal to solvent is about 1:5 to about 1:20 (w/w). In a further embodiment, the ratio is about 1:6 to about 1:12 (w/w). In an embodiment, the ratio is about 1:8 to about 1:10 (w/w).

In a further embodiment of the disclosure, the mixing solvent comprises water or an aqueous solution comprising a polysaccharide, a salt, such as sodium chloride, potassium chloride, or calcium chloride, or an alcohol. In an embodiment, the mixing solvent is water. In another embodiment, the polysaccharide is guar gum.

In an embodiment, the pH of the protein slurry is adjusted to a pH of about 6.5 to about 10.0. In a further embodiment, the pH of the protein slurry is adjusted to a pH of about 7.0 to about 9.0.

In another embodiment of the disclosure, the mixture is separated by centrifugation or hydrocyclone to separate the fiber from the mixture and form the protein slurry. In a further embodiment, the mixture is separated by centrifugation to separate the fiber from the mixture and form the protein slurry. In an embodiment, the mixture is centrifuged at a speed of about 1,000 rpm to about 2,000 rpm. In a further embodiment, the mixture is centrifuged at a speed of about 1,400 to about 1,600 rpm. In an embodiment, the mixture is centrifuged using a decanter centrifuge.

In another embodiment of the disclosure, mixing the protein slurry with additional partially defatted, fully defatted or protein-enriched meal is repeated at least once. In a further embodiment, mixing the protein slurry with additional partially defatted, fully defatted or protein-enriched meal is repeated at least two to seven times.

In an embodiment of the disclosure, the extraction solvent comprises water, methanol, ethanol, isopropanol, or mixtures thereof. In an embodiment, the extraction solvent comprises ethanol. In another embodiment, the extraction solvent comprises at least about 50% ethanol. In an embodiment, the extraction solvent comprises at least about 70% ethanol. In a further embodiment, the extraction solvent comprises at least about 90% ethanol.

In a further embodiment, the extract is separated from the washed insoluble protein fraction using centrifugation, vacuum filtration, pressure filtration, decantation or gravity draining. In an embodiment, the extract is separated from the washed insoluble protein fraction using centrifugation.

In another embodiment of the disclosure, wherein steps iv) and v) are repeated at least twice.

In a further embodiment, the process further comprises the step of drying the washed insoluble protein fraction to form the protein concentrate. In an embodiment, the protein concentrate is dried in a vacuum dryer, fluidized bed dryer, hot air dryer ring dryer or spray dryer.

In another embodiment, the protein concentrate comprises a hydrolyzed protein concentrate. In another embodiment, the protein concentrate is hydrolyzed to produce peptides and free amino acids. In another embodiment, the hydrolyzed protein concentrate comprises peptides and/or free amino acids.

In an embodiment of the disclosure, the partially defatted, fully defatted or protein-enriched meal comprises a canola, rapeseed, mustard seed, broccoli seed, flax seed, cotton seed, hemp seed, safflower seed, sesame seed or soybean meal. In another embodiment, the partially defatted, fully defatted or protein-enriched meal comprises a canola meal.

In an embodiment, the protein concentrate comprises a protein content of about 60% to about 90% on a dry weight basis.

In another embodiment of the disclosure, there is also provided a process for the production of a protein isolate from an oilseed meal, comprising:
 i) mixing the partially defatted, fully defatted or protein-enriched meal with a blending solvent, optionally water or alkaline water, to form a mixture and optionally treating the mixture with phytase at a temperature and a pH suitable for phytase activity;
 ii) optionally adjusting the pH of the mixture to a pH of about 7.0 to about 10.0;
 iii) separating fiber from the mixture to form a first protein slurry, wherein the first protein slurry comprises a soluble protein fraction and an insoluble protein fraction;
 iv) separating the first protein slurry to form a protein solids fraction and a soluble protein fraction;
 v) optionally mixing the protein solids fraction with a second blending solvent, optionally water, to form a second protein slurry;
 vi) optionally separating the second protein slurry to form a second protein solids fraction and a second soluble protein fraction;
 vii) optionally repeating steps v) and vi) at least once;
 viii) separating the soluble protein fractions to form a clarified soluble protein fraction and a residual insoluble protein fraction;
 ix) optionally adjusting the pH of the clarified soluble protein fraction to a pH of about 6 to about 9;
 x) separating the clarified soluble protein fraction, optionally by filtering the clarified soluble protein fraction by membrane filtration; and
 xi) optionally drying the clarified soluble protein fraction.

In another embodiment of the disclosure, the ratio of partially defatted, fully defatted or protein-enriched meal to water or alkaline water is about 1:4 to about 1:30 (w/w). In another embodiment, the ratio of partially defatted, fully defatted or protein-enriched meal to water or alkaline water is about 1:5 to about 1:20 (w/w). In a further embodiment, the ratio is about 1:6 to about 1:12 (w/w). In an embodiment, the ratio is about 1:8 to about 1:10 (w/w).

In an embodiment of the disclosure, the pH of the alkaline water is about 7 to about 12. In another embodiment, the pH of the first protein slurry is adjusted to about 8.0 to about 9.5. In a further embodiment, the pH of the first protein slurry is adjusted to about 8.5 to about 9.0.

In another embodiment of the disclosure, the mixture is separated by centrifugation or hydrocyclone to separate the fiber from the mixture and form the protein slurry. In a further embodiment, the mixture is separated by centrifugation to separate the fiber from the mixture and form the protein slurry. In an embodiment, the mixture is centrifuged at a speed of about 1,000 rpm to about 2,000 rpm. In a further embodiment, the mixture is centrifuged centrifuge at a speed of about 1,400 to about 1,600 rpm. In an embodiment, the mixture is centrifuged using a decanter centrifuge.

In another embodiment, the first protein slurry is centrifuged, optionally using a disc stack centrifuge, to separate the protein solids fraction from the soluble protein fraction. In a further embodiment, the first protein slurry is centrifuged at a speed of about 4,000 rpm to about 8,000 rpm. In a further embodiment, the first protein slurry is centrifuged at a speed of about 6,500 to about 7,500 rpm.

In another embodiment of the disclosure, the ratio of the protein solids fraction to water is about 1.0:0.5 to about 1.0:3.0 (w/w). In a further embodiment, the ratio of the protein solids fraction to water is about 1.0:1.0 to about 1.0:2.0 (w/w).

In an embodiment, the soluble protein fractions are centrifuged to form the clarified soluble protein fraction and the residual insoluble protein fraction. In an embodiment, the soluble protein fractions are centrifuged using a disc stack centrifuge at a speed of about 7,000 rpm to about 10,000 rpm. In a further embodiment, the soluble protein fractions are centrifuged using a disc stack centrifuge at a speed of about 7,500 rpm to about 8,500 rpm.

In another embodiment of the disclosure, the pH of the clarified soluble protein fraction is adjusted with alkali. In a further embodiment, the pH of the clarified soluble protein fraction is adjusted with sodium hydroxide.

In an embodiment, the clarified soluble protein fraction is filtered using an ultrafiltration apparatus. In a further embodiment, the ultrafiltration apparatus comprises a membrane to filter proteins larger than about 10,000 daltons.

In another embodiment of the disclosure, the process further comprises the step of filtering the clarified soluble protein fraction using a diafiltration apparatus.

In another embodiment, the clarified soluble protein fraction is dried in a vacuum dryer, fluidized bed dryer, ring dryer or spray dryer to form the protein isolate.

In an embodiment of the disclosure, the partially defatted, fully defatted or protein-enriched meal comprises a canola, rapeseed, mustard seed, broccoli seed, flax seed, cotton seed, hemp seed, safflower seed, sesame seed or soybean meal. In another embodiment, the partially defatted, fully defatted or protein-enriched meal comprises a canola meal.

In another embodiment, the protein isolate comprises a hydrolyzed protein isolate. In another embodiment, the protein isolate is hydrolyzed to produce peptides and free amino acids. In another embodiment, the hydrolyzed protein isolate comprises peptides and/or free amino acids.

In another embodiment of the disclosure, the protein isolate comprises a protein content of greater than about 90% on a dry weight basis.

In another embodiment of the disclosure, there is also provided a process for the production of a hydrolyzed protein concentrate from an oilseed meal, comprising:
 i) mixing the oilseed meal with a blending solvent, optionally water, to form a first mixture and optionally treating the mixture with phytase at a temperature and a pH suitable for phytase activity;
 ii) optionally adjusting the pH of the first mixture to a pH of about 6.5 to about 10.0;
 iii) separating the first mixture to remove fiber from the first mixture and form a protein slurry and an insoluble fiber fraction, wherein the protein slurry comprises a soluble protein fraction and an insoluble protein fraction and the insoluble fiber fraction comprises insoluble fiber and a second insoluble protein fraction;
 iv) optionally mixing the insoluble fiber fraction with a second blending solvent, optionally water, to form a washed insoluble fiber fraction and an extract;
 v) separating the washed insoluble fiber fraction from the extract;
 vi) optionally mixing the washed insoluble fiber fraction with a blending solvent, optionally water, to form a second mixture;
 vii) optionally adjusting the pH of the second mixture to a pH suitable for enzymatic activity;
 viii) mixing the second mixture with at least one protease to form a hydrolyzed protein extract;
 ix) separating the hydrolyzed protein extract from the second mixture to form the hydrolyzed protein concentrate and a second insoluble fiber fraction; and
 x) optionally drying the hydrolyzed protein concentrate.

In another embodiment of the disclosure, the ratio of partially defatted, defatted or protein-enriched meal to water is about 1:4 to about 1:30 (w/w). In another embodiment, the ratio of partially defatted, fully defatted or protein-enriched meal to water is about 1:5 to about 1:20 (w/w). In a further embodiment, the ratio is about 1:6 to about 1:12 (w/w). In an embodiment, the ratio is about 1:8 to about 1:10 (w/w).

In another embodiment, the pH of the first mixture is adjusted to about 8.0 to about 9.5. In a further embodiment, the pH of the first mixture is adjusted to about 8.5 to about 9.0.

In another embodiment of the disclosure, the first mixture is separated by centrifugation or hydrocyclone to separate the fiber from the first mixture and form the protein slurry. In a further embodiment, the mixture is separated by centrifugation to separate the fiber from the mixture and form the protein slurry. In an embodiment, the first mixture is centrifuged at a speed of about 1,000 rpm to about 2,000 rpm. In a further embodiment, the first mixture is centrifuged centrifuge at a speed of about 1,400 to about 1,600 rpm. In an embodiment, the mixture is centrifuged using a decanter centrifuge.

In another embodiment, the ratio of the insoluble fiber fraction or washed insoluble fiber fraction to water is about 1.0:0.5 to about 1.0:3.0 (w/w). In a further embodiment, the ratio of the insoluble fiber fraction or washed insoluble fiber fraction to water is about 1.0:1.0 to about 1.0:2.0 (w/w).

In another embodiment, the washed insoluble fiber fraction is centrifuged to separate the washed insoluble fiber fraction from extract. In a further embodiment, the washed insoluble fiber fraction is centrifuged at a speed of about 2,000 rpm to about 6,000 rpm. In a further embodiment, washed insoluble fiber fraction is centrifuged at a speed of about 3,000 to about 5,500 rpm.

In another embodiment of the disclosure, the pH of the second mixture is adjusted to about 8.0 to about 9.0.

In an embodiment of the disclosure, the ratio of the second mixture to the protease is about 100:1 to about 5000:1 (w/w).

In an embodiment of the disclosure, the second mixture is mixed with a protease at a temperature of about 40° C. to about 60° C. In another embodiment, the second mixture is mixed with a protease at a temperature of about 45° C. to about 55° C.

In another embodiment, the at least one protease comprises a protease from *Bacillus Licheniformis*.

In a further embodiment, the process further comprises the step of mixing the second mixture with a second protease.

In an embodiment, the ratio of the second mixture to the second protease is about 250:1 to about 5000:1 (w/w).

In another embodiment, the second mixture is mixed with the second protease at a temperature of about 50° C. to about 70° C. In an embodiment, the second mixture is mixed with the second protease at a temperature of about 55° C. to about 65° C.

In a further embodiment, the second protease comprises a fungal protease/peptidase complex from *Aspergillus oryzae*.

In another embodiment, the hydrolyzed protein concentrate is dried in a vacuum dryer, fluidized bed dryer, ring dryer or spray dryer to form the protein isolate.

In an embodiment of the disclosure, the partially defatted, fully defatted or protein-enriched meal comprises a canola, rapeseed, mustard seed, broccoli seed, flax seed, cotton seed, hemp seed, safflower seed, sesame seed or soybean meal. In another embodiment, the partially defatted, fully defatted or protein-enriched meal comprises a canola meal.

In a further embodiment, the hydrolyzed protein concentrate comprises a protein content of about 60% to about 90% on a dry weight basis.

In another embodiment, the process further comprises mixing the hydrolyzed protein extract with water to form a third mixture. In a further embodiment, the process further comprises filtering the third mixture fraction and the filtering comprises ultrafiltration. In an embodiment, the ultrafiltration comprises contacting the third mixture with an ultrafiltration apparatus that comprises a membrane to filter proteins larger than about 1,000 daltons.

In another embodiment, the process further comprises mixing the second insoluble fiber fraction to form a washed hydrolyzed protein extract and a washed second insoluble fiber fraction and separating the form the washed hydrolyzed protein extract from the washed second insoluble fiber fraction. In another embodiment, the washed hydrolyzed protein extract is combined with the hydrolyzed protein extract.

In an embodiment of the disclosure, there is also provided a process for the production of a protein concentrate from an oilseed meal comprising:

i) mixing the oilseed meal with a blending solvent, optionally water, a saline solution or a polysaccharide solution, to form a mixture and optionally treating the mixture with phytase at a temperature and a pH suitable for phytase activity;

ii) optionally adjusting the pH of the mixture to a pH of about 2.0 to about 10.0;

iii) separating fiber from the mixture to form a protein slurry, wherein the protein slurry comprises a first soluble protein fraction and an insoluble protein fraction;

iv) optionally repeating steps i)-iii) by mixing the protein slurry with additional oilseed meal;

v) separating the soluble protein fraction from the insoluble protein fraction;

vi) washing the insoluble protein fraction with a second blending solvent, optionally water, saline solution or polysaccharide solution, to form a washed insoluble protein fraction and a second soluble protein fraction;

vii) separating the washed insoluble protein fraction and the second soluble protein fraction;

viii) combining and separating the first and second soluble protein fractions to form a protein concentrate, optionally by filtering the first and second soluble protein fractions to form a protein concentrate or isolate;

ix) combining the washed insoluble protein fraction with the protein concentrate to form a combined protein concentrate or isolate; and x) optionally drying the combined protein concentrate.

In another embodiment of the disclosure, the ratio of partially defatted, fully defatted or protein-enriched meal to water is about 1:3 to about 1:30 (w/w). In another embodiment, the ratio of partially defatted, fully defatted or protein-enriched meal to water is about 1:5 to about 1:20 (w/w). In a further embodiment, the ratio is about 1:6 to about 1:12 (w/w). In an embodiment, the ratio is about 1:8 to about 1:10 (w/w).

In an embodiment, the pH of the mixture is adjusted to a pH of about 6.5 to about 10.0. In another embodiment, the pH of the mixture is adjusted to a pH of about 7.0 to about 9.0.

In another embodiment of the disclosure, the mixture is separated by centrifugation or hydrocyclone to separate the fiber from the mixture and form the protein slurry. In a further embodiment, the mixture is separated by centrifugation to separate the fiber from the mixture and form the protein slurry. In an embodiment, the mixture is centrifuged at a speed of about 1,000 rpm to about 2,000 rpm. In a further embodiment, the mixture is centrifuged at a speed of about 1,400 to about 1,600 rpm. In an embodiment, the mixture is centrifuged using a decanter centrifuge.

In another embodiment, the protein slurry is centrifuged to separate the protein solids fraction from the soluble protein fraction. In an embodiment, the protein slurry is centrifuged at a speed of about 6,000 rpm to about 8,500 rpm in a disc stack centrifuge. In another embodiment, the protein slurry is centrifuged at a speed of about 6,500 to about 7,500 rpm.

In another embodiment, the ratio of the insoluble protein fraction to water is about 1.0:0.5 to about 1.0:3.0 (w/w). In a further embodiment, the ratio of the insoluble protein fraction to water is about 1.0:1.0 to about 1.0:2.0 (w/w).

In another embodiment, the washed insoluble protein fraction and the second soluble protein fraction are separated using a centrifuge. In an embodiment, the washed insoluble protein fraction and the second soluble protein fraction are centrifuged at a speed of about 6,000 rpm to about 8,500 rpm in a disc stack centrifuge. In a further embodiment, the washed insoluble protein fraction and the second soluble protein fraction are centrifuged at a speed of about 6,500 to about 7,500 rpm.

In another embodiment, the first and second soluble protein fractions are filtered using an ultrafiltration apparatus. In a further embodiment, the ultrafiltration apparatus comprises a membrane to filter proteins larger than about 10,000 daltons. In an embodiment, the process further comprises the step of filtering the first and second soluble protein fractions using a diafiltration apparatus.

In another embodiment, the combined protein concentrate is dried in a vacuum dryer, fluidized bed dryer, ring dryer or spray dryer to form the dried protein concentrate.

In an embodiment of the disclosure, the partially defatted, fully defatted or protein-enriched meal comprises a canola, rapeseed, mustard seed, broccoli seed, flax seed, cotton seed, hemp seed, safflower seed, sesame seed or soybean meal. In another embodiment, the partially defatted, fully defatted or protein-enriched meal comprises a canola meal.

In another embodiment, the protein concentrate comprises a hydrolyzed protein concentrate. In another embodiment, the protein concentrate is hydrolyzed to produce peptides and free amino acids. In another embodiment, the hydrolyzed protein concentrate comprises peptides and/or free amino acids.

In a further embodiment, the protein concentrate comprises a protein content of about 60% to about 90% on a dry weight basis.

In an embodiment of the disclosure, there is also provided a process for the production of a protein isolate from an oilseed meal comprising:

i) mixing the oilseed meal with a blending solvent, optionally water, to form a mixture and optionally treating the mixture with phytase at a temperature and a pH suitable for phytase activity;

ii) optionally adjusting the pH of the mixture to a pH of about 2.0 to about 10.0;

iii) separating fiber from the mixture to form a protein slurry, wherein the protein slurry comprises a soluble protein fraction and an insoluble protein fraction;

iv) washing the fiber with a second blending solvent, optionally water, to form a washed fiber fraction;

vi) separating the washed fiber fraction to form a second protein slurry and washed fiber solids;

vii) combining and separating the first and second protein slurries to form a protein concentrate, optionally by filtering the first and second soluble protein fractions to form a protein concentrate; and ix) optionally drying the protein concentrate.

In another embodiment of the disclosure, the ratio of partially defatted, fully defatted or protein-enriched meal to water is about 1:3 to about 1:30 (w/w). In another embodiment, the ratio of partially defatted, fully defatted or protein-enriched meal to water is about 1:5 to about 1:20 (w/w). In a further embodiment, the ratio is about 1:6 to about 1:12 (w/w). In an embodiment, the ratio is about 1:8 to about 1:10 (w/w).

In an embodiment, the pH of the mixture is adjusted to a pH of about 6.5 to about 10.0. In another embodiment, the pH of the mixture is adjusted to a pH of about 7.0 to about 9.0.

In another embodiment of the disclosure, the mixture is separated by centrifugation or hydrocyclone to separate the fiber from the mixture and form the protein slurry. In a further embodiment, the mixture is separated by centrifugation to separate the fiber from the mixture and form the protein slurry. In an embodiment, the mixture is centrifuged at a speed of about 1,000 rpm to about 2,000 rpm. In a further embodiment, the mixture is centrifuged centrifuge at a speed of about 1,400 to about 1,600 rpm. In an embodiment, the mixture is centrifuged using a decanter centrifuge.

In another embodiment, the ratio of the fiber fraction to water is about 1.0:0.5 to about 1.0:3.0 (w/w). In a further embodiment, the ratio of the insoluble protein fraction to water is about 1.0:1.0 to about 1.0:2.0 (w/w).

In another embodiment of the disclosure, the washed fiber fraction is separated by centrifugation, gravity sedimentation, a gravity table or hydrocyclone to separate the fiber solids and form second the protein slurry. In a further embodiment, the washed fiber fraction is separated by centrifugation to separate the fiber and form the second protein slurry. In an embodiment, the mixture is centrifuged at a speed of about 1,000 rpm to about 2,000 rpm. In a further embodiment, the fiber fraction is centrifuged centrifuge at a speed of about 1,400 to about 1,600 rpm. In an embodiment, the fiber fraction is centrifuged using a decanter centrifuge.

In another embodiment, the first and second slurries are filtered using an ultrafiltration/microfiltration apparatus. In a further embodiment, the ultrafiltration/microfiltration apparatus comprises a membrane to filter proteins larger than about 10,000 daltons. In an embodiment, the process further comprises the step of filtering the first and second slurries using a diafiltration apparatus.

In another embodiment, the protein concentrate is dried in a vacuum dryer, fluidized bed dryer, ring dryer or spray dryer to form the dried protein concentrate.

In an embodiment of the disclosure, the partially defatted, fully defatted or protein-enriched meal comprises a canola, rapeseed, mustard seed, broccoli seed, flax seed, cotton seed, hemp seed, safflower seed, sesame seed or soybean meal. In another embodiment, the partially defatted, fully defatted or protein-enriched meal comprises a canola meal.

In another embodiment, the protein isolate comprises a hydrolyzed protein isolate. In another embodiment, the protein isolate is hydrolyzed to produce peptides and free amino acids. In another embodiment, the hydrolyzed protein isolate comprises peptides and/or free amino acids.

In a further embodiment, the protein concentrate comprises a protein content of about 60% to about 90% on a dry weight basis.

In another embodiment of the disclosure, there is also provided a process for the removal of fiber from a partially defatted, fully defatted or protein-enriched meal, comprising:
  i) mixing an oilseed meal with a blending solvent, optionally water, an aqueous solution or protein containing solution, to form a mixture and optionally treating the mixture with phytase at a temperature and a pH suitable for phytase activity;
  ii) optionally adjusting the pH of the protein slurry to a pH of about 2 to about 10; and
  iii) separating the mixture to form a protein slurry comprising soluble and insoluble proteins and an insoluble fiber fraction.

In another embodiment of the disclosure, there is also included protein concentrates and protein isolates, produced in accordance with the processes of the disclosure. Accordingly, in an embodiment of the disclosure, there is provided an oilseed protein isolate having a protein content of at least 90% (w/w), wherein the canola protein isolate has a solubility of at least 85% (w/w), wherein the solubility is measured at a concentration of about 1% and a pH of about 6.5 to about 7.5 in a borate-phosphate buffer solution. In another embodiment, the oilseed protein isolate has a solubility of at least 95% (w/w) in a borate-phosphate buffer solution. In a further embodiment, the oilseed protein isolate has a solubility of at least 99% (w/w) in a borate-phosphate buffer solution. In a further embodiment, the oilseed protein isolate has a solubility of at least 99.5% (w/w) in a borate-phosphate buffer solution.

In another embodiment of the disclosure, the oilseed protein isolate has a solubility of at least 85% (w/w) at a concentration of about 1% and a pH of about 6.5 to about 7.0 in a borate-phosphate buffer solution. In a further embodiment, the oilseed protein isolate has a solubility of at least 85% (w/w) at a concentration of about 1% and a pH of about 6.7 to about 7.0 in a borate-phosphate buffer solution.

In another embodiment of the disclosure, the oilseed protein isolate has a solubility of at least 85% (w/w) at a concentration of about 1% and a pH of about 6.5 to about 7.0 in a borate-phosphate buffer solution at a temperature of about 35° C. to about 45° C. In another embodiment of the disclosure, the oilseed protein isolate has a solubility of at least 85% (w/w) at a concentration of about 1% and a pH of about 6.5 to about 7.0 in a borate-phosphate buffer solution at a temperature of about 38° C. to about 40° C.

In another embodiment, the oilseed protein isolate comprises,
  i) a first class of proteins having a molecular weight of about 60 kDa to about 80 kDa, the first class of proteins comprising about 60% to about 90% (w/w) of the oilseed isolate;
  ii) a second class of proteins having a molecular weight of about 10 kDa to about 30 kDa, the second class of proteins comprising about 10% to about 30% (w/w) of the oilseed isolate; and
  iii) a third class of proteins having a molecular weight of less than about 10 kDa, the third class of proteins comprising about 2% to about 10% (w/w) of the oilseed isolate.

In another embodiment, the oilseed protein isolate comprises,
  i) a first class of proteins having a molecular weight of about 60 kDa to about 80 kDa, the first class of proteins comprising about 60% to about 70% (w/w) of the oilseed isolate;
  ii) a second class of proteins having a molecular weight of about 10 kDa to about 30 kDa, the second class of proteins comprising about 20% to about 30% (w/w) of the oilseed isolate; and
  iii) a third class of proteins having a molecular weight of less than about 10 kDa, the third class of proteins comprising about 5% to about 10% (w/w) of the oilseed isolate.

In a further embodiment, the oilseed protein isolate comprises
  i) a first class of proteins having a molecular weight of about 65 kDa to about 75 kDa, the first class of proteins comprising about 60% to about 90% (w/w) of the oilseed isolate;
  ii) a second class of proteins having a molecular weight of about 10 kDa to about 20 kDa, the second class of proteins comprising about 10% to about 30% (w/w) of the oilseed isolate; and
  iii) a third class of proteins having a molecular weight of less than about 10 kDa, the third class of proteins comprising about 2% to about 10% (w/w) of the oilseed isolate.

In another embodiment, the oilseed protein isolate comprises
  i) a first class of proteins having a molecular weight of about 65 kDa to about 70 kDa, the first class of proteins comprising about 60% to about 70% (w/w) of the oilseed isolate;

ii) a second class of proteins having a molecular weight of about 10 kDa to about 20 kDa, the second class of proteins comprising about 20% to about 30% (w/w) of the oilseed isolate; and iii) a third class of proteins having a molecular weight of less than about 10 kDa, the third class of proteins comprising about 5% to about 10% (w/w) of the oilseed isolate.

In another embodiment of the disclosure, the oilseed protein isolate comprises a canola, rapeseed, mustard seed, broccoli seed, flax seed, cotton seed, hemp seed, safflower seed, sesame seed or soybean oilseed protein isolate. In another embodiment, the oilseed comprises a canola oilseed.

In another embodiment, the oilseed protein isolate has an antinutritional concentration less than about 0.5% (w/w), optionally less than 0.1%. In a further embodiment, the oilseed protein isolate has a threonine content of at least about 4.1% (w/w) and a valine content of at least about 5.1% (w/w).

In another embodiment of the disclosure, there is also included a oilseed protein hydrolyzate having a protein content of about 60% to about 90% and having a protein dispersibility index of at least 95.0% and wherein a 1.0% solution (w/w) in water of the protein hydrolyzate has a visible light transmittance of least 90.0%. In a further embodiment, the oilseed protein hydrolyzate has a protein dispersibility index of at least 99.0%. In an embodiment, the oilseed protein hydrolyzate has a protein dispersibility index of at least 99.8%.

In another embodiment of the disclosure, a 1.0% solution (w/w) of the protein hydrolyzate has a visible light transmittance of least 95.0%. In a further embodiment, a 1.0% solution (w/w) of the protein hydrolyzate has a visible light transmittance of least 97.0%. In an embodiment, the oilseed protein hydrolyzate contains less than 1% by weight of fiber.

In another embodiment, the oilseed protein hydrolyzate has an antinutritional concentration less than about 0.5% (w/w). In a further embodiment, the oilseed protein hydrolyzate has a threonine content of at least about 4.1% (w/w), a valine content of at least about 5.1% (w/w), a methionine content of at least about 1.7% (w/w) and an isoleucine content of at least about 5.0% (w/w).

In another embodiment of the disclosure, there is also included an oilseed protein concentrate having a protein content of about 60% to about 90%, wherein the protein has a methionine content at least 1.90% by weight and a cysteine content at least 1.60% by weight. In an embodiment, the oilseed protein concentrate has a methionine content at least 1.95% by weight. In an embodiment, the oilseed protein concentrate has a methionine content at least 2.02% by weight. In an embodiment, the oilseed protein concentrate has a cysteine content at least 1.65% by weight. In an embodiment, the oilseed protein concentrate has a cysteine content at least 1.68% % by weight.

In another embodiment, the protein concentrate further has a threonine content of at least 4.0% by weight, a valine content of at least 5.1% (w/w) and a leucine content of at least 8.25% (w/w) of the total protein weight. In another embodiment, the oilseed protein concentrate has an antinutritional concentration less than about 0.5% (w/w), optionally less than 0.1%.

In another embodiment, the protein concentrate has a glucosinolate content of less than about 1 μmol/g of the protein concentrate, and optionally less than about 0.5 μmol/g.

The present disclosure relates to processes for the production of protein concentrates and protein isolates, in addition to hydrolyzed protein concentrates and isolates, in which the oilseed meal is subjected to low g-forces to separate the fiber from the insoluble and soluble protein fractions.

Accordingly, the present disclosure includes a process for the production of a protein concentrate from an oilseed meal comprising:

i) mixing the oilseed meal with a first blending solvent to form a mixture;

ii) optionally treating the mixture with phytase at a temperature and a pH suitable for phytase activity;

iii) optionally adjusting the pH of the mixture to a pH between 6.0 and 10.0;

iv) subjecting the mixture to a g-force sufficient to separate the mixture to form
  a) a fiber fraction, and
  b) protein fractions comprising an insoluble protein fraction and a soluble protein fraction;

v) optionally mixing the fiber fraction with a second blending solvent and repeating step iv);

vi) optionally adjusting the pH of the protein fractions to a pH between 4.0 and 6.0;

vii) optionally heating the protein fractions to a temperature between 80° C. and 100° C. to precipitate the proteins; and viii) separating the precipitated proteins from the protein fraction to form the protein concentrate.

In another embodiment, the first and second blending solvents comprise water, a saline solution or a polysaccharide solution. In a further embodiment, the first and second blending solvents comprise water.

In an embodiment of the disclosure, the partially defatted, fully defatted or protein-enriched oilseed meal comprises a canola, rapeseed, mustard seed, broccoli seed, flax seed, cotton seed, hemp seed, safflower seed, sesame seed or soybean meal. In another embodiment, the partially defatted, fully defatted or protein-enriched oilseed meal comprises a canola meal.

In an embodiment of the disclosure, the ratio of the oilseed meal to the first blending solvent is 1:3 to 1:30 (w/w) of meal to water, optionally about 1:8 to about 1:10 (w/w).

In an embodiment of the disclosure, the phytase is added in an amount between 0.01% and 0.1% (w/w) based on the weight of the oilseed meal. In a further embodiment, the temperature suitable for phytase activity is between 20° and 60° C. In a further embodiment, the pH suitable for phytase activity is between 2.0 and 7.0.

In another embodiment of the disclosure, the mixture is subjected to a g-force of between 100 g and 500 g, optionally between 150 g and 400 g, suitably between 180 g and 350 g.

In another embodiment, separating the mixture comprises using a centrifuge or a hydrocyclone. In another embodiment, the centrifuge comprises a decanter centrifuge or disc stack centrifuge.

In a further embodiment, separating the precipitated proteins comprises using a centrifuge or a hydrocyclone. In another embodiment, separating the precipitated proteins comprises using a centrifuge. In another embodiment, centrifuging the precipitated proteins comprises a g-force between 2,500 g and 9,500 g.

In another embodiment of the disclosure, the process further comprises the step of drying the protein concentrate to a moisture content of between 4% and 8% (w/w).

In another embodiment, the protein concentrate comprises a hydrolyzed protein concentrate. In another embodiment, the protein concentrate is hydrolyzed to produce peptides and free amino acids. In another embodiment, the hydrolyzed protein concentrate comprises peptides and/or free amino acids.

In another embodiment, there is also included a protein concentrate having a protein content of at least 60% and less than 90% protein comprising:

i) a first protein fraction comprising between 30% and 70% 2S protein;

ii) a second protein fraction comprising between 20% and 50% 12S protein.

The present disclosure also includes a process for the production of a protein concentrate from an oilseed meal comprising:

i) mixing the oilseed meal with a first blending solvent to form a mixture;

ii) optionally treating the mixture with phytase at a temperature and a pH suitable for phytase activity;

iii) optionally adjusting the pH of the mixture to a pH between 6.0 and 10.0;

iv) subjecting the mixture to a g-force sufficient to separate the mixture to form
    a) a fiber fraction, and
    b) protein fractions comprising an insoluble protein fraction and a soluble protein fraction;

v) optionally mixing the fiber fraction with a second blending solvent and repeating step iv);

vi) optionally adjusting the pH of the protein fractions to a pH between 4.0 and 6.0;

vii) mixing the protein fractions with a mixing solvent to form a protein slurry and precipitate the proteins;

viii) separating the precipitated proteins from the protein slurry to form the protein concentrate; and viii) optionally, repeating steps vi) and vii) with the precipitated proteins.

In another embodiment, the first and second blending solvents comprise water, a saline solution or a polysaccharide solution. In a further embodiment, the first and second blending solvents comprise water.

In an embodiment of the disclosure, the partially defatted, fully defatted or protein-enriched oilseed meal comprises a canola, rapeseed, mustard seed, broccoli seed, flax seed, cotton seed, hemp seed, safflower seed, sesame seed or soybean meal. In another embodiment, the partially defatted, fully defatted or protein-enriched oilseed meal comprises a canola meal.

In an embodiment of the disclosure, the ratio of the oilseed meal to the first blending solvent is 1:3 to 1:30 (w/w) of meal to water, optionally about 1:8 to about 1:10 (w/w).

In an embodiment of the disclosure, the phytase is added in an amount between 0.01% and 0.1% (w/w) based on the weight of the oilseed meal. In a further embodiment, the temperature suitable for phytase activity is between 20° and 60° C. In a further embodiment, the pH suitable for phytase activity is between 2.0 and 7.0.

In another embodiment of the disclosure, the mixture is subjected to a g-force of between 100 g and 500 g, suitably between 150 g and 400 g, optionally between 180 g and 350 g.

In another embodiment, separating the mixture comprises using a centrifuge or a hydrocyclone. In another embodiment, the centrifuge comprises a decanter centrifuge or a disc stack centrifuge.

In another embodiment of the disclosure, the mixing solvent comprises an ethanol:water mixture, wherein the ethanol is present in an amount between 90% and 100% (v/v).

In another embodiment, separating the precipitated proteins comprises using a centrifuge or a hydrocyclone. In another embodiment, separating the precipitated proteins comprises using a centrifuge. In another embodiment, centrifuging the precipitated proteins comprises a g-force between 2,500 g and 9,500 g.

In another embodiment of the disclosure, steps vii) and viii) are repeated at least twice.

In another embodiment, the process further comprises the step of drying the protein concentrate to a moisture content of between 4% and 8% (w/w).

In another embodiment, the protein concentrate comprises a hydrolyzed protein concentrate. In another embodiment, the protein concentrate is hydrolyzed to produce peptides and free amino acids. In another embodiment, the hydrolyzed protein concentrate comprises peptides and/or free amino acids.

In another embodiment, there is also included a protein concentrate having a protein content of at least 60% and less than 90% protein comprising:

i) a first protein fraction comprising between 30% and 70% 2S protein;

ii) a second protein fraction comprising between 20% and 50% 12S protein.

The present disclosure also includes a process for the production of a protein isolate from an oilseed meal comprising:

i) mixing the oilseed meal with a first blending solvent to form a mixture;

ii) optionally treating the mixture with phytase at a temperature and a pH suitable for phytase activity;

iii) optionally adjusting the pH of the mixture to a pH between 6.0 and 10.0;

iv) subjecting the mixture to a g-force sufficient to separate the mixture to form
    a) a fiber fraction, and
    b) protein fractions comprising an insoluble protein fraction and a soluble protein fraction;

v) optionally mixing the fiber fraction with a second blending solvent and repeating step iv);

vi) separating the insoluble protein fraction from the soluble protein fraction to recover therefrom an insoluble protein concentrate and a soluble protein extract; and vii) subjecting the soluble protein extract to filtration to recover therefrom the protein isolate.

In another embodiment, the first and second blending solvents comprise water, a saline solution or a polysaccharide solution. In a further embodiment, the first and second blending solvents comprise water.

In an embodiment of the disclosure, the partially defatted, fully defatted or protein-enriched oilseed meal comprises a canola, rapeseed, mustard seed, broccoli seed, flax seed, cotton seed, hemp seed, safflower seed, sesame seed or soybean meal. In another embodiment, the partially defatted, fully defatted or protein-enriched oilseed meal comprises a canola meal.

In an embodiment of the disclosure, the ratio of the oilseed meal to the first blending solvent is 1:3 to 1:30 (w/w) of meal to water, optionally about 1:8 to about 1:10 (w/w).

In an embodiment of the disclosure, the phytase is added in an amount between 0.01% to 0.1% (w/w) based on the weight of the oilseed meal. In a further embodiment, the temperature suitable for phytase activity is between 20° and 60° C. In a further embodiment, the pH suitable for phytase activity is between 2.0 and 7.0.

In another embodiment of the disclosure, the mixture is subjected to a g-force of between 100 g and 500 g, suitably between 150 g and 400 g, optionally between 180 g and 350 g.

In another embodiment, separating the mixture comprises using a centrifuge or a hydrocyclone. In an embodiment, the centrifuge comprises a decanter centrifuge or a disc stack centrifuge.

In another embodiment, separating the insoluble protein fraction from the soluble protein fraction comprises using a centrifuge or a hydrocyclone. In a further embodiment separating the insoluble protein fraction from the soluble protein fraction comprises using a centrifuge. In another embodiment, centrifuging to separate the insoluble protein fraction from the soluble protein fraction comprises a g-force between 2,500 g and 9,500 g.

In another embodiment, the process further comprises the step of drying the protein isolate to a moisture content of between 4% and 8% (w/w).

In another embodiment, the protein isolate comprises a hydrolyzed protein isolate. In another embodiment, the protein isolate is hydrolyzed to produce peptides and free amino acids. In another embodiment, the hydrolyzed protein isolate comprises peptides and/or free amino acids.

In another embodiment, there is also included a protein isolate having a protein content of at least 90% protein comprising:
  i) a first protein fraction comprising between 10% and 40% 2S protein;
  ii) a second protein fraction comprising between 30% and 70% 12S protein.

In another embodiment of the disclosure, there is also provided a process for the production of a protein concentrate from an oilseed meal comprising:
  i) mixing the oilseed meal with a first blending solvent to form a mixture;
  ii) optionally treating the mixture with phytase at a temperature and a pH suitable for phytase activity;
  iii) optionally adjusting the pH of the mixture to solubilize proteins in the mixture;
  iv) subjecting the mixture to a g-force sufficient to separate the mixture to form
    a) a fiber fraction, and
    b) a protein fraction comprising
      (i) an insoluble protein fraction, and
      (ii) a soluble protein fraction;
  v) separating the fiber fraction from the protein fraction and mixing the fiber fraction with a second blending solvent to form a fiber mixture;
  vi) treating the fiber mixture with a protease at a temperature and a pH suitable for protease activity;
  vii) subjecting the fiber mixture to a g-force sufficient to separate the fiber mixture to form:
    a) a second fiber fraction, and
    b) a hydrolyzed protein fraction, comprising
      (i) an insoluble protein fraction comprising partially hydrolyzed and un-hydrolyzed protein, and
      (ii) a soluble hydrolyzed protein fraction;
  viii) optionally adjusting the pH of the protein fraction from step iv(b) to a pH suitable to precipitate proteins;
  ix) separating the precipitated proteins from the protein fraction;
  x) optionally combining the precipitated proteins and the hydrolyzed protein fraction to form the protein concentrate.

In another embodiment, the process further comprises mixing the fiber fraction with the first blending solvent and repeating step iv) once, twice or three times and/or mixing the second fiber fraction with the second blending solvent and repeating step vii) once, twice or three times.

In another embodiment, the first and second blending solvents comprise water, a saline solution or a polysaccharide solution, optionally water, and wherein the ratio of the oilseed meal to the first blending solvent is 1:3 to 1:30 (w/w) of meal to water.

In another embodiment, the temperature suitable for phytase activity is between 20° and 60° C. and the pH suitable for phytase activity is between 2.0 and 7.0 and the temperature suitable for protease activity is between 30° and 70° C. and the pH suitable for protease activity is between 5.0 and 9.0.

In another embodiment, the mixture and/or the fiber mixture is subjected to a g-force of between 100 g and 500 g, optionally between 150 g and 400 g, or between 170 g and 350 g. In an embodiment, separating the mixture and/or the fiber mixture comprises using a centrifuge or a hydrocyclone.

In a further embodiment, the pH suitable to precipitate the proteins in the protein fraction is between 4.0 and 6.0.

In another embodiment, the process further comprises the step of drying the protein concentrate to a moisture of between 4% and 8% (w/w). In another embodiment, the protein concentrate also comprises peptides and free amino acids.

In another embodiment, the oilseed meal comprises a canola, rapeseed, mustard seed, broccoli seed, flax seed, cotton seed, hemp seed, safflower seed, sesame seed or soybean meal, optionally canola meal.

The present disclosure also includes a process for the production of a protein concentrate from an oilseed meal comprising:
  i) mixing the oilseed meal with a first blending solvent to form a mixture;
  ii) optionally treating the mixture with phytase at a temperature and a pH suitable for phytase activity;
  iii) optionally adjusting the pH of the mixture to solubilize proteins in the mixture;
  iv) subjecting the mixture to a g-force sufficient to separate the mixture to form
    a) a fiber fraction, and
    b) a protein fraction comprising
      (i) an insoluble protein fraction, and
      (ii) a soluble protein fraction;
  v) separating the fiber fraction from the protein fraction and mixing the fiber fraction with a second blending solvent to form a fiber mixture;
  vi) treating the fiber mixture with a protease at a temperature and a pH suitable for protease activity;
  vii) subjecting the fiber mixture to a g-force sufficient to separate the fiber mixture to form:
    a) a second fiber fraction, and
    b) a hydrolyzed protein fraction, comprising
      (i) an insoluble protein fraction comprising partially hydrolyzed and un-hydrolyzed protein, and
      (ii) a soluble hydrolyzed protein fraction;
  viii) mixing the protein fraction with a mixing solvent to precipitate proteins;
  ix) separating the precipitated proteins from the protein fraction; and
  x) optionally combining the precipitated proteins and the hydrolyzed protein fraction to form the protein concentrate.

In another embodiment, the process further comprises mixing the fiber fraction with the first blending solvent and repeating step iv) once, twice or three times and/or mixing the second fiber fraction with the second blending solvent and repeating step vii) once, twice or three times.

In another embodiment, the first and second blending solvents comprise water, a saline solution or a polysaccharide solution, optionally water, and wherein the ratio of the oilseed meal to the first blending solvent is 1:3 to 1:30 (w/w) of meal to water.

In another embodiment, the temperature suitable for phytase activity is between 20° and 60° C. and the pH suitable for phytase activity is between 2.0 and 7.0 and the temperature suitable for protease activity is between 30° and 70° C. and the pH suitable for protease activity is between 5.0 and 9.0.

In another embodiment, the mixture and/or the fiber mixture is subjected to a g-force of between 100 g and 500 g, optionally between 150 g and 400 g, or between 170 g and 350 g. In an embodiment, separating the mixture and/or the fiber mixture comprises using a centrifuge or a hydrocyclone.

In another embodiment, the mixing solvent comprises an ethanol:water mixture, wherein the ethanol is present in an amount between 80% and 100% (v/v).

In another embodiment, the process further comprises the step of drying the protein concentrate to a moisture of between 4% and 8% (w/w). In another embodiment, the protein concentrate also comprises peptides and free amino acids.

In another embodiment, the oilseed meal comprises a canola, rapeseed, mustard seed, broccoli seed, flax seed, cotton seed, hemp seed, safflower seed, sesame seed or soybean meal, optionally canola meal.

In another embodiment, the present disclosure also includes a process for the production of a protein isolate from an oilseed meal comprising:
i) mixing the oilseed meal with a first blending solvent to form a mixture;
ii) optionally treating the mixture with phytase at a temperature and a pH suitable for phytase activity;
iii) optionally adjusting the pH of the mixture to solubilize proteins in the mixture;
iv) subjecting the mixture to a g-force sufficient to separate the mixture to form
  a) a fiber fraction, and
  b) a protein fraction comprising
    (i) an insoluble protein fraction, and
    (ii) a soluble protein fraction;
vi) separating the insoluble protein fraction from the soluble protein fraction to recover therefrom an insoluble protein concentrate and a soluble protein extract; and
vii) subjecting the soluble protein extract to membrane filtration to recover therefrom the protein isolate.

In another embodiment, the process further comprises mixing the fiber fraction with the first blending solvent and repeating step iv) once, twice or three times.

In another embodiment, the first and second blending solvents comprise water, a saline solution or a polysaccharide solution, optionally water, and wherein the ratio of the oilseed meal to the first blending solvent is 1:3 to 1:30 (w/w) of meal to water.

In another embodiment, the temperature suitable for phytase activity is between 20° and 60° C. and the pH suitable for phytase activity is between 2.0 and 7.0 and the temperature suitable for protease activity is between 30° and 70° C. and the pH suitable for protease activity is between 5.0 and 9.0.

In another embodiment, the mixture and/or the fiber mixture is subjected to a g-force of between 100 g and 500 g, optionally between 150 g and 400 g, or between 170 g and 350 g. In an embodiment, separating the mixture and/or the fiber mixture comprises using a centrifuge or a hydrocyclone.

In another embodiment, the process further comprises the step of drying the protein concentrate to a moisture of between 4% and 8% (w/w). In another embodiment, the protein concentrate also comprises peptides and free amino acids.

In another embodiment, the oilseed meal comprises a canola, rapeseed, mustard seed, broccoli seed, flax seed, cotton seed, hemp seed, safflower seed, sesame seed or soybean meal, optionally canola meal.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

Embodiments of the invention will be described in relation to the drawings in which.

DETAILED DESCRIPTION OF THE DISCLOSURE

(I) Definitions

Figure 1:
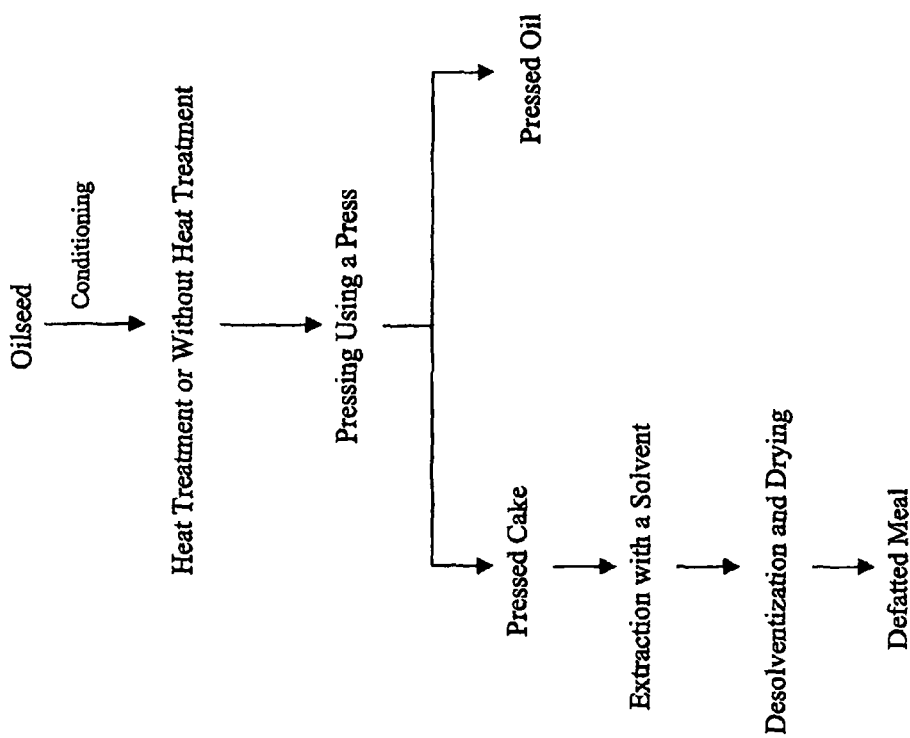
FIG. 1 is a schematic representation showing a preparation of defatted meal of an oilseed.

The term "peptide" as used herein refers to various natural compounds containing two or more amino acids linked by the carboxylic acid group of one amino acid to the amino group of another amino acid. Peptides generally have 4-100 amino acids (US Patent Office Classification Index Glossary) and a molecular weight of less than about 10,000 Daltons.

The term "protein" as used herein refers to peptides with more than about 50-100 amino acids and a molecular weight in excess of about 10,000 Daltons. The US Patent Office Classification Index Glossary defines protein as peptides with more then 100 amino acids.

The term "partially defatted meal" (alternatively called "seedcake" or "presscake") as used herein refers to an oilseed meal in which the oilseed has been pressed to remove the oil contained within. The pressing of the oilseed results in pressed oil and a partially defatted meal, which contains from about 15% to about 50% of protein on a dry weight basis and from about 10% to about 20% oil, optionally about 14% to 16%, on a dry weight basis.

The term "defatted meal" (alternatively called "fully defatted meal") as used herein refers to an oilseed which has been ii) pressed to remove oil, which forms a seedcake and pressed oil, and ii) subjected to solvent extraction, using, for example, hydrophobic and low-boiling solvents, such as butane, pentane, hexane and/or other refrigerants such as iodotrifluoromethane (ITFM) and R134a (1,1,1,2-tetrafluoroethane), to remove or reduce residual oil from the seedcake and form the defatted meal. A defatted meal will typically have a protein content of about 25% to about 55%, optionally 30% to about 50%, suitably about 35% to about 50%, on a dry weight basis, and from about 0% to about 4% oil, optionally about 0.5% to about 4%, optionally about 1% to about 3%, on a dry weight basis.

The term "protein-enriched meal" as used herein refers to a defatted meal as described above, which has subsequently been treated to remove fiber from the defatted meal. Accordingly, the defatted meal is typically subjected to a milling step and a screening step to remove fiber and obtain a protein-enriched meal having a protein content of about 30% to about 60%, optionally 40% to 55%, suitably 50% to 55% on a dry weight basis, and about 5% to about 6.5% fiber, optionally less than about 6%. Collectively, a partially defatted meal, fully defatted meal and a protein-enriched meal may be referred to as "meal".

The term "protein concentrate" as used herein refers to a defatted or protein-enriched meal that has been treated using the processes of the present disclosure to increase the protein content, where the protein concentrate has greater than 60% protein content but less than 90% protein content on a dry weight basis. The balance may comprise carbohydrate, ash, fiber and oil. In an embodiment, the protein concentrate is generally produced from the insoluble protein fraction or soluble/insoluble protein fractions of a protein mixture. In one embodiment, the protein concentrate also includes hydrolyzed protein concentrate.

The term "hydrolyzed protein concentrate" as used herein refers to a protein concentrate that has been treated to hydrolyze the proteins within the protein concentrate into amino acids and smaller peptides. Proteins can be hydrolyzed using various chemicals, such as strong acids and bases, and enzymes, preferably proteases.

The term "protease" as used herein refers to any enzyme that hydrolyzes proteins by hydrolysis of the peptide bonds that link amino acids together in the polypeptide chain forming the protein. Examples of proteases include, but are not limited to, Alcalase®, Flavourzyme® and Protamex®. The proteases solubilize and partially hydrolyse proteins trapped within the fiber fraction and to release insoluble proteins from the fiber fraction using a dosage of a single protease.

The term "protein isolate" as used herein refers to a defatted or protein-enriched meal that has been treated using the processes of the present disclosure to increase the protein content, where the protein isolate has 90% or greater than 90% protein on a dry weight basis. The balance may comprise carbohydrate, ash, and oil. In an embodiment, the protein isolate is generally produced from the soluble protein fraction of a protein mixture.

The term "hydrolyzed protein isolate" as used herein refers to a protein isolate that has been treated with proteases to hydrolyze the proteins within the protein isolate into amino acids and smaller peptides.

The term "mixing solvent" as used herein refers to a solvent that forms a protein slurry or mixture when mixed with a partially defatted, fully defatted or protein-enriched meal. In addition, the fiber present in the meal possesses minimal solubility in the mixing solvent (eg. typically less than 1% (w/w) solubility, or about 0% solubility), and suitably, is not soluble in the mixing solvent. Examples of mixing solvents include, but are not limited to, water, alcohols, such as methanol, ethanol or isopropanol, polysaccharide solutions such as guar gum solution, saline solutions, or mixtures of any of the above.

The term "blending solvent" as used herein refers to any aqueous solvent (typically at least: 80%, 85%, 90%, 95%, 98% or 99% water by weight) that forms a slurry or mixture when mixed with a partially defatted, fully defatted or protein-enriched meal. Typically the blending solvent is free from organic solvents, such as methanol, ethanol, propanol, iso-propanol, tetrahydrofuran since these solvents are not desirable as residues in a protein isolate, concentrate or hydrosylate for human consumption, however, if organic solvents are present, they are in the blending solvent in small amount (eg. typically equal to or less than: 20%, 10%, 10%, 5% or 1%) so that their presence in the final product is negligible. Examples of blending solvents include water, acidic water, alkaline water, saline salt solutions (such as sodium chloride, potassium chloride, calcium chloride), polysaccharide solutions (such as guar gum), and aqueous protein solutions.

The invention contemplates using a variety of solvents, which could include blending solvents, mixing solvents or other combinations or alcohols (eg. 80% ethanol), water and/or aqueous solvents. The use of the term blending solvents should not be construed as precluding the use of organic solvents in processes as disclosed herein.

The term "extraction solvent" as used herein refers to a solvent which is capable of solubilizing antinutritional compounds, or other constituents, that are present in the oilseed and which are desirably removed. Examples of antinutritionals include, but are not limited to, glucosinolates, phytic acid, phytates and other compounds that reduce the nutritional or commercial value of the protein concentrate or protein isolate. Antinutritional compounds are compounds that are, for example, not digestible by mammals (e.g humans), have adverse effects, such as toxicity or are bitter tasting, and are desirably removed from the protein product. Accordingly, the concentration of antinutritionals in a protein product produced in accordance with a process of the present disclosure is less than about 1% (w/w), optionally less than about 0.5% (w/w), optionally less than about 0.1% (w/w), and optionally less than about 0.05% (w/w). Examples of other compounds include, but are not limited to, materials that undesirably effect the quality, color, taste, odor, appearance or characteristics of the end product. Examples include compounds that cause a darkening or variation in the color, cause a bitter taste or a pungent odor, such as sinapine or sinigrin, or affect the handling or agglomeration of the end product. While the antinutritionals or other components are not desirable in the protein concentrates or isolates they may constitute commercially valuable side products which can have utility as medicinal or industrial ingredients or end products once separated from the protein concentrate or isolate. Examples of extraction solvents include, but are not limited to, water, alcohols, such as methanol, ethanol, isopropanol, or mixtures of any of the above. Other extractions solvents which are useful include tetrahydrofuran (THF), dimethylformamide (DMF), and ethers, such as methyl t-butyl ether. However, it will be known to those skilled in the art that solvents such as THF, DMF or ethers, as a result of their higher toxicity as compared to, for example, ethanol, require lower limits in the protein product.

The term "homogeneous agitation" as used herein refers to the mixing of a protein meal, such as a partially defatted meal, a fully defatted meal or a protein-enriched meal with a solvent to form a homogenous mixture or suspension. Such agitation is accomplished, for example, by mixing the slurry or mixture at a speed of about 30 rpm to about 300 rpm in a standard mixer.

The term "washed" used herein refers to a protein fraction that has been mixed with an extraction solvent, such as ethanol, to remove antinutritional compounds, or other constituents, from the protein fraction.

The term "protein slurry" as used herein refers to protein, for example, the protein in a defatted or protein-enriched meal, that has been mixed with a mixing solvent to form a suspension of protein, and optionally fiber and other antinutritional compounds, in the mixing solvent.

The terms "soluble protein fraction" and "insoluble protein fraction" as used herein refer to specific protein fractions which are either soluble or insoluble, respectively, in a particular solvent, such as a blending solvent, mixing solvent or an extraction solvent. In an embodiment, the insoluble protein fraction is generally composed of insoluble globulin and denatured proteins. The insoluble protein fraction is generally composed of insoluble globulin proteins. In another embodiment, the soluble protein fraction is generally composed of albumin, soluble globulin and undenatured proteins. The soluble protein fraction is generally composed of soluble albumin and soluble globulin proteins.

The term "water" as used herein refers to any source of water, for example, tap water, distilled water or reverse osmosis water.

The term "alkaline water" as used herein refers to water which has a basic pH of greater than about 7.0, optionally about 7.0 to about 12.0. The alkalinity of the water results from the addition of a base to water, for example, an alkali hydroxide such as sodium hydroxide. For example, a solution of sodium hydroxide at a concentration of about 5% to about 15% (w/w), optionally 11%.

The term "suitable for phytase activity" as used herein refers to the conditions, such as the temperature and pH, and optionally includes the length of time, in which the phytase enzyme is able to hydrolyze the phosphate groups on phytate or phytic acid, and accordingly, reduce the amount of phytates or phytic acid in the mixture. In an embodiment, the temperature suitable for phytase activity is between 20° C. and 60° C., optionally between 40° C. and 55° C., suitably between 50° C. and 55° C. In another embodiment, the pH suitable for phytase activity is between 2.0 and 7.0, optionally between 4.0 and 6.0, suitably between 4.5 and 5.5, optionally 5.0 to 5.5. In another embodiment, the concentration of the phytase enzyme is between 0.01% to 1.0% (w/w) based on the weight of the oilseed meal, optionally 0.01% and 0.5% optionally 0.01% and 0.1%. It will be understood that the conditions suitable for phytase activity apply to all of the processes of the present disclosure.

The term "suitable for protease activity" as used herein refers to the conditions, such as the temperature and pH, and optionally includes the length of time, in which a protease enzyme is able to hydrolyze proteins. In an embodiment, the temperature suitable for protease activity is between 30° C. and 70° C., optionally between 35° C. and 70° C. In another embodiment, the pH suitable for protease activity is between 5.0 and 9.0, optionally between 5.5 and 8.5. In another embodiment, the concentration of the protease enzyme is between 0.01% to 1.0% (w/w) based on the weight of the oilseed meal, optionally 0.01% and 0.5% optionally 0.01% and 0.1%. It will be understood that the conditions suitable for protease activity apply to all of the processes of the present disclosure.

The term "g-force sufficient to separate the mixture" as used herein refers to the force necessary to separate the insoluble fiber fraction in the mixture from the protein fractions. In an embodiment, the g-force is between 100 g and 500 g, suitably between 150 g and 400 g, optionally between 170 g and 350 g. It will be understood that when the mixture is subjected to a sufficient g-force, the insoluble fiber, due to its relative higher density and/or greater particle size, will separate from the protein fractions. It should also be recognized that forces greater than the ranges necessary to separate the phases are not desirable as they can result in the high concentrations of the insoluble protein being deposited in the fiber phase. In addition, as a result of the insoluble protein fraction having a higher relative density and/or particle size compared to the soluble protein, the insoluble protein fraction will separate from the soluble protein fraction. It will be understood though that not all of the protein will separate from the insoluble fiber fraction, and likewise, not all of the insoluble fiber will separate from the protein fraction. Moreover, not all of the insoluble protein fraction will separate from the soluble protein fraction. Accordingly, when the mixture has been subjected to a g-force sufficient to separate the mixture, the insoluble fiber fraction will comprise at least 10% crude fiber, optionally 15%, 20%, 25, 30% crude fiber on a dry weight basis. Likewise, the protein fraction will comprise less than 10% crude fiber, optionally less than 5%, 4%, 3%, 2%, 1% and less than 1% crude fiber with the majority of other material comprising soluble and insoluble proteins, carbohydrate, ash and oil. In an embodiment, the g-force sufficient to separate the mixture is obtained by rotating a centrifuge at a speed of about 500 RPM to about 2,500 RPM. It will be understood that a centrifuge will have a rotational radius which will vary depending on the size of the centrifuge. In another embodiment, the g-force sufficient to separate the mixture is obtained by using a hydrocyclone with a g-force of between 50 g and 250 g.

(II) Protein Concentrates and Isolates

The present disclosure relates to processes for the production of a protein concentrate or a protein isolate from oilseed. A protein concentrate is an isolated protein extract of pressed oilseed, wherein the extract has greater than 60% protein content but less than 90% protein content on a dry weight basis. A protein concentrate has been treated to separate protein in the oilseed from the fiber and other unwanted antinutritional factors. A protein isolate is an isolated protein extract of pressed oilseed, wherein the extract has greater than or equal to 90% protein content on a dry weight basis. Typically, the protein isolate has up to 98%, 99%, 99.5% or 100% protein content on a dry weight basis. Examples of pressed oilseed include seedcake, defatted meal or protein-enriched meal, as explained below. Typically, the non-protein content includes non-protein compounds such as antinutritional substances, fiber, and other components or impurities such as coloring agents.

In an embodiment, the disclosure provides a process for the removal of fiber, antinutritionals and other constituents, that are present within the oilseed. A person skilled in the art would recognize that antinutritionals include glucosinolates, phytic acid, phytates and other compounds that reduce the nutritional or commercial value of the protein concentrate or protein isolate. For example, antinutritional compounds may not be digestible by mammals (e.g humans), have adverse effects, such as toxicity, and are desirably removed from the protein product. Certain antinutritionals have other undesirable properties, such as undesirable organoleptic properties. Examples of such compounds are sinapine, which has a bitter taste, and sinigrin which has a pungent and very bitter flavor. Further, other antinutritional constituent of oilseeds that are typically removed include, but are not limited to, coloring agents and/or other inert compounds. In an embodiment, the constituents which are removed or are reduced to safe or acceptable levels, are undesirable constituents or impurities using the processes of the present disclosure. A person skilled the art would recognize the safe and/or acceptable levels of particular antinutritionals in the final protein product.

The term protein-enriched meal refers to a meal that possesses a protein content of about 30% to about 60%, optionally 30% to 55%, suitably 50% to 55%, on a dry weight basis. Such protein-enriched meals are useful to prepare the concentrates and isolates of the disclosure, which may be further processed.

In another embodiment of the disclosure, there is also included protein concentrates and protein isolates, produced in accordance with the processes of the disclosure. Accordingly, in an embodiment of the disclosure, there is provided an oilseed protein isolate having a protein content of at least 90%, wherein the canola protein isolate has a solubility of at least 85% (w/w) at a concentration of about 1% and a pH of about 6.5 to about 7.5 in a borate-phosphate buffer solution. In another embodiment, the oilseed protein isolate has a solubility of at least 95% (w/w) in a borate-phosphate buffer solution. In a further embodiment, the oilseed protein isolate has a solubility of at least 99% (w/w) in a borate-phosphate buffer solution. In a further embodiment, the oilseed protein isolate has a solubility of at least 99.5% (w/w) in a borate-phosphate buffer solution.

In another embodiment of the disclosure, the oilseed protein isolate has a solubility of at least 85% (w/w) at a concentration of about 1% and a pH of about 6.5 to about 7.0 in a borate-phosphate buffer solution. In a further embodiment, the oilseed protein isolate has a solubility of at least 85% (w/w) at a concentration of about 1% and a pH of about 6.7 to about 7.0 in a borate-phosphate buffer solution.

In another embodiment of the disclosure, the oilseed protein isolate has a solubility of at least 85% (w/w) at a concentration of about 1% and a pH of about 6.5 to about 7.0 in a borate-phosphate buffer solution at a temperature of about 35° C. to about 45° C. In another embodiment of the disclosure, the oilseed protein isolate has a solubility of at least 85% (w/w) at a concentration of about 1% and a pH of about 6.5 to about 7.0 in a borate-phosphate buffer solution at a temperature of about 38° C. to about 40° C.

In another embodiment, the oilseed protein isolate comprises,
i) a first class of proteins having a molecular weight of about 60 kDa to about 80 kDa, the first class of proteins comprising about 60% to about 90% (w/w) of the oilseed isolate;
ii) a second class of proteins having a molecular weight of about 10 kDa to about 30 kDa, the second class of proteins comprising about 10% to about 30% (w/w) of the oilseed isolate; and
iii) a third class of proteins having a molecular weight of less than about 10 kDa, the third class of proteins comprising about 2% to about 10% (w/w) of the oilseed isolate.

In another embodiment, the oilseed protein isolate comprises,
i) a first class of proteins having a molecular weight of about 60 kDa to about 80 kDa, the first class of proteins comprising about 60% to about 70% (w/w) of the oilseed isolate;
ii) a second class of proteins having a molecular weight of about 10 kDa to about 30 kDa, the second class of proteins comprising about 20% to about 30% (w/w) of the oilseed isolate; and
iii) a third class of proteins having a molecular weight of less than about 10 kDa, the third class of proteins comprising about 5% to about 10% (w/w) of the oilseed isolate.

In a further embodiment, the oilseed protein isolate comprises
i) a first class of proteins having a molecular weight of about 65 kDa to about 75 kDa, the first class of proteins comprising about 60% to about 90% (w/w) of the oilseed isolate;
ii) a second class of proteins having a molecular weight of about 10 kDa to about 20 kDa, the second class of proteins comprising about 10% to about 30% (w/w) of the oilseed isolate; and
iii) a third class of proteins having a molecular weight of less than about 10 kDa, the third class of proteins comprising about 2% to about 10% (w/w) of the oilseed isolate.

In another embodiment, the oilseed protein isolate comprises
i) a first class of proteins having a molecular weight of about 65 kDa to about 70 kDa, the first class of proteins comprising about 60% to about 70% (w/w) of the oilseed isolate;
ii) a second class of proteins having a molecular weight of about 10 kDa to about 20 kDa, the second class of proteins comprising about 20% to about 30% (w/w) of the oilseed isolate; and
iii) a third class of proteins having a molecular weight of less than about 10 kDa, the third class of proteins comprising about 5% to about 10% (w/w) of the oilseed isolate.

In an embodiment of the disclosure, the protein isolate produced in accordance with a process of the present disclosure contains greater than 90% protein content (w/w) on a dry weight basis, optionally 90% to about 99% (w/w), optionally 90% to about 98% (w/w), and optionally 90% to about 95% (w/w). In another embodiment, a protein isolate produced in accordance with a process of the present disclosure contains less than about 1% (w/w) fiber, optionally less than about 0.5% (w/w) fiber, and optionally less than about 0.1% (w/w) fiber.

In another embodiment, the protein isolate produced in accordance with a process of the present disclosure contains greater than 90%, and contains
(i) a first class of proteins having a molecular weight between 225 and 275 kDa, optionally about 250 kDa, the first class of proteins comprising between 50-70%, optionally about 50%;
(ii) a second class of proteins having a molecular weight between 40 and 60 kDa, optionally about 50 kDa, the second class of proteins comprising between 3-8%, optionally about 5%;
(iii) a third class of proteins having a molecular weight between 20 and 40 kDa, optionally about 30 kDa, the third class of proteins comprising between 2-6%, optionally about 4%;
(iv) a fourth class of proteins having a molecular weight between 7 and 15 kDa, optionally about 12 kDa, the fourth class of proteins comprising between 10-20%, optionally about 15%;
(v) a fifth class of proteins having a molecular weight between 3 and 10 kDa, optionally about 6 kDa, the fifth class of proteins comprising between 10-20%, optionally about 15%; and
(vi) a sixth class of proteins having a molecular weight of less than about 5 kDa and comprising less than about 1% of the protein isolate.

In another embodiment of the disclosure, the oilseed protein isolate comprises a canola, rapeseed, mustard seed, broccoli seed, flax seed, cotton seed, hemp seed, safflower seed, sesame seed or soybean oilseed protein isolate. In another embodiment, the oilseed comprises a canola oilseed.

In an embodiment of the disclosure, oilseed protein isolates, such as a canola protein isolate, produced in accordance with the processes of the present disclosure, have excellent emulsifying and foaming properties. For example, with respect to emulsifying capacity, a 0.5% (w/w) canola protein isolate solution possessed a similar emulsifying capacity as compared to a 5% egg yolk solution. Further, the protein isolates of the present disclosure, such as a canola protein isolate, possess excellent foaming capacity. Further, oilseed protein isolates, such as a canola protein isolate, produced in accordance with the processes of the present disclosure, have excellent properties of gel formation and water immobilization, and therefore, act as stabilizers.

In another embodiment of the disclosure, there is also included a oilseed protein hydrolyzate having a protein content of about 60% to about 90% and having a protein dispersibility index of at least 95.0% and wherein a 1.0% solution (w/w) in water of the protein hydrolyzate has a visible light transmittance of least 90.0%. In a further embodiment, the oilseed protein hydrolyzate has a protein dispersibility index of at least 99.0%. In an embodiment, the oilseed protein hydrolyzate has a protein dispersibility index of at least 99.8%.

In another embodiment of the disclosure, a 1.0% solution (w/w) of the protein hydrolyzate has a visible light transmittance of least 95.0%. In a further embodiment, a 1.0% solution (w/w) of the protein hydrolyzate has a visible light transmittance of least 97.0%. In another embodiment, a protein hydrolyzate produced in accordance with a process of the present disclosure contains less than about 1% (w/w) fiber, optionally less than about 0.5% (w/w) fiber, and optionally less than about 0.1% (w/w) fiber.

In another embodiment of the disclosure, there is also included an oilseed protein concentrate having a protein content of about 60% to about 90%, wherein the protein has a methionine content at least 1.90% by weight and a cysteine content at least 1.60% by weight. In an embodiment, the oilseed protein concentrate has a methionine content at least 1.95% by weight. In an embodiment, the oilseed protein concentrate has a methionine content at least 2.02% by weight. In an embodiment, the oilseed protein concentrate has a cysteine content at least 1.65% by weight. In an embodiment, the oilseed protein concentrate has a cysteine content at least 1.68% % by weight.

In another embodiment of the disclosure, a protein concentrate produced in accordance with a process of the present disclosure, contains less than about 5% (w/w) of fiber, optionally about 0.5% to about 5% (w/w).

In an embodiment, the protein concentrate possessing a protein content of about 60% to about 70% produced in accordance with the processes of the present disclosure are utilized as a protein ingredient in aquafeeds for fish, swine and pet foods.

In another embodiment, the protein concentrate possessing a protein content of about 70% to about 75% produced in accordance with the processes of the present disclosure are useful as a protein ingredient for baked food products such as bread, rolls, cake and pastry products (including mixtures for preparing baked food products), cookies, biscuits, crackers, pancakes, pastries, doughnuts, and other pasta products. In addition, this protein concentrate is useful as a protein ingredient in meat products such as baked meat, hot dogs, bologna, analogs, ham and sausages. Further, this protein concentrate is also useful as a protein ingredient in vegetarian foods. It will be understood by a person skilled in the art that this protein concentrate is also useful for other applications where a lower grade of protein concentrate is sufficient, such as in aquafeeds and pet foods as described above.

In another embodiment, the protein concentrate possessing a protein content of about 75% to less than 90% produced in accordance with the processes of the present disclosure is useful as a protein ingredient in breakfast cereals, and baked goods, as well as meat products such as bologna, frankfurters, luncheon loaves and ham. Further, this protein concentrate is useful in candies, confections, desserts, dietary items, Asian foods, soup mixes, gravies and other similar food items. Again, it will be understood by a person skilled in the art that this protein concentrate is also useful for other applications where a lower grade of protein concentrate is sufficient, such as in aquafeeds, pet foods, bakery products and meat products, as described above.

In another embodiment, the protein isolate possessing a protein content of greater than 90% produced in accordance with the processes of the present disclosure is useful as a protein ingredient in nutritional beverages such as protein fortified soft drinks, sports drinks, fruit juices and other high protein drinks. In addition, this protein isolate is useful as a protein ingredient for nutritional supplements, special diet products, and high protein nutritional tablets. In addition, the protein isolate is useful as a protein ingredient in infant formulas, as well as an ingredient in comminuted and emulsified meats, simulated meats, combination meat products and cured or uncured meat products. Further, the protein isolate is useful as a protein ingredient in pasta (eg. macaroni), bread and other bakery products, pancakes, waffles, crackers, donuts, pie crusts, soups, egg replacements, dried milk replacements and dairy analogs. Again, it will be understood by a person skilled in the art that this protein isolate is also useful for other applications where a lower grade of protein is sufficient, such as in aquafeeds, pet foods, and meat products, as described above.

In another embodiment, the hydrolyzed protein isolate possessing a protein content of greater than 90% produced in accordance with the processes of the present disclosure is useful as a protein ingredient in nutritional beverages such as protein fortified soft drinks, sports drinks, fruit juices and other high protein drinks. In addition, the hydrolyzed protein isolate is useful as a cosmetic ingredient. Further, the hydrolyzed protein isolate is useful as a protein ingredient for healthy food applications to improve absorption and digestibility. Again, it will be understood by a person skilled in the art that this hydrolyzed protein isolate is also useful for other applications where a lower grade of protein is sufficient, such as in aquafeeds, pet foods, bakery products and meat products, as described above.

In another embodiment, there is also included a protein concentrate having a protein content of at least 60% and less than 90% protein comprising:

i) a first protein fraction comprising between 30% and 70% 2S protein, optionally between 40% and 60%, optionally 45% and 55%;

ii) a second protein fraction comprising between 20% and 50% 12S protein, optionally between 25% and 45%, optionally between 30% and 40%, optionally between 35% and 40%.

In another embodiment, there is also included a protein isolate having a protein content of at least 90% protein comprising:

i) a first protein fraction comprising between 10% and 40% 2S protein, optionally between 15% and 30%;

ii) a second protein fraction comprising between 30% and 70% 12S protein, optionally 40% and 60%, optionally between 50% and 60%.

(III) Processes of the Disclosure

Figure 2:
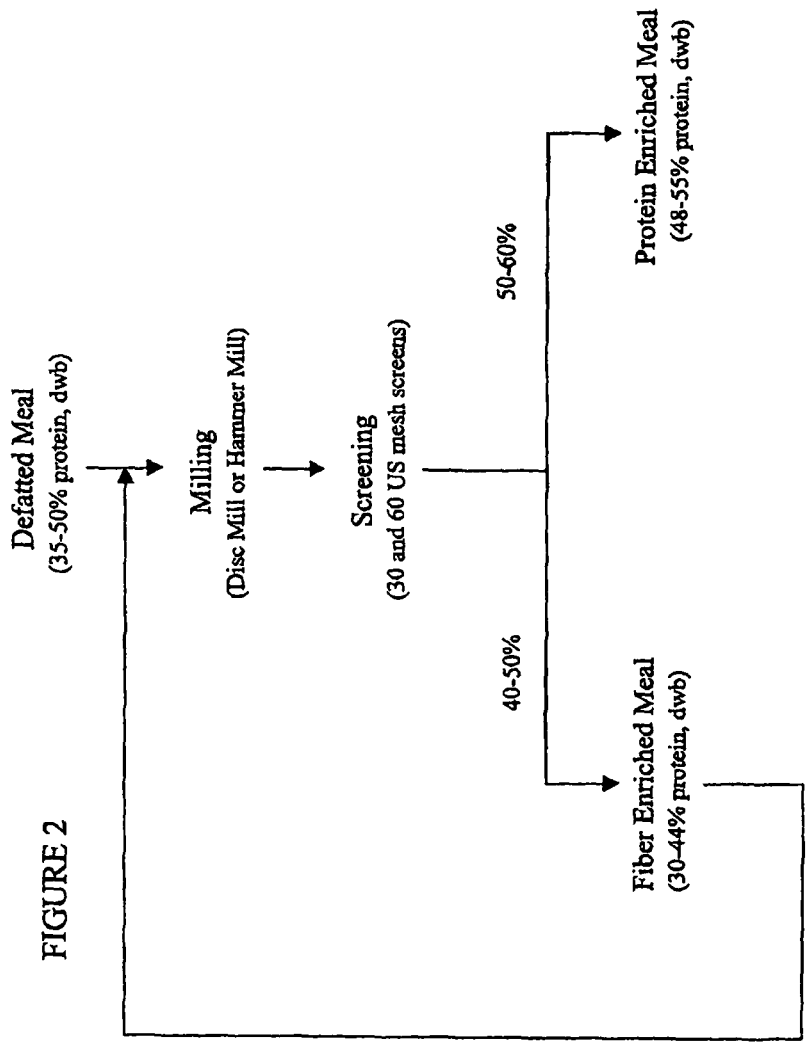
FIG. 2 is a schematic representation showing a preparation of a protein-enriched meal from the defatted meal of an oilseed.

A person skilled in the art would be able to produce a protein-enriched meal using methods that are well known in the art. A general method for obtaining a protein-enriched meal is shown in FIGS. 1 and 2. For example, when beginning with an oilseed, such as canola, rapeseed, mustard seed, broccoli seed, flax seed, cotton seed, hemp seed, safflower seed, sesame seed or soybean meal, in particular canola, the moisture content of the oilseed is adjusted. The moisture adjusted oilseed is optionally exposed to a heat treatment. In an embodiment of the processes of the present disclosure, the oilseed is heat treated to a temperature of about 60° C. to about 120° C., optionally about 70° C. to about 100° C., or about 80° C. to about 90° C., or about 80° C. In another embodiment, the heat treatment is carried out at a temperature of 100° C. The heat treatment of the oilseed results in the inactivation of the enzymes present in the oilseed, for example, myrosinase, lipase, phospholipase. If the oilseed is not heat treated, the enzymes (such as myrosinase, lipase, phospholipase), as a result of their enzymatic action, can degrade the oil and breakdown glucosinolates releasing sulphur into oil. However, a heat treatment can also denature the proteins in the concentrate or isolate. At a temperature of about 75-100° C., the enzymes are deactivated, and are therefore not able to degrade the oil and breakdown glucosinolates releasing sulphur into oil, while the protein within the oilseed is not denatured. The selection of a heat treatment temperature is a compromise between the opposing effects on oil quality, meal quality and economics. Accordingly, in an embodiment, a heat treatment temperature of 75-100° C. results in a reasonably high protein dispersibility index (PDI), lower sulphur, FFA and phosphorus in pressed and butane/R134a extracted oils.

Alternatively, in an embodiment, the oilseed is not exposed to a heat treatment and its moisture content is not adjusted. It will be understood by a person skilled in the art that the moisture content of the seed is typically in the range of about 7% to about 10% for a pressing operation. If the moisture content of the seed is not in this range, the moisture of the seed is optionally adjusted to about 7% to about 10% by adding water or drying, which is followed by blending and tempering.

The oilseed is then pressed to remove the oil from within the oilseed. Generally, an oilseed such as canola, rapeseed, mustard seed, broccoli seed, flax seed, cotton seed, hemp seed, safflower seed, sesame seed or soybean, contains about 15% to about 50% oil (w/w), depending on the particular oilseed. Typically, oil is removed from an oilseed by pressing the oil from the oilseed to form a pressed oilseed. Examples of pressed oilseeds are a seedcake (or a presscake), while a defatted meal or a protein-enriched meal begin from a seedcake (or presscake), as explained below. It will be understood that a seedcake and a presscake define the same pressed seed meal. Methods of pressing oil from an oilseed are well known in the art. A typical pressing will remove about 30% to about 70% of the oil in the oilseed, and results in pressed oil and a pressed seedcake (or presscake).

In an embodiment, the removal of much of the remaining oil from the seedcake is accomplished by solvent extraction of the seedcake. Solvent extraction is a well known process in the art and utilizes low boiling solvents, such as hexane, methyl pentane or other refrigerants such as ITFM and R134a (1,1,1,2-tetrafluoroethane), to remove residual oil from the seedcake.

In another embodiment, the remaining oil in the seedcake is removed using solvent extraction, wherein the solvent is ethanol, which has been heated close to its boiling point.

The solvent extraction process results in a defatted seedcake meal and a solution of solvent and oil. The oil is separated from the solvent and utilized for other purposes. Generally, depending on the extraction process, the seedcake will contain residual amounts of solvent that are removed from the seedcake. Typically, the removal of the residual solvent from seedcake is accomplished by heating the seedcake in a desolventizer toaster (DT), flash desolventizer (such as a ring dryer) or vacuum oven, which causes the residual solvent to evaporate. The seedcake is subsequently dried. The above process removes much of the oil from the pressed oilseed and leaves material known as defatted meal. In an embodiment, the defatted meal will contain less than about 6% of oil, optionally about 0.5% to about 3% (w/w).

The defatted meal is then subjected to a milling step and a screening step to obtain a pressed oilseed known as a protein-enriched meal.

The defatted meal is typically milled, for example with a disc mill or a hammer mill, to reduce the particle size of the defatted meal. When using a disc mill, the defatted meal is forced through two rotating discs which crush the defatted meal. When a hammer mill is used to reduce the particle size of the defatted meal, the meal is loaded into the hammer mill, wherein the hammers reduce the particle size of the defatted meal.

After the particle size of the defatted meal has been sufficiently reduced, the milled defatted meal is screened through mesh screens, which results in an initial separation of a fiber fraction from the defatted meal, resulting in a protein-enriched meal. Fiber tends to have a larger particle size which is not able to pass through the screen. However, a portion of the fiber will be able to pass through the screen, and as such, only a portion of the fiber is removed by screening. Typically, about a 45 US mesh screen is used for the initial fiber separation. This is a dry screening process which results in a fiber enriched meal, which does not pass through the screen, and the protein-enriched meal, which does pass through the screen. The protein-enriched meal, however, still contains a significant amount of fiber and other antinutritional factors. From the milled defatted material, about a 30% to about 60% by weight protein-enriched meal is typically obtained, while the fiber fraction constitutes about 40% to about 70% of the original weight of the defatted material. The protein-enriched meal possesses a protein content of about 40% to about 60%, optionally 50% to about 55%, while the fiber fraction possesses about 35% to about 48% protein content. In an embodiment of the disclosure, it is this protein-enriched meal that is utilized to produce the protein concentrates and protein isolates of the present disclosure. However, in another embodiment, it will be apparent to those skilled in the art that a seedcake, defatted meal or protein-enriched meal is utilized with the processes of the present disclosure. The use of such a defatted or protein-enriched meal, and processing with a minimum amount of heat during conditioning, pressing, solvent extraction, desolventization and drying, leads to better protein concentrates and protein isolates.

In an embodiment of the present disclosure, there is a process for removing fiber from a partially defatted, fully defatted or protein-enriched meal or "meal"). In particular, the process relates to separating and removing fiber from a meal based on the density and particle size differences between the fiber particles and the protein particles. The separation and removal of fiber is accomplished by using separation methods, at specific speeds, which can separate particles based on their density or particle size such as centrifugation, gravity sedimentation, a gravity table or hydrocyclone to separate the fiber from the mixture and form the protein slurry. In an embodiment, the separation is accomplished using centrifugation. In another embodiment, the separation is accomplished using a decanter centrifuge. In another embodiment, the separation is accomplished using a decanter centrifuge at a speed of about 1,000 rpm to about 2,000 rpm. In another embodiment, the separation is accomplished using a decanter centrifuge at a speed of about 1,500 rpm. In an embodiment, the centrifugation of a meal mixture results in three layers: i) an insoluble fiber layer and a protein slurry on top of the fiber, which is comprised of ii) an insoluble protein fraction and iii) a soluble protein fraction. Separation of the top and middle layers (the soluble protein extract and the insoluble fine protein fraction) from the bottom layer (coarse fiber solids), results in a protein slurry with fiber removed.

Figure 3:
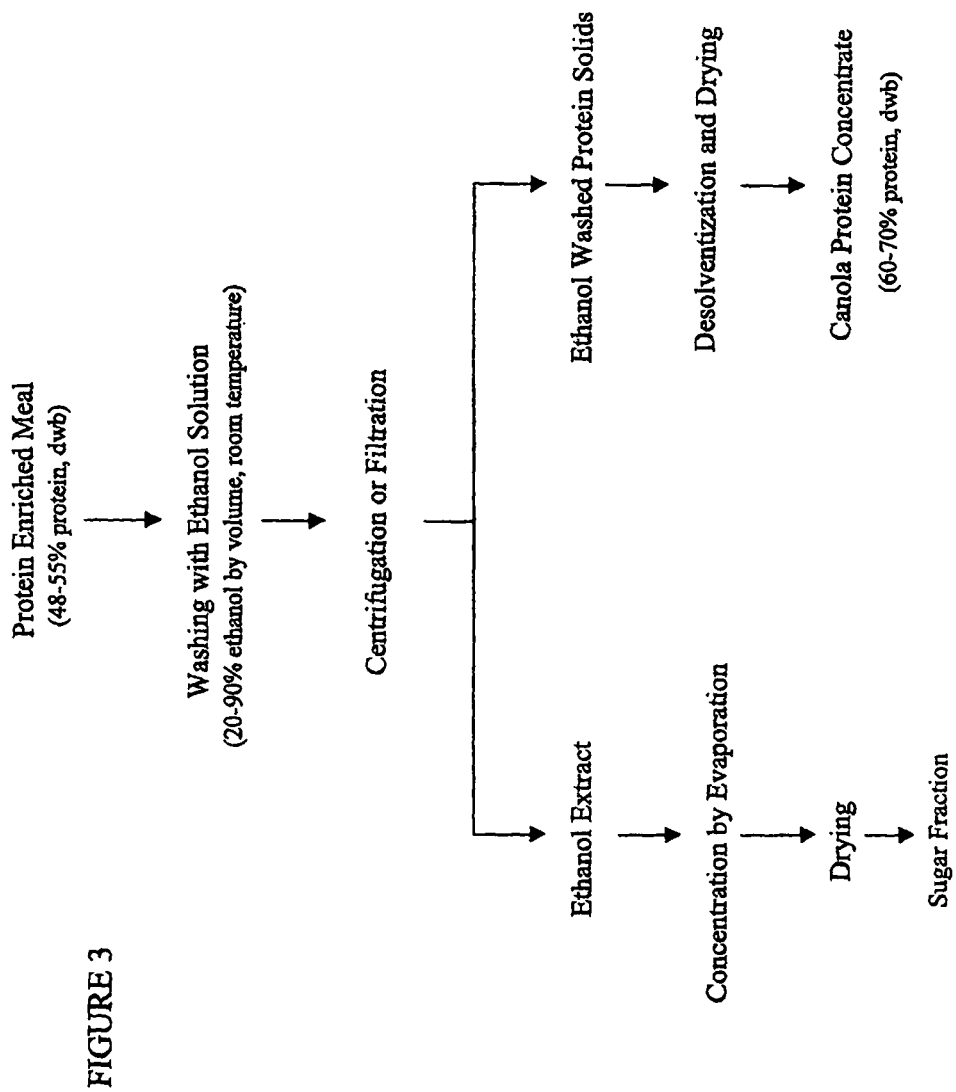
FIG. 3 is schematic representation showing a preparation of a protein concentrate from a protein-enriched meal.
Figure 4:
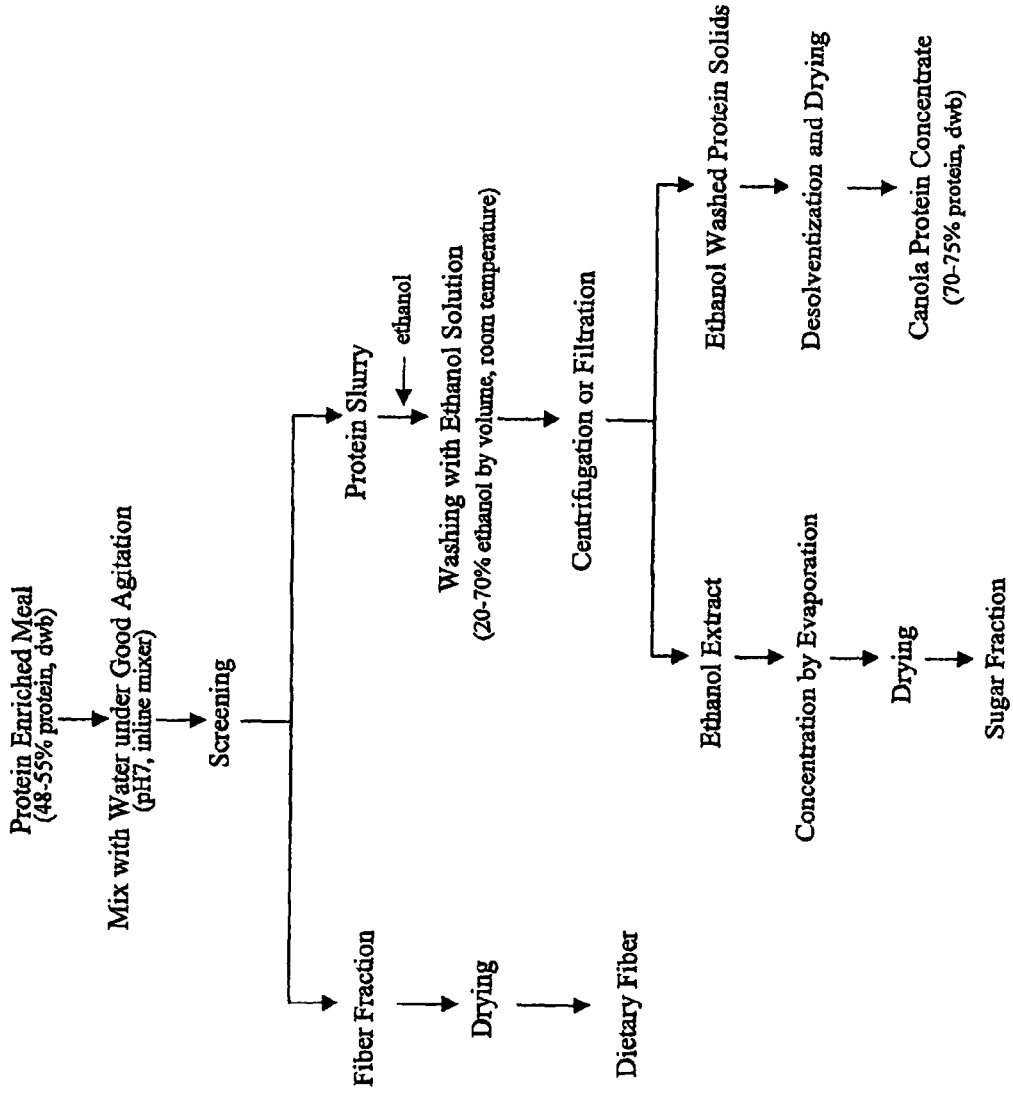
FIG. 4 is a schematic representation of a first embodiment showing the removal of fiber during a preparation of a protein concentrate from a protein-enriched meal.
Figure 5:
FIG. 5 is a schematic representation of a second embodiment showing the removal of fiber during a preparation of a protein concentrate from a protein-enriched meal.
Figure 6:
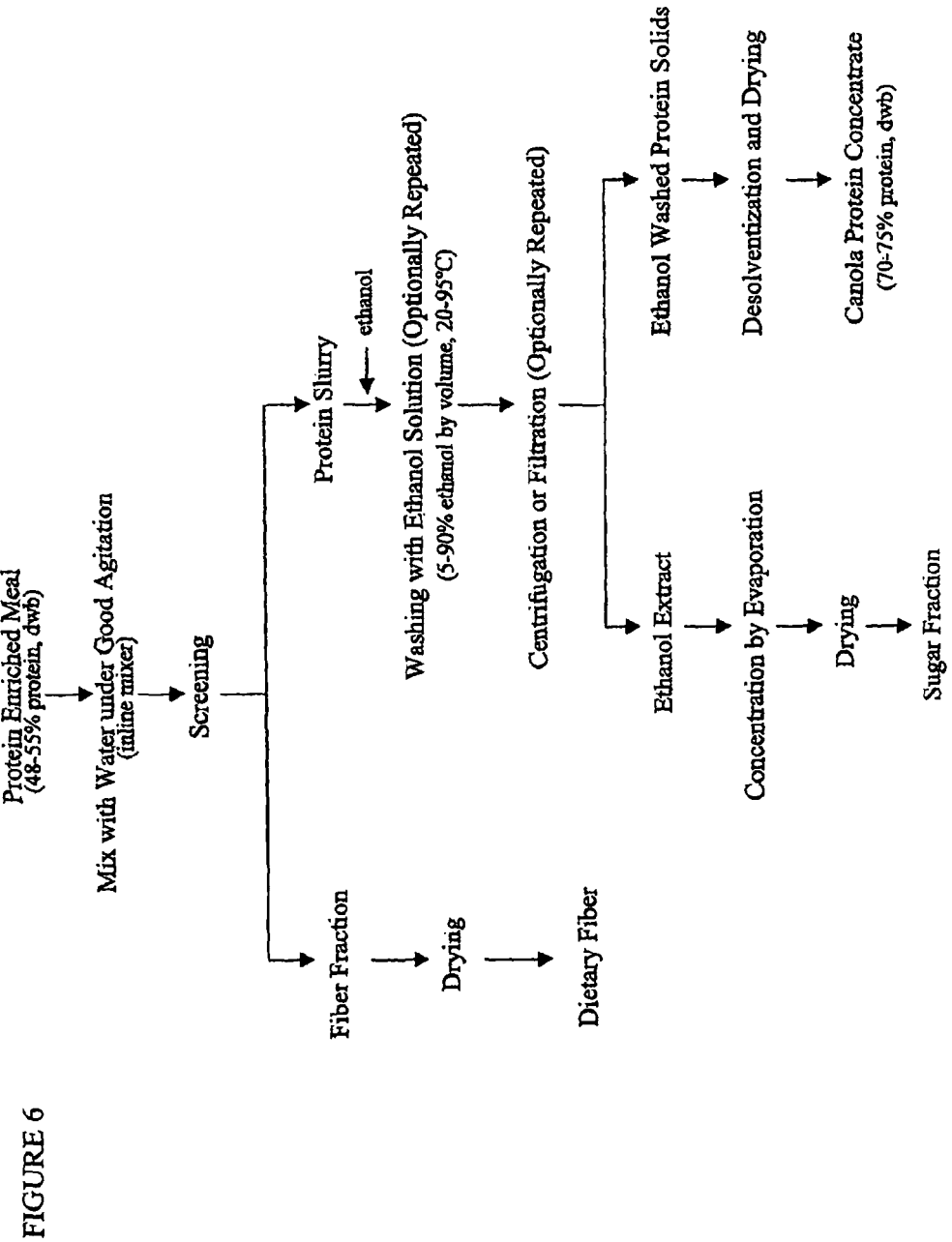
FIG. 6 is a schematic representation of a third embodiment showing the removal of fiber during a preparation of a protein concentrate from a protein-enriched meal.
Figure 7:
FIG. 7 is a schematic representation of a fourth embodiment showing the removal of fiber during the preparation of a protein concentrate from a protein-enriched meal.

In an embodiment of the present disclosure, a process for the production of a protein concentrate possessing a protein content of about 60% to about 70% is obtained from a defatted or protein-enriched meal. An optional general process for the production of a protein concentrate is illustrated in FIG. 3.

In an embodiment, a defatted or protein-enriched meal is produced by the process above, and is then washed at least once with about 5% to about 100%, optionally about 20% to about 90%, or about 40% to about 80% (v/v) ethanol in water, resulting in an ethanol extract and an ethanol washed defatted or protein-enriched meal. Other alcohols, such as methanol or isopropanol, can be utilized for washing the defatted or protein-enriched meal. In an embodiment, ethanol is used for washing the defatted or protein-enriched meal because it is less toxic than other alcohols, and a higher percentage of ethanol residue is allowed in the final product.

In another embodiment, the defatted or protein-enriched meal is washed once with ethanol, wherein the ratio of ethanol to the protein-enriched meal is about 1:3 to about 1:15, typically about 1:4 to about 1:8, optionally 1:6, on a weight-to-weight basis of protein-enriched meal to ethanol.

In another embodiment, the defatted or protein-enriched meal is washed twice with ethanol, wherein the amount of ethanol added to the protein-enriched meal results in a ratio of about 1:2 to about 1:15, typically about 1:5 to about 1:8, optionally 1:6, on a weight-to-weight basis of protein-enriched meal to ethanol. Typically, washing the defatted or protein-enriched meal at least twice results in the removal of more impurities from the defatted or protein-enriched meal and therefore increases the protein content in the protein concentrate.

In a further embodiment, the defatted or protein-enriched meal is washed in a counter-current extractor. In this embodiment, the defatted or protein-enriched meal is washed about 2 times to about 10 times, wherein the ratio of solvent to the defatted or protein-enriched meal is about 1 to about 10 of meal to about 1 of meal.

In another embodiment, the defatted or protein-enriched meal is washed with ethanol at a temperature of about 10° C. to about 90° C., optionally 20° C. to about 60° C., suitably at a temperature of about 40° C. to about 60° C.

The ethanol extract is optionally separated from the ethanol washed defatted or protein-enriched meal by centrifugation, filtration, vacuum filtration, pressure filtration, sedimentation, decantation or gravity draining. With respect to centrifugation, the ethanol mixture is typically fed to a decanter centrifuge or a basket centrifuge. The ethanol extract is then separated from the ethanol washed defatted or protein-enriched meal by centrifugal force. For the decanter centrifuge, a screw conveyer is contained within a solid bowl and both rotate at high speeds. Solids settling on the bowl are conveyed by the screw conveyer out of the centrifuge. For a basket centrifuge, which consists of a perforated basket rotating inside a stationary housing, the ethanol mixture is fed into the basket and centrifugal force pushes it against the filter liner. The solids are retained by the liner while the liquid passes through. For filtration, the ethanol extract is typically separated from the ethanol washed defatted or protein-enriched meal by draining through a perforated belt or basket in a reactor. For vacuum filtering or pressure filtering, the separation is aided by vacuum or pressure. In an embodiment, the ethanol extract is concentrated by evaporation of the ethanol to form a high sugar fraction, optionally containing antinutritional factors that can be further purified. The antinutritional compounds may be purified into valuable pharmaceutical, medicinal or chemical compounds, such as glucosinolates, phytic acid or phytates, sinapine and sinigrin. In an embodiment, the ethanol extract is heated under vacuum at about 30° C. to about 90° C., which results in the evaporation of ethanol and water, and soluble solids are left behind. Ethanol is further separated from water by distillation and re-used in the process. The concentrated high-sugar fraction is dried by spray drying, rotary drum drying, vacuum drying, flash drying, ring drying, microwave drying, freeze drying or using a fluidized bed dryer.

In another embodiment, the washed defatted or protein-enriched meal is dried to form the protein concentrate, possessing a protein content of about 60% to about 70%. In a further embodiment, the washed protein-enriched meal is dried in a spray dryer, drum dryer, vacuum dryer, fluidized bed dryer or ring dryer to form the protein concentrate possessing a protein content of about 60% to about 70%. These dryers remove the solvent by drying the protein concentrate under a vacuum or at atmospheric pressure at elevated temperatures of about 30° C. to about 100° C.

In an embodiment, the protein concentrate is dried to a moisture content of about 1% to about 10%, optionally about 4% to about 8%.

In another embodiment, the ethanol that is removed through drying is recovered and recycled so it can be used again in further ethanol extractions. The ethanol is recovered through evaporation and distillation.

In another embodiment, the dried protein concentrate possessing a protein content of about 60% to about 70% is further milled into powder form without coarse particles.

In another embodiment of the present disclosure, there is provided a process for producing a protein concentrate possessing a protein content of about 70% to about 75% on a dry weight basis. In an embodiment, a general process for the production of a protein concentrate possessing a protein content of about 70% to about 75% is illustrated in FIGS. 4-7, where the removal of fiber is also detailed. In an embodiment, the use of an extraction solvent, such as ethanol, leads to a protein concentrate or protein isolate having superior organoleptic properties, as well as superior water solubility properties, which therefore possesses better functional properties.

Accordingly, in an embodiment of the present disclosure, a process for the production of a protein concentrate from a defatted or protein-enriched meal is disclosed, comprising:
1) removing fiber from the defatted or protein-enriched meal, comprising either:
  i) mixing the defatted or protein-enriched meal with a mixing solvent to form a first mixture;
    screening the first mixture through a mesh screen of about 10 to about 200 US mesh size to remove the fiber; or
  ii) mixing the defatted or protein-enriched meal with water to form a second mixture;
    optionally adjusting the pH of the second mixture to a pH of about 3 to about 7; and
    adding cellulase complex to the second mixture and heating to a temperature of about 30° C. to about 60° C. to hydrolyze the fiber;
2) washing the first or second mixture with an extraction solvent to form an extract and a washed defatted or protein-enriched meal;
3) separating the extract from the washed defatted or protein-enriched meal;
4) optionally repeating steps 2) and 3) at least one more time; and 5) desolventizing the washed defatted or protein-enriched meal to form a protein concentrate.

In an embodiment of the present disclosure, the mixing solvent is any solvent which forms a slurry with the defatted or protein-enriched meal when mixed together and is able to suspend the protein within the mixture. In another embodiment, the mixing solvent comprises water, methanol, ethanol, or isopropanol, or mixtures thereof. In a further embodiment, the mixing solvent comprises water or ethanol, and mixtures thereof.

In another embodiment, the defatted or protein-enriched meal comprises a canola, rapeseed, mustard seed, broccoli seed, flax seed, cotton seed, hemp seed, safflower seed, sesame seed or soybean meal. In a further embodiment, the protein-enriched meal comprises a canola meal, a soybean meal, a mustard seed meal or a flax seed meal.

In an embodiment of the disclosure, the defatted or protein-enriched meal is mixed with a mixing solvent in a ratio of about 3 to about 10 parts solvent to about 1 part of the defatted or protein-enriched meal, on a weight-to-weight basis.

In an embodiment of the present disclosure, the pH of the first mixture is adjusted to a pH of about 3.0 to about 10.0, optionally about 6.8 to about 7.2 with a solution of an alkali metal base or an acid, such as phosphoric, hydrochloric or sulphuric acid. In a further embodiment, a solution of an alkali metal base comprising about 1% to about 40% by weight, optionally about 5% to about 30%, of the alkali metal base and water is added to the first mixture. In another embodiment, the alkali metal base comprises sodium hydroxide (NaOH).

In another embodiment of the present disclosure, the first mixture is thoroughly agitated. In another embodiment, an inline mixer is used for thorough mixing of the first mixture. Thorough mixing of the first mixture disperses the protein particles and releases natural sugar compounds that are trapped inside the insoluble protein particles in the mixing solvent. In addition, the agitation suspends the solids of the protein-enriched meal in the mixing solvent.

In a further embodiment, the thoroughly mixed first mixture is wet screened resulting in a separation of the fiber from the mixture which contains the protein. In another embodiment of the disclosure, the mesh screen comprises a US mesh screen of about 20 to about 200 US mesh. In a further embodiment, the mesh screen is a vibratory screen. A person skilled in the art would recognize that other screens, for example revolving screens, shaking screens or oscillating screens, could be used in place of vibratory screens to perform substantially the same function of vibrating the mixture which aids in separation of the first mixture from the fiber. In an embodiment of the disclosure, the fiber in the meal swells upon addition of the mixing solvent, increasing the particle size of the fiber. Consequently, the mesh screen prevents the fiber from passing through, while the protein in the first mixture passes through the screen, resulting in a separation of the fiber from the protein. In an embodiment, the fiber fraction is dried and can be used in dietary fiber products. The fiber fraction optionally contains protein and carbohydrates.

In another embodiment of the present disclosure, the defatted or protein-enriched meal is thoroughly mixed with water to form the second mixture. In an embodiment, wet milling is used to mix the second mixture. In another embodiment, an inline mixer is used to thoroughly mix the second mixture. In an embodiment, the mixing of the defatted or protein-enriched meal in water, results in the internal fiber structure being exposed, which allows for the cellulase complex to efficiently hydrolyze the fiber.

In a further embodiment of the disclosure, the pH of the second mixture is optionally adjusted with an acid. In an embodiment, the pH of the second mixture is adjusted to a pH that is suitable for the activity of an enzyme within the second mixture. In an embodiment, the pH of the second mixture is adjusted to a pH of about 3 to about 7. The pH of the second solution is adjusted with an acid solution. In an embodiment, the acid solution is phosphoric acid, hydrochloric acid or sulfuric acid. In an embodiment, the natural pH of the second mixture is about 6.8 to about 7.2, and therefore the pH of the second mixture is not adjusted.

In another embodiment of the present disclosure, the cellulase complex is added to the second mixture in an amount of about 1 to about 10 grams (about 0.1% to about 1%) to about 1 kg of dried solids in the second mixture. In a further disclosure, the cellulase complex is mixed with the second mixture for about 0.5 hours to about 5 hours. In another embodiment, the cellulase complex is mixed with the second mixture for about 1 to about 3 hours. It will be apparent to those skilled in the art that cellulase complex contains different types of cellulase enzyme. For example, cellulase complex contains at least one of endocellulase, exocellulase, cellobiohydrolase, cellobiase, endohemicellulase and exohemicellulase. Cellulase enzymes possess enzymatic activity which are able to hydrolyze the fiber to constituent sugars within the second mixture.

In another embodiment of the present disclosure, the first or second mixture is washed at least once with about 5% to about 100%, optionally about 25% to about 85%, or about 50% to about 85%, or about 60% to about 85%; of the extraction solvent (v/v) in water. The addition of the extraction solvent precipitates proteins in the first or second mixture, while the carbohydrates from the oilseed and from the hydrolyzation of the fiber remain in the extraction solvent, which allows for separation. It will be understood that an extraction solvent will be any solvent which dissolves the carbohydrates and other undesirable compounds, but precipitates the protein. In embodiment, the extraction solvent is water, methanol, ethanol or isopropanol, and mixtures thereof. In another embodiment, the extraction solvent is ethanol. It will be understood by a person skilled in the art that if the extraction solvent comprises 100% extraction solvent, no water will be present in the extraction solvent. For example, the extraction solvent could be 100% ethanol. In another embodiment, the extraction solvent is 60% ethanol in water.

In an embodiment of the present disclosure, the extraction solvent is added in an amount to adjust the ratio of the extraction solvent to the first or second mixture of about 5% to about 95%, optionally about 10% to about 90%, or about 40% to about 80% (v/v) of the extraction solvent.

In an embodiment of the present disclosure, the first or second mixture is washed with an extraction solvent at a temperature of about 10° C. to about 90° C. In another embodiment, the first or second mixture is washed with the extraction solvent at a temperature of about 20° C. to about 60° C. In a further embodiment, the first or second mixture is washed with the extraction solvent at a temperature of about 20° C. to about 25° C.

In an embodiment of the present disclosure, the extract is separated from the washed defatted or protein-enriched meal by centrifugation, vacuum filtration, pressure filtration, decantation or gravity draining. In an embodiment, the extract is concentrated by evaporation of the extraction solvent dried to form a high sugar fraction, as is performed above.

In another embodiment of the disclosure, steps 2) and 3) are optionally repeated at least once. In an embodiment, steps 2) and 3) are repeated at least twice. Repeating steps 2) and 3) results in a protein product containing less impurities, such as fiber and other antinutritional factors.

In another embodiment, the washed defatted or protein-enriched meal is dried to form the protein concentrate, possessing a protein content of about 70% to about 75% on a dry weight basis. In a further embodiment, the washed defatted or protein-enriched meal is dried in a vacuum dryer, fluidized bed dryer, spray dryer or ring dryer to form the protein concentrate possessing a protein content of about 70% to about 75%.

In another embodiment, the washed defatted or protein-enriched meal is dried to a moisture content of about 0.5% to about 12%, optionally about 1% to about 10%, or about 4% to about 8%. In a further embodiment, the washed defatted or protein-enriched meal is dried to a moisture content of about 6%.

In another embodiment of the disclosure, the extraction solvent that is removed through drying is recovered and recycled so it can be used again in further extractions.

In another embodiment, the dried protein concentrate possessing a protein content of about 70% to about 75% is further milled into powder form.

Figure 8:
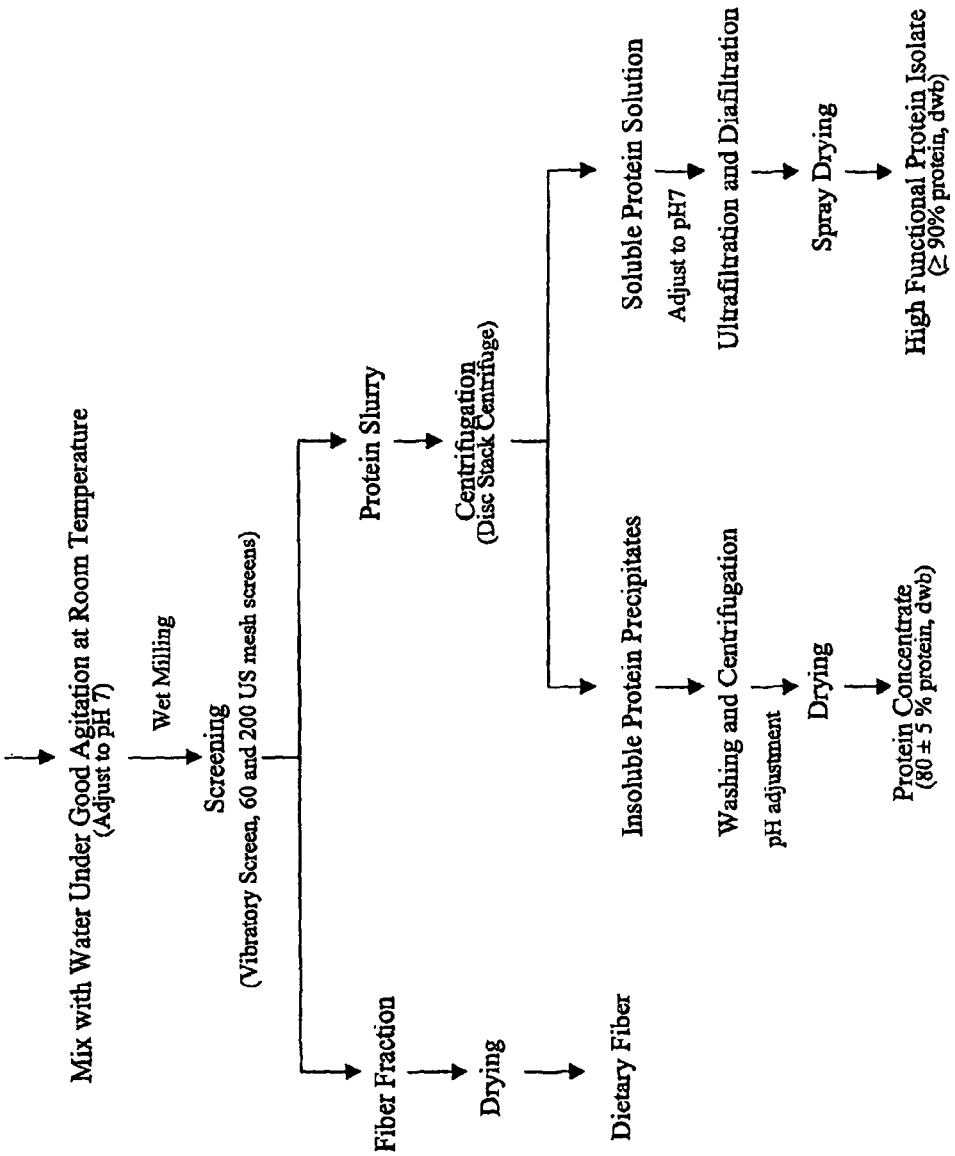
FIG. 8 is a schematic representation of a first embodiment showing a preparation of a protein concentrate and a protein isolate from a protein-enriched meal.
Figure 9:
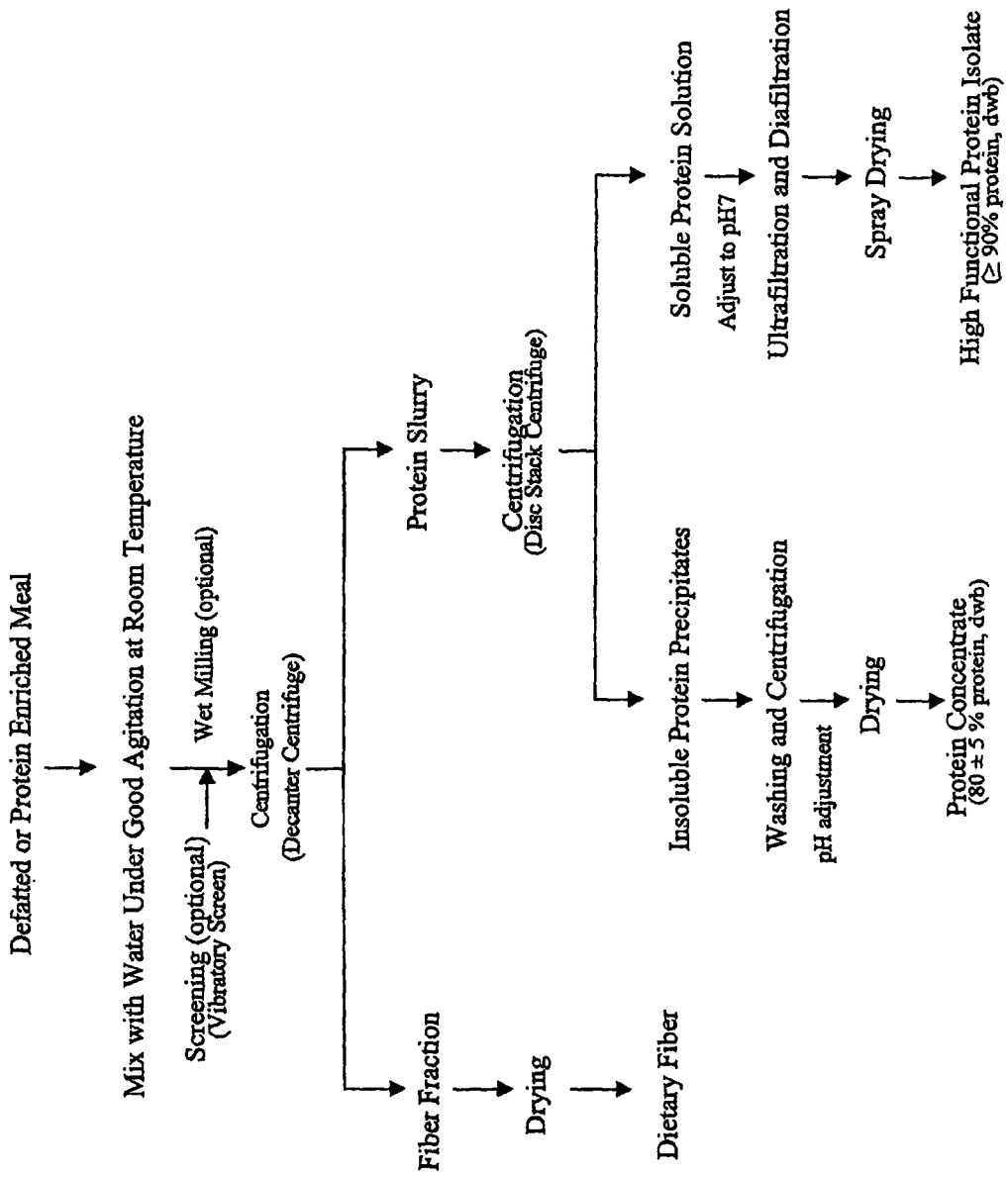
FIG. 9 is a schematic representation of a second embodiment showing a preparation of a protein concentrate and a protein isolate from a protein-enriched meal.

In another embodiment of the present disclosure, there is disclosed a process for the production of a protein concentrate comprising a protein content of about 75% to less than 90% on a dry weight basis. In an embodiment, a general process for the production of a protein concentrate possessing a protein content of about 80% and a protein isolate having a protein content greater than 90% is illustrated in FIGS. 8-9.

Accordingly, a process for the production of a protein concentrate from a defatted or protein-enriched meal is disclosed, comprising:
  removing fiber from the defatted or protein-enriched meal, comprising:
    i) mixing the defatted or protein-enriched meal with a mixing solvent to form a mixture;
      optionally screening the mixture through a mesh screen of about 10 to about 200 US mesh size to remove fiber,
      optionally adjusting the pH of the mixture to a pH of about 7;
      optionally milling the mixture;
      centrifuging the mixture to remove fiber, and forming a protein slurry; and
    ii) centrifuging the protein slurry to form a protein precipitate and a soluble protein fraction;
    iii) washing the protein precipitate with an extraction solvent at least once and centrifuging to form a purified protein precipitate;
    iv) drying the purified protein precipitate to form the protein concentrate.

It will be understood by a person skilled in the art that the steps of the process do not have to be followed exactly. For example, a person skilled in the art would recognize that the milling step could be performed before the screening step.

In another embodiment, the defatted or protein-enriched meal comprises a canola, rapeseed, mustard seed, broccoli seed, flax seed, cotton seed, hemp seed, safflower seed, sesame seed or soybean meal. In a further embodiment, the protein-enriched meal comprises a canola meal. In an embodiment, the protein-enriched meal comprises a soybean meal. In another embodiment, the protein-enriched meal comprises mustard seed meal. In a further embodiment, the protein-enriched meal comprises flax seed meal.

In an embodiment of the disclosure, the mixing solvent is any solvent which forms a slurry with the defatted or protein-enriched meal and is able to suspend the protein within the mixture. In another embodiment, the mixing solvent comprises water, methanol, ethanol, or isopropanol, and mixtures thereof. In a further embodiment, the solvent comprises water or ethanol, and mixtures thereof.

In an embodiment, the defatted or protein-enriched meal is mixed with the mixing solvent to form a mixture in a ratio of defatted or protein-enriched meal to mixing solvent of about 1:3 to about 1:20, optionally about 1:6 to about 1:10, or about 1:6 to about 1:8.

In a further embodiment, the mixture is wet screened resulting in a separation of the fiber from the mixture which contains the protein. In another embodiment of the disclosure, the mesh screen comprises a US screen of size about 20 to about 200 mesh. In a further embodiment, the mesh size is 40 US mesh size. In a further embodiment, the mesh screen is a vibratory screen. The mesh screen prevents the fiber from passing through, while the protein in the mixture passes through the screen, resulting in a separation of the fiber from the protein. In an embodiment, the fiber fraction is dried and can be used in dietary fiber products. In an embodiment, protein and carbohydrates are present in the fiber fraction.

In another embodiment, the pH of the mixture is adjusted to about 7 with the addition of aqueous sodium hydroxide. In a further embodiment, the aqueous sodium hydroxide is a solution of about 1% to about 40%, optionally about 5% to about 30%, by weight of sodium hydroxide in water.

In another embodiment, the mixture is optionally milled using a wet milling process. In an embodiment, the wet milling of the mixture results in thorough mixing of the defatted or protein-enriched meal with the mixing solvent. Thorough mixing of the mixture disperses the protein particles and releases natural sugar compounds that are trapped inside the insoluble protein particles in the mixing solvent. In addition, the mixing suspends the solids of the protein-enriched meal in the mixing solvent.

In another embodiment of the present disclosure, the mixture is centrifuged using a decanting centrifuge. In an embodiment, the mixture is centrifuged with a decanting centrifuge at a speed of about 1000 rpm to about 2000 rpm. In another embodiment, the speed is about 1500 rpm.

In another embodiment, the protein slurry is then centrifuged using a disc stack centrifuge to separate insoluble proteins from soluble proteins, forming a protein precipitate and a soluble protein fraction. In an embodiment, the protein slurry is pumped to a disc centrifuge. The centrifuge has a bowl which spins at about 7500 rpm. As the slurry enters the centrifuge bowl, the slurry is brought up to the same speed as the bowl, which results in high centrifugal forces, about 6500 times the force of gravity acting on the mixture. The heavier protein precipitate is forced to the outside of the bowl. The soluble protein fraction is forced towards the axis of the bowl. The heavy precipitate collects around the outside of the bowl which are removed from the bowl periodically or continuously. The protein slurry is fed to the centrifuge continuously while the liquid soluble protein fraction is pumped out continuously. In an embodiment, the disc centrifuge operates at a speed of about 6500 rpm to about 8500 rpm.

In a further embodiment, the protein precipitate is washed with an extraction solvent to purify the protein precipitate and dissolve residual sugars and other non-desirable compounds. It will be understood that an extraction solvent will be any solvent which dissolves the carbohydrates and other non-desirable compounds. In an embodiment, the extraction solvent is water, methanol, ethanol or isopropanol, and mixtures thereof. In another embodiment, the extraction solvent is water or ethanol, and mixtures thereof. In another embodiment, the extraction solvent is water. In an embodiment, the protein precipitate is washed at least twice with the extraction solvent.

In another embodiment, the washed protein precipitate is then centrifuged again with a disc stack centrifuge at a speed of about 6500 rpm to about 8500 rpm to obtain a protein precipitate. In another embodiment, the washing extracts from the centrifugation are added to the soluble protein fraction.

In another embodiment, the washed protein precipitate is dried to form a protein concentrate comprising a protein content of about 75% to about 90% on a dry weight basis. In a further embodiment, the washed protein precipitate is dried in a vacuum dryer, fluidized bed dryer or ring dryer to form the protein concentrate possessing a protein content of about 75% to less than 90%. It will be understood by a person skilled in the art that the washed protein precipitate can be used as a protein isolate without drying. However, the dried protein isolate has a better shelf life as removal of the solvent, for example water, results in a more stable protein isolate.

Figure 10:
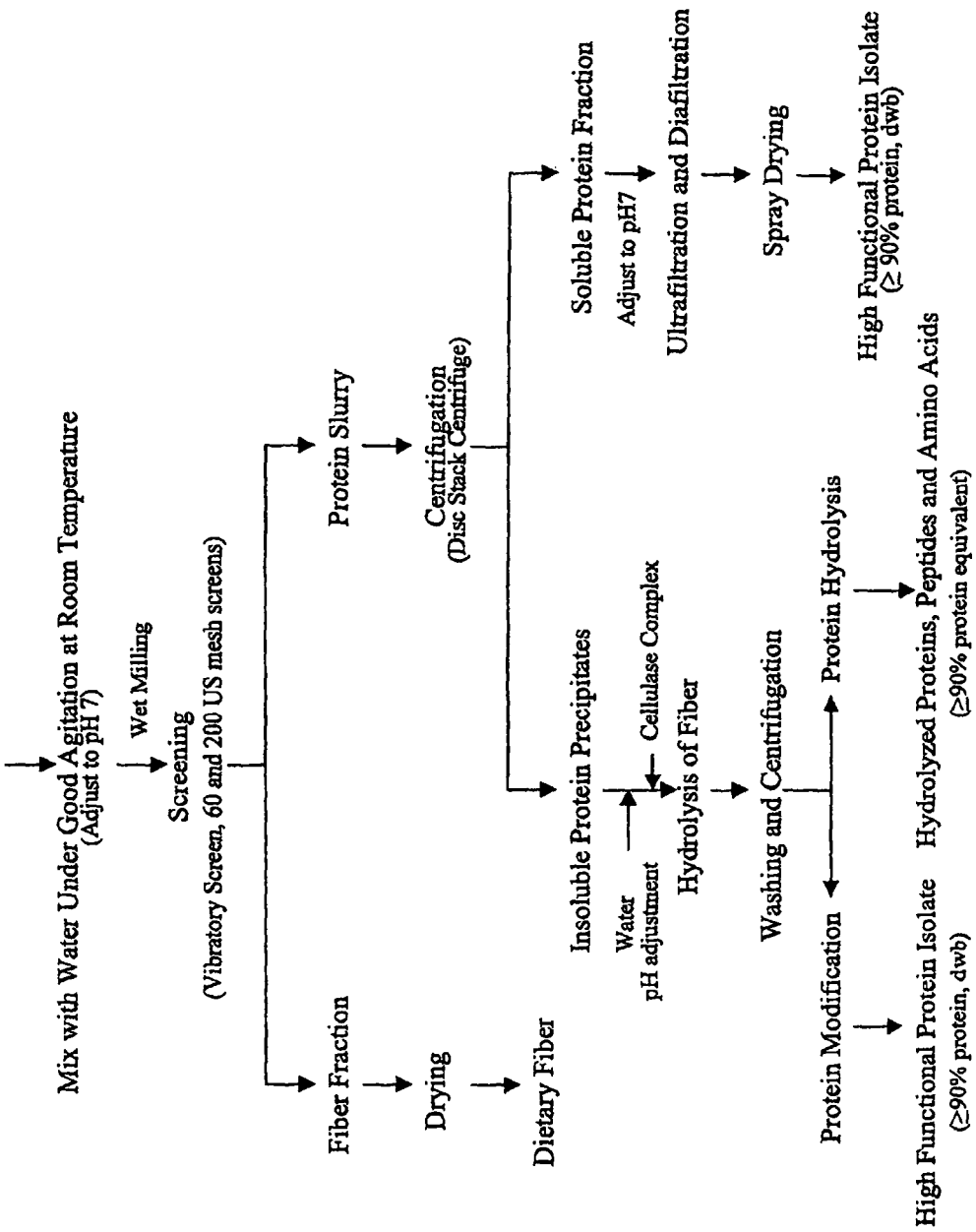
FIG. 10 is a schematic representation of a first embodiment showing a preparation of a protein isolate from a protein-enriched meal.
Figure 11:
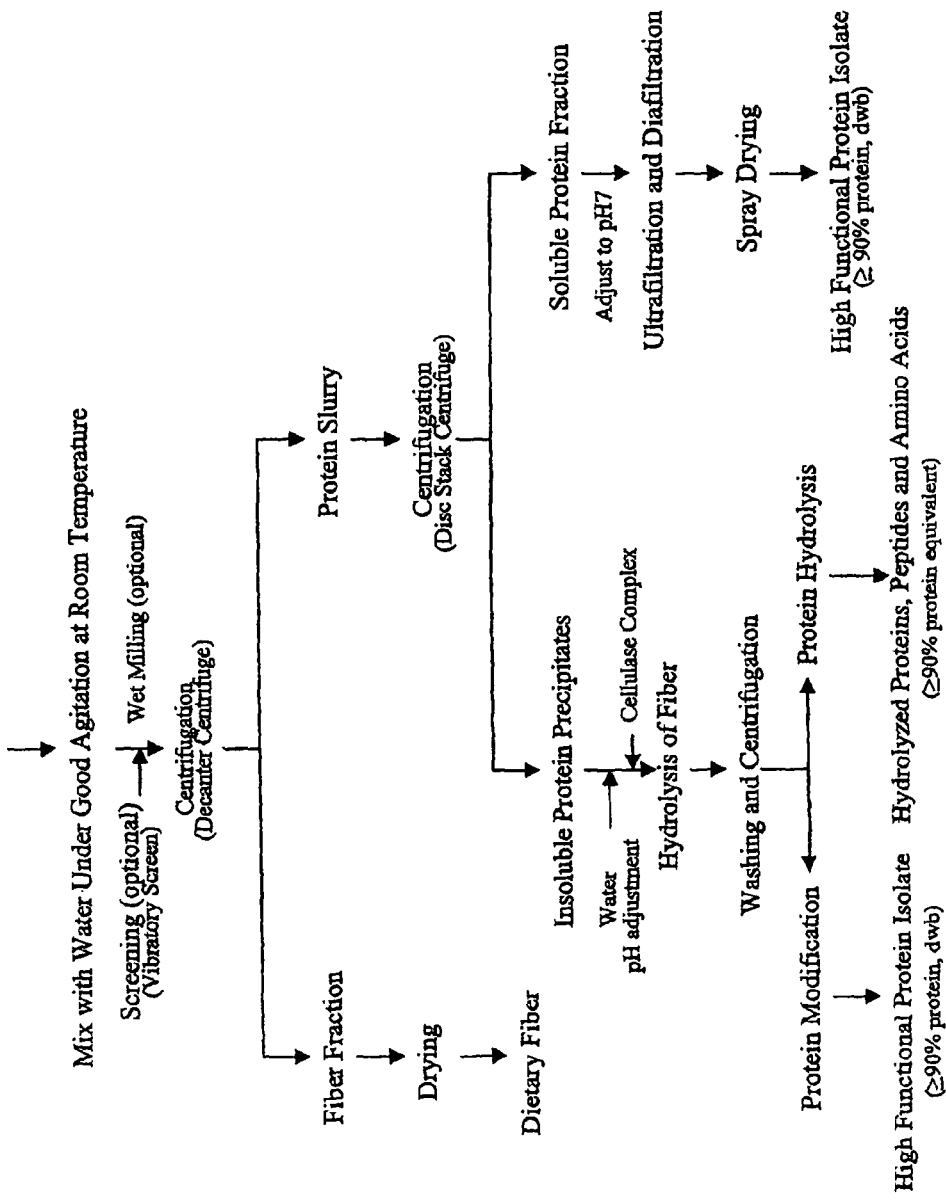
FIG. 11 is a schematic representation of a second embodiment showing a preparation of a protein isolate from a protein-enriched meal.

In another embodiment of the present disclosure, there is provided a process for the production of a protein isolate comprising a protein content of greater than 90% on a dry weight basis. In an embodiment, a general process for the production of a protein isolate and hydrolyzed proteins having a protein content greater than 90% is illustrated in FIGS. 10-11.

Accordingly, a process for the production of a protein isolate from a defatted or protein-enriched meal is disclosed, comprising:
    removing fiber from the defatted or protein-enriched meal, comprising:
        i) mixing the defatted or protein-enriched meal with a mixing solvent to form a mixture;
            screening the mixture through a mesh screen of about 10 to about 200 US mesh size to remove fiber,
            optionally adjusting the pH of the mixture to a pH of about 7;
            optionally milling the mixture; and
            centrifuging the mixture to remove fiber,
            and forming a protein slurry;
        ii) centrifuging the protein slurry to form a protein precipitate and a soluble protein fraction;
        iii) filtering the soluble protein fraction; and
        iv) drying the soluble protein to form the protein isolate.

In an embodiment, the soluble protein fraction is obtained using the same process as described above.

It will be understood by a person skilled in the art that the steps of the process do not have to be followed exactly. For example, a person skilled in the art would recognize that the milling step could be performed before the screening step.

In another embodiment, the defatted or protein-enriched meal comprises a canola, rapeseed, mustard seed, broccoli seed, flax seed or soybean meal. In a further embodiment, the protein-enriched meal comprises a canola meal. In an embodiment, the protein-enriched meal comprises a soybean meal. In another embodiment, the protein-enriched meal comprises mustard seed meal. In a further embodiment, the protein-enriched meal comprises flax seed meal.

In an embodiment of the disclosure, the mixing solvent comprises water or a salt solution. In an embodiment, the salt solution comprises less than 5%, optionally about 3% to about 4%, or 3.5% by weight of salt in solution. In a further embodiment, the mixing solvent comprises water. In another embodiment, the ratio of defatted or protein-enriched meal to the mixing solvent is about 1:3 to about 1:20. In a further embodiment, the ratio is about 1:6 to about 1:10. In an embodiment, the ratio is about 1:6 to about 1:8.

In an embodiment, the soluble protein fraction is purified by ultrafiltration and diafiltration using a membrane filtration apparatus. In an embodiment, when ultrafiltration is utilized, the soluble protein fraction is heated to a temperature of about 1° C. to about 60° C., optionally 40° C. to about 55° C., before being passed through an ultrafiltration apparatus fitted with membranes to filter proteins larger than about 10,000 daltons, optionally about 30,000, or about 100,000 daltons. The filtered protein is recycled back to the feed tank while the liquid is discarded. The ultrafiltration process is continued until the amount of protein that has been filtered in the feed tank is equal to about 30% to about 40% of its initial weight of the soluble protein fraction.

In a further embodiment, when diafiltration is utilized, it is conducted at about 1° C. to about 60° C., optionally about 40° C. to about 55° C., using the diafiltration unit, which is fitted with the membranes to filter proteins larger than about 10,000 daltons, optionally about 30,000, or about 100,000 daltons. The original volume of soluble protein fraction in the feed tank is held constant by adding water to make up for the removed liquid. The filtered protein is recycled back to the feed tank. The amount of water added to maintain the original volume of protein solution is about 2 times the original volume of soluble protein fraction. For example, if 100 L of soluble protein fraction is used, 200 L of water is added to the soluble protein fraction in the feed tank during the cycle of diafiltration. The volume of the feed tank is kept constant at 100 L with the continued addition of water to the feed tank while the liquid is removed from the system through diafiltration.

In an embodiment, after the soluble protein fraction has been filtered, the filtered soluble protein is spray dried to form a high functional protein isolate comprising a protein content of greater than about 90% on a dry weight basis. It will be understood by a person skilled in the art that spray drying is the transformation of a feed from a fluid state into a dried form by spraying the feed into a circulating hot air medium. Generally, spray drying transforms the filtered protein into many droplets which are then exposed to a fast current of hot air. As a result of the very large surface area of the droplets the water in the protein evaporates almost instantaneously and the droplets are transformed into powdery dry protein particles. In an embodiment, the inlet temperature is about 180° C. to about 220° C. which is the temperature of the hot air entering the spray dryer chamber, the outlet temperature is about 75° C. to about 90° C., which is the temperature of the exhaust, and the feed temperature is about 40° C. to about 50° C. It will be understood by a person skilled in the art that the washed protein precipitate can be used as a protein isolate without drying. However, the dried protein isolate has a better shelf life as removal of the solvent, for example water, results in a more stable protein isolate.

In another embodiment of the present disclosure, there is provided a process for the production of a protein isolate which is subsequently modified or hydrolyzed to form a high functional protein isolate or a mixture of hydrolyzed proteins, peptides and amino acids comprising a protein content of greater than 90% on a dry weight basis.

Accordingly, in an embodiment of the present disclosure, a process for the production of a protein isolate from a defatted or protein-enriched meal is disclosed, comprising:
    removing fiber from the defatted or protein-enriched meal, comprising:
        i) mixing the defatted or protein-enriched meal with a mixing solvent to form a mixture;

optionally screening the mixture through a mesh screen of about 10 to about 200 US mesh size to remove fiber, optionally adjusting the pH of the mixture to a pH of about 7;
optionally milling the mixture; and
centrifuging the mixture to remove fiber,
and forming a protein slurry;
ii) centrifuging the protein slurry to form a protein precipitate and a soluble protein fraction;
iii) mixing the protein precipitate with water to form a protein precipitate mixture and optionally adjusting the pH of the mixture to a pH of about 3 to about 7;
iv) adding cellulase complex to the protein precipitate mixture to hydrolyze residual fiber;
v) washing the protein precipitate with an extraction solvent and centrifuging to form a protein isolate.

It will be understood by a person skilled in the art that the steps of the process do not have to be followed exactly. For example, a person skilled in the art would recognize that the milling step could be performed before the screening step.

In another embodiment, the defatted or protein-enriched meal comprises a canola, rapeseed, mustard seed, broccoli seed, flax seed or soybean meal. In a further embodiment, the protein-enriched meal comprises a canola meal. In an embodiment, the protein-enriched meal comprises a soybean meal. In another embodiment, the protein-enriched meal comprises mustard seed meal. In a further embodiment, the protein-enriched meal comprises flax seed meal.

In another embodiment of the disclosure, the mixing solvent comprises water or a salt solution. In an embodiment, the salt solution comprises less than 5%, optionally about 3% to about 4%, or 3.5% by weight of salt in solution. In a further embodiment, the mixing solvent comprises water. In another embodiment, the ratio of defatted or protein-enriched meal to the mixing solvent is about 1:3 to about 1:20. In a further embodiment, the ratio is about 1:6 to about 1:10. In an embodiment, the ratio is about 1:6 to about 1:8.

In a further embodiment, the mixture is wet screened resulting in a separation of the fiber from the mixture which contains the protein. In another embodiment of the disclosure, the mesh screen comprises a US mesh screen of size about 20 to about 200 mesh. In an embodiment, the mesh screen is of size 40 US mesh size. In a further embodiment, the mesh screen is a vibratory screen. The mesh screen prevents the fiber from passing through, while the protein in the mixture passes through the screen, resulting in a separation of the fiber from the protein. This results in a mixture of protein which passes through the screen and a fiber fraction which is trapped by the screen. In an embodiment, the fiber fraction is dried and can be used in dietary fiber products. In an embodiment, some protein and carbohydrates are present in the fiber fraction.

In another embodiment, the pH of the mixture is optionally adjusted to about 7 with the addition of aqueous sodium hydroxide. In a further embodiment, the aqueous sodium hydroxide is a solution of about 1% to about 40%, optionally about 5% to about 30%, by weight of sodium hydroxide in water.

In another embodiment, the mixture is optionally milled using a wet milling process. In an embodiment, the wet milling of the mixture results in thorough mixing of the defatted or protein-enriched meal with the mixing solvent.

In another embodiment of the present disclosure, the mixture is centrifuged using a decanting centrifuge. In an embodiment, the mixture is centrifuged with a decanting centrifuge at a speed of about 1000 rpm to about 2000 rpm. In another embodiment, the speed is about 1500 rpm.

In another embodiment, the protein slurry is centrifuged using a disc stack centrifuge to separate insoluble proteins from soluble proteins, forming a protein precipitate and a soluble protein fraction. In an embodiment, the soluble protein fraction is filtered as described above. In an embodiment, the disc centrifuge operates continuously at a speed of about 6500 rpm to about 8500 rpm at a temperature of about 1° C. to about 60° C., optionally about 20° C. to about 40° C., or optionally at about 20° C. to about 25° C.

In an embodiment of the disclosure, the precipitated protein is mixed with water and its pH optionally adjusted for the addition of cellulase complex, in a similar manner as described above. This additional enzymatic step hydrolyzes residual fiber and allows the removal of fiber from the protein precipitate.

In another embodiment, after treatment with the cellulase complex, the protein precipitate is washed at least once with an extraction solvent to remove water-soluble sugar compounds as a result of the fiber hydrolyzation by the cellulase complex. In an embodiment, the extraction solvent is water. In an embodiment, the protein precipitate mixture is washed at least twice with the extraction solvent. In an embodiment, the ratio of extraction solvent to the precipitated protein is about 10:1 to about 1:1, optionally about 4:1 to about 2:1. The mixture is then further centrifuged to obtain a protein precipitate that has been further purified.

In an embodiment, the further purified protein precipitate is then subjected to high pressure jet cooking to obtain a high functional protein isolate having a protein content of greater than about 90% on a dry weight basis. In an embodiment, the jet cooking of the protein isolate occurs at a temperature of about 90° C. to about 120° C. for about 1 second to about 2 minutes, optionally about 3 seconds to about 30 seconds. As will be understood by a person skilled in the art, jet cooking involves the injection of steam into the purified protein, and results in the pasteurization of the protein and improves the functional properties of the protein isolate.

In another embodiment, the further purified protein precipitate is hydrolyzed using proteases to form a hydrolyzed protein extract containing hydrolyzed proteins, peptides and amino acids having a protein content of greater than about 90% on a dry weight basis. In an embodiment, the proteases are, for example, Alcalase® and Flavourzyme®. Alcalase® and Flavourzyme® were obtained from Novozymes North America, Inc., Franklinton, N.C. USA. This step hydrolyzes the protein in the protein precipitate into smaller peptides and amino acids, which are soluble in nutritional drinks and are easily adsorbed. In an embodiment, the purified protein precipitate is mixed with water to form a protein slurry, which is optionally followed by pH adjustment to a pH of about 6.0 to about 10.0, optionally about 7.5 to about 8.5. In an embodiment, the Alcalase® is added in a ratio of about 0.5% based on the dry weight of the protein slurry. In a further embodiment, the temperature is adjusted to about 20° C. to about 65° C., optionally about 50° C. to about 60° C., or about 60° C., for about 1 to about 4 hours. The hydrolyzed protein slurry is then cooled to about 30° C. to about 50° C., or about 40° C. to about 50° C., or about 50° C. The pH of the mixture is then adjusted to a pH of about 5.0 to about 7.0, or about 6.0 to about 7.0, or about 6.5, and a protease to form a hydrolyzed protein extract, such as Flavourzyme®, is then added to the mixture. In an embodiment, the protease to form a hydrolyzed protein extract, such as Flavourzyme®, is added in a ratio of about 0.5% based on the dry weight of the protein slurry. In a further embodiment, the mixture is then heated to a temperature of about 20° C. to about 60° C., optionally about 40° C. to about 60° C., or about 45° C. to about 55° C., for about 1 to about 4 hours. The hydrolyzed protein mixture is then centrifuged to separate the hydrolyzed protein extract from the insoluble solids. The soluble hydrolyzed protein extract is then spray dried as described above, while the extract from the centrifugation is added to the soluble protein fraction as described above.

In another embodiment of the disclosure, there is a provided a process for the production of a protein concentrate from a partially defatted, fully defatted or protein-enriched meal, comprising:
i) mixing the partially defatted, fully defatted or protein-enriched meal with a mixing solvent to form a mixture;
ii) optionally adjusting the pH of the mixture to a pH of about 2.0 to about 10.0;
iii) separating fiber from the mixture to form a protein slurry, wherein the protein slurry comprises a soluble protein fraction and an insoluble protein fraction;
iv) optionally repeating steps i)-iii) by mixing the protein slurry with additional partially defatted, fully defatted or protein-enriched meal;
v) mixing the protein slurry with an extraction solvent to form an extract and a washed insoluble protein fraction;
vi) separating the extract from the washed insoluble protein fraction;
vii) optionally repeating steps v) and vi) at least once; and
viii) desolventizing the washed insoluble protein fraction to form a protein concentrate.

In another embodiment of the disclosure, the ratio of partially defatted, fully defatted or protein-enriched meal to mixing solvent is about 1:3 to about 1:30 (w/w). In another embodiment, the ratio of partially defatted, fully defatted or protein-enriched meal to solvent is about 1:5 to about 1:20 (w/w). In a further embodiment, the ratio is about 1:6 to about 1:12 (w/w). In an embodiment, the ratio is about 1:8 to about 1:10 (w/w).

In a further embodiment of the disclosure, the mixing solvent comprises water or an aqueous solution comprising a polysaccharide, a salt or an alcohol. In an embodiment, the mixing solvent is water. In another embodiment, the polysaccharide is guar gum.

In an embodiment, the pH of the protein slurry is adjusted to a pH of about 6.5 to about 10.0. In a further embodiment, the pH of the protein slurry is adjusted to a pH of about 7.0 to about 9.0.

In an embodiment, the mixture is centrifuged to separate the fiber from mixture and form the protein slurry. In an embodiment, the mixture is centrifuged at a speed of about 1,000 rpm to about 2,000 rpm. In a further embodiment, the mixture is centrifuged at a speed of about 1,400 to about 1,600 rpm. In an embodiment, the mixture is centrifuged using a decanter centrifuge.

The centrifugation of the mixture results in three layers: i) an insoluble fiber layer and a protein slurry on top of the fiber, which was comprised of ii) an insoluble protein fraction and iii) a soluble protein fraction. Separation of the top and middle layers (the soluble protein extract and the insoluble fine protein fraction) from the bottom layer (coarse fiber solids), resulted in the protein slurry with fiber removed. In an embodiment, the bird decanter was operated at a low pool depth with a bowl speed of between about 1,000 rpm and about 2,000 rpm, optionally 1,400 to about 1,600 rpm, suitably about 1,500 rpm. It was determined that when the speed of the centrifugation is too high, for example at 5,000 rpm, the insoluble protein fraction settles with the fiber. If the speed of the centrifugation is too low, fiber will remain in the protein slurry. Accordingly, in an embodiment, when the speed of the centrifugation is between about 1,000 rpm and about 2,000 rpm, optionally 1,400 to about 1,600 rpm, suitably about 1,500 rpm, the fiber in the mixture is separated from both the soluble and insoluble protein.

In another embodiment of the disclosure, mixing the protein slurry with additional partially defatted, fully defatted or protein-enriched meal is repeated at least once. In a further embodiment, mixing the protein slurry with additional partially defatted, fully defatted or protein-enriched meal is repeated at least two to seven times. In an embodiment, recycling the protein slurry with additional partially defatted, fully defatted or protein-enriched meal increases the solid content of the meal being processed, and accordingly, reduces the overall processing volume.

In an embodiment of the disclosure, the extraction solvent comprises water, methanol, ethanol, isopropanol, or mixtures thereof. In an embodiment, the extraction solvent comprises ethanol. In another embodiment, the extraction solvent comprises at least about 50% ethanol. In an embodiment, the extraction solvent comprises at least about 70% ethanol. In a further embodiment, the extraction solvent comprises at least about 90% ethanol.

In a further embodiment, the extract is separated from the washed insoluble protein fraction using centrifugation, vacuum filtration, pressure filtration, decantation or gravity draining. In an embodiment, the extract is separated from the washed insoluble protein fraction using centrifugation.

In another embodiment of the disclosure, wherein steps iv) and v) are repeated at least twice.

In a further embodiment, the process further comprises the step of drying the washed insoluble protein fraction to form the protein concentrate. In an embodiment, the protein concentrate is dried in a vacuum dryer, fluidized bed dryer, hot air dryer ring dryer or spray dryer.

In an embodiment of the disclosure, the partially defatted, fully defatted or protein-enriched meal comprises a canola, rapeseed, mustard seed, broccoli seed, flax seed, cotton seed, hemp seed, safflower seed, sesame seed or soybean meal. In another embodiment, the partially defatted, fully defatted or protein-enriched meal comprises a canola meal.

In an embodiment, the protein concentrate comprises a protein content of about 60% to about 90% on a dry weight basis.

In another embodiment of the disclosure, there is also provided a process for the production of a protein isolate from a partially defatted, fully defatted or protein enriched meal, comprising:
i) mixing the partially defatted, fully defatted or protein-enriched meal with alkaline water to form a mixture;
ii) optionally adjusting the pH of the mixture to a pH of about 6.0 to about 10.0;
iii) separating fiber from the mixture to form a first protein slurry, wherein the first protein slurry comprises a soluble protein fraction and an insoluble protein fraction;
iv) separating the first protein slurry to form a protein solids fraction and a soluble protein fraction;
v) mixing the protein solids fraction with water to form a second protein slurry;
vi) separating the second protein slurry to form a second protein solids fraction and a second soluble protein fraction;
vii) optionally repeating steps v) and vi) at least once;
viii) separating the soluble protein fractions to form a clarified soluble protein fraction and a residual insoluble protein fraction;
ix) optionally adjusting the pH of the clarified soluble protein fraction to a pH of about 7;

x) separating the clarified soluble protein fraction, optionally by filtering the clarified soluble protein fraction by membrane filtration; and xi) optionally drying the clarified soluble protein fraction.

In another embodiment of the disclosure, the ratio of partially defatted, fully defatted or protein-enriched meal to alkaline water is about 1:3 to about 1:30 (w/w). In another embodiment, the ratio of partially defatted, fully defatted or protein-enriched meal to alkaline water is about 1:5 to about 1:20 (w/w). In a further embodiment, the ratio is about 1:6 to about 1:12 (w/w). In an embodiment, the ratio is about 1:8 to about 1:10 (w/w).

In an embodiment of the disclosure, the pH of the alkaline water is about 7 to about 12. In another embodiment, the pH of the first protein slurry is adjusted to about 8.0 to about 9.5. In a further embodiment, the pH of the first protein slurry is adjusted to about 8.5 to about 9.0.

In an embodiment, the mixture is centrifuged to separate the fiber from the protein slurry and form the protein extract. In an embodiment, the mixture is centrifuged at a speed of about 1,000 rpm to about 2,000 rpm. In a further embodiment, the mixture is centrifuged at a speed of about 1,400 to about 1,600 rpm. In an embodiment, the mixture is centrifuged using a decanter centrifuge.

In another embodiment, the first protein slurry is centrifuged to separate the protein solids fraction from the soluble protein fraction. In a further embodiment, the first protein slurry is centrifuged at a speed of about 4,000 rpm to about 8,500 rpm. In a further embodiment, the first protein slurry is centrifuged at a speed of about 5,000 to about 8,500 rpm.

In another embodiment of the disclosure, the ratio of the protein solids fraction to water is about 1.0:0.5 to about 1.0:3.0 (w/w). In a further embodiment, the ratio of the protein solids fraction to water is about 1.0:1.0 to about 1.0:2.0 (w/w).

In an embodiment, the soluble protein fractions are centrifuged to form the clarified soluble protein fraction and the residual insoluble protein fraction. In an embodiment, the soluble protein fractions are centrifuged using a disc stack centrifuge at a speed of about 7,000 rpm to about 10,000 rpm. In a further embodiment, the soluble protein fractions are centrifuged using a disc stack centrifuge at a speed of about 8,400 rpm to about 8,600 rpm.

In another embodiment of the disclosure, the pH of the clarified soluble protein fraction is adjusted with alkali. In a further embodiment, the pH of the clarified soluble protein fraction is adjusted with sodium hydroxide.

In an embodiment, the clarified soluble protein fraction is filtered using an ultrafiltration apparatus. In a further embodiment, the ultrafiltration apparatus comprises a membrane to filter proteins larger than about 10,000 daltons. In another embodiment, the separation of the clarified soluble protein fraction is accomplished by adjusting the pH of the solution to the isoelectric point of the proteins (about pH of 4.5), and consequently, the proteins are precipitated out of solution. In another embodiment, the proteins are cooked to precipitate the proteins from solution.

In another embodiment of the disclosure, the process further comprises the step of filtering the clarified soluble protein fraction using a diafiltration apparatus.

In another embodiment, the clarified soluble protein fraction is dried in a vacuum dryer, fluidized bed dryer, freeze dryer, ring dryer or spray dryer to form the protein isolate.

In an embodiment of the disclosure, the partially defatted, fully defatted or protein-enriched meal comprises a canola, rapeseed, mustard seed, broccoli seed, flax seed, cotton seed, hemp seed, safflower seed, sesame seed or soybean meal. In another embodiment, the partially defatted, fully defatted or protein-enriched meal comprises a canola meal.

In another embodiment of the disclosure, the protein concentrate comprises a protein content of greater than about 90% on a dry weight basis.

In another embodiment of the disclosure, there is also provided a process for the production of a hydrolyzed protein concentrate from a partially defatted, fully defatted or protein-enriched meal, comprising:

i) mixing the partially defatted, fully defatted or protein-enriched meal with water to form a mixture;

ii) optionally adjusting the pH of the mixture to a pH of about 6.0 to about 10.0;

iii) separating the mixture to remove fiber from the mixture and form a first protein slurry, wherein the first protein slurry comprises a soluble protein fraction and an insoluble protein fraction;

iv) optionally adjusting the pH of the first protein slurry to a pH of about 7.0;

v) separating the first protein slurry to form a first protein solids fraction and a first soluble protein fraction;

vi) mixing the first protein solids fraction with water to form a second protein slurry;

vii) separating the second protein slurry to form a second protein solids fraction and a second soluble protein fraction;

viii) mixing the second protein solids fraction with water to form a third protein slurry;

ix) adjusting the pH of the third protein slurry to a pH of about 7.0 to about 9.0;

x) mixing the third protein slurry with at least one protease to form a hydrolyzed protein extract;

xi) separating the hydrolyzed protein extract from the third protein slurry to form the hydrolyzed protein concentrate.

In another embodiment of the disclosure, the ratio of partially defatted, fully defatted or protein-enriched meal to water is about 1:3 to about 1:30 (w/w). In another embodiment, the ratio of partially defatted, fully defatted or protein-enriched meal to water is about 1:5 to about 1:20 (w/w). In a further embodiment, the ratio is about 1:6 to about 1:12 (w/w). In an embodiment, the ratio is about 1:8 to about 1:10 (w/w).

In another embodiment, the pH of the mixture is adjusted to about 8.0 to about 9.0. In a further embodiment, the pH of the mixture is adjusted to about 8.5 to about 9.0.

In an embodiment, the mixture is centrifuged to separate the fiber from the protein slurry and form the protein extract. In an embodiment, the mixture is centrifuged at a speed of about 1,000 rpm to about 2,000 rpm. In a further embodiment, the mixture is centrifuged centrifuge at a speed of about 1,400 to about 1,600 rpm. In an embodiment, the mixture is centrifuged using a decanter centrifuge.

In another embodiment, the first protein slurry is centrifuged to separate the protein solids fraction from the soluble protein fraction. In a further embodiment, the first protein slurry is centrifuged at a speed of about 4,000 rpm to about 8,000 rpm. In a further embodiment, the first protein slurry is centrifuged at a speed of about 5,000 to about 8,500 rpm.

In another embodiment, the ratio of the first and second protein solids fraction to water is about 1.0:0.5 to about 1.0:3.0 (w/w). In a further embodiment, the ratio of the first and second protein solids fraction to water is about 1.0:1.0 to about 1.0:2.0 (w/w).

In another embodiment of the disclosure, the pH of the third protein slurry is adjusted to about 8.0 to about 8.5.

In an embodiment of the disclosure, the ratio of the third protein slurry to the protease is about 100:1 to about 5000:1 (w/w).

In an embodiment of the disclosure, the third protein slurry is mixed with a protease at a temperature of about 50° C. to about 70° C. In another embodiment, the third protein slurry is mixed with a protease at a temperature of about 55 to about 65° C.

In another embodiment, the at least one protease comprises a protease from *Bacillus Licheniformis*.

In a further embodiment, the process further comprises the step of mixing the third protein slurry with a second protease.

In an embodiment, the ratio of the third protein slurry to the second protease is about 100:1 to about 5000:1 (w/w).

In another embodiment, the third protein slurry is mixed with the second protease at a temperature of about 40° C. to about 60° C. In an embodiment, the third protein slurry is mixed with the second protease at a temperature of about 45° C. to about 55° C.

In a further embodiment, the second protease comprises a fungal protease/peptidase complex from *Aspergillus oryzae*.

In an embodiment, the hydrolyzed protein extract is separated using a centrifuge. In a further embodiment, the hydrolyzed protein extract is separated using a decanter centrifuge at a speed of about 3,800 to about 5,200 rpm.

In another embodiment, the clarified soluble protein fraction is dried in a vacuum dryer, fluidized bed dryer, ring dryer or spray dryer to form the protein isolate.

In an embodiment of the disclosure, the partially defatted, fully defatted or protein-enriched meal comprises a canola, rapeseed, mustard seed, broccoli seed, flax seed, cotton seed, hemp seed, safflower seed, sesame seed or soybean meal. In another embodiment, the partially defatted, fully defatted or protein-enriched meal comprises a canola meal.

In a further embodiment, the hydrolyzed protein concentrate comprises a protein content of greater than about 70% on a dry weight basis.

In an embodiment, the use of an extraction solvent, such as ethanol, leads to a protein concentrate or protein isolate having superior organoleptic properties, as well as superior protein solubility properties, which therefore possesses better functional properties. In an embodiment, the use of an extraction solvent, such as ethanol, results in the protein concentrates containing fewer impurities. Consequently, the protein concentrates are generally of higher quality and have better functional properties.

The present disclosure relates to processes for the production of protein concentrates and protein isolates, in which the oilseed meal is subjected to low g-forces to separate the fiber from the insoluble and soluble protein fractions. Removing the fiber from a protein mixture using low g-forces, separates the insoluble fiber from the protein fraction, and in particular the insoluble protein fraction, which consequently increases the amount of recoverable protein from an oilseed meal.

Accordingly, the present disclosure includes a process for the production of a protein concentrate from an oilseed meal comprising:
   i) mixing the oilseed meal with a first blending solvent to form a mixture;
   ii) optionally treating the mixture with phytase at a temperature and a pH suitable for phytase activity;
   iii) optionally adjusting the pH of the mixture to a pH between 6.0 and 10.0;
   iv) subjecting the mixture to a g-force sufficient to separate the mixture to form
     a) a fiber fraction, and
     b) protein fractions comprising an insoluble protein fraction and a soluble protein fraction;
   v) optionally mixing the fiber fraction with a second blending solvent and repeating step iv);
   vi) optionally adjusting the pH of the protein fraction to a pH between 4.0 and 6.0;
   vii) heating the protein fraction to a temperature between 80° C. and 100° C. to precipitate the proteins; and
   viii) separating the precipitated proteins from the protein fraction to form the protein concentrate.

In another embodiment, the first and second blending solvents comprise water, a saline solution or a polysaccharide solution. In a further embodiment, the first and second blending solvents comprise water.

In an embodiment of the disclosure, the ratio of the oilseed meal to the first blending solvent is 1:3 to 1:30 (w/w) of meal to water, optionally about 1:8 to about 1:10 (w/w).

In an embodiment, the temperature suitable for phytase activity is between 20° C. and 60° C., optionally between 40° C. and 55° C., suitably between 50° C. and 55° C. In another embodiment, the pH suitable for phytase activity is between 2.0 and 7.0, optionally between 4.0 and 6.0, suitably between 4.5 and 5.5, optionally 5.0 to 5.5. In another embodiment, the concentration of the phytase enzyme is between 0.01% to 1.0% (w/w) based on the weight of the oilseed meal, optionally 0.01% and 0.5% optionally 0.01% and 0.1%. In another embodiment, the mixture is incubated with the phytase enzyme under good agitation. The addition of phytase enzyme to the protein mixture results in the hydrolysis of phytates and/or phytic acid present in the oilseed meal to organic phosphates and inositol. It is known to those skilled in the art that phytates and phytic acid may constitute undesirable anti-nutritional compounds in a protein meal, and accordingly, are desirably removed from the oilseed meal and the final protein products. Accordingly, the addition of phytase enzyme results in the hydrolysis of the phytates and/or phytic acid which are subsequently removed from the mixture. In addition, it has also been determined that phytates and/or phytic acid complex with proteins to form an insoluble gel complex. Accordingly, in an embodiment, when filtration, such as diafiltration or ultrafiltration, is utilized to purify and separate protein concentrates and/or protein isolates, the insoluble protein/phytate (or phytic acid) gel complexes block the filtration apparatus, reducing the flow through the filtration apparatus, and accordingly, reducing the amount of recoverable protein and filtration efficiency. It will be understood that the addition of phytase to the mixture and the conditions recited for reduction or removal of phytates and/or phytic acid apply to all of the processes and embodiments of the present disclosure.

In another embodiment of the disclosure, after treating the mixture with the phytase enzyme, the pH of the mixture is optionally adjusted to a pH of about 6.0 to about 10.0, optionally 6.5 to about 9.5, suitably 7.0 to 8.0, using a base, such as sodium hydroxide, potassium hydroxide, etc. In an embodiment, adjusting the pH of the mixture results in the protein becoming more soluble in the blending solvent, such as water, which consequently increases the yield of the protein concentrate.

In another embodiment of the disclosure, the mixture is subjected to a g-force sufficient to separate the mixture to form a fiber fraction and protein fractions comprising an insoluble protein fraction and a soluble protein fraction. The separation of the mixture using a sufficient g-force is described herein with reference to a centrifuge, such as a decanter centrifuge or a disc stack centrifuge, but a person skilled in the art would understand that other methods of separation that create a separation force, including a hydrocyclone, are also included. Accordingly, in an embodiment, when the mixture is subjected to a sufficient g-force using a centrifuge, the mixture separates into three-phases as a result of the sedimentation principle: (i) an insoluble fiber fraction, and (ii) protein fractions comprising (ii.a) an insoluble protein fraction, and (ii.b) a soluble protein fraction. The centripetal acceleration acting on the mixture results in the insoluble fiber fraction, which has a relatively higher density and/or greater particle size compared to the other fractions, moving further along the radial direction in which the centripetal force is acting (perpendicular to the axis of rotation). When a centrifuge is utilized, the insoluble fiber fraction (or phase) moves towards the bottom of the centrifuge tube, as a result of its relatively higher density and/or greater particle size, resulting in one of the phases of separation. As a result of the proteins in the insoluble protein fraction having a lower relative density and/or smaller particle size as compared to the insoluble fiber fraction, the insoluble protein fraction forms another phase of separation (the middle phase). Finally, the proteins in the soluble protein fraction, being soluble in the blending solvent and/or having a lower relative density compared to the fiber fraction and insoluble protein fraction, remain near the top of the centrifuge tube. If oil seed meal is partially defatted meal, a fourth phase may also form on top of the soluble protein phase comprising residual oil. It will be understood that subjecting the mixture to a sufficient g-force will not result in a total separation of the three fractions, and accordingly, a minor amount of fiber will be present in the protein fraction, while protein will be present in the insoluble fiber fraction. There will be a certain amount of protein trapped within the structure of the insoluble fiber fraction that is not separable using mechanical means (i.e. using a centrifuge). In an embodiment, the amount of protein trapped within the fiber fraction will be 30%, optionally 20%, 10%, 5%, 1%. In another embodiment, proteases (such as Protamex, Alcalase 2.4L FG and/or Flavourzyme 1000L) are used to hydrolyze the protein trapped within the fiber fraction, which releases the protein from the fiber, and can be recovered therefrom, and such a process is also included in the present disclosure. In this embodiment, the hydrolyzed protein is separated from the fiber using any of the means disclosed herein (e.g. centrifugation, hydrocyclone). It will be understood that the disclosure concerning the g-force sufficient to separate the mixture as described above applies to all of the processes and embodiments of the present disclosure.

In an embodiment, the mixture is subjected to a g-force of between 100 g and 500 g, suitably between 150 g and 400 g, optionally between 180 g and 350 g. Calculation of g-force (or relative centrifugal force) optionally involves the RPMs (revolutions per minute) of the device, as well as the rotational radius (in centimeters):

$$\text{g-force} = (\text{RPM})^2 \times (\text{rotational radius}) \times (0.00001118)$$

A person skilled in the art will readily be able to calculate the g-force from the RPMs of a given separation device, such as a centrifuge or a hydrocyclone.

In another embodiment, separating the mixture comprises using a centrifuge or a hydrocyclone. In another embodiment, the centrifuge comprises a decanter centrifuge or a disc stack centrifuge.

In another embodiment, as there will be a residual amount of protein in the separated fiber fraction, the separated fiber fraction is washed with a second blending solvent, optionally at least once, optionally twice or more than twice, and the mixture is then again subjected to a g-force to separate the mixture to form a fiber fraction and a protein fraction comprising an insoluble protein fraction and a soluble protein fraction.

In another embodiment, the separation of the insoluble fiber fraction from the protein fractions, results in fiber solids which are dried and consequently constitute a high fiber canola meal containing a low concentration of anti-nutritional factors, such as phytates and/or phytic acid.

In another embodiment, the pH of the protein fraction comprising the insoluble protein fraction and soluble protein fraction is adjusted using an acid, such as phosphoric acid, nitric acid, citric acid, sulfuric acid, and the pH is adjusted to between 4.0 and 6.0, optionally 4.0 and 5.0, suitably 4.0 and 4.5. In an embodiment, adjusting the pH of the protein fraction using an acid results in undesirable ash becoming soluble in the protein fraction, and therefore, separable from the final protein concentrate.

In another embodiment, the protein fraction comprising the insoluble protein fraction and the soluble protein fraction is heated to a temperature between 80° C. and 100° C., optionally 90° C. and 100° C., suitably 95° C. and 100° C., for a time period of between 5 minutes and 60 minutes, optionally 5 minutes and 45 minutes, suitably between 10 minutes and 30 minutes. Increasing the temperature of the protein fractions denatures some of the undenatured proteins in the soluble protein fraction, rendering them insoluble, and therefore increasing the yield of the insoluble protein concentrate.

In a further embodiment, separating the precipitated proteins comprises using a centrifuge or a hydrocyclone. In another embodiment, separating the precipitated proteins comprises using a centrifuge, such as decanter centrifuge or a disc stack centrifuge. In another embodiment, centrifuging the precipitated proteins comprises a g-force between 2,500 g and 9,500 g. When the centrifuge is operated at such a g-force, the precipitated proteins move along the radial axis to the bottom of the centrifuge tube and are easily separated from the supernatant.

In another embodiment of the disclosure, the process further comprising the step of drying the protein concentrate to a moisture content of between 4% and 8%, optionally 6% (w/w). In another embodiment, the drying is performed using a fluidized bed dryer, conveyor dryer, rotary dryer, drum dryer, spray drier or a ring drier.

In another embodiment, there is also included a protein concentrate having a protein content of at least 60% and less than 90% protein comprising:

i) a first protein fraction comprising between 30% and 70% 2S protein, optionally between 40% and 60%, optionally 45% and 55%;

ii) a second protein fraction comprising between 20% and 50% 12S protein, optionally between 25% and 45%, optionally between 30% and 40%, optionally between 35% and 40%.

In another embodiment, the protein concentrate comprises a hydrolyzed protein concentrate. In another embodiment, the hydrolyzed protein concentrate comprises peptides and/or free amino acids.

The present disclosure also includes a process for the production of a protein concentrate from an oilseed meal comprising:

i) mixing the oilseed meal with a first blending solvent to form a mixture;

ii) optionally treating the mixture with phytase at a temperature and a pH suitable for phytase activity;

iii) optionally adjusting the pH of the mixture to a pH between 6.0 and 10.0;

iv) subjecting the mixture to a g-force sufficient to separate the mixture to form
   a) a fiber fraction, and
   b) protein fractions comprising an insoluble protein fraction and a soluble protein fraction;
v) optionally mixing the fiber fraction with a second blending solvent and repeating step iv);
vi) optionally adjusting the pH of the protein fraction to a pH between 4.0 and 6.0;
vii) mixing the protein fraction with a mixing solvent to form a protein slurry and precipitate the proteins;
viii) separating the precipitated proteins from the protein slurry to form the protein concentrate; and
ix) optionally repeating steps vii) and viii) with the precipitated proteins.

In another embodiment, the first and second blending solvents comprise water, a saline solution or a polysaccharide solution. In a further embodiment, the first and second blending solvents comprise water.

In an embodiment of the disclosure, the ratio of the oilseed meal to the first blending solvent is 1:3 to 1:30 (w/w) of meal to water, optionally about 1:8 to about 1:10 (w/w).

In an embodiment, the temperature suitable for phytase activity is between 20° C. and 60° C., optionally between 40° C. and 55° C., suitably between 50° C. and 55° C. In another embodiment, the pH suitable for phytase activity is between 2.0 and 7.0, optionally between 4.0 and 6.0, suitably between 4.5 and 5.5, optionally 5.0 to 5.5. In another embodiment, the concentration of the phytase enzyme is between 0.01% to 1.0% (w/w) based on the weight of the oilseed meal, optionally 0.01% and 0.5% optionally 0.01% and 0.1%. In another embodiment, the mixture is incubated with the phytase enzyme under good agitation.

In another embodiment of the disclosure, after treating the mixture with the phytase enzyme, the pH of the mixture is optionally adjusted to a pH of about 6.0 to about 10.0, optionally 6.5 to about 9.5, suitably 7.0 to 8.0, using a base, such as sodium hydroxide, potassium hydroxide, etc. In an embodiment, adjusting the pH of the mixture results in the protein becoming more soluble in the blending solvent, such as water, which consequently increases the yield of the protein concentrate.

In another embodiment of the disclosure, the mixture is subjected to a g-force of between 100 g and 500 g, suitably between 150 g and 400 g, optionally between 180 g and 350 g.

In another embodiment, separating the mixture comprises using a centrifuge or a hydrocyclone. In another embodiment, the centrifuge comprises a decanter centrifuge or disc stack centrifuge.

In another embodiment, as there will be a residual amount of protein in the separated fiber fraction, the separated fiber fraction is washed with a second blending solvent, optionally at least once, optionally twice or more than twice, and the mixture is then again subjected to a g-force to separate the mixture to form a fiber fraction and a protein fraction comprising an insoluble protein fraction and a soluble protein fraction.

In another embodiment, the separation of the insoluble fiber fraction from the protein fraction, results in fiber solids which are dried and consequently constitute a high fiber canola meal containing a low concentration of anti-nutritional factors, such as phytates and/or phytic acid.

In another embodiment, the pH of the protein fraction comprising the insoluble protein fraction and soluble protein fraction is adjusted using an acid, such as phosphoric acid, nitric acid, citric acid, sulfuric acid, hydrochloric acid, and the pH is adjusted to between 4.0 and 6.0, optionally 4.0 and 5.0, suitably 4.0 and 4.5. In an embodiment, adjusting the pH of the protein fraction using an acid results in undesirable ash becoming soluble in the protein fraction, and therefore, separable from the final protein concentrate.

In another embodiment of the disclosure, the protein fraction is mixed with a mixing solvent comprising an ethanol:water mixture, wherein the ethanol is present in an amount between 80% and 100%, optionally 85% and 100% (v/v), optionally 90% and 100% (v/v), optionally 95% and 100% (v/v). It will be understood that 100% ethanol may contain a small percentage of impurities such as water, etc., which cannot be removed from the ethanol. In an embodiment, mixing solvent is added to the protein fraction at a ratio of between 2:1 and 1:2 (v/v of mixing solvent:protein fraction), optionally 1:1. In an embodiment, when the mixing solvent comprises an alcohol, such as ethanol (80%, 90%, 95% ethanol in water or 100% ethanol), proteins in the protein slurry precipitate from solution, as a result the proteins being less soluble in the mixing solvent (such as ethanol) than in the blending solvent (such as water), and therefore increases the yield of the protein concentrate.

In another embodiment, separating the precipitated proteins comprises using a centrifuge or a hydrocyclone. In another embodiment, separating the precipitated proteins comprises using a centrifuge, such as decanter centrifuge or disc stack centrifuge. In another embodiment, centrifuging the precipitated proteins comprises a g-force between 2,500 g and 9,500 g. When the centrifuge is operated at such a g-force, the precipitated proteins move along the radial axis to the bottom of the centrifuge tube and are easily separated from the supernatant.

In another embodiment of the disclosure, steps viii) and viii) are repeated at least twice, such that the precipitated proteins are washed with mixing solvent to remove impurities.

In another embodiment, the process further comprises the step of drying the protein concentrate to a moisture content of between 4% and 8% (w/w), optionally 6% (w/w). In another embodiment, the drying is performed using a fluidized bed dryer, spray dryer or a ring drier.

In another embodiment, there is also included a protein concentrate having a protein content of at least 60% and less than 90% protein comprising:
   i) a first protein fraction comprising between 30% and 70% 2S protein, optionally between 40% and 60%, optionally 45% and 55%;
   ii) a second protein fraction comprising between 20% and 50% 12S protein, optionally between 25% and 45%, optionally between 30% and 40%, optionally between 35% and 40%.

In another embodiment, the protein concentrate comprises a hydrolyzed protein concentrate. In a further embodiment, the hydrolyzed protein concentrate comprises peptides and/or free amino acids.

The present disclosure also includes a process for the production of a protein isolate from an oilseed meal comprising:
   i) mixing the oilseed meal with a first blending solvent to form a mixture;
   ii) optionally treating the mixture with phytase at a temperature and a pH suitable for phytase activity;
   iii) optionally adjusting the pH of the mixture to a pH between 6.0 and 10.0;
   iv) subjecting the mixture to a g-force sufficient to separate the mixture to form
      a) a fiber fraction, and b) protein fractions comprising an insoluble protein fraction and a soluble protein fraction;

v) optionally mixing the fiber fraction with a second blending solvent and repeating step iv);

vi) separating the insoluble protein fraction from the soluble protein fraction to recover therefrom an insoluble protein concentrate and a soluble protein extract; and vii) subjecting the soluble protein extract to filtration to recover therefrom the protein isolate.

In another embodiment, the first and second blending solvents comprise water, a saline solution or a polysaccharide solution. In a further embodiment, the first and second blending solvents comprise water.

In an embodiment of the disclosure, the ratio of the oilseed meal to the first blending solvent is 1:3 to 1:30 (w/w) of meal to water, optionally 1:8 to 1:10 (w/w).

In an embodiment, the temperature suitable for phytase activity is between 20° C. and 60° C., optionally between 40° C. and 55° C., suitably between 50° C. and 55° C. In another embodiment, the pH suitable for phytase activity is between 2.0 and 7.0, optionally between 4.0 and 6.0, suitably between 4.5 and 5.5, optionally 5.0 and 5.5. In another embodiment, the concentration of the phytase enzyme is between 0.01% and 1.0% (w/w) based on the weight of the oilseed meal, optionally 0.01% and 0.5% optionally 0.01% and 0.1%. In another embodiment, the mixture is incubated with the phytase enzyme under good agitation.

In another embodiment of the disclosure, after treating the mixture with the phytase enzyme, the pH of the mixture is optionally adjusted to a pH of between 6.0 and about 10.0, optionally 7.0 and 9.0, suitably 7.0 and 8.0, using a base, such as sodium hydroxide, potassium hydroxide, etc. In an embodiment, adjusting the pH of the mixture results in the protein becoming more soluble in the blending solvent, such as water, which consequently increases the yield of the protein isolate.

In another embodiment of the disclosure, the mixture is subjected to a g-force of between 100 g and 500 g, suitably between 150 g and 400 g, optionally between 180 g and 350 g.

In another embodiment, separating the mixture comprises using a centrifuge or a hydrocyclone. In an embodiment, the centrifuge comprises a decanter centrifuge or disc stack centrifuge.

In another embodiment, as there will be a residual amount of protein in the separated fiber fraction, the separated fiber fraction is washed with a second blending solvent, optionally at least once, optionally twice or more than twice, and the mixture is then again subjected to a g-force to separate the mixture to form a fiber fraction and a protein fraction comprising an insoluble protein fraction and a soluble protein fraction.

In another embodiment, the separation of the insoluble fiber fraction from the protein fraction, results in fiber solids which are dried and consequently constitute a high fiber canola meal containing a low concentration of anti-nutritional factors, such as phytates and/or phytic acid.

In another embodiment, separating the insoluble protein fraction from the soluble fiber fraction comprises using a centrifuge or a hydrocyclone. In a further embodiment separating the insoluble protein fraction from the soluble protein fraction comprises using a centrifuge, such as a decanter centrifuge or disc stack centrifuge.

In another embodiment, centrifuging to separate the insoluble protein fraction from the soluble protein fraction comprises a g-force between 2,500 g and 9,500 g. In another embodiment, the separation of the insoluble protein fraction from the soluble protein fraction results in a wet protein concentrate that can be subsequently dried. The extract from the separation of the insoluble protein fraction from the soluble protein fraction comprises the soluble protein, which is subsequently filtered through a filtration apparatus, such as ultrafiltration and/or diafiltration, resulting in the protein isolate. As described above, phytates and/or phytic acid can complex and bind to the proteins, and consequently block the filtration apparatus. The removal of the phytates and/or phytic acid from the oilseed meal mixture (oilseed meal and blending solvent) using phytase as described above, such that the filtration apparatus is not blocked with such complexes, resulting the filtration apparatus performing efficiently to produce the protein isolate.

In another embodiment, the process further comprises the step of drying the protein isolate to a moisture content of between 4% and 8% (w/w), optionally 6% (w/w). In another embodiment, the drying is performed using a spray drier or a ring drier.

In another embodiment, there is also included a protein isolate having a protein content of at least 90% protein comprising:

i) a first protein fraction comprising between 10% and 40% 2S protein, optionally between 15% and 30%;

ii) a second protein fraction comprising between 30% and 70% 12S protein, optionally 40% and 60%, optionally between 50% and 60%.

In a further embodiment, the protein isolate comprises a hydrolyzed protein isolate. In another embodiment, the hydrolyzed protein concentrate comprises peptides and/or free amino acids.

The present disclosure also includes a process for obtaining a protein concentrate from an oilseed meal comprising:

i) mixing the oilseed meal with a first blending solvent to form a mixture;

ii) optionally treating the mixture with phytase at a temperature and a pH suitable for phytase activity;

iii) optionally adjusting the pH of the mixture to a pH suitable to solubilize proteins in the mixture;

iv) subjecting the mixture to a g-force sufficient to separate the mixture to form
   a) a fiber fraction, and
   b) a protein fraction comprising
      (i) an insoluble protein fraction, and
      (ii) a soluble protein fraction;

v) separating the fiber fraction from the protein fraction and mixing the fiber fraction with a second blending solvent to form a fiber mixture;

vi) treating the fiber mixture with a protease at a temperature and a pH suitable for protease activity;

vii) subjecting the fiber mixture to a g-force sufficient to separate the fiber mixture to form:
   a) a second fiber fraction, and
   b) a hydrolyzed protein fraction, comprising
      (i) an insoluble protein fraction comprising partially hydrolyzed and un-hydrolyzed protein, and
      (ii) a soluble hydrolyzed protein fraction;

viii) optionally adjusting the pH of the protein fraction from step iv(b) to a pH suitable to precipitate the proteins;

x) separating the precipitated proteins from the protein fraction;

xi) optionally combining the precipitated proteins and the hydrolyzed protein fraction to form the protein concentrate.

In one embodiment, the pH of the mixture (oilseed meal and first blending solvent) is optionally adjusted to solubilize proteins (undenatured proteins) into the first blending solvent. In an embodiment, the pH of the mixture is adjusted to a pH between 6 and 8, optionally between 6.5 and 7.5, optionally about 7.0, using a base such as sodium hydroxide, which solubilizes some of the proteins present in the oilseed meal, and upon low g-force separation, increases the amount of protein in the protein fraction. In addition, adjusting the pH to about 7.0 results in the fiber fraction (after low g-force separation of the mixture) having a neutral pH as a by-product.

In another embodiment, the process further comprises mixing the fiber fraction with the first blending solvent and repeating step iv) once, twice or three times and/or mixing the second fiber fraction with the second blending solvent and repeating step vii) once, twice or three times. The repeated washing of the fiber fractions with the blending solvent increases the amount of protein that is recovered for the protein concentrate as the repeated washings separates additional protein that is trapped within the fiber structure.

In another embodiment, the first and second blending solvents comprise water, a saline solution or a polysaccharide solution, optionally water, and wherein the ratio of the oilseed meal to the first blending solvent is 1:3 to 1:30 (w/w) of meal to water, optionally 1:8.

In another embodiment, the temperature suitable for phytase activity is between 20° and 60° C. and the pH suitable for phytase activity is between 2.0 and 7.0 and the temperature suitable for protease activity is between 30° and 70° C. and the pH suitable for protease activity is between 5.0 and 9.0.

In another embodiment, the mixture and/or the fiber mixture is subjected to a g-force of between 100 g and 500 g, optionally between 150 g and 400 g, or between 170 g and 350 g. In an embodiment, separating the mixture and/or the fiber mixture comprises using a centrifuge or a hydrocyclone, optionally a decanter centrifuge.

In a further embodiment, the pH of the protein fraction from step iv(b) is adjusted to precipitate proteins in the protein fraction. The protein fraction comprises (i) an insoluble protein fraction, and (ii) a soluble protein fraction, and the adjustment of the pH precipitates proteins from the soluble protein fraction, and therefore increases the yield of the protein concentrate. In one embodiment, the pH of the protein fraction is adjusted to the isoelectric point of the soluble protein, at which point the soluble protein precipitates from solution. In one embodiment, the pH suitable to precipitate the proteins in the protein fraction is between 4.0 and 6.0, optionally 4.0 and 5.0, suitably 4.0 and 4.5 using an acid such as phosphoric acid, nitric acid, sulfuric acid, hydrochloric acid, optionally phosphoric acid having a concentration of 40% to 60% (w/w), optionally about 50%. In another embodiment, adjusting the pH of the protein fraction using an acid results in undesirable ash becoming soluble in the protein fraction, and therefore, separable from the final protein concentrate.

In another embodiment, separating the precipitated proteins comprises using a centrifuge or a hydrocyclone. In another embodiment, separating the precipitated proteins comprises using a centrifuge, such as decanter centrifuge or disc stack centrifuge. In another embodiment, centrifuging the precipitated proteins comprises a g-force between 2,500 g and 9,500 g. When the centrifuge is operated at such a g-force, the precipitated proteins move along the radial axis to the bottom of the centrifuge tube and are easily separated from the supernatant.

In another embodiment, the process further comprises the step of drying the protein concentrate to a moisture of between 4% and 8% (w/w). In another embodiment, the protein concentrate also comprises peptides and free amino acids.

In another embodiment, the oilseed meal comprises a canola, rapeseed, mustard seed, broccoli seed, flax seed, cotton seed, hemp seed, safflower seed, sesame seed or soybean meal, optionally canola meal.

In another embodiment, any of the above processes is conducted using a counter-current process.

The present disclosure also includes a process for the production of a protein concentrate from an oilseed meal comprising:
  i) mixing the oilseed meal with a first blending solvent to form a mixture;
  ii) optionally treating the mixture with phytase at a temperature and a pH suitable for phytase activity;
  iii) optionally adjusting the pH of the mixture to a pH suitable to solubilize proteins in the mixture;
  iv) subjecting the mixture to a g-force sufficient to separate the mixture to form
    a) a fiber fraction, and
    b) a protein fraction comprising
      (i) an insoluble protein fraction, and
      (ii) a soluble protein fraction;
  v) separating the fiber fraction from the protein fraction and mixing the fiber fraction with a second blending solvent to form a fiber mixture;
  vi) treating the fiber mixture with a protease at a temperature and a pH suitable for protease activity;
  vii) subjecting the fiber mixture to a g-force sufficient to separate the fiber mixture to form:
    a) a second fiber fraction, and
    b) a hydrolyzed protein fraction, comprising
      (i) an insoluble protein fraction, and
      (ii) a soluble hydrolyzed protein fraction;
  ix) mixing the protein fraction with a mixing solvent to precipitate proteins;
  x) separating the precipitated proteins from the protein fraction; and
  xi) optionally combining the precipitated proteins and the hydrolyzed protein fraction to form the protein concentrate.

In one embodiment, the pH of the mixture (oilseed meal and first blending solvent) is optionally adjusted to solubilize proteins (undenatured proteins) into the first blending solvent. In an embodiment, the pH of the mixture is adjusted to a pH between 6 and 8, optionally between 6.5 and 7.5, optionally about 7.0, using a base such as sodium hydroxide, which solubilizes some of the proteins present in the oilseed meal, and upon low g-force separation, increases the amount of protein in the protein fraction. In addition, adjusting the pH to about 7.0 results in the fiber fraction (after low g-force separation of the mixture) having a neutral pH as a by-product.

In another embodiment, the process further comprises mixing the fiber fraction with the first blending solvent and repeating step iv) once, twice or three times and/or mixing the second fiber fraction with the second blending solvent and repeating step vii) once, twice or three times. The repeated washing of the fiber fractions with the blending solvent increases the amount of protein that is recovered for the protein concentrate as the repeated washings separates additional protein that is trapped within the fiber structure.

In another embodiment, the first and second blending solvents comprise water, a saline solution or a polysaccharide solution, optionally water, and wherein the ratio of the oilseed meal to the first blending solvent is 1:3 to 1:30 (w/w) of meal to water, optionally 1:8.

In another embodiment, the temperature suitable for phytase activity is between 20° and 60° C. and the pH suitable for phytase activity is between 2.0 and 7.0 and the temperature suitable for protease activity is between 30° and 70° C. and the pH suitable for protease activity is between 5.0 and 9.0.

In another embodiment, the mixture and/or the fiber mixture is subjected to a g-force of between 100 g and 500 g, optionally between 150 g and 400 g, or between 170 g and 350 g. In an embodiment, separating the mixture and/or the fiber mixture comprises using a centrifuge or a hydrocyclone, optionally a decanter centrifuge.

In another embodiment, the pH of the protein fraction from step iv(b) is adjusted using an acid, such as phosphoric acid, nitric acid, citric acid, sulfuric acid, hydrochloric acid, and the pH is adjusted to between 4.0 and 6.0, optionally 4.0 and 5.0, suitably 4.0 and 4.5. In an embodiment, adjusting the pH of the protein fraction using an acid results in undesirable ash becoming soluble in the protein fraction, and therefore, separable from the final protein concentrate.

In another embodiment of the disclosure, the protein fraction is mixed with a mixing solvent comprising an ethanol:water mixture, wherein the ethanol is present in an amount between 80% and 100%, optionally 90% and 100%, optionally 95% and 100% (v/v). It will be understood that 100% ethanol may contain a small percentage of impurities such as water, etc., which cannot be removed from the ethanol. In an embodiment, mixing solvent is added to the protein fraction at a ratio of between 2:1 and 1:2 (v/v of mixing solvent:protein fraction), optionally 1:1. In an embodiment, when the mixing solvent comprises an alcohol, such as ethanol (80%, 90%, 95% ethanol in water or 100% ethanol), soluble proteins in the protein fraction precipitate from solution, as a result the proteins being less soluble in the mixing solvent (such as ethanol) than in the blending solvent (such as water), and therefore increases the yield of the protein concentrate.

In another embodiment, the mixing solvent comprises an ethanol:water mixture, wherein the ethanol is present in an amount between 80% and 100% (v/v). The addition of the mixing solvent to the protein fraction from step iv(b) causes proteins in the protein fraction to precipitate as a result of the proteins having a lower solubility in such a solvent (such as ethanol/water mixture). Accordingly, the amount of protein recovered is increased upon separation.

In another embodiment, separating the precipitated proteins comprises using a centrifuge or a hydrocyclone. In another embodiment, separating the precipitated proteins comprises using a centrifuge, such as decanter centrifuge or disc stack centrifuge. In another embodiment, centrifuging the precipitated proteins comprises a g-force between 2,500 g and 9,500 g. When the centrifuge is operated at such a g-force, the precipitated proteins move along the radial axis to the bottom of the centrifuge tube and are easily separated from the supernatant.

In another embodiment, the process further comprises the step of drying the protein concentrate to a moisture of between 4% and 8% (w/w). In another embodiment, the protein concentrate also comprises peptides and free amino acids.

In another embodiment, the oilseed meal comprises a canola, rapeseed, mustard seed, broccoli seed, flax seed, cotton seed, hemp seed, safflower seed, sesame seed or soybean meal, optionally canola meal.

In another embodiment, any of the above processes is conducted using a counter-current process.

In another embodiment, the present disclosure also includes a process for the production of a protein isolate from an oilseed meal comprising:

i) mixing the oilseed meal with a first blending solvent to form a mixture;

ii) optionally treating the mixture with phytase at a temperature and a pH suitable for phytase activity;

iii) optionally adjusting the pH of the mixture to a pH suitable to solubilize proteins;

iv) subjecting the mixture to a g-force sufficient to separate the mixture to form
   a) a fiber fraction, and
   b) a protein fraction comprising
      (i) an insoluble protein fraction, and
      (ii) a soluble protein fraction;

vi) separating the insoluble protein fraction from the soluble protein fraction to recover therefrom an insoluble protein concentrate and a soluble protein extract; and vii) subjecting the soluble protein extract to filtration to recover therefrom the protein isolate.

In one embodiment, the pH of the mixture (oilseed meal and first blending solvent) is optionally adjusted to solubilize proteins (undenatured proteins) into the first blending solvent. In an embodiment, the pH of the mixture is adjusted to a pH between 6 and 8, optionally between 6.5 and 7.5, optionally about 7.0, which solubilizes some of the proteins present in the oilseed meal, and upon low g-force separation, increases the amount of protein in the protein fraction. In addition, adjusting the pH to about 7.0 results in the fiber fraction (after low g-force separation of the mixture) having a neutral pH as a by-product.

In another embodiment, the process further comprises mixing the fiber fraction with the first blending solvent and repeating step iv) once, twice or three times. The repeated washing of the fiber fraction with the blending solvent increases the amount of protein that is recovered for the protein concentrate as the repeated washings separates additional protein that is trapped within the fiber structure.

In another embodiment, the first and second blending solvents comprise water, a saline solution or a polysaccharide solution, optionally water, and wherein the ratio of the oilseed meal to the first blending solvent is 1:3 to 1:30 (w/w) of meal to water.

In another embodiment, the temperature suitable for phytase activity is between 20° and 60° C. and the pH suitable for phytase activity is between 2.0 and 7.0 and the temperature suitable for protease activity is between 30° and 70° C. and the pH suitable for protease activity is between 5.0 and 9.0.

In another embodiment, the mixture and/or the fiber mixture is subjected to a g-force of between 100 g and 500 g, optionally between 150 g and 400 g, or between 170 g and 350 g. In an embodiment, separating the mixture and/or the fiber mixture comprises using a centrifuge or a hydrocyclone, optionally in a decanter centrifuge.

In another embodiment, centrifuging to separate the insoluble protein fraction from the soluble protein fraction comprises a g-force between 2,500 g and 9,500 g. In another embodiment, the separation of the insoluble protein fraction from the soluble protein fraction results in a wet protein concentrate that can be subsequently dried. The extract from the separation of the insoluble protein fraction from the soluble protein fraction comprises the soluble protein, which is subsequently filtered through a filtration apparatus, such as ultrafiltration and/or diafiltration, resulting in the protein isolate. As described above, phytates and/or phytic acid can complex and bind to the proteins, and consequently block the filtration apparatus. The removal of the phytates and/or phytic acid from the oilseed meal mixture (oilseed meal and blending solvent) using phytase as described above, such that the filtration apparatus is not blocked with such complexes, resulting the filtration apparatus performing efficiently to produce the protein isolate.

In another embodiment, the process further comprises the step of drying the protein concentrate to a moisture of between 4% and 8% (w/w). In another embodiment, the protein concentrate also comprises peptides and free amino acids.

In another embodiment, the oilseed meal comprises a canola, rapeseed, mustard seed, broccoli seed, flax seed, cotton seed, hemp seed, safflower seed, sesame seed or soybean meal, optionally canola meal.

In another embodiment, any of the above processes is conducted using a counter-current process.

In another embodiment, there is also included a process for treating an oilseed meal comprising a fiber fraction and a protein fraction, wherein the protein fraction comprises (i) an insoluble protein fraction and (ii) a soluble protein fraction, to separate the fiber fraction from the protein fraction comprising:

i) mixing the oilseed meal with a first blending solvent to form a mixture;

ii) optionally adjusting the pH of the mixture to a pH suitable to solubilize proteins in the mixture;

iv) subjecting the mixture to a g-force sufficient to separate the mixture to form
 a) a fiber fraction, and
 b) a protein fraction comprising
  (i) an insoluble protein fraction, and
  (ii) a soluble protein fraction; and v) separating the fiber fraction from the protein fraction.

In one embodiment, the separation at a g-force of between 150 to 300 g, optionally 150 to 200 g, optionally 175 to 180 g, comprises using any means to achieve such g-forces, such as a centrifuge, such as a decanter centrifuge, or a hydrocylcone.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The following non-limiting examples are illustrative of embodiments of the present disclosure:

EXAMPLES

Reagents and Materials

Canola seeds (*Brassica juncea* and *Brassica napus*) were obtained from Viterra, North Battleford, Saskatchewan, Canada. Commercial methyl pentane was purchased from Univar Canada Ltd., Saskatoon, Saskatchewan, Canada. Enzyme samples of Cellulase (Celluclast® 1.5L), Cellulase Complex, Alcalase® 2.4L FG, and Flavourzyme® were obtained from Novozymes North America, Inc., Franklinton, N.C. USA. Pea protein isolate was obtained from Roquette America, Inc., Keokuk, Iowa, USA. Soy protein isolate was obtained from Protient, ABF Ingredients Company, St. Paul, Minn., USA Analysis Mixing of the materials was performed using a Ribbon Blender (Torco Model R-12, Toronto Coppersmithing International Ltd., Scarborough, Ontario, Canada). Heat treatments of seed samples were conducted using an Infra Red Cereal Processing System (Micronizing Company Limited, Framlingham, Sulfolk, England) or a two-tray Simon-Rosedown cooker (Laboratory cooker-press, Simon-Rosedowns Limited, Hull, England). Pressing of the oil seeds is performed using a Gusta Laboratory Screw Press. Ultrafiltration was carried out using a Millipore® Ultrafiltration Unit (Model A60, Millipore® Corporation, Bedford, Mass., USA). Protein content of the samples was determined by the Leco® Protein Analyzer (Model FP-428, Leco® Corporation, ST. Joseph, Mich. U.S.A.) based on AOCS Official Method Ba 4e-93. Moisture content of the samples was determined by drying samples in a 105±2° C. convection oven for 16 hours or to a constant weight based on AOCS Official Method Ba 2a-38. Oil content of the samples was determined based on AOCS Official Method Ba 3-38 with the following changes: (a) 2 g of sample was used instead of 5 g in the analysis; (b) extraction continued for 4 hours, and (c) extraction flask was heated to remove residual petroleum ethers. Ash content of the samples was determined based on AOCS Official Method Ba 5a-49 with the following changes: (a) samples were pre-ashed on a hot plate prior to being placed into the muffle furnace; (b) samples were incinerated for 18 hours in muffle furnace; and (c) nitric acid was added if sample remained black. Crude fiber content of the samples was determined based on AOCS Official Method Ba 6-84 with the following changes: (a) samples with oil contents below 3% were not defatted and (b) digest was dried for 2 hours at 130° C. Protein dispersibility index (PDI) of the samples was determined based on A.O.C.S. Official Method Ba 10-65. Free fatty acid (FFA) of the oil samples was determined based on AOCS Official Method Ca 5a-40. Phosphorus and sulphur of the samples were determined based on the modified methods of AOCS Ca20-99 and AOCS Ca 17-01 (modified), respectively. Crude fiber content of the samples was determined based on AOCS Official Method Ba 6-84 with the following changes: (a) samples with oil contents below 3% were not defatted and (b) digest was dried for 2 hours at 130° C. Protein dispersibility index (PDI) of the samples was determined based on A.O.C.S. Official Method Ba 10-65. Glucosinolate content of the samples was determined based on the Method of the Canadian Grain Commission, Grain Research Laboratory (Daun, J. K. and McGregor, D. I., Glucosinolate Analysis of Rapeseed (Canola), Dec. 15, 1981). Solvent residues were determined using GC/MS techniques based on a modified method of A.O.C.S. Official Method, Ba 13-87.

Example 1(a)

Effect of Heat Treatment on Canola Seed (*Brassica juncea*) at Temperatures Between 75° C.-95° C.

Seven samples containing about 4 kg of canola seed (28 kg in total) were adjusted from an original moisture content of about 6.25% to about 11% by adding water to the canola seed in a plastic pail with manual agitation for a few minutes. The canola seed in the pails was then covered and tempered overnight in the laboratory.

After the canola seed had been tempered overnight, six samples containing about 4 kg of the tempered seed (about 24 kg in total) were subjected to individual heat treatments with a combination of high temperatures and short residence times using a lab scale as listed in Table 1. For control, a control sample (about 4 kg) of canola seed was heated in a microwave oven for 2 minutes (heat to 85-95° C.). The canola seed was then covered with an aluminum foil and heated at 95° C. in a forced air oven for 30 minutes (Table 1).

After heat treatment, seven samples (about 4 kg each) of the heat treated canola seeds were flaked using a lab flaking mill and then pressed, resulting in pressed oils and pressed protein cakes. The pressed oils were analyzed for sulfur and free fatty acid (FFA) contents. The pressed cakes were stored in a freezer.

Seven samples (about 1 kg each) of the pressed cakes from the six heat treatment trials and one control were extracted using a solvent mixture of butane and R-134a (1,1,1,2-tetrafluoroethane) to produce extracted oils and defatted canola meals. The press cake was loaded in a column and the solvent mixture under 300 PSI pressure was flowed through the press cake to fluidize the press cake particles. The oil was extracted from the cake at 50° C. The solvent mixture with oil in a liquid form was pumped to a low pressure zone and the pressure was released. The solvent mixture turns into gas while the oil remains in a liquid state for the separation of oil from the solvent mixture. The defatted canola meals were analyzed for protein dispersibility index (PDI), the results of which are shown in Table 3. The extracted oil samples were analyzed for sulfur, phosphorus and FFA contents, the results of which are shown in Tables 4-6.

The remaining pressed cakes were extracted with methyl pentane for five hours using a lab Soxhlet system. Approximately 6-8 L of fresh methyl pentane were required for each extraction lot. The extracted oil was recovered by evaporation and desolventization to remove the solvent from the miscella under vacuum at 60° C. The extracted oil was analyzed for sulfur, phosphorus and FFA contents. The methyl pentane extracted meals were desolventized in a laboratory fume hood for three days at room temperature. The moisture and oil contents of the pressed cake are shown in Table 7.

Example 1(b)

Effect of Heat Treatment on Canola Seed (*Brassica juncea*) at Temperatures Between 100° C.-130° C.

Five samples containing about 4 kg (about 20 kg in total) of canola seed were adjusted from an original moisture content of about 6.25% to about 11% by adding water to the canola seed in a plastic pail with manual agitation for a few minutes. The canola seed in the pails was then covered and tempered overnight in the laboratory.

After the canola seed had been tempered overnight, five samples containing about 4 kg of the tempered seed (about 20 kg in total) were subjected to individual heat treatments with a combination of high temperatures and short residence times using a lab scale as listed in Table 2. After heat treatment, the five samples (about 4 kg each) of the heat treated canola seeds were flaked using a lab flaking mill, and then pressed. The pressed oils were analyzed for sulfur, phosphorus and FFA contents. The pressed cakes were stored in a freezer.

Five samples (about 1.5 kg each) of the pressed cakes from the five heat treatment trials were extracted using a solvent mixture of butane and R-134a (1,1,1,2-tetrafluoroethane) to produce extracted oils and defatted canola meals. The extracted oils were analyzed for sulfur and FFA contents. The defatted canola meals were analyzed for protein dispersibility index (PDI).

Discussion

In the heat treatment process, rapid heating makes it possible to expose the canola seed to an increased temperature very quickly and thus to inactivate the enzymes (e.g. myosinase, lipase, phospholipase, etc.) This is a more economical way for consistent inactivation of enzymes without loss of lysine or other heat sensitive amino acids.

As shown in Table 3, the increase in the heat treatment temperature from 75° C. to 100° C. resulted in the gradual decrease in the PDI of the defatted meal. The decrease in PDI of the defatted meal accelerated when the temperature was increased from 105° C. to 130° C. The sharp drop in PDI occurred when the temperature was above 110° C. Typically, the higher the heat treatment temperature, the higher the percentage of protein molecules being denatured and thus the lower the PDI of the defatted meal.

The sulphur content in the pressed oil from canola seed without heat treatment was 46.9 ppm, which decreased sharply to 21.5 ppm and 9.77 ppm with heat treatment at 75° C. and 80° C. for 15 seconds, respectively. Heat treatment at higher temperatures from 80° C. to 130° C. did not have any major effect on the sulphur content in the pressed oil (as shown in Table 4).

The sulphur in the butane/R134a extracted oil decreased from the level of 303 ppm without heat treatment to 99.3 ppm at 75° C. and 101 ppm at 80° C. The sulphur level showed continuous reduction with increase in the temperature of heat treatment except at 85° C.

The sulphur content in the methyl pentane extracted crude oil decreased continuously in relation to the increase in temperature from 222 ppm at 75° C. to 34.5 ppm at 95° C. Methyl pentane extracted oil had higher sulphur levels at 75° C. and 80° C., but lower at 85-95° C. as compared with butane/R134a extracted oils.

The sulphur content in the pressed oil, the butane/R134a and methyl pentane extracted oils of the control samples were high. In the heat treatment of the control samples, the canola seed was covered using an aluminum foil and heated at 95° C. in a forced air oven for 0.5 hour. Because the heat transfer efficiency is low, the temperature of the seed in the oven might have been lower than 95° C. even though the oven temperature was set at that temperature. Therefore, myrosinase was still mostly active, causing the breakdown of glucosinolates and release of the sulphur into the pressed and extracted oils.

The free fatty acid in the pressed oil decreased slightly with the increase in the heat treatment temperature from 75° C. to 95° C. (as shown in Table 5). A sharp drop in FFA occurred at 100° C. and FFA showed little change from 100-130° C. The FFA in the butane/R134a extracted oil showed significant decrease with the increase in temperature from 75-100° C., however a further increase in temperature gained little benefit for the reduction in FFA (Table 5). The FFA in methyl pentane extracted oil also decreased with the increase in temperature from 75 to 95° C. The increase in heat treatment temperature enhanced the degree of inactivation of lipase, which in return reduced the hydrolysis of oil by lipase and thus reduced the FFA content.

The FFA content in the oil is mainly dependent on the quality of seed. Improper handling or storage can cause elevated levels of FFA.

The phosphorus content of butane/R134a extracted oil was very low ranging from 2.93 ppm at 75° C. to 22.8 ppm at 95° C. as listed in seen in Table 6. The phosphorus content of the pressed oil was also low at heat treatment temperatures of 100, 105, 110, and 130° C. The phosphorus content of pressed oil from the heat treatment of 120° C. was 117 ppm.

The selection of a heat treatment temperature is a compromise between the opposing effects on oil quality, meal quality and economics. Accordingly, in an embodiment, a heat treatment temperature of 100° C. results in a reasonably high PDI, lower sulphur, FFA and phosphorus in pressed and butane/R134a extracted oils.

Heat treatment of canola seed above 80° C. reduced the sulphur content in pressed oil to levels below 10 ppm. The pressed oil accounted for about 50-60% of total crude oil from the crushing operation. The heat treatment of canola seed reduced the sulphur content of butane/R134a and methyl pentane extracted oils substantially with an increase in temperature. The high sulphur in the extracted oil is related to high glucosinolates content in the canola seed. The canola seed (*B. juncea*) contained about 22.95 μmoles/g of glucosinolates on a dry weight basis. If canola seed with a glucosinolate content of 12 μmoles/g or lower is used, the sulphur content in the extracted oil can be reduced further using the same heat treatment condition.

For a heat treatment of 100° C. for 15 seconds, the phorphorus content in the pressed and butane/R134a extracted oils was below 50 ppm.

Example 2

Protein Concentrate of about 65% Protein (a) Defatted Meal

Approximately 4 kg of canola seed (*B. juncea*) was adjusted from the original 6.25% moisture to 11% moisture by adding water to canola seed in a plastic pail with manual agitation for a few minutes. The canola seed in the pail was then covered and tempered overnight in the laboratory. The tempered canola seed was then heat treated at 100° C. for 15 seconds.

After heat treatment, the canola seed was flaked using a lab flaking mill and then pressed. The pressed cake was stored in a freezer before solvent extraction. The pressed oil was recovered and stored in a freezer. The pressed cake was extracted with 6-8 liters of methyl pentane at about 58-67° C. for 5 hours using a lab scale Soxhlet system. The extracted oil was recovered by evaporation and desolventization to remove the solvent from the miscella under vacuum at 60° C. The extracted oil was stored in a freezer. The methyl pentane extracted meal or defatted meal was desolventized in a laboratory fume hood for three days at ambient temperature. Approximately 2 kg of defatted meal was produced and stored at ambient temperature before further evaluation.

(b) Protein Enriched Meal

Approximately 2 kg of defatted meal was ground using a coffee grinder for 15-20 seconds. The ground meal was screened through a 60 US mesh screen. Approximately 0.94 kg of fine meal (protein-enriched meal) and 1.06 kg of coarse meal (fiber enriched meal) were obtained.

(c) 65% Protein Concentrate

Approximately 0.94 kg of protein-enriched meal was extracted by mixing with 5.64 kg of 65% (v/v) ethanol at ambient temperature for 1 hour. The mixture was centrifuged at 4,000 g force for 15 minutes to separate the liquid sugar extract from the protein solids using a lab centrifuge. The sugar extracts were combined together and concentrated using a lab Buchi Rotavapor at 80° C., which was followed by freeze drying of the concentrated sugar extract using a lab freeze dryer. The washed protein-enriched meal was desolventized in a lab fume hood, which was followed by drying in a lab forced air oven. Approximately 0.67 kg of protein concentrate containing 65% protein on a dry weight basis and 0.21 kg of dried sugar fraction were produced, respectively. The analysis of the defatted meal, protein-enriched meal and 65% protein concentrate are shown in Table 8.

Example 3

Protein Concentrate of about 70% Protein (a) Ethanol Washing and Screening

The process for preparation of the protein-enriched meal was the same as in Example 2 except for (1) canola seed was cooked at 80° C. for 25 minutes before pressing, and (2) the defatted meal was milled using a disc mill before screening through a 60 US mesh screen as described below.

Approximately 1 kg of protein-enriched meal was mixed under homogeneous agitation with 6 kg of 80% (v/v) ethanol at 50° C.±5° C. for 1 hour, which was followed by screening the mixture through a 40 mesh US screen to remove fiber. The screened mixture was centrifuged at 4,000 g force using a lab centrifuge for 15 minutes to separate the sugar extract from the protein solids. The protein-solids were mixed under homogeneous agitation with 6 kg of 80% (v/v) ethanol at 50° C.±5° C. for 0.5 hour. The washed protein solids was separated from the sugar extract by centrifugation at 4,000 g force for 0.5 hour. The protein solids were again washed 6 kg of 80% (v/v) ethanol for at 50° C.±5° C. 0.5 hour, which was followed by centrifugation at 4,000 g force for 15 minutes. Finally the washed protein solids were dried to give a protein concentrate containing 70% protein on a dry weight basis. The ethanol was recovered from the combined sugar extract through evaporation under vacuum at 80° C. using a lab Buchi Rotavapor. The concentrated sugar extract was spray dried into a dried sugar sample.

Example 4

Canola Protein Concentrate Having about 65-70% Protein Content

Three samples of a protein concentrate from *Brassica juncea* were prepared in the following manners (the processing conditions for Samples 1-3 are compared in Table 13):

(1) Sample 1—Moisture Adjustment

Approximately 2,919 kg of canola seed was adjusted from the original about 6.25% moisture content to about 11% moisture by adding 54 kg of water to the canola seed under mixing. The moisture adjustment and mixing were executed as 14 batches due to the capacity constraint of the Ribbon Blender (Table 9). After the moisture adjustment, the canola seed was stored in bins, covered and tempered overnight before pressing.

Pressing

The tempered canola seed was divided into two portions,
(i) 300.5 kg of seed for pressing trial without flaking and
(ii) the remainder of the tempered seed (2,676 kg) for flaking and pressing.

Approximately 300.5 kg of tempered seed was heat treated using a two-tray cooker. The temperature of the top tray was 50-72° C., while the temperature for the bottom tray was 75-96° C. The resident time for top and bottom trays was 20 minutes, respectively. After heat treatment, the seed was fed into the press and was pressed to produce 181.6 kg of press cake (Sample 1a). Press cake is a term that is synonymous with seed cake.

Approximately 2,676 kg of tempered seed was flaked to produce flaked canola seed with an average thickness of 0.3±0.1 mm using a flaking mill. The flaked canola seed was heat treated using a two-tray cooker. The temperature for the top tray was 50-72° C., while the temperature for the bottom tray was 75-96° C. The resident time for the top and bottom trays was 20 minutes, respectively. After heat treatment, the flaked seed was fed into the press and was pressed to produce 1,566 kg of press cake (Sample 1b). Approximately 945 kg of press oil was produced from the pressing trials of non-flaked and flaked seeds. Approximately 42.9 kg of fine particles (foots) was produced in the pressing trials. Approximately 85.3 kg of canola seed was lost as floor sweeps, which are waste materials that drop on the floor.

Solvent Extraction

Approximately (i) 181.6 kg and (ii) 1,566 kg of press cakes from non-flaked and flaked canola seeds were extracted using a solvent mixture of butane/R124a to produce extracted (defatted) canola meals from the non-flaked press cake (Sample 1c) and the flaked press cake (Sample 1d), in addition to extracted oils. The solvent extraction of the press cakes was conducted at 50° C. for 1.5 hours.

As shown in Tables 10, 11 and 14, the press cake (Sample 1a) from the non-flaking trial contained a high crude oil content of 26.81-32.37% on a dry weight basis.

Milling and Screening

Approximately 1,231 kg of extracted (defatted) meal (Sample 1d) was produced from 1,566 kg of flaked press cake through solvent extraction at 50° C. for 1.5 hours using a solvent mixture of butane and R134a. The extracted meal was milled using a disc mill equipped with #8114 stationary and rotating plates (The Bauer Bros. Co., Springfield, Ohio, U.S.A.) at 0.02" gap, 2340 rpm rotational speed and 200 kg/hr throughput. Only one pass through the disc mill was conducted. Approximately 1,142 kg of milled canola meal was produced. Approximately 88.9 kg of material was lost in the milling operation with a recovery yield of 92.78%.

The milled canola meal was screened through a 43-45 US mesh screen using the Rotex® Vibratory Screen (from Rotex®, Ohio, USA) at a feed rate of 200 kg/hr. Only one pass through the screen was conducted. Approximately 423.66 kg of protein enriched meal (fine fraction) and 717.00 kg of fiber enriched meal (coarse fraction) were produced, respectively. Approximately 1.64 kg of material was lost in the screening operation with a recovery yield of 99.86%. After screening, 37.14% of the total material was protein enriched meal (Sample 1e) and 62.86% was fiber enriched meal (Sample 1f), respectively, as seen in Table 12.

Preparation of Protein Concentrate from Protein Enriched Meal

Approximately 412 kg of protein enriched meal containing 6.90% moisture and 53.92% protein (dwb) was mixed with about 2,400 kg of 80% ethanol (v/v) in two 2600 L stainless steel tanks under homogeneous agitation at room temperature for 1 hour. After extraction, the protein slurry was centrifuged continuously using a decanter centrifuge (Model CA220-21-33, Westfalia® Separator, GEA Westfalia Separator® Inc., Northvale, N.J., USA) to separate insoluble protein solids from the sugar extract. The protein solids were mixed with 2,400 kg of 80% ethanol (v/v) under homogeneous agitation at room temperature for 1 hour, which was followed by centrifugation of the protein slurry using the decanter to separate the washed protein solids from the washing sugar extract. Finally, the washed protein solids were mixed with 2,400 kg of 80% ethanol (v/v) under homogeneous agitation at room temperature for 1 hour. The protein slurry was centrifuged using the decanter to separate the final washed protein solids from the washing sugar extract. The final washed protein solids were desolventized and dried at 54±3° C. for 18 hours in a Littleford® vacuum dryer (Littleford Day®, Inc., Florence, Ky., USA) until the moisture content of the dried solids reached 5±1%. The desolventized and dried protein solids were milled using a Fitz mill fitted with a 0.033" screen (The Fitzpatrick Co., Elmhurst, Ill., U.S.A.). The milled protein solids were screened using a Rotex Vibratory Screen (Model 111 A-MS/MS, Rotex Inc., Cincinnati, Ohio, U.S.A.) fitted with a 43-45 US mesh screen (POS #54 screen). Approximately 248.3 kg of protein concentrate containing (Sample 1g) 65.80% protein (dwb) and 5.51% moisture was produced.

(2) Sample 2—Preparation of Defatted Meal

Approximately 4.5 kg of extracted (defatted) canola meal (Sample 2a) was produced from non-flaked press cake through extraction using a solvent mixture of butane and R134a at 50° C. for 2 hours. The non-flaked press cake was produced from canola seed (*B. juncea*) by heat treatment of canola seed at 80° C. for 0.5 hour before pressing in a French Oil Machinery press.

Milling and Screening

Approximately 3.5 kg the defatted meal (Sample 2a) was milled for 1 minute using a lab Waring® Blender, which was followed by manual screening using a 45 US mesh Rotex screen to generate a protein fraction (fine fraction) and a coarse fraction. The coarse fraction was re-milled in the lab Warring Blender for 1 minute. This was followed by manual screening using the 45 US mesh Rotex screen to generate the $2^{nd}$ protein fraction and a coarse fraction. Finally, the coarse fraction was milled in the Warring Blender for 1 minute and the milled material was manually screened using the 45 US mesh Rotex screen to generate the $3^{rd}$ protein fraction and the fiber enriched meal. Approximately, 1.5 kg of combined $1^{st}$, $2^{nd}$ and $3^{rd}$ protein fractions and 2 kg of fiber enriched meal were produced, respectively. Therefore, 42.85% of the total material was the protein enriched meal (Sample 2b) and 57.15% was the fiber enriched meal (Sample 2c), as seen in Table 12.

Preparation of Protein Concentrate from Protein Enriched Meal

Approximately 1.5 kg of protein enriched meal containing 6.16% moisture and 54.77% protein (dwb) was mixed with 9 kg of 80% ethanol (v/v) in a stainless steel pot under homogeneous agitation using an over head stirrer at room temperature for 1 hour. After extraction the slurry was centrifuged batch wise at 4,414 g (4,000 rpm) for 10 minutes to separate insoluble protein solids from the sugar extract. For a second extraction, the protein solids were mixed with 9 kg of 80% ethanol (v/v) under homogeneous agitation at room temperature for 1 hour, which was followed by centrifugation of the protein slurry at 4,414 g (4,000 rpm) for 10 minutes to separate the washed protein solids from the washing sugar extract. Finally, the washed protein solids were extracted for a $3^{rd}$ time with 9 kg of 80% ethanol (v/v) under homogeneous agitation at room temperature for 1 hour. The protein slurry was centrifuged at 4,414 g (4,000 rpm) for 10 minutes to separate the final washed protein solids from the washing sugar extract. The final washed protein solids were desolventized and dried in a lab fume hood for over 3 days, which was followed by drying in a forced air oven at 50° C. for 15 hours to reduce the ethanol residue. The desolventized and dried protein solids were milled twice using a lab pin mill. Approximately 1.1 kg of protein concentrate (Sample 2d) containing 68.69% protein (dwb) and 5.52% moisture was produced.

(3) Sample 3—Preparation of Defatted Meal

Approximately 13.1 kg of defatted canola meal (Sample 3a) was produced from non-flaked press cake through extraction using a solvent mixture of butane and R134a at 50° C. for 1.5 hours. The non-flaked press cake was produced from canola seed (*B. juncea*) by heat treatment of canola seed at 80° C. for 0.5 hour before pressing in a French Oil Machinery press.

Milling and Screening

Approximately 13.1 kg of the defatted meal (Sample 3a) was milled using a disc mill equipped with #8114 stationary and rotating plates (The Bauer Bros. Co., Springfield, Ohio, U.S.A.) at 0.02" gap and a speed of 1150 rpm for the rotating plate. The milled meal was screened using a Rotex Vibratory Screen (Model 111 A-MS/MS, Rotex Inc., Cincinnati, Ohio, U.S.A.) fitted with a 43-45 US mesh screen (POS #54 screen) to generate 4.1 kg of protein enriched meal (fine fraction) and 8.8 kg of coarse fraction. The coarse fraction was fed to the disc mill at 0.015" gap stationary and rotating plates of #8114 and a speed of 1150 rpm for the rotating plate. The milled coarse fraction was screened using a Rotex Vibratory Screen fitted with a 43-45 US mesh screen (POS #54 screen) to generate 1.1 kg of protein enriched meal (fine fraction) and 7.7 kg of fiber enriched meal. After screening, 40.31% of the total material was protein enriched meal (Sample 3b) while 59.69% was fiber enriched meal (Sample 3c) (see. Table 12).

Preparation of Protein Concentrate from Protein Enriched Meal

Approximately 3.9 kg of protein enriched meal containing 6.5% moisture and 52.62% protein (dwb) was mixed with 23.4 kg of 80% ethanol (v/v) in a stainless steel pot under homogeneous agitation using an over head stirrer at room temperature for 1 hour. After extraction the slurry was centrifuged batch wise at 4,414 g (4,000 rpm) for 10 minutes to separate the insoluble protein solids from the sugar extract. The protein solids were mixed with 23.4 kg of 80% ethanol (v/v) under homogeneous agitation at room temperature for 1 hour, which was followed by centrifugation of the protein slurry at 4,414 g (4,000 rpm) for 10 minutes to separate washed protein solids from the washing sugar extract. Finally, the washed protein solids were extracted for a $3^{rd}$ time with 23.4 kg of 80% ethanol (v/v) under homogeneous agitation at room temperature for 1 hour. The protein slurry was centrifuged at 4,414 g (4,000 rpm) for 10 minutes to separate the final washed protein solids from the washing sugar extract. The final washed protein solids were desolventized and dried in a lab fume hood for over 3 days. The desolventized and dried protein solids were milled using a lab hammer milled fitted with a 14 US mesh screen, which was followed by further milling through a lab pin mill twice. The milled protein solids were manually screened using a lab Rotex screen fitted with a 60 US mesh screen to obtain 2.38 kg of protein concentrate (Sample 3d) containing 69.6% protein (dwb) and 0.25 kg of coarse fraction containing 59.1% protein (dwb). The protein concentrate was dried in a forced air oven at 50° C. for 15 hours to reduce the ethanol residue.

Vacuum Drying of Samples 1-3

One kilogram samples of Samples 1c, 1d, 2a, 2d, 3a and 3d were loaded into 6 metal trays, which were placed in a freeze dryer (Model 50 SRC-6 Subliminator, Virtis Company, Gardiner, N.Y.). Drying was started at 50° C. and a maximum vacuum attainable (absolute pressure of 150-500 µHg) by the dryer. Drying was continued at 50° C. for 15 hours. After drying, nitrogen was injected into the dryer while vacuum was released slowly. The samples were tested for solvent residues.

Discussion

Figure 12:
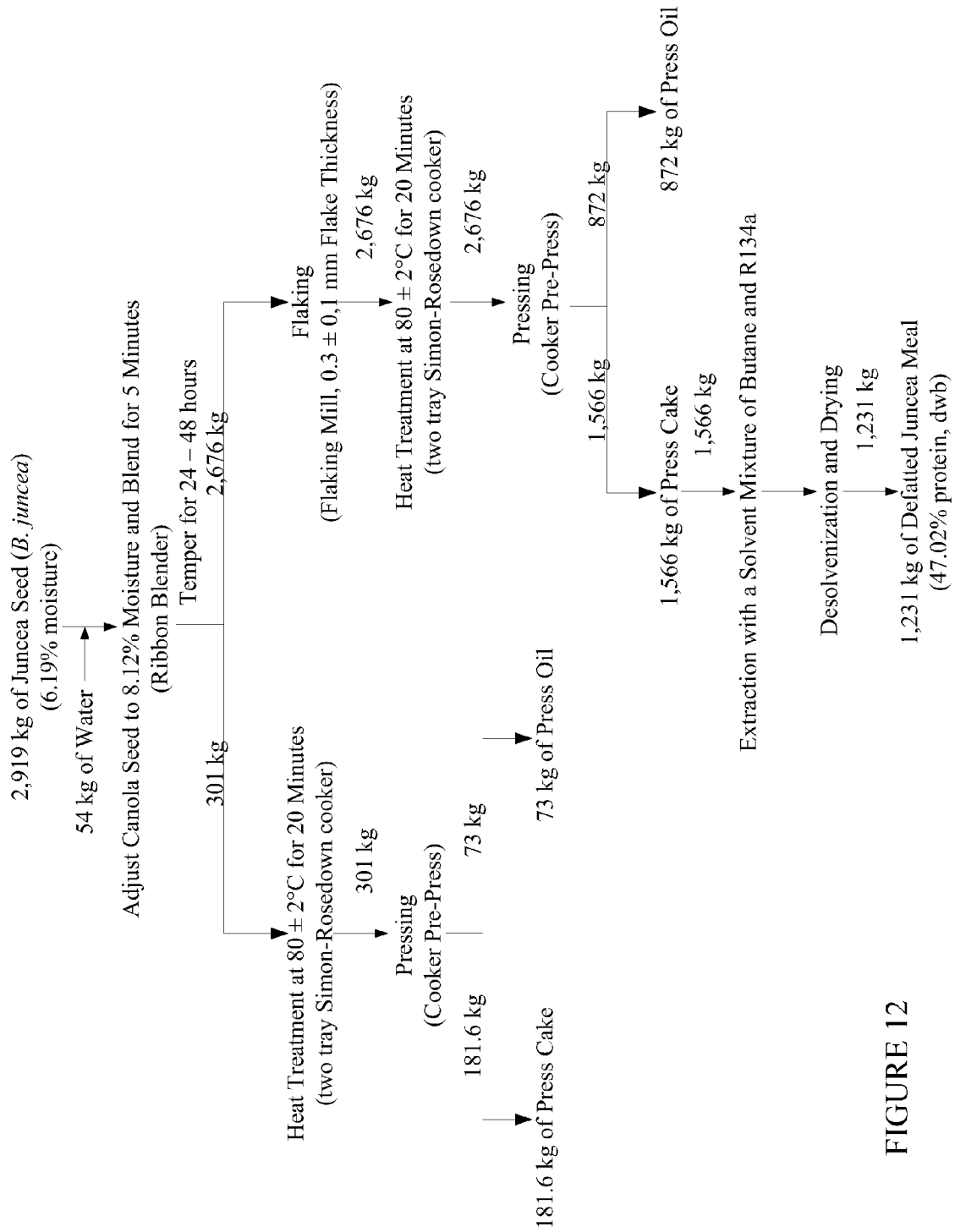
FIG. 12 is a schematic representation of a first embodiment for crushing of *Juncea* Seed and preparation of defatted *Juncea* meal.

The mass balance data for flaking and pressing trials for Samples 1a and 1b are shown in Table 10 and FIG. 12, while the proximate analysis results for the Samples are listed in Table 11. Further, the moisture and oil contents of the press cakes of Sample 1 are given in Tables 14 and 15.

The average oil content in the flaked press cake (Sample 1b) as calculated from the results in Table 15 is 15.18% (dwb). The average moisture content in the flaked press cake (Sample 1b) is 7.87%. The oil content in the starting canola seed is 44.39% (dwb) (Table 11). Moreover, 1,566 kg of flaked press cake (Sample 1b) contained 219 kg of crude oil, while the starting 2,676 kg of canola seed after the moisture adjustment contained 1,091 kg of crude oil (see FIG. 12). Approximately 872 kg of crude oil or 79.93% of the total crude oil was pressed out of the flaked seed during the pressing operations.

The average oil content in the non-flaked press cake (Sample 1a) as calculated from the results in Tables 10 and 11 was 29.83% (dwb). The average moisture content in the non-flaked press cake (Sample 1a) was 8.31% (Tables 11 & 14). Moreover, 181.6 kg of non-flaked press cake Sample 1a) contained 49.7 kg of crude oil, while the 301 kg of starting canola seed after the moisture adjustment contained 122.8 kg of crude oil. Approximately 73.1 kg of crude oil or 59.52% of the total crude oil was pressed out of the non-flaked seed during the pressing operation.

Non-flaked press cake (Sample 1a) contained much higher crude oil content than that of flaked press cake (Sample 1b). Higher ratio of press oil was obtained from the flaked seed than from the non-flaked seed in the pressing operation. After solvent extraction, defatted canola meal (Sample 1c) from non-flaked press cake still contained a high oil content of 8.75%-12.73% (dwb) while defatted meal (Sample 1d) from flaked press cake contained less than 3.13% of crude oil (Tables 14 & 16). Visual inspection of the non-flaked press cake showed that it contained many intact seeds, making it difficult for oil extraction by the solvent mixture of butane and R134a. Flaking would be required to rupture the oil cells before pressing to obtain high ratio of press oil in the pressing operation and lower oil content in the solvent extracted meal. Defatted meal (Sample 1d) from flaked press cake was used as the starting material for the preparation of a protein concentrate. Defatted meal from non-flaked press cake was not used for the preparation of protein concentrate due to its high oil content.

The fractions of protein enriched and fiber enriched meals (Samples 1e and 1f) from milling and screening trials are shown in Table 12, while the results of the proximate analysis are given in Table 17. As seen in Table 12 for Sample 1e, approximately 42.33% to 57.23% of the total material was generated as protein enriched fraction and 42.76% to 57.66% as fiber enriched fraction (Sample 1f). From the screening trial of this milled *juncea* meal, approximately 37.14% was protein enriched meal while 62.86% was fiber enriched meal.

As shown in Table 17, the protein content was increased from 47.02-49.98% (dwb) in the extracted or defatted meals to 52.62-54.77% (dwb) in the protein enriched meals by the milling and screening operation (Samples 1d, 2a and 3a compared to Samples 1e, 2b and 3b). The crude fiber content was reduced from 8.28-9.79% (dwb) in the extracted meals to 4.82-5.49% (dwb) in the protein enriched meals (Samples 1f, 2c and 3c compared to Samples 1e, 2b and 3b). A simple step of dry milling and screening generated a starting material with higher protein and lower fiber contents for protein concentrate preparation.

Figure 13:
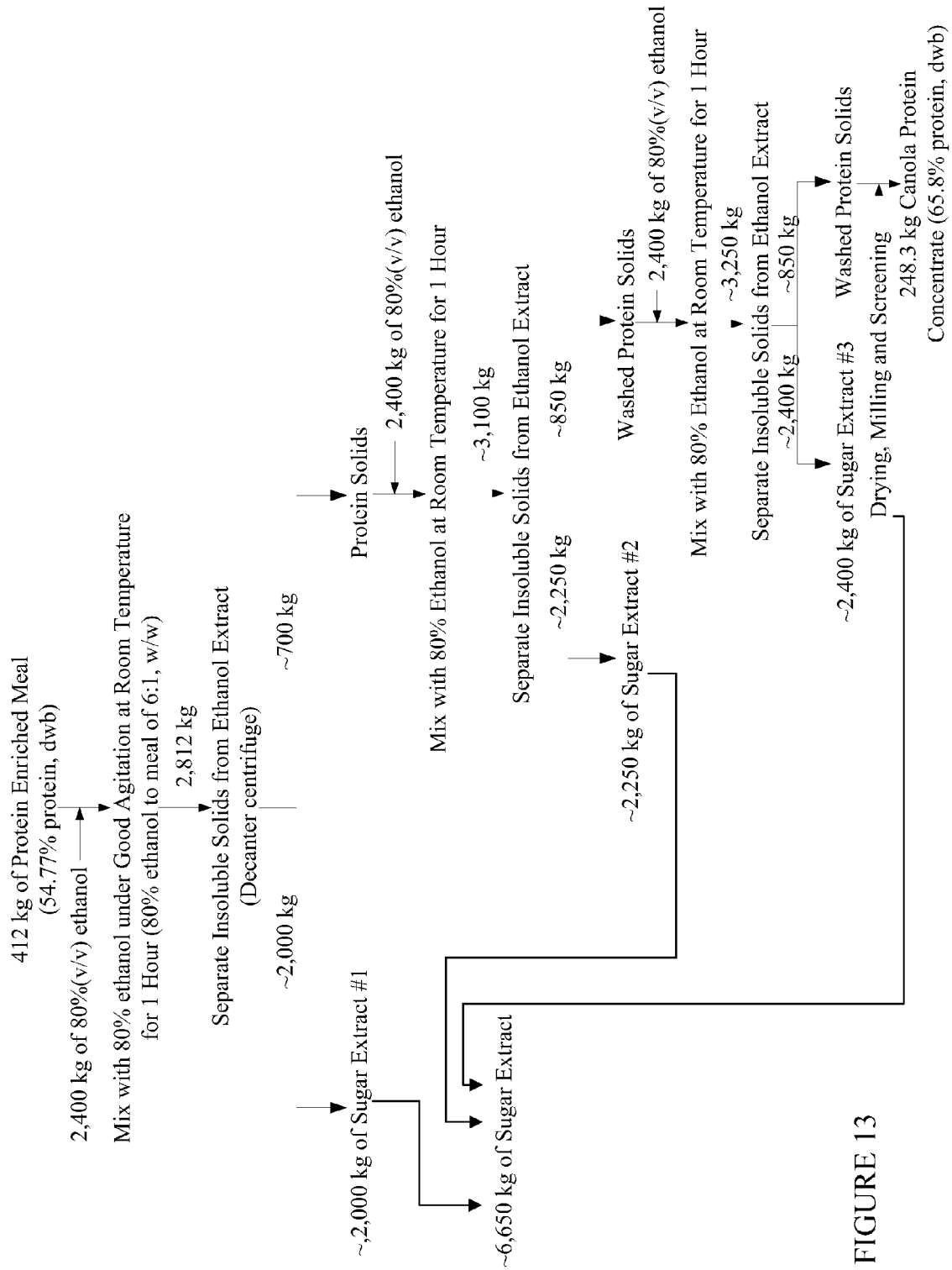
FIG. 13 is a schematic representation of a first embodiment showing a preparation of a protein concentrate from a protein enriched meal.
Figure 14:
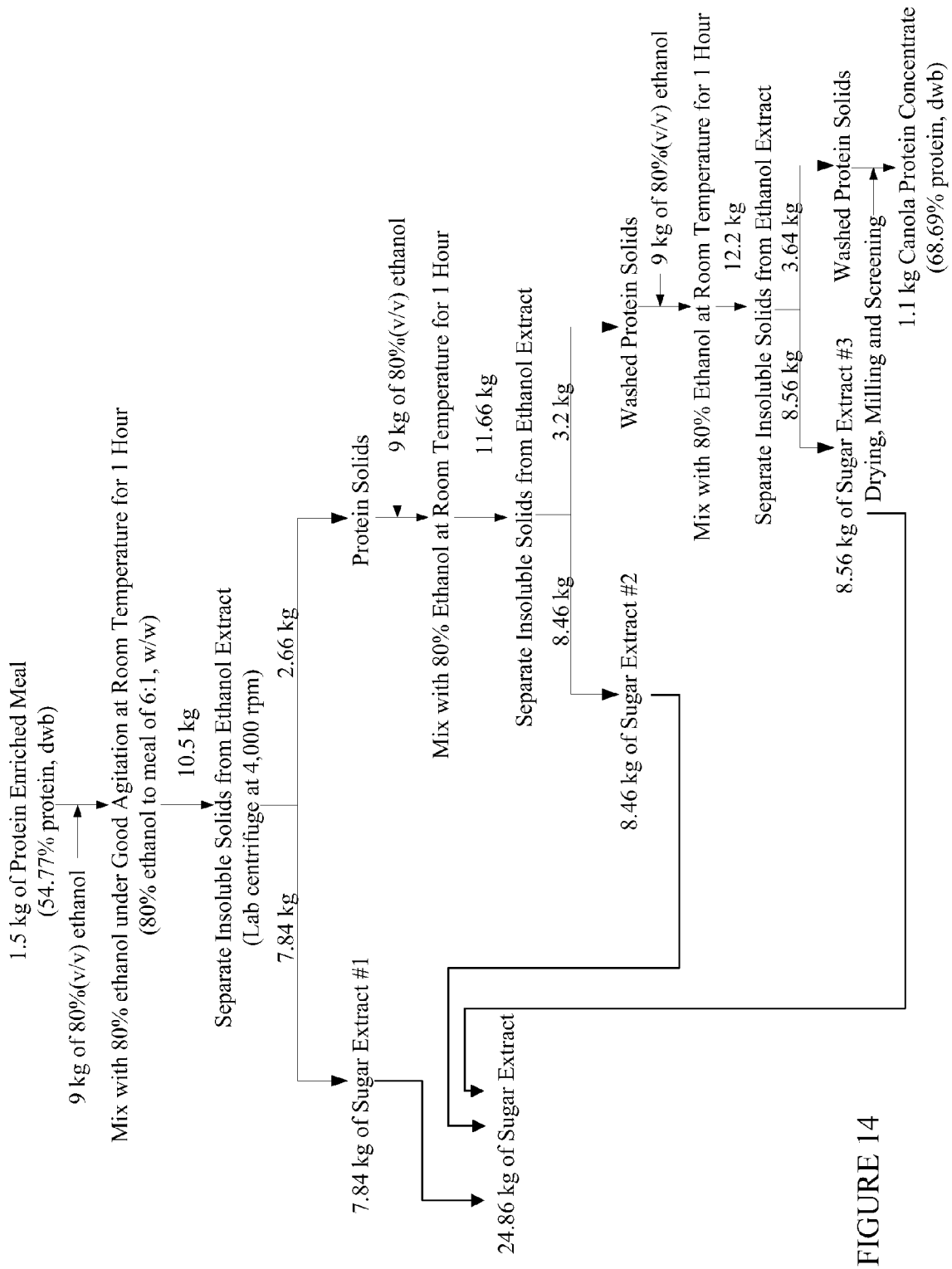
FIG. 14 is a schematic representation of a second embodiment showing a preparation of a protein concentrate from a protein enriched meal.
Figure 15:
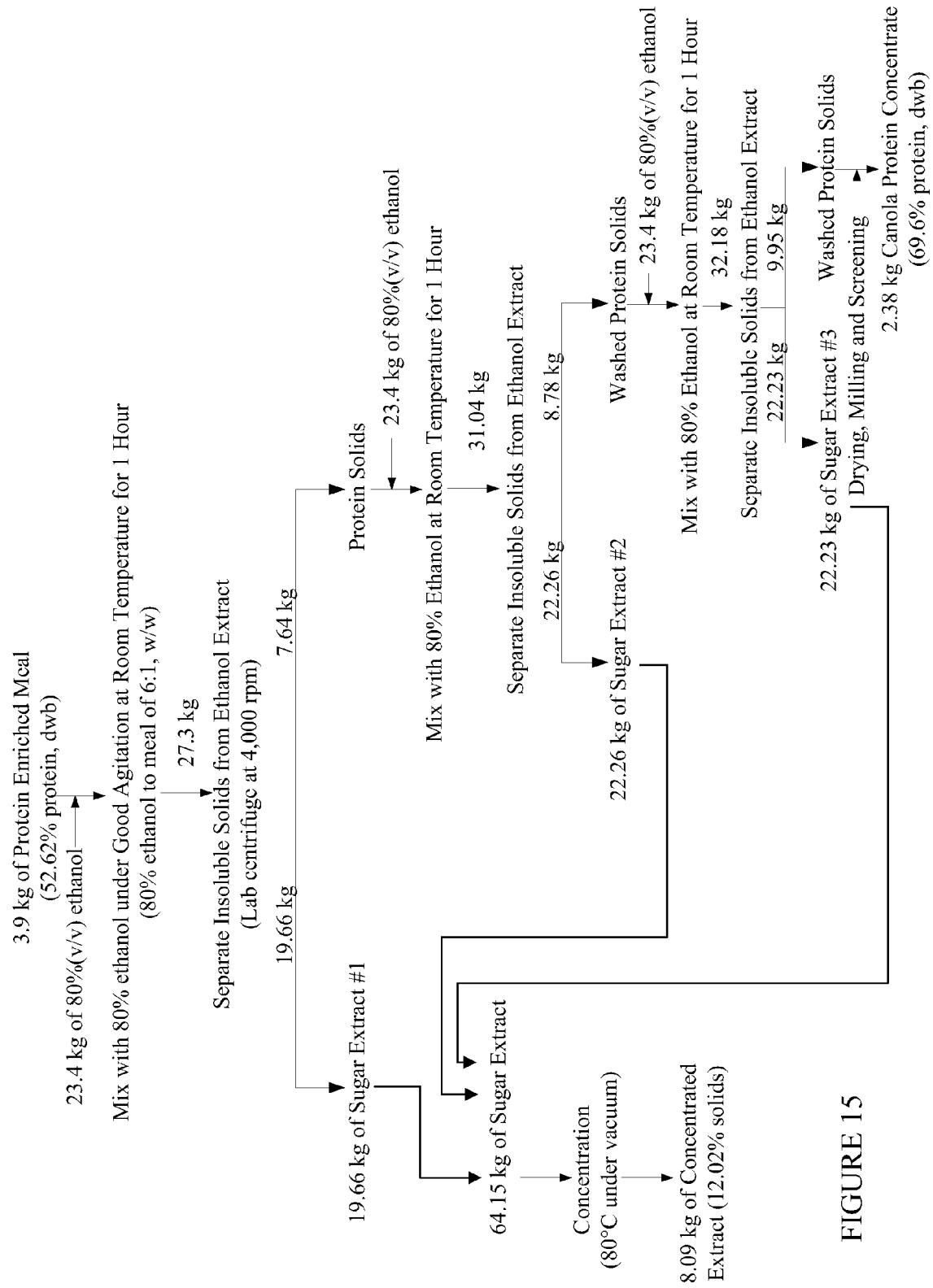
FIG. 15 is a schematic representation of a third embodiment showing a preparation of a protein concentrate from a protein enriched meal.

The mass balance flow charts for preparation of protein concentrates (Samples 1g, 2d and 3d) from protein enriched meals are shown in FIGS. 13, 14 and 15. As seen in Table 17, the moisture content of protein concentrates was in the range of 5.32-5.52%, the protein content of protein concentrates (Samples 1g, 2d and 3d) was in the range of 65.80-69.60% (dwb). The crude oil content of protein concentrates was in the range of 0.02-0.41% (dwb) (Samples 1g, 2d and 3d), while the crude fiber content of protein concentrates was in the range of 6.37-7.16% (dwb). The yield of protein concentrates is listed in Table 18. Approximately 0.6-0.733 kg of protein concentrate containing 65.80-69.60% protein (dwb) was produced from 1 kg of protein enriched meal containing 52.62-54.77% protein (dwb).

Protein concentrates from Samples 1g, 2d and 3d contained 65.80%, 68.69% and 69.60% protein (dwb). Protein concentrates contained 6.37-7.16% crude fiber on a dry weight basis (Table 17), which was higher than the crude fiber content of around 3.8-4.5% for soy protein concentrate.

Ethanol extraction was effective to increase the protein content from 52.62-54.77% (dwb) in the protein enriched meals to 65.8-69.6% (dwb) in the protein concentrates (Samples 1g, 2d and 3d). Ethanol washing was also effective in reducing the crude oil content from 0.51-1.49% (dwb) in protein enriched meals to 0.02-0.41% (dwb) in the protein concentrates.

Sample 2d was analyzed for its components and the test results are listed in Table 19. The amino acid profile Sample 2d is given in Table 20. Samples 1d, 2a and 3a; 1f, 2c and 3c; and 1g, 2d and 3d were analyzed. Results are shown in Tables 21, 22 and 23 for the contents of antinutritional factors such as glucosinolates, phytates and sinapines.

The glucosinolate and sinapine contents were reduced significantly by using 80% ethanol washings when protein concentrate (Samples 1g, 2d and 3d) was produced from Samples 1d, 2a and 3a (Tables 21-23).

The results of solvent residues analysis are listed in Table 24. The results of solvent residue analysis after desolventization and drying are shown in Table 25.

Samples 1d, 1f, 2a, 2c, 3a and 3c contained high solvent residues of butane and R134a before vacuum drying. After vacuum drying, the solvent residues of had been reduced significantly. The residues of butane and R134a in Samples 1d, 1f, 2a and 2c were reduced to below the detention limit of 10 ppm respectively. After drying of Samples 2d and 3d at 50° C. for 15 hours in the forced air oven and drying of Sample 1g at 54±3° C. for 18 hour in the Littleford® vacuum dryer, they contained less than 10 ppm of butane and less than 10 ppm of R134a.

In the pressing and extraction trials of Sample 1, non-flaked press cake (Sample 1a) contained much higher crude oil content than that of flaked press cake (Sample 1b). After solvent extraction the defatted canola meal from non-flaked press cake (Sample 1c) contained a high oil content of 8.75%-12.73% (dwb) while the defatted meal from flaked press cake (Sample 1d) contained less than 3.13% (dwb) residual crude oil. Visual inspection of the non-flaked press cake showed that it contained many intact seeds, making it difficult for efficient oil extraction by the solvent mixture of butane and R134a. Flaking would be required to rupture the oil cells before pressing to increase the ratio of press oil and obtain a lower oil content in the solvent extracted meal.

Milling of Sample 1d using a disc mill went smoothly with a throughput of 200 kg per hour. 47.93% protein enriched (Sample 1d) and 52.07% fiber enriched meals (Sample 1f) were produced in lab screening trials of the milled extracted meal using a Rotex screen of 45 US mesh. In these screening trials, up to 57.23% protein enriched meal (Sample 1e) was obtained. 37.14-40.31% protein enriched and 59.69-62.86% fiber enriched meals were produced from the screening of the milled extracted meals. The protein enriched meals (Samples 1e, 2b and 3b) contained 52.62-54.77% protein on a dry weight basis.

Protein concentrates (Samples 1g, 2d and 3d) containing 65.80-69.60% protein on a dry weight basis were prepared from protein enriched meals subjected to three 80% ethanol (v/v) washings. 60.27-73.33% recovery yields for protein concentrates were obtained based on the weight of starting protein enriched meals. Antinutritional factors such as glucosinolates and sinapines were reduced dramatically by 80% ethanol washings of protein enriched meals. Protein concentrates contained 6.37-7.16% crude fiber on a dry weight basis, which was still higher than the crude fiber content of around 3.8-4.5% for soy protein concentrate. A wet separation method was utilized to reduce the crude fiber content to 3.20-4.88% (dwb) in the canola protein concentrates (Samples 1g, 2d and 3d) using a decanter centrifuge to separate the fiber from insoluble and soluble proteins based on the difference in density.

Samples 1d, 2s and 3a, and 1f, 2c and 3c contained high solvent residues of butane and R134a before vacuum drying. After vacuum drying, the solvent residues had been reduced significantly.

Example 5(a)

Figure 16:
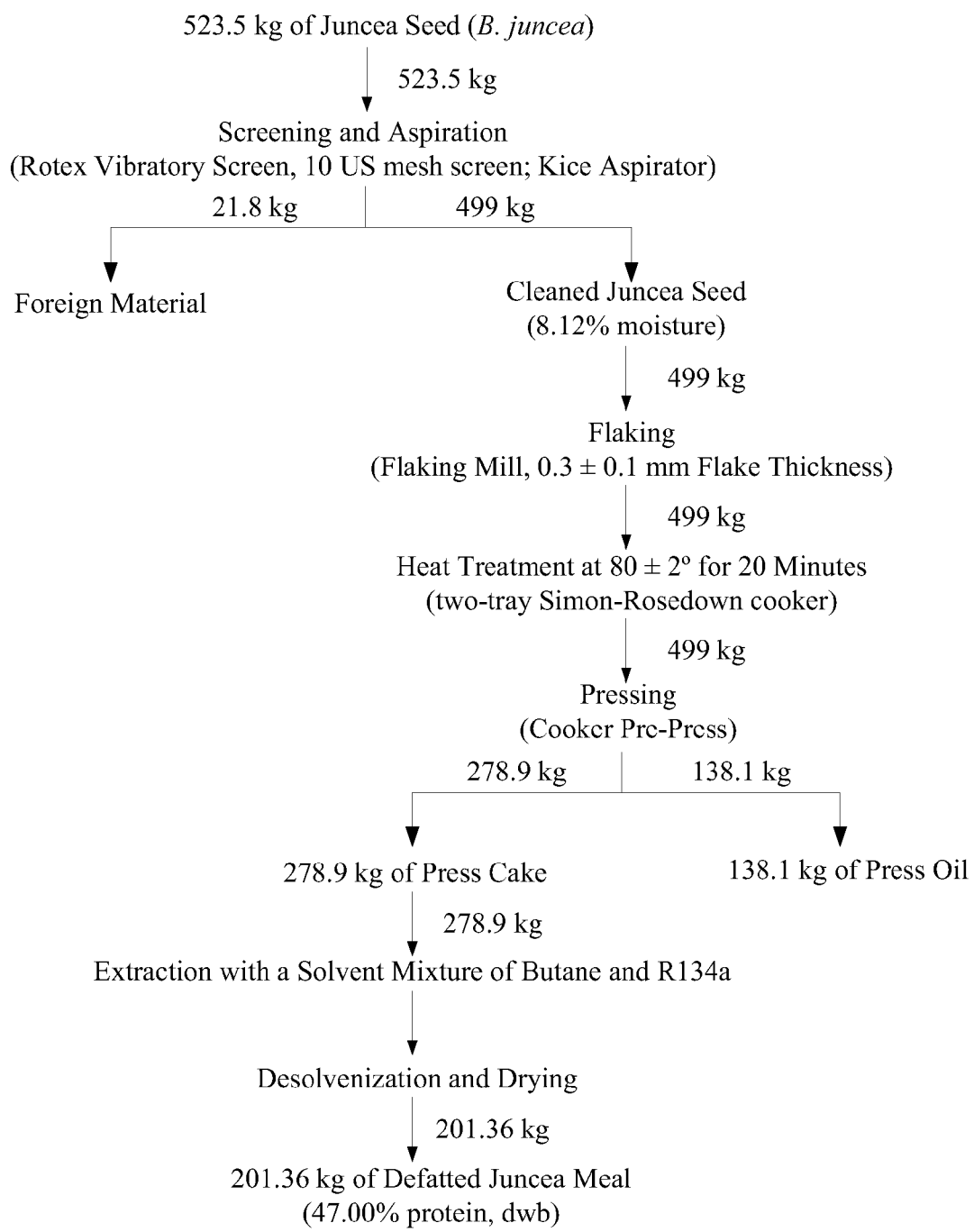
FIG. 16 is a schematic representation of a second embodiment showing the crushing of *Juncea* seed and preparation of defatted *Juncea* meal.

Canola Protein Concentrate Having about 70% Protein Content (i) Screening and Aspiration of Canola Seed Approximately 523.5 kg of canola seed (*Brassica juncea*) was screened through a Rotex vibratory Screen (Model 111 A-MS/MS, Rotex Inc., Cincinnati, Ohio, U.S.A.) fitted with a 10 US mesh screen to separate the seed from large size of foreign materials. The screened canola seed was fed to a Kice Aspirator (Kice Metal Products Company Inc., Wichita, Kans., USA) and aspirated into two fractions, the clean seed and the light foreign materials. Approximately 21.8 kg of foreign materials and 499 kg of clean seed were produced from the screening and aspiration operations. The clean seed contained 8.12% moisture. A schematic flowchart for screening and aspiration of canola seed is shown in FIG. 16.

(ii) Screw Pressing of Cleaned Canola Seed

Approximately 499 kg of the cleaned canola seed was flaked to produce flaked seed with an average thickness of 0.3±0.1 mm using a flaking mill (Model S28, Lauhoff Corporation, Detroit, U.S.A.). The flaked canola seed was heat treated using a two tray cooker. The temperature for the top tray was 52-59° C., while the temperature for the bottom tray was 68-90° C. The resident time for the top and bottom trays was 20 minutes, respectively. After heat treatment, the flaked seed was fed into the press and pressed to produce 278.9 kg of press cake and 138.1 kg of press oil.

(iii) Solvent Extraction of Press Cake

Approximately 278.9 kg of press cake was subjected to a solvent extraction which was conducted at 50° C. for 1.5 hours using a solvent mixture of butane and R134a. Approximately 201.4 kg of defatted (extracted) meal containing 47.0% protein on a dry weight basis was produced from 278.9 kg of press cake.

(iv) Milling and Screening of Defatted Meal

Figure 17:
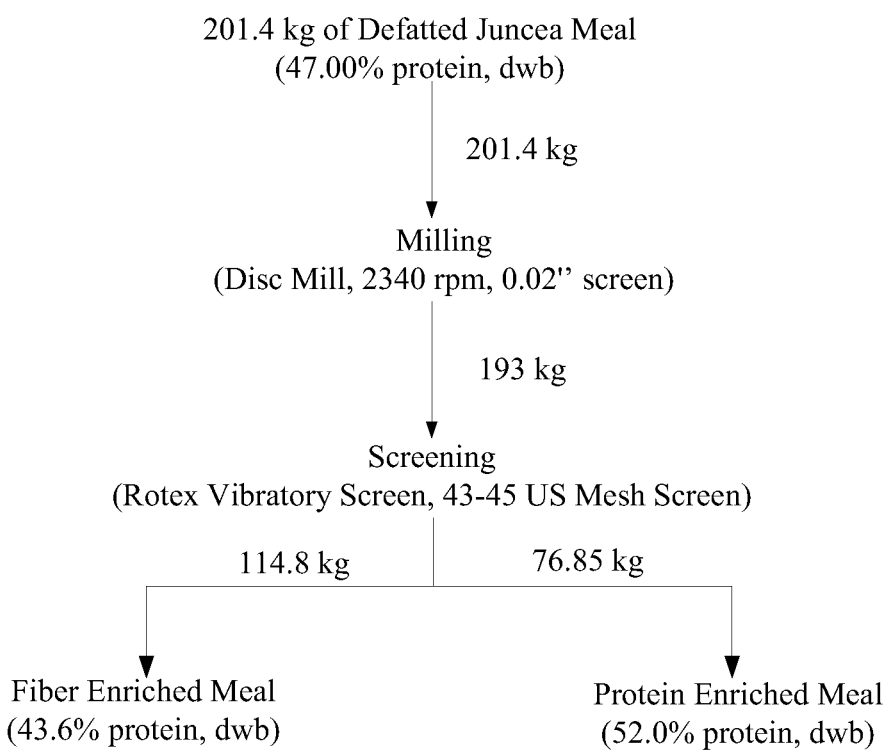
FIG. 17 is a schematic representation showing the milling and screening of defatted *Juncea* meal.

The defatted meal (201.4 kg) was milled using a disc mill equipped with #8114 stationary and rotating plates (The Bauer Bros. Co., Springfield, Ohio, U.S.A.) at 0.02" gap, 2340 rpm rotational speed and 100 kg/h throughput. Only one pass through the disc mill was conducted. A schematic flowchart for milling and screening of the defatted meal is shown in FIG. 17. Approximately 193 kg of milled defatted canola meal was produced. Approximately 8.4 kg of material was lost in the milling operation with a recovery yield of 95.83%.

The milled defatted canola meal was screened through a 45 US mesh screen using the Rotex Vibratory Screen at a feed rate of 100 kg/hr. Only one pass through the screen was conducted. Approximately 76.85 kg of protein enriched meal (fine fraction) and 114.8 kg of fiber-enriched meal (coarse fraction) were produced, respectively. Approximately 1.35 kg of material was lost in the screening operation with a recovery yield of 99.30%. After screening, 40.1% of the total material was protein enriched meal and 59.9% was fiber enriched meal, respectively.

(v) Wet Separation to Remove Fiber

Figure 18:
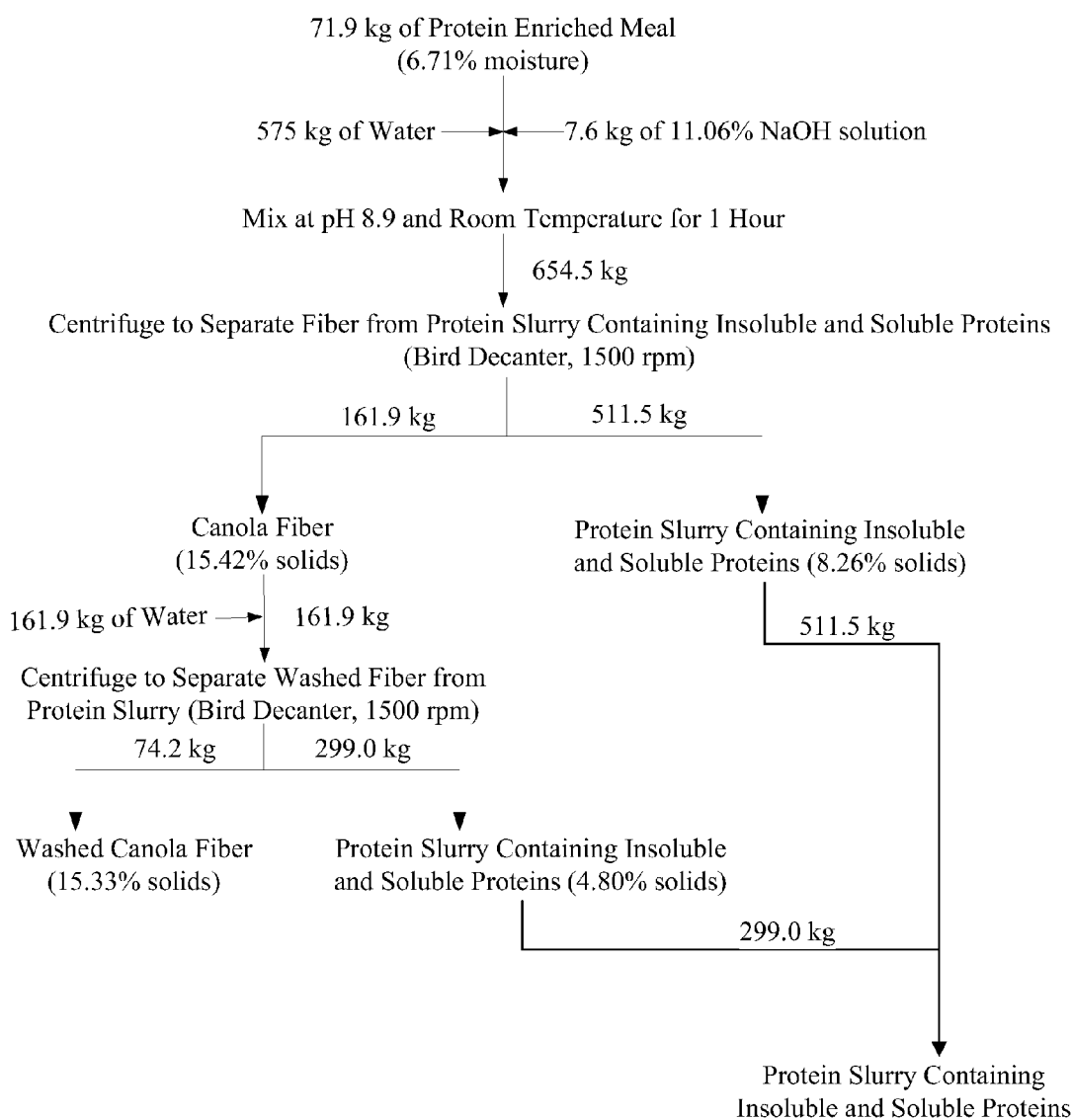
FIG. 18 is a schematic representation illustrating a separation and removal of fiber from a protein slurry containing insoluble and soluble proteins.

Approximately 71.9 kg of protein enriched meal was mixed with 575 kg of tap water at a ratio of about 1 to 8 (by weight) under homogeneous agitation to form a protein slurry. The protein slurry was adjusted to pH 8.9 by slow addition of 7.6 kg of 11.06% NaOH solution under homogeneous agitation. This was followed by centrifugation at room temperature using a Bird Decanter Centrifuge (Bird 6" Continuous Bowl Centrifuge, Bird Machine Company of Canada, Saskatoon, Saskatchewan). The protein slurry was pumped through the Bird Decanter at ambient temperature and a feed rate of 150 kg/h and it was operated at a bowl speed of 1,500 rpm with a low pool depth to separate the coarse fiber solids from the soluble and insoluble protein fractions. Approximately 161.9 kg of wet fiber solids containing 15.42% solids and 511.5 kg of protein slurry containing soluble and insoluble proteins at 8.26% solids were produced, respectively. 161.9 kg of wet fiber solids was mixed with 161.9 kg of water in a tank for 0.5 hour as a second extraction, which was followed by centrifugation at room temperature using the Bird Decanter at a bowl speed of 1,500 rpm and a feed rate of 160 kg/hr. Approximately 74.2 kg of washed wet fiber and 299 kg of protein slurry containing soluble and insoluble proteins were produced. Protein slurries containing soluble and insoluble proteins from these two centrifugations were combined and approximately 810.5 kg of the combined protein slurry was obtained. A schematic flowchart illustrating the wet separation of fiber is shown in FIG. 18.

Discussion

The Bird Decanter can operated at a bowl speed of 1,000-5,000 rpm (100-2130 g) and a pool depth of 5 to 19 mm. A spin down of the protein slurry sample in a centrifuge tube using a bench top centrifuge showed three layers, liquid extract as the top layer, insoluble protein cake of fine protein particles as the middle layer and the coarse fiber solids as the bottom layer. The objective was to separate the top and middle layers (the soluble protein extract and the insoluble fine protein solids) from the bottom layer (coarse fiber solids). The bird decanter was operated at a low pool depth and a bowl speed of 1,000, 1,500, 2,000, 2,500 and 3,000 rpm and the separation efficiency was evaluated by spin down tests of the feed, the fiber fraction and the protein slurry using the bench top centrifuge. Separation of the coarse fiber solids from the insoluble fine protein solids and the soluble protein extract was obtained at a bowl speed of about 1,000 rpm to about 2,000 rpm, optionally about 1,500 rpm (~760 g) and a low pool depth.

(vi) Preparation of Protein Concentrate Containing 70% Protein

Figure 19:
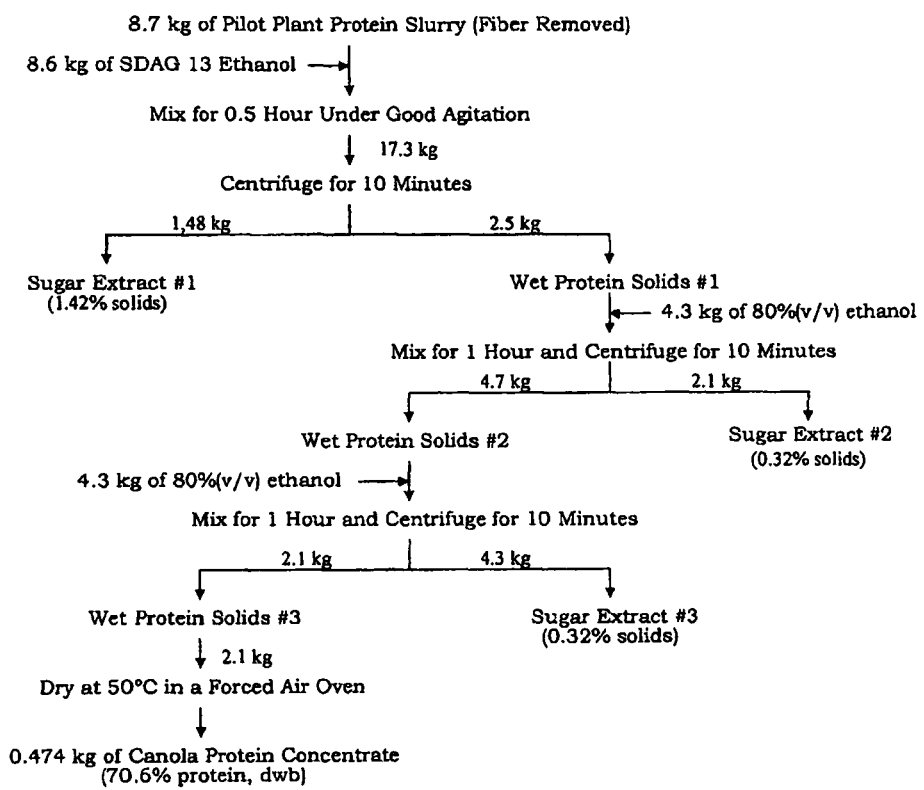
FIG. 19 is a schematic representation illustrating a preparation of a protein concentrate from a protein slurry with fiber removed.

Approximately 8.7 kg of protein slurry containing soluble and insoluble proteins after the fiber removal using the Bird Decanter was mixed with 8.6 kg of SDAG-13 denatured ethanol (containing 99% ethanol and 1% ethyl acetate) for 0.5 hours at room temperature. This was followed by centrifugation for 10 minutes using a lab centrifuge at 4,200 rpm to obtain 14.8 kg of a first sugar extract containing 1.42% solids and 2.5 kg of a first wet protein solid fraction. The wet protein solid fraction (2.5 kg) was further mixed with 4.3 kg of SDAG-13 denatured ethanol for 1 hour at room temperature. This was again followed by centrifugation for 10 minutes using the lab centrifuge at 4,200 rpm to obtain 4.7 kg of a second sugar extract and 2.1 kg of a second wet protein solid fraction. Finally, the wet protein solid fraction (2.1 kg) was mixed with 4.3 kg of SDAG 13 denatured ethanol for 1 hour at room temperature, which was followed by centrifugation for 10 minutes using the lab centrifuge at 4,200 rpm to obtain 4.3 kg of a third sugar extract and 2.1 kg of a third wet protein solid fraction. The wet protein solids were dried in a lab forced air oven at 50° C. until the moisture content was about 6%. The dried protein solids were milled using a lab pin mill to obtain the final protein concentrate containing 70.6% protein on a dry weight basis. A schematic flowchart illustrating the preparation of a protein concentrate containing 70.6% protein is shown in FIG. 19.

Example 5(b)

Canola Protein Isolate

Approximately 770 kg of a protein slurry containing soluble and insoluble proteins prepared in the same manner as in Example 5a(i)-(v) (including fiber removal using the Bird Decanter), was centrifuged using a Westfalia® Decanter (Model CA 225-010, Centrico Inc., Northvale, N.J., USA) at ambient temperature and a bowl speed of 5,200 rpm (3,300 g) to separate the soluble protein extract from insoluble protein solids. Approximately 650 kg of a first protein extract containing soluble proteins and 120 kg of a first protein solid fraction were produced. The first protein solid fraction was mixed with 360 kg of water at room temperature for 0.5 hour under homogeneous agitation, which was followed by centrifugation using the Westfalia® Decanter to obtain 368.5 kg of a second protein extract containing soluble proteins and 91.3 kg of a second protein solids fraction.

The first and second protein extracts were combined together and the combined extract was centrifuged using a Westfalia® Disc Stack Centrifuge (Model SA14-02-073, Centrico., Northvale, N.J., USA) at ambient temperature and a bowl speed of 8,500 rpm (6,549 g) to remove trace insoluble solids in the soluble protein extract. Approximately 978.5 kg of clarified protein extract and 21.9 kg of a third protein solids fraction were produced.

The clarified protein extract was adjusted to pH 7.0 by addition of 1.8 kg of 11% NaOH solution, which was followed by concentration of the protein extract in the feed tank from 978.5 kg to 140 kg at ambient using a Millipore® Ultrafiltration Unit from Millipore®, Mass., USA. The Ultrafiltration Unit (UF) was fitted with three hollow fiber cartridges with a molecular weight cutoff of 10,000 daltons, with each cartridge containing 5 $m^2$ of membrane surface area. The protein extract was pumped through the hollow fiber cartridges at a rate of 800-1000 kg/hr. The retentate was recycled back to the feed tank and the permeate was collected in another tank. The UF unit was operated at an inlet pressure of 25 psi maximum and a retentate back pressure of 15 psi maximum. The flux rate or permeate rate was about 120 kg/hr initially and gradually decreased to about 70 kg/hr and stabilized at that level for a period of time before decreasing further. Back flushing was conducted to increase the flux rate periodically. The ultrafiltration process continued until the amount of protein solution in the feed tank was equal to about 15% of its initial weight.

Approximately 60 kg of water was added into the feed tank and diafiltration was conducted at ambient temperature using the same UF unit fitted with the same three hollow fiber cartridges. The original volume of protein solution in the feed tank was held constant by adding water to make up for the removed permeate. The retentate was recycled back to the feed tank. The amount of water added to maintain the original volume of protein solution was about 2.8 times the original volume of protein solution or 560 kg.

Figure 20:
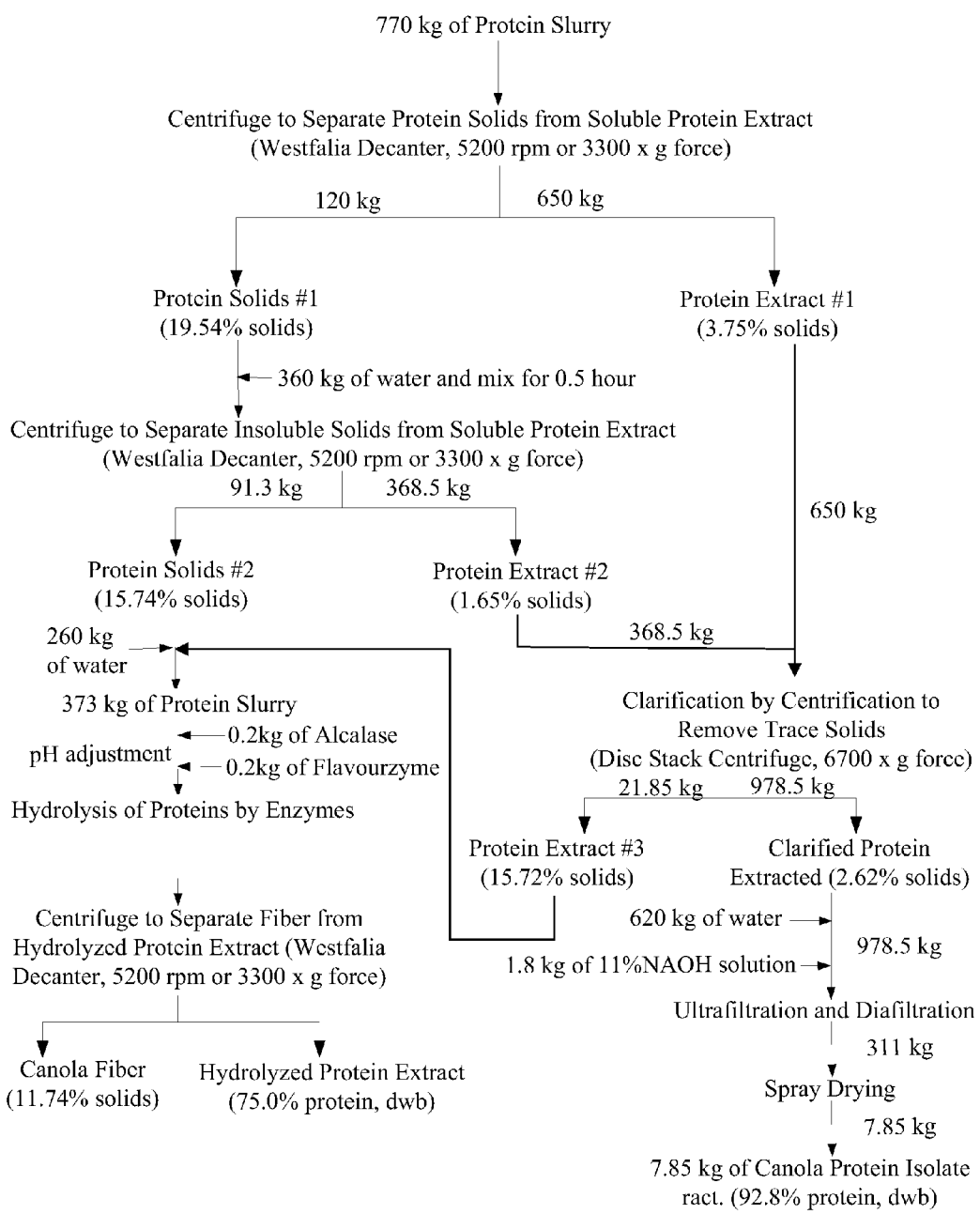
FIG. 20 is a schematic representation illustrating a preparation of a protein isolate and a hydrolyzed protein extract.

Approximately 311 kg of purified protein extract was obtained from the ultrafiltration and diafiltration process. The purified protein extract was heated to 40±10° C. using a heat exchanger prior to being fed to a Komline Sanderson® spray dryer (Komline Sanderson® Ltd., Brampton, Ontario, Canada) by pumping at a feed rate of 150-165 kg per hour. The spray drying operation was conducted at an inlet air temperature of 185±5° C. and an outlet air temperature of 85±5° C. Approximately 7.85 kg of spray dried protein isolate was produced. A schematic flowchart illustrating the preparation of a canola protein isolate is shown in FIG. 20.

Using gel permeation chromatography, the canola protein isolate had a molecular weight profile wherein the isolate contains 64.7% of the proteins have a molecular weight of 70 kDa, 26.2% at 12 kDa and 9.1% at <10 kDa.

Example 5(c)

Preparation of Hydrolyzed Protein Concentrates

Approximately 91.3 kg of the second protein solid fraction and 21.9 kg of the third protein solid fraction (obtained from Example 5(b)) were added to 260 kg of water in a tank, resulting in a slurry of about 5% solids in a 2000 L scraped surface tank. This was followed by pH adjustment to 8.3±0.1 using 8% NaOH solution. Approximately 200 g of a first protease (Alcalase® 2.4L FG) was added to the slurry. The slurry was then heated to 60±2° C. and held at temperature for 4 hours. The slurry was cooled down to 50±2° C. and 200 g of a second protease (Flavourzyme®) was added to the slurry, which was followed by holding at 50±2° C. for 4 hours. The slurry was centrifuged using the Westfalia® Decanter at 3300×g to separate the hydrolyzed protein extract from the insoluble fiber fraction. The insoluble fiber was washed further with 100 kg of filtered tap water, which was again followed by centrifugation at 3300×g to separate the washed protein extract from the washed fiber solids using the Westfalia® Decanter. A sample of the washed protein extract was taken to analyze the protein content.

Hydrolyzed protein concentrates were also produced from the combined protein slurry after fiber removal using the Bird Decanter (Example 5a(i)-(v)). Approximately 7.48 kg of protein slurry containing soluble and insoluble proteins was adjusted from pH 8.3 to pH 7.0 by addition of 25% phosphoric acid. After pH adjustment, the protein slurry was centrifuged at 4,000 RPM to separate the soluble protein extract from the insoluble solids. Approximately 1.15 kg of insoluble solids was mixed with 3.4 kg of water, which was followed by centrifugation at 4,000 RPM to separate the first washing extract from the first washed solids fraction. Approximately 1.07 kg of the first washed solids was mixed with 3.4 kg of water. This was followed by centrifugation at ambient temperature at 4,000 RPM to separate the second washing extract from the second washed solids fraction.

Figure 21:
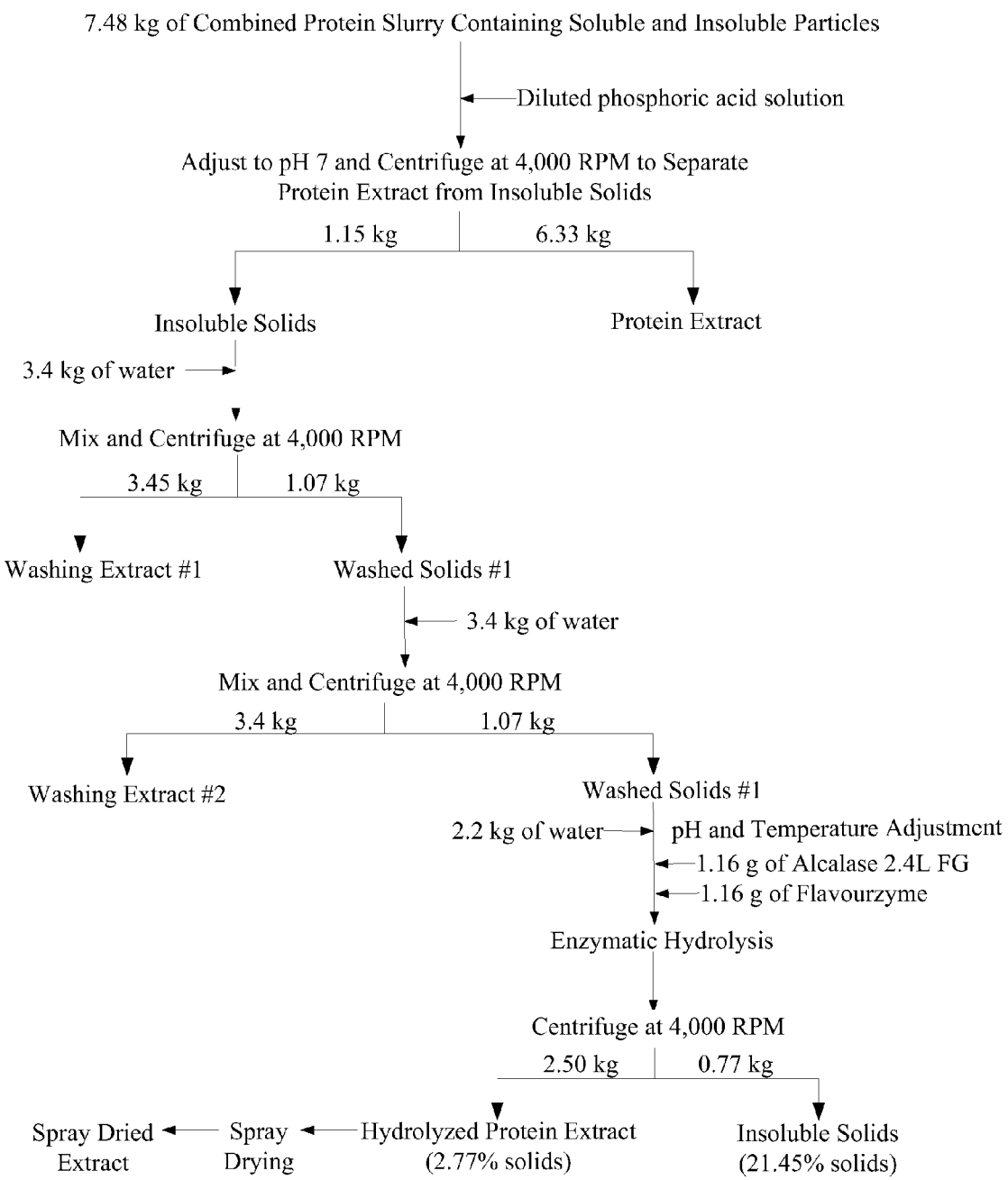
FIG. 21 is a schematic representation illustrating a preparation of a hydrolyzed protein extract.

Approximately 1.07 kg of the second washed solids fraction was mixed with 2.2 kg of water to obtain a slurry, which was followed by pH adjustment to 8.2 with the addition of 1M NaOH solution. Approximately 1.16 g of a first proteinase (Alcalase® 2.4L FG) was added to the slurry. The slurry was heated to about 62° C. and held at this temperature for 4 hours. The slurry was cooled down to about 50° C. and approximately 1.16 g of a second proteinase (Flavourzyme®) was added to the slurry, which was followed by holding at 50° C. for 4 hours. Finally, the slurry was centrifuged at 4,000 rpm for 10 minutes to separate the hydrolyzed protein extract from the insoluble fiber fraction. The hydrolyzed protein extract was spray dried into hydrolyzed protein concentrate using a lab spray dryer. A schematic flowchart illustrating the preparation of hydrolyzed protein extract is shown in FIGS. 20 and 21.

Using gel permeation chromatography, the hydrolyzed protein had a molecular weight profile wherein 63.3% of the hydrolyzed protein has an approximate molecular weight of 9,500 daltons while 16.4% hydrolyzed protein has approximate molecular weight of 7,000 daltons. The remaining 20.3% of the hydrolyzed protein has an approximate molecular weight of less than 5,000 daltons.

Discussion

The results of the proximate analysis for canola seed, press cake, defatted meal, protein enriched meal, fiber enriched meal, protein concentrate, hydrolyzed protein concentrate and protein isolate are shown in Table 26.

As shown in Table 26, dry separation by milling using a disc mill and screening using a vibratory screen of 45 US mesh increased the protein content from 47% in the extracted meal to 52% in the protein enriched meal on a dry weight basis. The fiber content was reduced from 7.75% in the extracted meal to 5.53% in the protein enriched meal by dry separation. Wet separation to remove fiber using the Bird Decanter and to remove sugar compounds by the ethanol extraction process further increased the protein content from 52% in the protein enriched meal to 70.6% in the protein concentrate. The fiber content was reduced from 5.53% in the protein enriched meal to 4.88% in the protein concentrate by wet separation using the bird decanter.

As shown in Table 27, wet separation to remove fiber by the Bird Decanter decreased the crude fiber content from 5.53% in the protein enriched meal (see Table 26) to 3.20% in the protein slurry (see Table 27) after the first fiber removal. The fiber fraction after the first fiber separation contained about 10.2% crude fiber. The fiber fraction was washed with water at a ratio of 1 to 1 by weight, which was followed by centrifugation using the Bird Decanter to separate the washed fiber fraction from the washing protein slurry. The washed fiber fraction contained 12.7% crude fiber. The fiber washing step was able to increase the crude fiber content in the fiber fraction from 10.2% to 12.7% on a dry weight basis. More importantly, the washing step significantly reduced the weight of fiber fraction from 161.9 kg to 74.2 kg or about 54% and thus increased the protein recovery yield in the final protein concentrate. The washed fiber fraction contained 11.34 kg of total dry solids (74.2 kg×15:33% solids=11.34 kg) or 16.91% of starting protein enriched meal on a dry weight basis.

After dry separation by screening, the protein enriched meal produced by this process still contained a high crude fiber content of 5.53% on a dry weight basis (see Table 26). A wet separation process was employed to separate and remove fiber from the soluble protein extract and the insoluble protein particles taking advantage of the difference in density and particle size between the fiber and insoluble protein particles.

Figure 22:
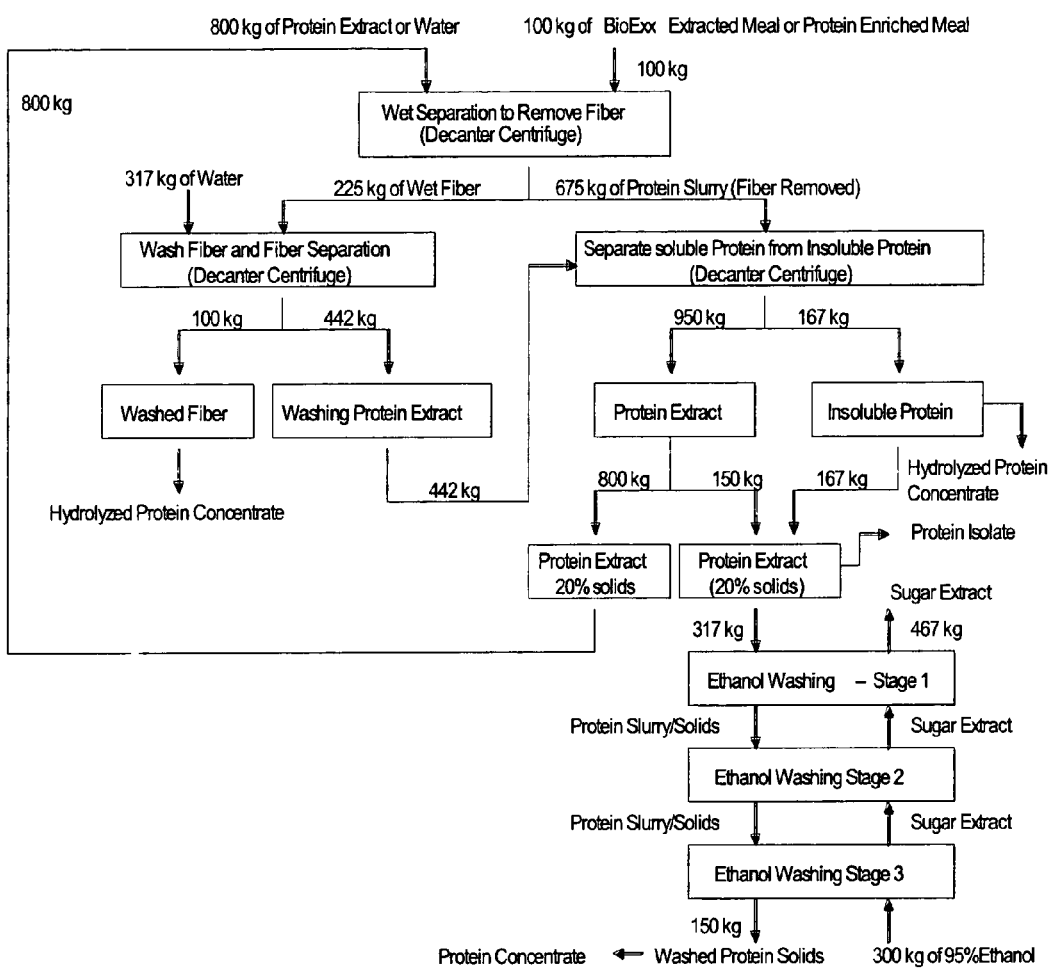
FIG. 22 is a schematic representation illustrating a wet fiber removal process.

Several spin down tests were performed on a protein slurry sample of 10.4% solids in a centrifuge tube in the laboratory using a lab centrifuge, three layers of top liquid layer, the middle protein particle layer and the bottom fiber layer were obtained in the tube. The fiber particles settled faster than the smaller insoluble protein particles. The settling rate was dependent on the g force—the higher the g force, the higher the settling rate. If the decanter centrifuge is run at a full bowl speed of 5,000 rpm or 3000 g force, both fiber and insoluble protein particles settle and would be separated from the liquid extract and be removed by the decanter as the combined insoluble solids. If the decanter is run at a lower bowl speed of 1,500 rpm or a lower g force of 750 g, the large fiber particles settle, but the fine protein particles have not yet had sufficient time to settle, therefore the fiber particles can be separated from the insoluble protein particles and the protein extract. The separation of fiber from protein particles is mainly caused by the difference in density between the insoluble fiber and protein particles. A schematic flowchart for the fiber removal process is illustrated in FIG. 22.

The protein enriched meal was mixed with water at a ratio of 1 to 8 by weight and pH was adjusted to 8.9. After 1 hour of hold time under agitation at room temperature, the protein slurry was centrifuged at a low bowl speed of 1,500 RPM (~750 g force) using the Bird Decanter. Larger fiber particles with higher density were separated from smaller insoluble protein particles with lower density as well as soluble protein solution. The fiber fraction was washed with water at a ratio of 1 to 1, which was followed by centrifugation at 1,500 RPM using the Bird Decanter to separate the large fiber particles with higher density from the insoluble smaller protein particles with lower density as well as protein extract. In an embodiment, the efficiency of a wet fiber separation is affected by viscosity and density of the liquid medium. The soluble protein extract would be cycled and re-used to increase the soluble solid content in order increase the density and viscosity of the liquid medium. This also helps to reduce the volume of water usage.

The results of the amino acid profiles for the canola protein concentrates and isolate on a dry weight basis are shown in Table 28. In addition, a comparison of amino acid profiles for the canola protein concentrate, canola protein isolate and commercially available soy and pea protein isolates is shown in Tables 29 and 30.

From the amino acid profiles as shown in Tables 28, 29 and 30, canola protein compares favorably to that of soy protein or pea protein. Canola protein is of high nutritional quality and capable of providing adequate amounts of all essential amino acids. Canola protein contains much higher sulphur containing amino acids such as methionine and cystine than soy and pea proteins. Canola protein contains 48-72% higher methionine than soy protein and 70-97% higher methionine than pea protein. Usually, cereals tend to be low in lysine but adequate in the sulphur containing amino acid methionine. Legumes are adequate in lysine but low in methionine. Canola protein is unique in that it contains both adequate lysine and sulphur containing amino acid methionine. Therefore, it exhibits a better amino acid balance than cereal proteins and legume proteins (such as pea protein and soy protein). Canola protein has excellent nutritional quality and can be used in applications such as baby formula and foods required for good nutrition.

From the essential amino acid profiles as shown in Table 30, canola protein is very rich in the muscle building essential amino acids such as valine, methionine, leucine and isoleucine. It also contains a much higher content of the essential amino acid threonine, which is important for brain activity.

Canola protein concentrate and isolate may be suitable ingredients for sports nutritional supplements.

With respect to the molecular weight and characterization of the canola protein concentrate, the concentrate obtained in Example 5(a) contained three major subunits as listed below:
10,000-12,000 dalton molecular weight
15,000-20,000 dalton molecular weight
25,000-37,000 dalton molecular weight The results obtained using a technique of Gel Permeation Chromatography show that canola protein isolate contains 64.7% of the proteins at molecular weight of 70 kDa, 26.2% at 12 kDa and 9.1% at <10 kDa.

With respect to the functional properties of the canola protein isolate, the emulsifying and foaming properties of the canola protein isolate (obtained in Example 5(b)) as compared to soy and pea protein isolates are shown in Table 31. As seen in Table 31, the canola protein isolate of the present disclosure has much better foaming capacity than soy and pea protein isolates at pH 7.0 and a protein concentration of 0.5%. At pH 7 and concentration of 1.0%, canola protein isolate has slightly lower foaming capacity than soy protein isolate, but much higher foaming capacity than pea protein isolate. The canola protein isolate has a much better foam stability than soy and pea protein isolates. Further, the canola protein isolate has similar emulsifying properties as compared to soy and pea protein isolates at pH 7 and concentrations of 0.5% and 1.0%, and also has similar emulsion stability at pH 7 and concentrations of 0.5% and 1.0%.

The foaming capacity of a protein is characterized by whipping the dissolved protein at 0.5% protein content with a milk foamer (Aeroflott™) at 20° C. for 1 minute. Foam height was determined in a 100 ml scaled cylinder for 1 hour. Additionally, the protein solution at 0.5% protein was heated at 60° C. for 15 minutes and then cooled to 20° C. before foam test The emulsifying capacity of a protein is defined as the maximum amount of oil which can be emulsified with a defined amount of protein forming a stable emulsion. The higher the emulsifying capacity, the higher the effectiveness of the protein substance. The emulsifying capacity is measured by using the following emulsifying conditions:
measuring temperature at 20° C.
protein concentration at 0.5%
stepwise addition of coloured plant oil (starting point at 50%)
Emulsification using Ultra-Turrax (13,000 min$^{-1}$; 60 s)
Evaluation of oil separation 30 minutes after emulsification.

As shown in Table 32, the emulsifying results of a 0.5% canola protein isolate solution were very good as compared to a 5% egg yolk solution. Further, as described in Table 32, the canola protein isolate possesses the functional property of gel formation and water immobilization, and therefore, would act as a stabilizer. The results of gel firmness for canola protein isolate are good and comparable to other vegetable proteins. The results of water immobilization of canola protein isolate gels are good as compared to that of whey protein isolate gels, which is an important parameter for stability and shelf-life of a final product containing canola protein isolate.

Because of its emulsifying and foaming properties, in an embodiment, the canola protein isolate is a suitable protein and functional ingredient in food applications that require good emulsifying and foaming capacity and stability such as in cakes, coffee toppings, and specialty coffee drinks, crèmes, dressings and pastes. In another embodiment, the canola protein isolate is used for laundry and cosmetic products that require good foaming capacity and stability such as in laundry detergents, bath soaps, conditioning shampoos, and cream hand and skin cleansers. In a further embodiment, the canola protein isolate is used for soups, salad dressings, sausages, bologna and other comminuted and emulsified meat products that require good emulsifying capacity.

As seen in Table 33, the solubility of the canola protein isolate, in addition to the solubility for pea and soy protein isolates is shown. The results show that 99.81% of the crude protein canola isolate crude is soluble. The test results demonstrate that the canola protein isolate of the present disclosure has 99.81% soluble crude protein as compared to 25.21% and 18.85% soluble crude protein for soy and pea protein isolates, respectively. Accordingly, in an embodiment, the canola protein isolate is a suitable protein ingredient for nutritional beverages such as protein fortified soft drinks, fruit juices, sports drinks and high protein drinks. In another embodiment, it is also useful for healthy food applications to improve absorption and digestibility.

As shown in Table 34, the concentrations of antinutritional factors in the canola protein isolate obtained in Example 5(b) are illustrated. Accordingly, the canola protein isolate contains very low levels of total glucosinolates, phytic acid and allyl isothiocyanate.

The results of glucosinolates in the canola seed, the canola press cake, the defatted meal, the protein and fiber enriched meals, the protein concentrates and isolate are shown in Table 35. The content of total aliphatic glucosinolates in seed, press cake, extracted meal, protein and fiber enriched meals is high and at similar level on an oil free basis. Dry separation by screening to separate the extracted meal into the protein and fiber enriched meals did not alter the concentration of total aliphatic glucosinolates significantly. Wet separation processing reduced the total aliphatic glucosinolates dramatically from 17.31 μmoles/g in the protein enriched meal to 0.11 μmole/g in canola protein concentrate, 0.23 μmole/g in hydrolyzed protein concentrate and 0.17-0.41 μmole/g in protein isolate.

Accordingly, based on the above described properties of the canola protein concentrates and isolates, the concentrates and isolates have:

Excellent nutritional value and the only vegetable protein product having high lysine and methionine. For example, protein isolates of the present disclosure will typically have greater than 4.5% lysine by weight and 2.0% methionine by weight of the isolate as a whole. Further, protein concentrates of the present disclosure will typically have greater than 5.4% lysine by weight and 1.9% methionine by weight of the concentrate as a whole;

Attractive labeling as GMO free and no food allergies;

Zero or very low fat. Typically, the protein isolates of the present disclosure will have less than 0.2% fat by weight of the protein isolate as a whole, while the protein concentrates will typically have less than 0.5% fat by weight of the protein concentrate as a whole;

Vegetable protein origin and green products;

Gluten free;

Low salt and low sugar contents. Typically, the protein isolates of the present disclosure will have less than 0.5% sugar by weight and less than 0.5% salt by weight of the protein isolate as a whole. Further, the protein concentrates of the present disclosure will have less than 0.5% sugar by weight and about 0% salt by weight of the protein isolate as a whole.

Example 6

Canola Protein Concentrate Having About 70% Protein Content (i) Milling and Screening of Defatted *Juncea* Meal Approximately 458.5 kg of defatted canola meal (prepared as in Example 4) was milled using a disc mill equipped with #8114 stationary and rotating plates (The Bauer Bros. Co., Springfield, Ohio, U.S.A.) at 0.02" gap, 2340 rpm rotational speed and 100 kg/hr throughput. Only one pass through the disc mill was conducted. Approximately 448 kg of milled canola meal was produced. Approximately 10.5 kg of material was lost in the milling operation with a recovery yield of 97.71%.

Figure 23:
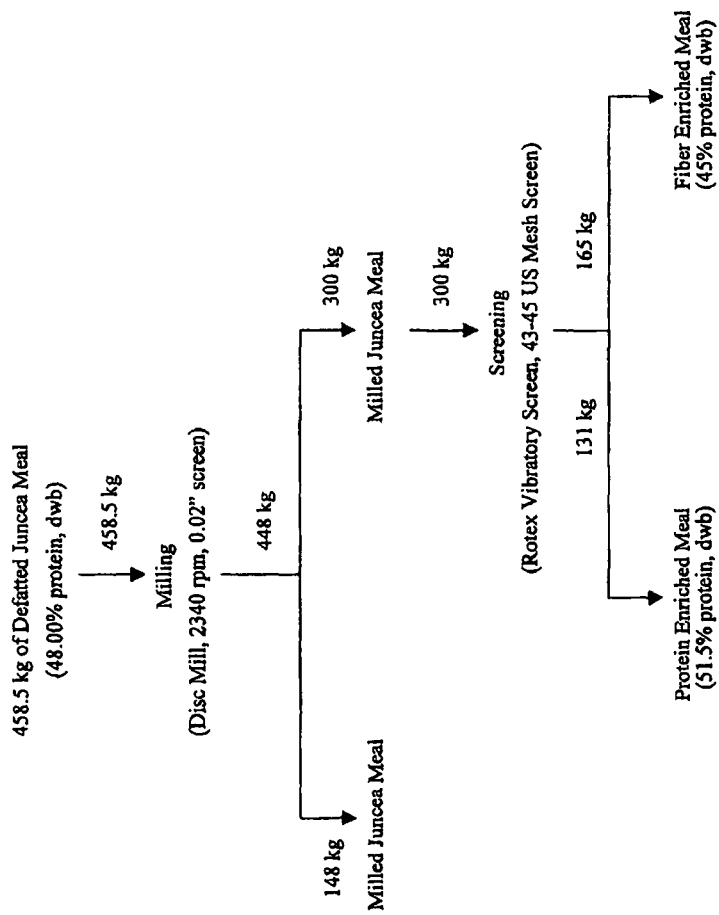
FIG. 23 is a schematic representation illustrating a milling and screening process of defatted *Juncea* meal.

Approximately 300 kg of the milled canola meal was screened through a 45 US mesh screen using the Rotex Vibratory Screen at a feed rate of 100 kg/hr. Only one pass through the screen was conducted. Approximately 131 kg of protein enriched meal (fine fraction) and 165 kg of fiber enriched meal (coarse fraction) were produced, respectively. Approximately 4 kg of material was lost in the screening operation with a recovery yield of 98.67%. After screening, 44.26% of the total material was protein enriched meal and 55.74% was fiber enriched meal, respectively. A schematic representation illustrating milling and screening of defatted *Juncea* meal is shown in FIG. 23.

(ii) Wet Separation to Remove Fiber

Figure 24:
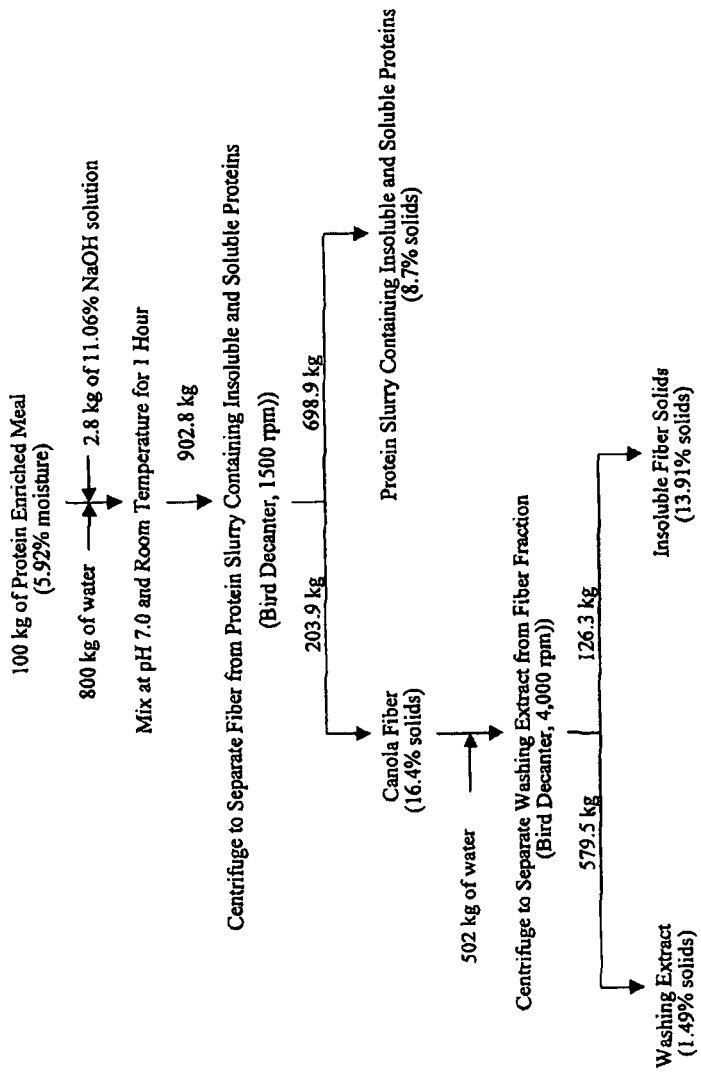
FIG. 24 is a schematic representation illustrating a separation and removal of fiber from a protein slurry containing insoluble and soluble proteins.

Approximately 100 kg of the protein enriched meal was mixed with 800 kg of tap water at a ratio of 1 to 8 (by weight) under homogeneous agitation. The protein slurry was adjusted to about pH 7 by slow addition of 2.8 kg of 11.06% NaOH solution under homogeneous agitation. This was followed by centrifugation at room temperature using a Bird Decanter Centrifuge (Bird 6" Continuous Bowl Centrifuge, Bird Machine Company of Canada, Saskatoon, Saskatchewan) at 1500 rpm bowl speed and a low pool depth. A schematic flowchart illustrating the wet separation and removal of fiber is shown in FIG. 24.

The protein slurry was pumped through the Bird Decanter at ambient temperature and a feed rate of 150 kg/hr and it was operated at a bowl speed of 1,500 rpm and a low pool depth to separate the coarse fiber solids from the soluble and insoluble protein fractions. Approximately 203.9 kg of wet fiber solids containing 16.4% solids and 698.9 kg of protein slurry containing soluble and insoluble proteins at 8.7% solids were produced, respectively. 698.9 kg of protein slurry containing soluble and insoluble proteins would be used to produce protein concentrate.

Approximately 203.9 kg of wet fiber solids was mixed with 502 kg of water in a tank for 0.5 hour, which was followed by centrifugation to separate the soluble liquid extract from the insoluble fiber solids at room temperature using the Bird Decanter at a bowl speed of 4,000 rpm and a feed rate of 350 kg/hr. Approximately 126.3 kg of insoluble fiber solids and 579.5 kg of soluble liquid extract were produced. The insoluble fiber solids are used to produce hydrolyzed protein concentrate.

(iii) Preparation of Protein Concentrate

Figure 25:
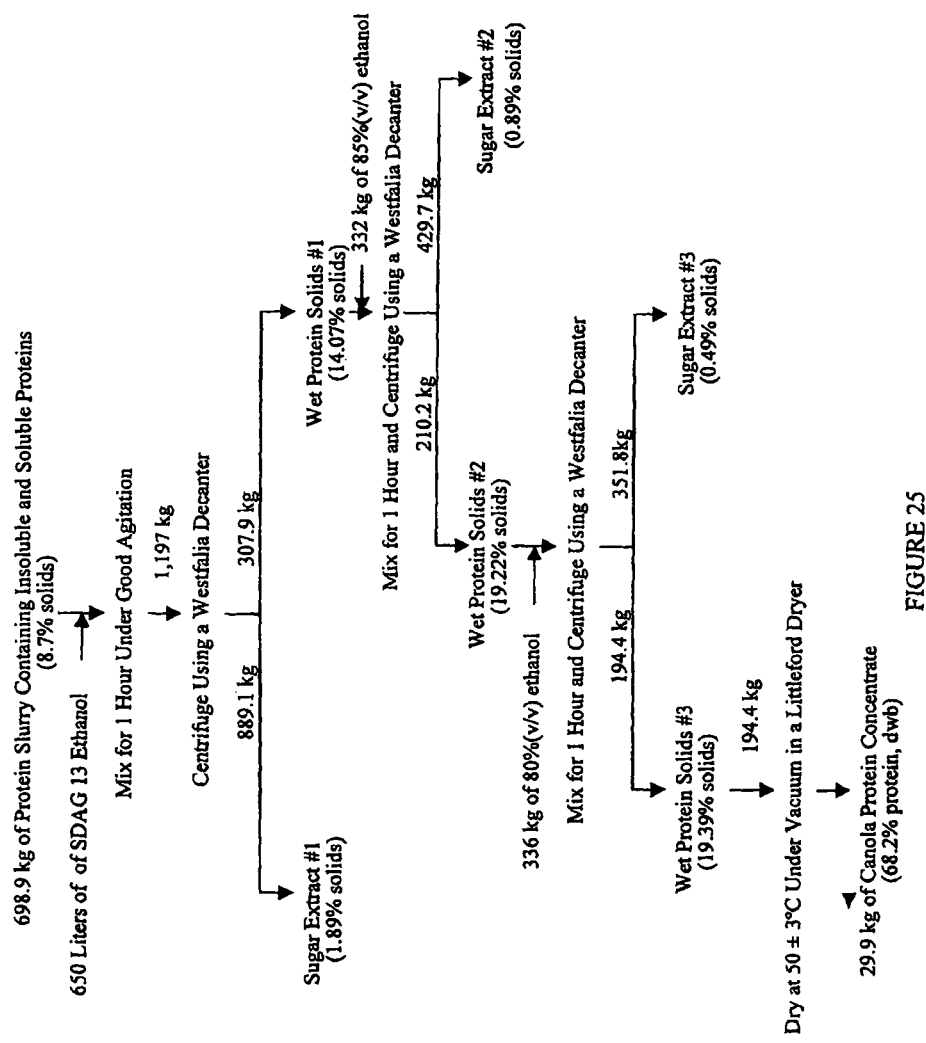
FIG. 25 is a schematic representation illustrating a preparation of a protein concentrate from a protein slurry after the removal of fiber.

Approximately 698.9 kg of protein slurry containing soluble and insoluble proteins after the fiber removal in the using the Bird Decanter was mixed with 650 liters of SDAG 13 denatured ethanol (containing 99% ethanol and 1% ethyl acetate) for 1 hour at room temperature. This was followed by centrifugation using a Westfalia® Decanter to obtain 889.1 kg of a first sugar extract containing 1.89% solids and 307.9 kg of a wet protein solids fraction containing 14.07% solids. The wet protein solids fraction (307.9 kg) was mixed with 332 kg of SDAG 13 denatured ethanol for 1 hour at room temperature. This was again followed by centrifugation using the Westfalia® Decanter to obtain 429.7 kg of a second sugar extract and 210.2 kg of a second wet protein solid fraction. Finally, the wet protein solids (210.2 kg) were mixed with 336 kg of SDAG 13 denatured ethanol for 1 hour at room temperature, which was followed by centrifugation using the Westfalia® Decanter to obtain 351.8 kg of a third sugar extract and 194.4 kg of a third wet protein solid fraction. The wet protein solids fractions were dried at 50±3° C. under vacuum using a Littleford® Dryer until the moisture content was about 7.83%. The protein concentrate contained 68.2% protein on a dry weight basis. A schematic flowchart illustrating the preparation of a protein concentrate is shown in FIG. 25.

(iv) Preparation of Hydrolyzed Protein Concentrate

Figure 26:
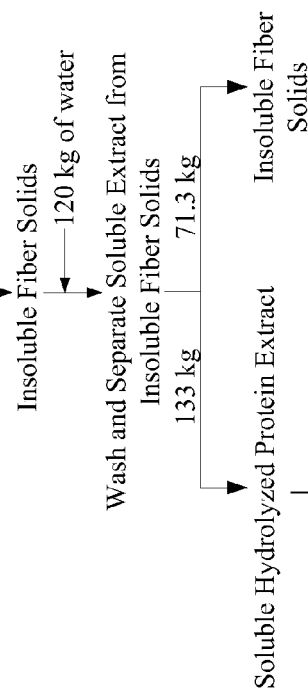
FIG. 26 is a schematic representation illustrating a preparation of a hydrolyzed protein concentrate.

Approximately 126.3 kg of insoluble fiber solids were mixed with 100 kg of water in a tank. This was followed by pH adjustment to 8.3±0.1 using 0.9 kg of 11.06% NaOH solution. Approximately 0.5 kg of a first protease (Alcalase® 2.4L FG) was added to the slurry. The slurry was then heated to 60±2° C. and held at this temperature for 4 hours. The slurry was cooled down to 50±2° C. and pH adjusted to 6.5. Approximately 0.5 kg of a second protease (Flavouzyme) was added to the slurry, which was followed by holding at 50±2° C. for 4 hours. The slurry was centrifuged using the Westfalia® Decanter at 3300×g to separate the hydrolyzed protein extract from the insoluble fiber fraction. The insoluble fiber was washed further with 120 kg of filtered tap water, which was again followed by centrifugation at 3300×g to separate the wash protein extract from the washed fiber solids using the Westfalia® Decanter. The hydrolyzed protein extract and the wash hydrolyzed protein extract were combined. The combined hydrolyzed protein extract was fed to a Millipore® Ultrafiltration Unit (Model A60, Millipore® Corporation, Bedford, Mass., USA) at ambient temperature. The Ultrafiltration Unit (UF) was fitted with three hollow fiber cartridges with a molecular weight cutoff of 10,000 daltons, with each cartridge containing 5 m² of membrane surface area. The hydrolyzed protein extract was pumped through the hollow fiber cartridges at a rate of 800-1000 kg/hr. The retentate was recycled back to the feed tank and the permeate was collected in another tank. The UF unit was operated at an inlet pressure of 25 psi maximum and a retentate back pressure of 15 psi maximum. The flux rate or permeate rate was about 190-300 kg/hr throughout the ultrafiltration process. The ultrafiltration process continued until about 40 kg of retentate remained in the feed tank. Approximately 260 kg of water was added continuously into the feed tank and ultrafiltration was conducted at ambient temperature using the same UF unit fitted with the same three hollow fiber cartridges. The original volume of retentate in the feed tank was held constant by adding water to make up for the removed permeate. The retentate was recycled back to the feed tank. The ultrafiltration process continued until all 260 kg of water was added to the retentate. A schematic flowchart illustrating the preparation of a hydrolyzed protein concentrate is shown in FIG. 26.

Approximately 540 kg of permeate and 47.7 kg of retentate were obtained from the ultrafiltration process. The permeate was spray dried to produce hydrolyzed protein concentrate using a Komline Sanderson® spray dryer (Komline Sanderson® Ltd., Brampton, Ontario, Canada). The spray drying operation was conducted at an inlet air temperature of 185±5° C. and an outlet air temperature of 85±5° C. Approximately 3.36 kg of spray dried hydrolyzed protein concentrate containing 82% protein (dwb) was produced.

Discussion

The results of the proximate analysis for defatted canola meal, protein enriched meal, fiber enriched meal, protein concentrate and hydrolyzed protein concentrate are shown in Table 36. As shown in Table 36, dry separation by milling using a disc mill and screening using a vibratory screen of 45 US mesh increased the protein content from 48% in the defatted meal to 51.5% in the protein enriched meal. The fiber content was reduced from 7.75% in the extracted meal to 5.48% in the protein enriched meal by dry separation. Wet separation to remove fiber using the Bird Decanter and to remove sugar compounds by the ethanol extraction process further increased the protein content from 51.5% in the protein enriched meal to 68.2% in the protein concentrate.

The enhancement in the protein content by ethanol washing is shown in Table 37. The protein content in the ethanol washed protein solids was increased to 61.4%, 66.3% and 67.8% in the ethanol precipitation, first and second ethanol washings. The large increase in the protein content was achieved in the 1$^{st}$ ethanol washing of the ethanol precipitated protein solids, from 61.4% protein to 66.3% protein.

In order to produce a protein concentrate containing about 70% protein (dwb), it is necessary to separate and remove fiber from the soluble protein extract and the insoluble protein particles taking advantage of the difference in density and particle size between the fiber and insoluble protein particles. The protein enriched meal was mixed with water at a ratio of 1 to 8 by weight and pH was adjusted to 7.0. After 1 hour of holding time under agitation at room temperature, the protein slurry was centrifuged at a low bowl speed of 1,500 RPM (~750 g force) using the Bird Decanter. Larger fiber particles with higher density were separated from smaller insoluble protein particles with lower density as well as soluble protein solution. In an embodiment, the soluble protein extract would be re-cycled and re-used to increase the soluble solid content in order increase the density and viscosity of the liquid medium, which would help to reduce the volume of water usage.

Hydrolyzed protein concentrate containing 82% protein (dwb) was obtained. The hydrolyzed protein concentrate was 100% water soluble and its solution was crystal clear since it was purified by a membrane filtration process. A shown in Table 38, the protein recovery yield through protein hydrolysis and membrane purification was about 85.15% before spray drying, which was calculated based on the hydrolyzed proteins including amino acids and peptides in the permeate of the ultrafiltration divided by the total proteins in the starting material of the insoluble fiber solids before the hydrolysis process (6.88 kg of protein weight in the permeate divided by 8.08 kg of protein weight in the insoluble fiber solids gave 85.15% protein recovery yield). The loss of proteins through membrane filtration is about 3.22% (0.26 kg of protein weight in the retentate divided by 8.08 kg of protein weight in the permeate gives 3.22% protein loss in the UF process).

The hydrolyzed protein concentrate produced in accordance with the processes of the present disclosure contained 82% protein (dwb). It was determined that the protein dispersibility index of the hydrolyzed protein concentrate was 99.8% and its solution was clear and transparent since it was purified by a membrane filtration process. The absorbance and transmittance of 1%, 3% and 5% hydrolyzed protein solutions using distilled water as the control is shown in Table 39. The absorbance and transmittance of 1% soy and pea protein isolate solutions were also determined for comparison. The absorbance and transmittance of the samples were determined at 720 nm wavelength using a Shimadzu® UV-Visible Spectrophotometer (UV-VIS 265, Mandel Scientific® Company Ltd., Guelph, Ontario, Canada).

In spectroscopy, the absorbance A and transmittance $I_{out}/I_{in}$ at 720 nm wavelength are defined as:

$$A_{720\,nm} = -\log_{10}(I_{out}/I_{in}) \qquad (I)$$

$I_{out}$ is the intensity of light at 720 nm wavelength that has passed through a sample (transmitted light intensity).

$I_{in}$ is the intensity of the light before it enters the sample.

As shown in Table 39, 97%, 89% and 87% light intensity passed through 1%, 3% and 5% hydrolyzed canola protein concentrate solutions at 720 nm wavelength. These hydrolyzed protein solutions were clear and transparent by visual inspection. In comparison, less than 0.016% light intensity had passed through 1% soy and pea protein isolate solutions. The soy and pea protein isolate solutions were not clear and transparent. The incident light was likely scattered by the dispersed particles in the soy and pea protein isolate solutions.

Example 7

Canola Protein Concentrate Having about 65-75% Protein Content (i) Preparation of Defatted Meal from Regular Canola Seed (*B. napus*)

Approximately 10 kg of regular canola seed (*B. napus*) was adjusted to 9% moisture by adding water to the canola seed in a plastic pail with manual agitation for a few minutes. The canola seed in the pail was then covered and tempered overnight in the laboratory. The moisture adjusted regular canola seed was then heated in a microwave oven for 2 minutes (heat to 85-95° C.). The canola seed was then covered with an aluminum foil and heated at 95° C. in a forced air oven for 30 minutes. After the heat treatment, the regular canola seed was flaked using a lab flaking mill. The flaked and heat treated seed was pressed using a Gusta Laboratory Screw Press. Approximately 3.26 kg of press oil and 6.32 kg of press cake were obtained from the pressing operation.

Approximately 6.32 kg of regular canola press cake was extracted with 16 liters of methyl pentane for 5 hours using a Soxhlet extraction system to obtain an extracted oil and a defatted canola meal. The extracted oil was recovered by evaporation and desolventization to remove the solvent from the miscella under vacuum at 60° C.

The methyl pentane defatted regular canola meal was desolventized in a laboratory fume hood for three days at room temperature. Approximately 5.02 kg of defatted regular canola meal was obtained after desolventization and drying.

(ii) Preparation of Defatted Meal from *Juncea* Seed (*B. juncea*)

Approximately 499 kg of cleaned *Juncea* seed containing 8.12% moisture was flaked to produce flaked seed with an average thickness of 0.3±0.1 mm using a flaking mill (Model S28, Lauhoff Corporation, Detroit, U.S.A.). The flaked canola seed was heat treated using a two tray cooker. The temperature for the top tray was 52-59° C., while the temperature for the bottom tray was 68-90° C. The resident time for the top and bottom trays was 20 minutes, respectively. After heat treatment, the flaked seed was fed into the press and pressed to produce 278.9 kg of press cake and 138.1 kg of press oil.

Approximately 10 kg of canola (*Juncea*) press cake was extracted with 32 liters of methyl pentane for 5 hours using a Soxhlet extraction system to obtain extracted oil and defatted canola meal. The extracted oil was recovered by evaporation and desolventization to remove the solvent from the miscella under vacuum at 60° C. The methyl pentane defatted canola meal was desolventized in a laboratory fume hood for three days at room temperature. Approximately 8.23 kg of defatted canola (*Juncea*) meal was obtained.

(iii) Lab Milling and Screening of Defatted Regular (*napus*) and *Juncea* Meals Approximately 4.01 kg of defatted regular canola meal was milled for 1 minute using a lab Warring Blender, which was followed by manual screening using a 45 US mesh Rotex screen to generate a protein enriched fraction (fine fraction) and a fiber enriched fraction (coarse fraction). The coarse fraction was re-milled in the lab Warring Blender for 1 minute. This was followed by manual screening using the 45 US mesh Rotex screen to generate a second protein enriched fraction and a coarse fraction. Finally, the coarse fraction was milled in the Warring Blender for 1 minute and the milled material was manually screened using the 45 US mesh Rotex screen to generate a third protein enriched fraction and the final fiber enriched meal. Approximately 1.76 kg of combined protein enriched fractions and 2.24 kg of fiber enriched meal were produced, respectively. Therefore, 43.89% of the total material was the protein enriched meal and 56.11% was the fiber enriched meal.

Approximately 3.52 kg of defatted *Juncea* meal was milled for 1 minute using a lab Warring Blender, which was followed by manual screening using a 45 US mesh Rotex screen to generate a protein enriched fraction (fine fraction) and a fiber enriched fraction (coarse fraction). The coarse fraction was re-milled in the lab Warring Blender for 1 minute. This was followed by manual screening using the 45 US mesh Rotex screen to generate a second protein enriched fraction and a coarse fraction. Finally, the coarse fraction was milled in the Warring Blender for 1 minute and the milled material was manually screened using the 45 US mesh Rotex screen to generate a third protein enriched fraction and the final fiber enriched meal. Approximately, 1.53 kg of combined protein enriched fractions and 1.84 kg of fiber enriched meal were produced, respectively. Therefore, 43.71% of the total material was the protein enriched meal and 56.29% was the fiber enriched meal. The mass balance data for preparation of defatted meals, protein and fiber enriched meals are given in Table 40.

(iv) Wet Separation to Remove Fiber

Approximately 0.75 kg regular (*napus*) protein enriched meal was mixed with 6 kg of water at a ratio of 1 to 8 by weight at ambient temperature for 1 hour under homogeneous agitation. The protein slurry was centrifuged at 4,000 rpm for 10 minutes using a lab centrifuge. Three layers of top liquid layer, the middle insoluble protein layer and the bottom insoluble fiber layer were obtained in the centrifuge bottles. The larger fiber particles with higher density settled faster than the smaller insoluble protein particles with lower density. Therefore, the larger fiber particles settled to the bottom of the bottles at first. The smaller insoluble protein particles with lower density settled on the top of the fiber layer. The liquid extract containing soluble proteins was at the top layer. The bottom fiber layer (0.347 kg) was separated manually from the middle insoluble protein layer (1.360 kg) and the top liquid extract layer (5.053 kg). After the fiber removal, the middle insoluble protein layer and the top liquid extract layer were combined and the combined slurry was mixed with 100% SDAG 13 ethanol at a ratio of 1 to 1 by volume for 10 minutes to precipitate proteins. The precipitation slurry was centrifuged at 4,000 rpm for 10 minutes to separate the soluble sugar extract from the insoluble protein solids using the lab centrifuge. The recovered protein solids were mixed with 4.5 kg of 80% ethanol (v/v) at ambient temperature for 1 hour, which was followed by centrifugation at 4,000 rpm for 10 minutes to separate the insoluble protein solids from the washing sugar extract. Finally, the insoluble protein solids were mixed with 4.5 kg of 80% ethanol (v/v) at ambient temperature for 1 hour. The slurry was once again centrifuged at 4,000 rpm to separate the washed protein solids from the soluble sugar extract. The washed protein solids were desolventized in a laboratory fume hood for 3 days before drying to 5.26% moisture at 50° C. using a forced air oven. The dried protein concentrate was milled into powder form using a lab pin mill.

Approximately 1 kg of *Juncea* protein enriched meal was mixed with 8 kg of water at a ratio of 1 to 8 by weight at ambient temperature for 1 hour under homogeneous agitation. The protein slurry was centrifuged at 4,000 rpm for 10 minutes using the lab centrifuge. Three layers of top liquid layer, the middle insoluble protein layer and the bottom insoluble fiber layer were obtained in the centrifuge bottles. The larger fiber particles with higher density settled faster than the smaller insoluble protein particles with lower density. Therefore, the larger fiber particles settled to the bottom of the bottles at first. The smaller insoluble protein particles with lower density settled on the top of the fiber layer. The liquid extract containing soluble proteins was at the top layer. The bottom fiber layer (0.430 kg) was separated manually from the middle insoluble protein layer (2.282 kg) and the top liquid extract layer (6.288 kg). After the fiber removal, the middle insoluble protein layer and the top liquid extract layer were combined and the combined slurry was mixed with 100% SDAG 13 ethanol at a ratio of 1 to 1 by volume for 10 minutes to precipitate proteins. The precipitation slurry was centrifuged at 4,000 rpm for 10 minutes to separate the soluble sugar extract from the insoluble protein solids using the lab centrifuge. The recovered protein solids were mixed with 6 kg of 80% ethanol (v/v) at ambient temperature for 1 hour, which was followed by centrifugation at 4,000 rpm for 10 minutes to separate the insoluble protein solids from the washing sugar extract. Finally, the insoluble protein solids were mixed with 6 kg of 80% ethanol (v/v) at ambient temperature for 1 hour. The slurry was once again centrifuged at 4,000 rpm to separate the washed protein solids from the soluble sugar extract. The washed protein solids were desolventized in a laboratory fume hood for 3 days before drying to 3.9% moisture at 50° C. using a forced air oven. The dried protein concentrate was milled into powder form using a lab pin mill. The mass balance data for the wet separation process to remove fiber and prepare protein concentrate are shown in Table 41.

Discussion

As shown in Table 42, the protein content was increased from 46.8% (dwb) in the defatted regular canola meal to 51.5% (dwb) in the regular protein enriched meal by the milling and screening operation. The crude fiber content was reduced from 9.90% (dwb) in the defatted regular canola meal to 7.09% (dwb) in the regular protein enriched meal. The protein content was increased from 48.7% (dwb) in the defatted *Juncea* meal to 52.8% (dwb) in the *Juncea* protein enriched meal by the milling and screening operation. The crude fiber content was reduced from 7.44% (dwb) in the defatted *Juncea* meal to 5.36% (dwb) in the *Juncea* protein enriched meal. A simple step of dry milling and screening was able to reduce fiber and increase protein content.

As shown in Table 43, the wet separation process to remove fiber by centrifugation based on the particle size and density difference of insoluble fiber and protein particles as well as to remove sugar compounds by the ethanol extraction process increased the protein content from 51.5% in the regular protein enriched meal to 66.9% in the regular protein concentrate. The protein content was increased from 52.8% in the *Juncea* protein enriched meal to 71.2% in the *Juncea* protein concentrate by the wet fiber separation and ethanol washing process.

The amino acid profile of defatted canola meals and protein concentrates is shown in Table 44. Canola protein concentrates generated from the methyl pentane defatted regular and *Juncea* canola meals contains higher lysine and sulphur containing amino acids methionine and cystine than the canola protein concentrate generated from the defatted *Juncea* meal using a solvent mixture of butane and R134a (see Example 5). From the amino acid profile, canola protein concentrates are of high nutritional quality and capable of providing adequate amounts of all essential amino acids. From the essential amino acid profiles as shown in Table 44, canola protein concentrates are rich in the muscle building essential amino acids such as valine, methionine, leucine and isoleucine. They also contain a high content of the essential amino acid threonine, which is important for brain activity. Both regular and *Juncea* canola protein concentrates generated from methyl pentane defatted meals contain similar content of essential amino acids.

In an embodiment of the disclosure, the canola protein concentrates produced in accordance with the present disclosure, contain about 2% to about 8% crude fiber and 65-75% protein on a dry weight basis. In a further embodiment, the protein concentrates have a minimum 25% soluble protein in a borate-phosphate buffer solution. In a further embodiment of the disclosure, the hydrolyzed canola protein concentrates contains typically less than about 5%, optionally 2% and suitably about 0% crude fiber, and greater than about 75% protein on a dry weight basis. In another embodiment, the hydrolyzed protein concentrate is at least about 95%, optionally about 98%, optionally about 99% and suitably about 100% water soluble. In an embodiment, the hydrolyzed protein concentrate has a 100% water solubility as defined by 100% PDI value (protein dispersibility index). In another embodiment of the disclosure, the canola protein isolates produced in accordance with the present disclosure typically contain about 0% crude fiber and greater than about 90% protein. In another embodiment, the protein isolates have a minimum of about 85% soluble protein in a borate-phosphate buffer solution. In another embodiment, the protein isolates have a typical molecular weigh profile of 64.7% at 70 kDa, 26.2% at 12 kDa and 9.1% at <kDa.

The results of protein solubility test on defatted canola meals and protein concentrates are shown in Table 45. The test results show that the defatted regular and *Juncea* meals have similar protein solubility of 30.36-31.48% while regular and *Juncea* proteins concentrates have protein solubility of 32.27-36.76%. They all have much higher protein solubility than commercially available samples of soy and pea protein isolates.

The results of antinutritional factors in defatted canola meals, canola protein concentrates, canola protein isolate and commercial samples of soy and pea protein isolates are shown in Table 46. The wet separation and ethanol washing process for preparation of canola protein concentrates from defatted meals had significantly reduced the sinapine content. Canola protein concentrates contain similar sinapine content as commercial samples of soy and pea protein isolates. Canola protein concentrates contain higher phytate content than soy and pea protein isolates. Canola protein isolate contains lower phytate content than soy and pea protein isolates.

Example 8

Canola Protein Concentrate Having about 73% Protein Content (i) Preparation of Defatted Meal A press cake was produced from *Juncea* seed (*B. juncea*) using the processing conditions similar to those listed in Example 5. Defatted *Juncea* meal was produced from the press cake through solvent extraction at 50° C. for 1.5 hours using a solvent mixture of butane and R134a. The defatted meal was milled using a disc mill equipped with #8114 stationary and rotating plates (The Bauer Bros. Co., Springfield, Ohio, U.S.A.) at 0.02" gap, 2340 rpm rotational speed and 100 kg/hr throughput. Only one pass through the disc mill was conducted.

Figure 27:
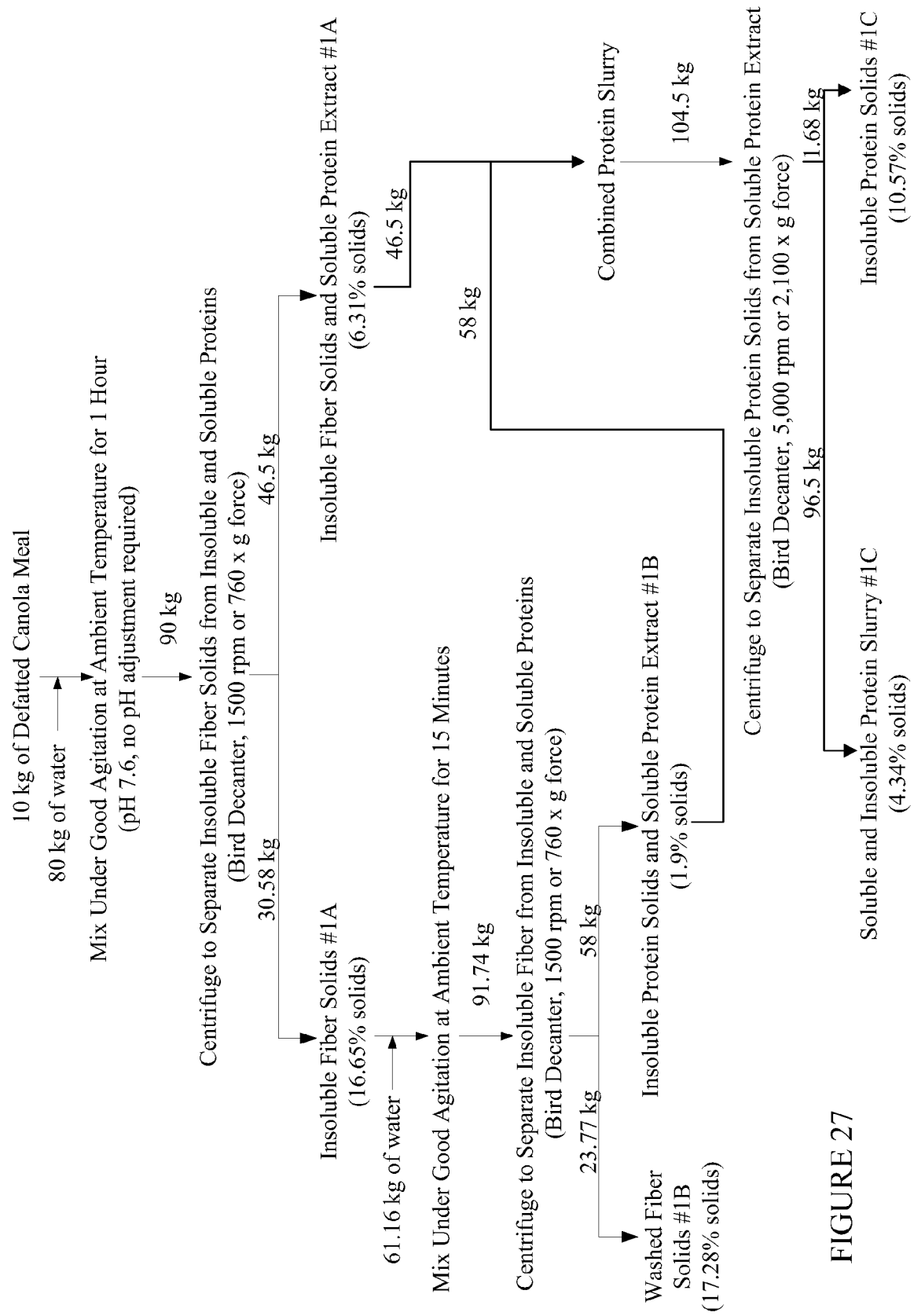
FIG. 27 is a schematic representation illustrating a wet fiber removal process.

(ii) Wet Separation to Remove Fiber (a) A schematic flowchart for wet fiber separation is shown in FIG. 27. Approximately 10 kg of defatted meal was mixed with 80 kg of tap water at a ratio of 1 to 8 (by weight) under homogeneous agitation for 1 hour. The pH of protein slurry was at 7.6 and no further pH adjustment was required. The canola meal slurry was centrifuged at ambient temperature using a Bird Decanter Centrifuge (Bird 6" Continuous Bowl Centrifuge, Bird Machine Company of Canada, Saskatoon, Saskatchewan) at 1500 rpm bowl speed and a low pool depth. The canola meal slurry was pumped through the Bird Decanter at ambient temperature and a feed rate of 150 kg/hr and it was operated at a bowl speed of 1,500 rpm and a low pool depth to separate the coarse fiber solids from the soluble and insoluble protein fractions. Approximately 30.58 kg of wet fiber solids #1A containing 16.65% solids and 46.5 kg of protein slurry #1A containing soluble and insoluble proteins at 6.31% solids were produced, respectively.

The wet fiber solids #1A was mixed with 61.16 kg of water in a tank for 15 minutes, which was followed by centrifugation to separate the washed fiber solids #1B from the insoluble protein solids and soluble protein extract #1B at room temperature using the Bird Decanter at a bowl speed of 1,500 rpm and a feed rate of 150 kg/hr. Approximately 23.77 kg of washed fiber solids #1B containing 17.28% solids and 58 kg of insoluble and soluble protein slurry #1B containing 1.9% solids were produced.

The insoluble protein solids and soluble protein extract #1A and #1B were combined, which was followed by centrifugation using the Bird Decanter at 5,000 rpm to separate the insoluble protein solids #1C from the soluble and insoluble protein slurry #1C. Approximately 1.68 kg of insoluble protein solids #1C containing 10.57% solids and 96.5 kg of soluble and insoluble protein slurry #1C containing 4.34% solids were produced.

Figure 28:
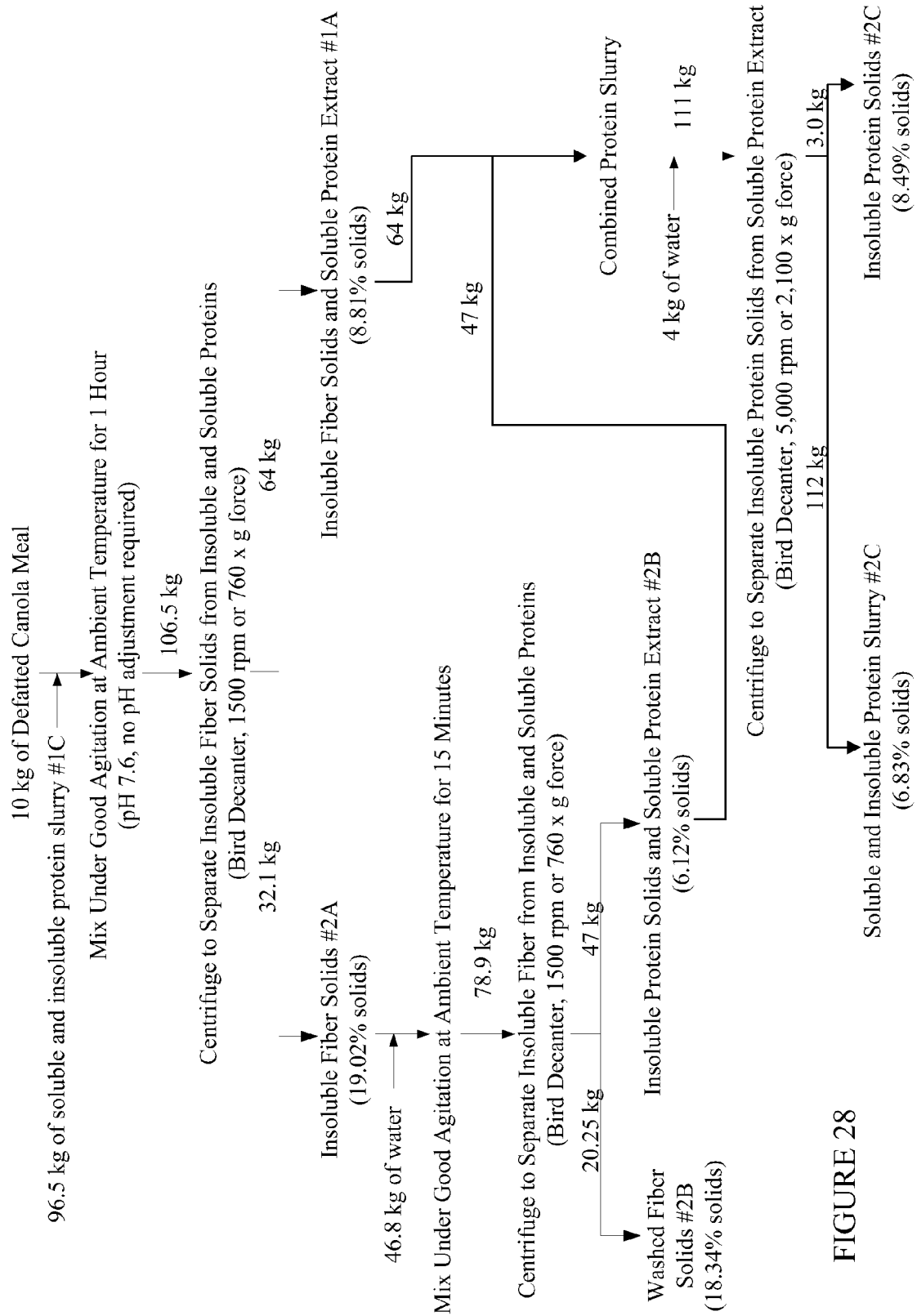
FIG. 28 is a schematic representation illustrating a first recycling of a protein fraction and a wet fiber removal process.

(b) Recycling of Protein Slurry Containing Soluble and Insoluble Protein Fractions A schematic flowchart for wet fiber separation and the $1^{st}$ recycle is shown in FIG. 28. Approximately 10 kg of defatted meal was mixed with 96.5 kg of soluble and insoluble protein slurry #1C generated from the previous wet fiber separation process under homogeneous agitation for 1 hour. The pH of protein slurry was at 7.6 and no further pH adjustment was required. The canola meal slurry was centrifuged at ambient temperature using a Bird Decanter Centrifuge (Bird 6" Continuous Bowl Centrifuge, Bird Machine Company of Canada, Saskatoon, Saskatchewan) at 1,500 rpm bowl speed and a low pool depth. The canola meal slurry was pumped through the Bird Decanter at ambient temperature and a feed rate of 150 kg/hr to separate the coarse fiber solids from the soluble and insoluble protein fractions. Approximately 32.1 kg of wet fiber solids #2A containing 19.02% solids and 64 kg of protein slurry #2A containing soluble and insoluble proteins at 8.81% solids were produced, respectively.

The wet fiber solids #2A was mixed with 46.8 kg of water in a tank for 15 minutes, which was followed by centrifugation to separate the washed fiber solids #2B from the insoluble protein solids and soluble protein extract #2B at ambient temperature using the Bird Decanter at a bowl speed of 1,500 rpm and a feed rate of 150 kg/hr. Approximately 20.25 kg of washed fiber solids #2B containing 18.34% solids and 47 kg of insoluble and soluble protein slurry #2B containing 6.12% solids were produced.

The insoluble protein solids and soluble protein extract #2A and #2B were combined, which was followed by centrifugation using the Bird Decanter at 5,000 rpm to separate the insoluble protein solids #2C from the soluble and insoluble protein slurry #2C. Approximately 3.0 kg of insoluble protein solids #2C containing 8.49% solids and 112 kg of soluble and insoluble protein slurry #2C containing 6.83% solids were produced.

(c) Second Recycling

Figure 29:
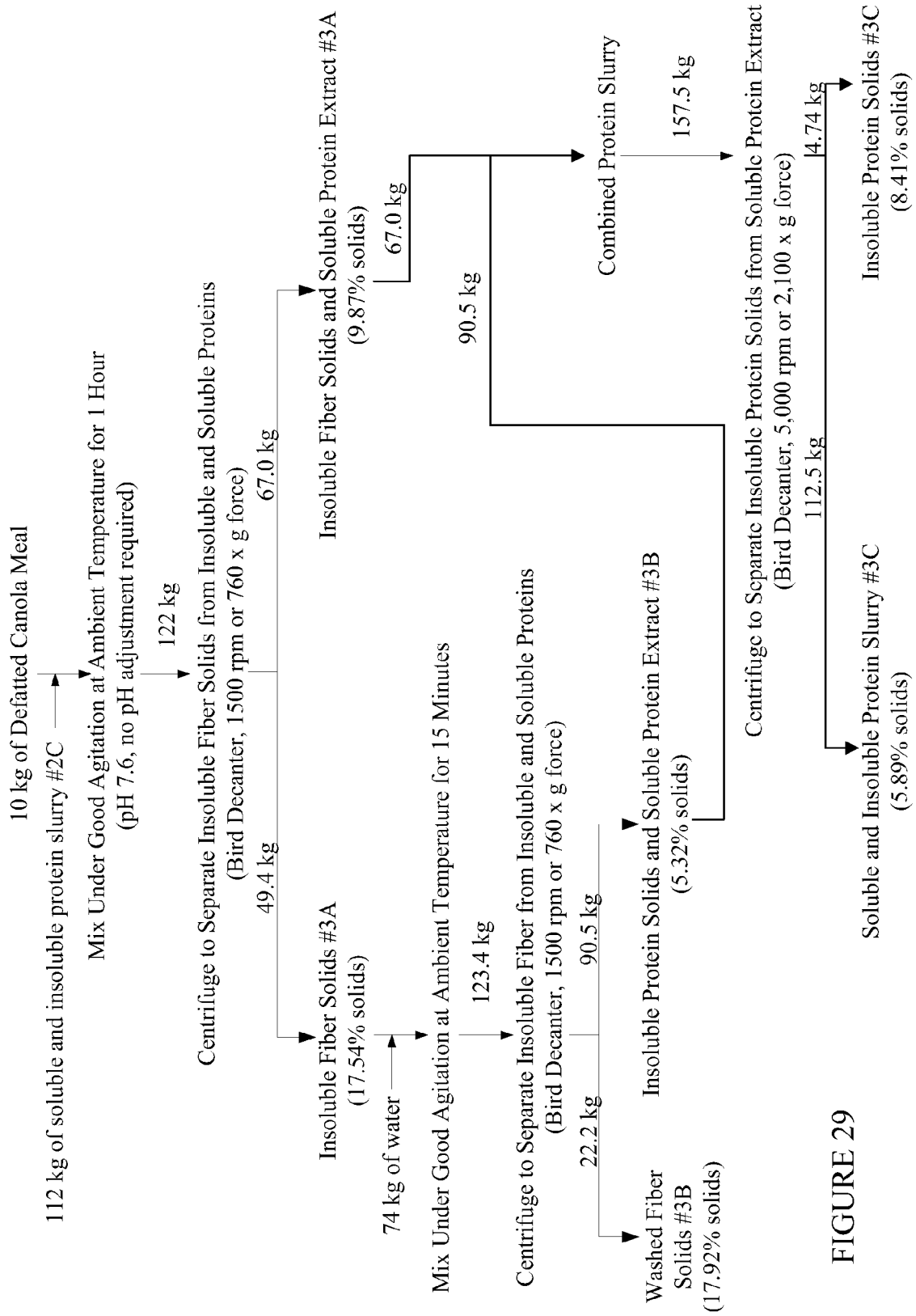
FIG. 29 is a schematic representation illustrating a second recycling of a protein fraction and a wet fiber removal process.

A schematic flowchart for wet fiber separation and the $2^{nd}$ recycle is shown in FIG. 29. Approximately 10 kg of defatted meal was mixed with 112 kg of soluble and insoluble protein slurry #2C generated from the previous wet fiber separation process under homogeneous agitation for 1 hour. The pH of protein slurry was at 7.6 and no further pH adjustment was required. The canola meal slurry was centrifuged at ambient temperature using a Bird Decanter Centrifuge (Bird 6" Continuous Bowl Centrifuge, Bird Machine Company of Canada, Saskatoon, Saskatchewan) at 1,500 rpm bowl speed and a low pool depth. The canola meal slurry was pumped through the Bird Decanter at ambient temperature and a feed rate of 150 kg/hr to separate the coarse fiber solids from the soluble and insoluble protein fractions. Approximately 49.4 kg of wet fiber solids #3A containing 17.54% solids and 67.0 kg of protein slurry #3A containing soluble and insoluble proteins at 9.87% solids were produced, respectively.

The wet fiber solids #3A was mixed with 74 kg of water in a tank for 15 minutes, which was followed by centrifugation to separate the washed fiber solids #38 from the insoluble protein solids and soluble protein extract #3B at ambient temperature using the Bird Decanter at a bowl speed of 1,500 rpm and a feed rate of 150 kg/hr. Approximately 22.2 kg of washed fiber solids #3B containing 17.92% solids and 90.5 kg of insoluble and soluble protein slurry #3B containing 5.32% solids were produced.

The insoluble protein solids and soluble protein extract #3A and #3B were combined, which was followed by centrifugation using the Bird Decanter at 5,000 rpm to separate the insoluble protein solids #3C from the soluble and insoluble protein slurry #3C. Approximately 4.74 kg of insoluble protein solids #3C containing 8.41% solids and 112.5 kg of soluble and insoluble protein slurry #3C containing 5.89% solids were produced.

(d) Third Recycling

Figure 30:
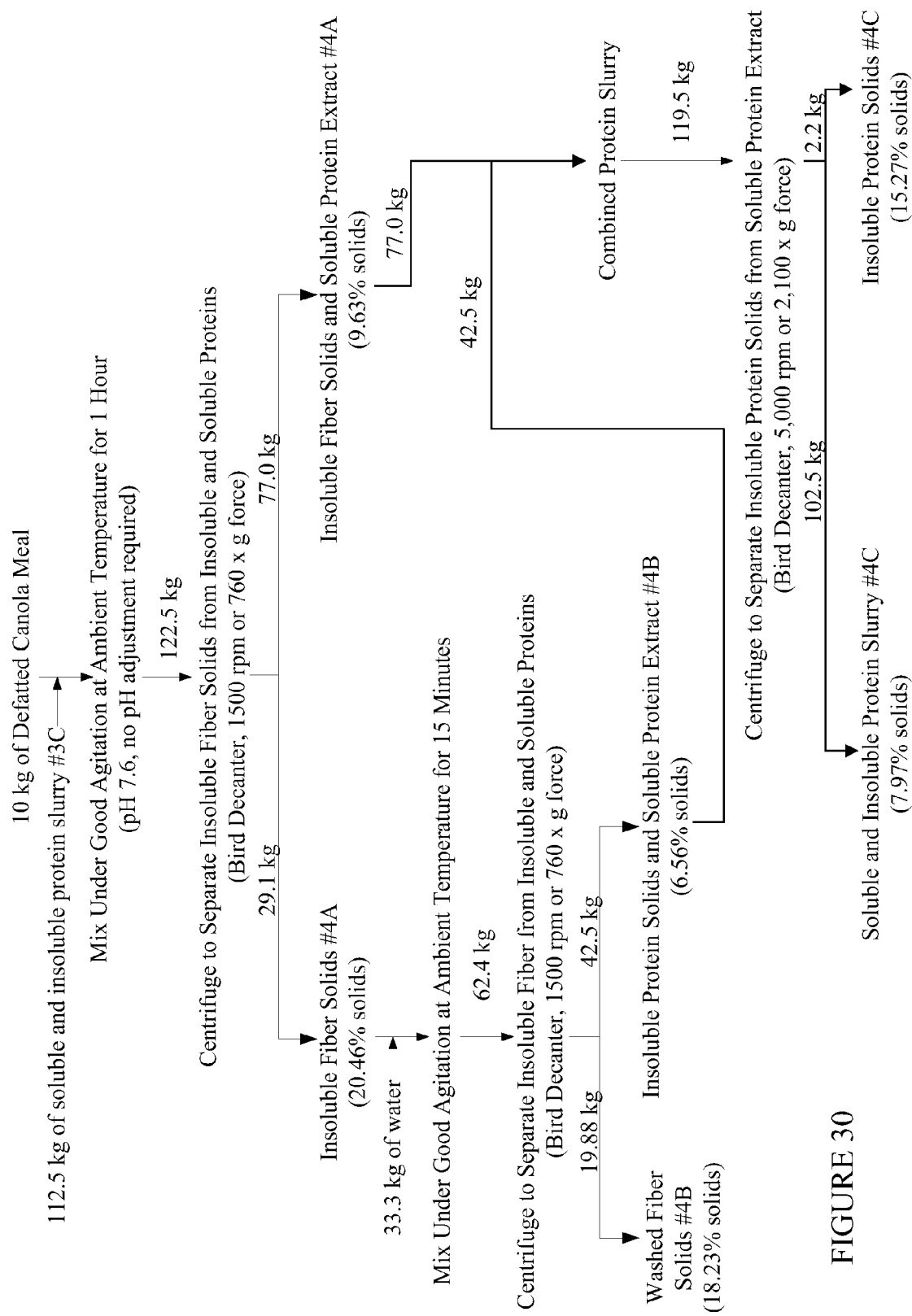
FIG. 30 is a schematic representation illustrating a third recycling of a protein fraction and a wet fiber removal process.

A schematic flowchart for wet fiber separation and the $3^{rd}$ recycle is shown in FIG. 30. Approximately 10 kg of defatted meal was mixed with 112.5 kg of soluble and insoluble protein slurry #3C generated from the previous wet fiber separation process under homogeneous agitation for 1 hour. The pH of protein slurry was at 7.6 and no further pH adjustment was required. The canola meal slurry was centrifuged at ambient temperature using a Bird Decanter Centrifuge (Bird 6" Continuous Bowl Centrifuge, Bird Machine Company of Canada, Saskatoon, Saskatchewan) at 1500 rpm bowl speed and a low pool depth. The canola meal slurry was pumped through the Bird Decanter at ambient temperature and a feed rate of 150 kg/hr to separate the coarse fiber solids from the soluble and insoluble protein fractions. Approximately 29.1 kg of wet fiber solids #4A containing 20.46% solids and 77.0 kg of protein slurry #4A containing soluble and insoluble proteins at 9.63% solids were produced, respectively.

The wet fiber solids #4A was mixed with 33.3 kg of water in a tank for 15 minutes, which was followed by centrifugation to separate the washed fiber solids #4B from the insoluble protein solids and soluble protein extract #4B at ambient temperature using the Bird Decanter at a bowl speed of 1,500 rpm and a feed rate of 150 kg/hr. Approximately 19.88 kg of washed fiber solids #4B containing 18.23% solids and 42.5 kg of insoluble and soluble protein slurry #4B containing 6.56% solids were produced.

The insoluble protein solids and soluble protein extract #4A and #4B were combined, which was followed by centrifugation using the Bird Decanter at 5,000 rpm to separate the insoluble protein solids #4C from the soluble and insoluble protein slurry #4C. Approximately 2.2 kg of insoluble protein solids #4C containing 15.27% solids and 102.5 kg of soluble and insoluble protein slurry #4C containing 7.97% solids were produced.

(e) Fourth Recycling

Figure 31:
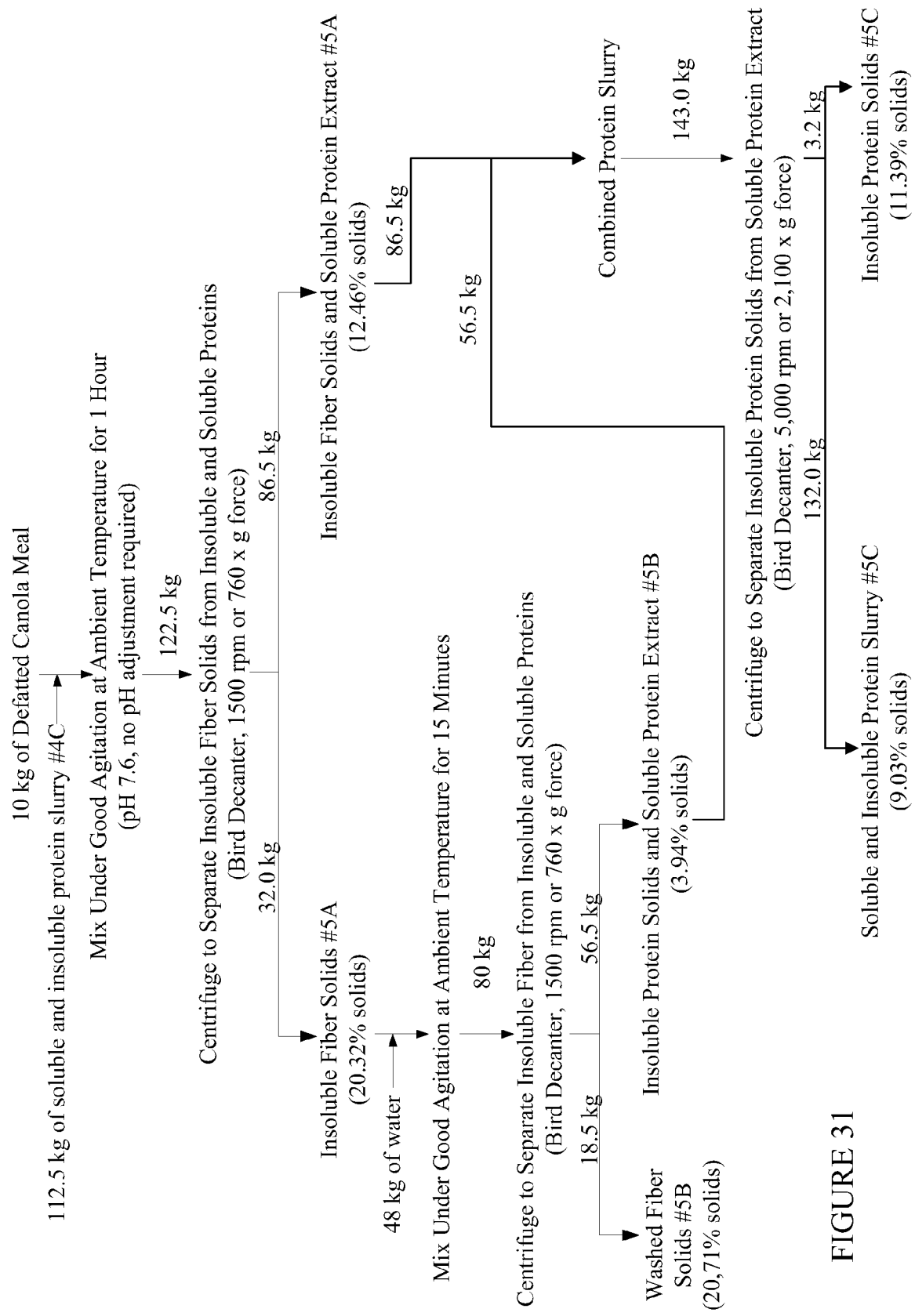
FIG. 31 is a schematic representation illustrating a fourth recycling of a protein fraction and a wet fiber removal process.

A schematic flowchart for wet fiber separation and the 4$^{th}$ recycle is shown in FIG. 31. Approximately 10 kg of defatted meal was mixed with 112.5 kg of soluble and insoluble protein slurry #4C generated from the previous wet fiber separation process under homogeneous agitation for 1 hour. The pH of protein slurry was at 7.6 and no further pH adjustment was required. The canola meal slurry was centrifuged at ambient temperature using a Bird Decanter Centrifuge (Bird 6" Continuous Bowl Centrifuge, Bird Machine Company of Canada, Saskatoon, Saskatchewan) at 1,500 rpm bowl speed and a low pool depth. The canola meal slurry was pumped through the Bird Decanter at ambient temperature and a feed rate of 150 kg/hr to separate the coarse fiber solids from the soluble and insoluble protein fractions. Approximately 32.0 kg of wet fiber solids #5A containing 20.32% solids and 86.5 kg of protein slurry #5A containing soluble and insoluble proteins at 12.46% solids were produced, respectively.

The wet fiber solids #5A was mixed with 48 kg of water in a tank for 15 minutes, which was followed by centrifugation to separate the washed fiber solids #5B from the insoluble protein solids and soluble protein extract #5B at ambient temperature using the Bird Decanter at a bowl speed of 1,500 rpm and a feed rate of 150 kg/hr. Approximately 18.5 kg of washed fiber solids #5B containing 20.71% solids and 56.5 kg of insoluble and soluble protein slurry #56 containing 3.94% solids were produced.

The insoluble protein solids and soluble protein extract #5A and #5B were combined, which was followed by centrifugation using the Bird Decanter at 5,000 rpm to separate the insoluble protein solids #5C from the soluble and insoluble protein slurry #5C. Approximately 3.2 kg of insoluble protein solids #5C containing 11.39% solids and 132 kg of soluble and insoluble protein slurry #5C containing 9.03% solids were produced.

(f) Fifth Recycling

Figure 32:
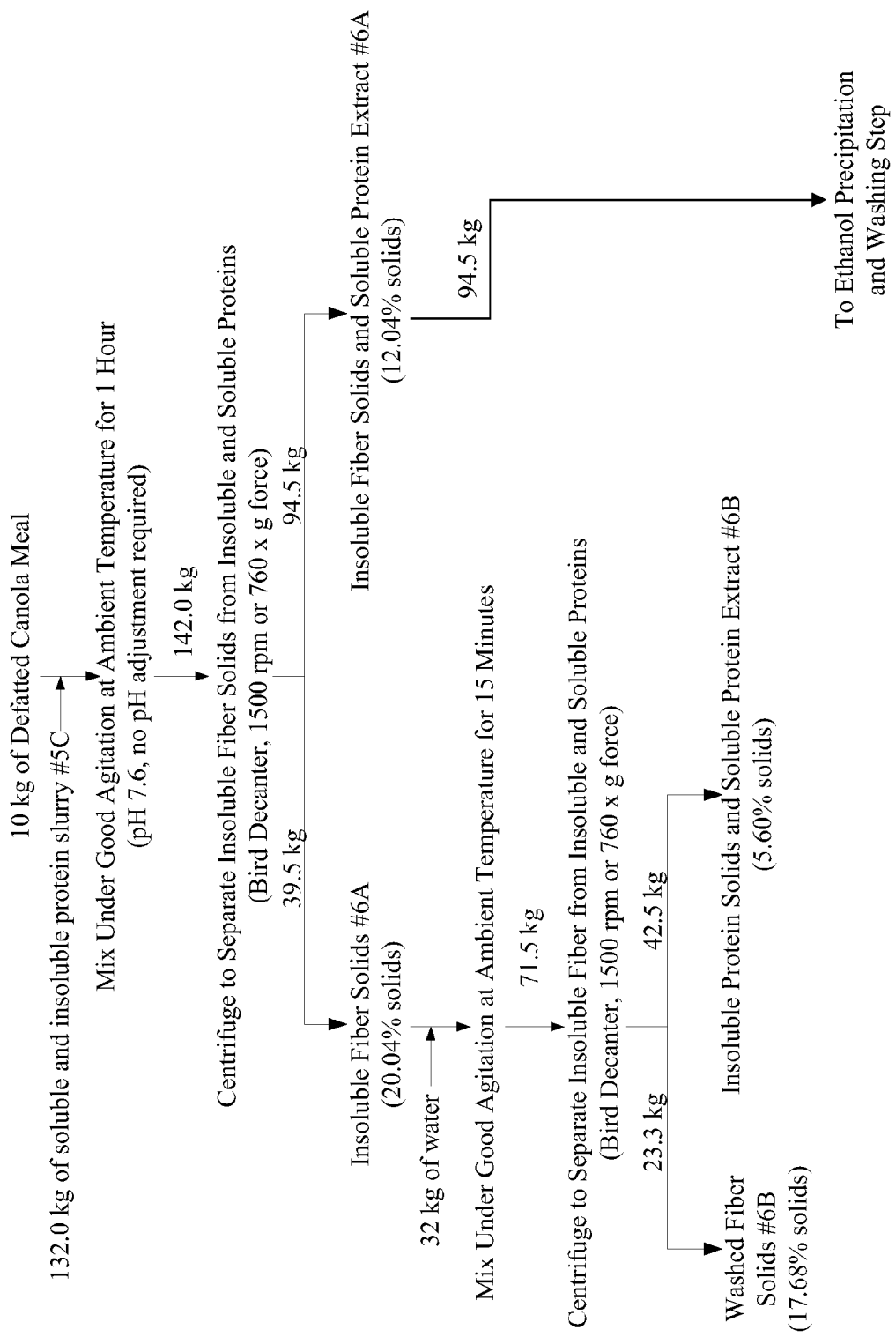
FIG. 32 is a schematic representation illustrating a fifth recycling of a protein fraction and a wet fiber removal process.

A schematic flowchart for wet fiber separation and the 5$^{th}$ recycle is shown in FIG. 32. Approximately 10 kg of defatted meal was mixed with 132 kg of soluble and insoluble protein slurry #5C generated from the previous wet fiber separation process under homogeneous agitation for 1 hour. The pH of protein slurry was at 7.6 and no further pH adjustment was required. The canola meal slurry was centrifuged at ambient temperature using a Bird Decanter Centrifuge (Bird 6" Continuous Bowl Centrifuge, Bird Machine Company of Canada, Saskatoon, Saskatchewan) at 1,500 rpm bowl speed and a low pool depth. The canola meal slurry was pumped through the Bird Decanter at ambient temperature and a feed rate of 150 kg/hr to separate the coarse fiber solids from the soluble and insoluble protein fractions. Approximately 39.5 kg of wet fiber solids #6A containing 20.04% solids and 94.5 kg of protein slurry #6A containing soluble and insoluble proteins at 12.04% solids were produced, respectively.

The wet fiber solids #6A was mixed with 32 kg of water in a tank for 15 minutes, which was followed by centrifugation to separate the washed fiber solids #6B from the insoluble protein solids and soluble protein extract #6B at ambient temperature using the Bird Decanter at a bowl speed of 1,500 rpm and a feed rate of 150 kg/hr. Approximately 23.3 kg of washed fiber solids #6B containing 17.68% solids and 42.5 kg of insoluble and soluble protein slurry #6B containing 5.60% solids were produced.

(iii) Preparation of Canola Protein Concentrate from Recycled Protein Slurry

Figure 33:
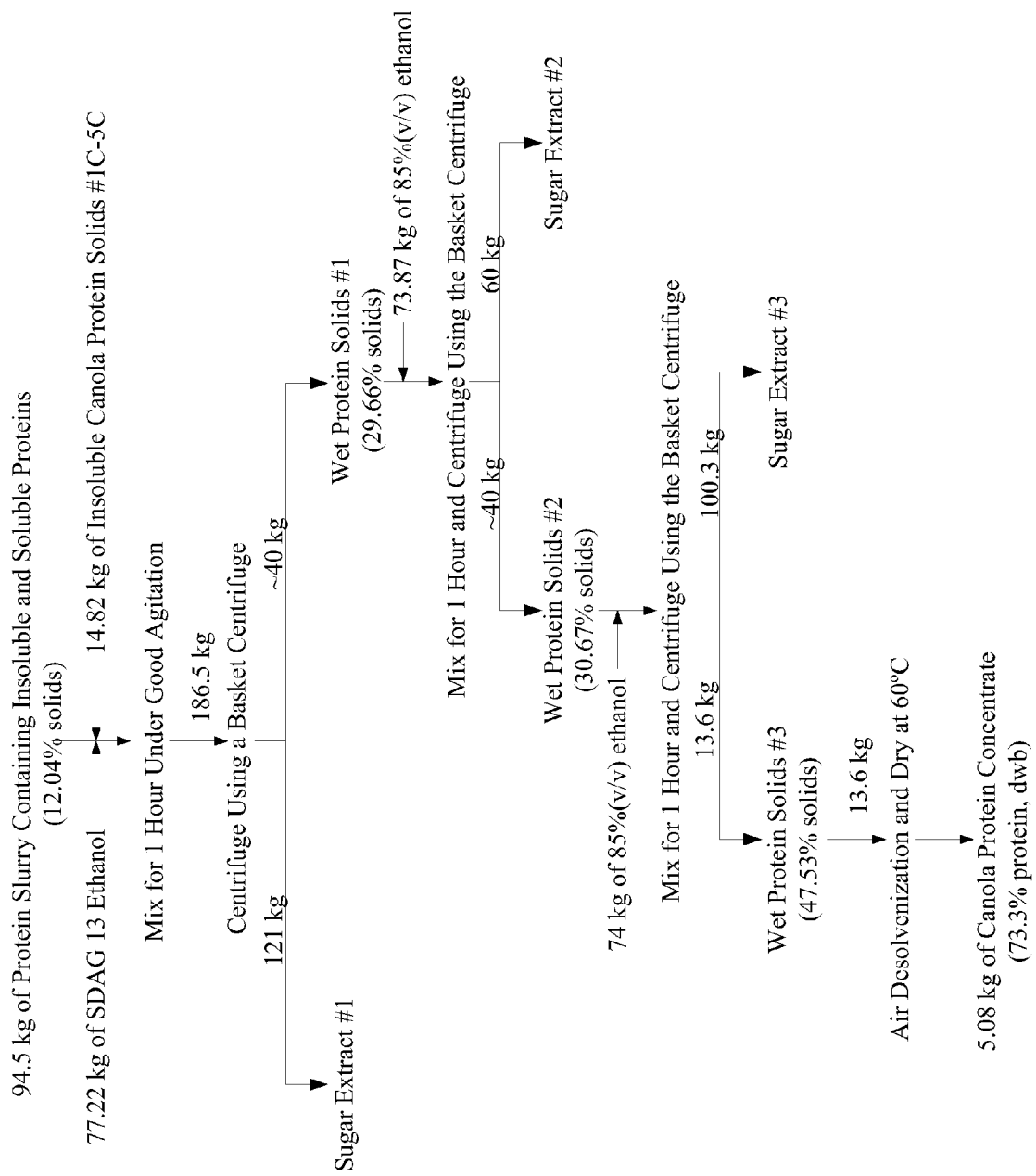
FIG. 33 is schematic representation illustrating a preparation of a protein concentrate produced by recycling a protein fraction.

A schematic flowchart for preparation of protein concentrate from the defatted meal slurry after the fiber removal is shown in FIG. 33. 94.5 kg of protein slurry containing soluble and insoluble proteins after the fiber removal and 14.82 kg of insoluble protein solids #1C-#5C were mixed with 77.22 kg of SDAG 13 denatured ethanol (containing 99% ethanol and 1% ethyl acetate) for 1 hour at room temperature. This was followed by centrifugation using a Basket Centrifuge (Tolhurst—26 in. Center-Slung, Ametek, Inc., East Moline, Ill., USA) to obtain 121 kg of sugar extract #1 and ~40 kg of wet protein solids #1 containing 29.66% solids. The wet protein solids (~40 kg) were mixed with 73.87 kg of 85% ethanol (v/v) for 1 hour at ambient temperature. This was again followed by centrifugation using the Basket Centrifuge to obtain 60 kg of sugar extract #2 and ~40 kg of wet protein solid #2 containing 30.67% solids. Finally, the wet protein solids (~40 kg) were mixed with 74 kg of 85% ethanol (v/v) for 1 hour at ambient temperature, which was followed by centrifugation using the Basket Centrifuge to obtain 100.3 kg of sugar extract #3 and 13.6 kg of wet protein solid #3 containing 47.53% solids. The wet protein solids #3 was air desolventized in a lab fume hood for 2 days, which was followed by drying at 60° C. in a forced air oven until the moisture content is below 7%. The protein concentrate contained 73.3% protein on a dry weight basis.

Discussion

As shown in Table 47, canola protein concentrate containing 73.3% protein (dwb) and 3.78% crude fiber (dwb) was produced from defatted canola meal (*B. juncea*) the wet fiber separation method based on the density and particle size difference between the insoluble fiber particles and the insoluble protein particles. In an embodiment, dry screening to prepare a protein enriched meal from defatted meal is not required, which increases the protein recovery yield in the protein concentrate.

As shown in Table 48, after the wet fiber separation by centrifugation, the protein slurry containing soluble and insoluble proteins is recycled to mix with the defatted meal before the fiber separation. The solid content of the protein slurry containing soluble and insoluble proteins was increased from 6.31% solids to 12.46% solids after 4 recycling trials. Higher solid content in the canola slurry did not affect the fiber separation by the wet fiber separation process. The protein content of the protein slurry containing insoluble and soluble proteins was increased while the crude fiber content remained at similar level with the increased in the solid content (Table 48). Interestingly, canola protein slurry #6A contained 57.6% protein (dwb) and 1.60% crude fiber (dwb) after the fiber separation and before ethanol precipitation. Canola protein concentrate containing 73.3% protein (dwb) and 3.78% crude fiber was produced. In an embodiment, the fiber separation by the decanter centrifuge based on the density difference results in a low crude fiber content in the protein slurry containing soluble and insoluble proteins after fiber separation and removal.

As shown in Table 49, the $1^{st}$ ethanol precipitation increased the protein content to 69.3% (dwb), the $1^{st}$ ethanol washing increased the protein content to 70.6% (dwb) and the $2^{nd}$ ethanol washing increased the protein content to 73.3% (dwb). In an embodiment, a one step ethanol precipitation is sufficient to produce a protein concentrate containing 70% protein (dwb) and a low fiber content comparable to soy protein concentrate. In another embodiment, a membrane filtration process is conducted on the protein slurry containing soluble and insoluble proteins at high solid content after fiber separation to concentrate and purify proteins before spray drying to produce protein concentrate containing 70% protein (dwb). In an embodiment, an ultrafiltration is utilized since the protein slurry at high solid content already has reasonable purity in terms of protein content.

In an embodiment, the increase in the solid content of the protein slurry containing soluble and insoluble proteins serves the purpose of reducing the processing volume and the amount of ethanol usage. This would reduce the size of the equipment, energy consumption, processing cost and capital investment.

Example 9

Figure 34:
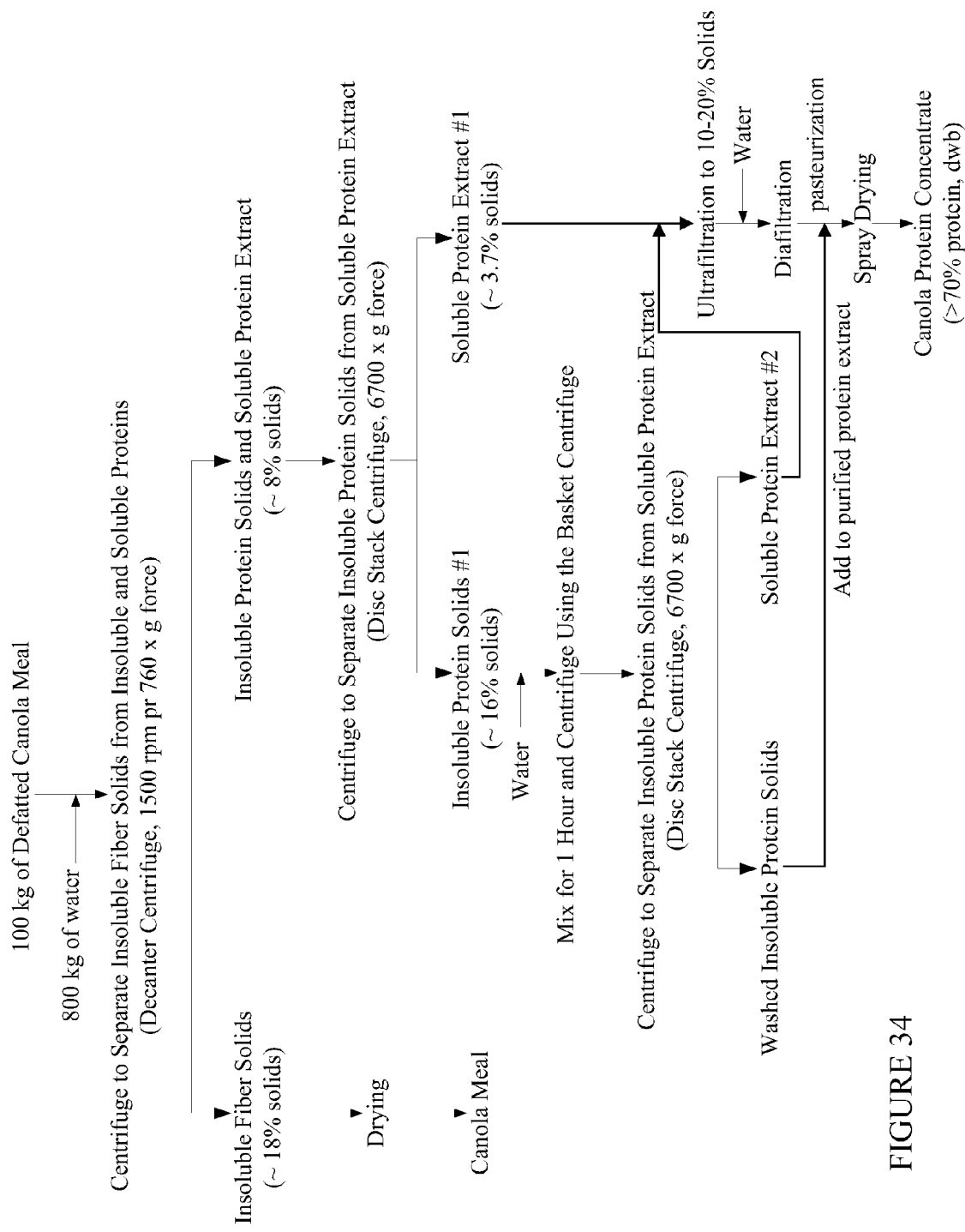
FIG. 34 is a schematic representation of a first embodiment illustrating a preparation of a protein concentrate.

Hypothetical Example of Preparation of Canola Protein Concentrate Containing Greater than 70% Protein A schematic representation for the preparation of canola protein concentrate by membrane filtration is shown in FIG. 34. 100 kg of defatted meal is mixed with 800 kg of water at a ratio of 1 to 8 (by weight) under homogeneous agitation. This is followed by centrifugation at room temperature using a Decanter Centrifuge at 1500 rpm bowl speed and a low pool depth to separate the insoluble fiber solids from the protein slurry containing insoluble and soluble proteins. The protein slurry containing soluble and insoluble proteins after the fiber removal is centrifuged using a Disc Stack Centrifuge at ambient temperature to separate the soluble protein extract #1 from the insoluble protein solids #1. The insoluble protein solids #1 is mixed with water at a ratio of 1 to 2 by weight at ambient temperature for 0.5 hour under homogeneous agitation, which is followed by centrifugation using the Disc Stack Centrifuge to separate soluble protein extract #2 from the washed insoluble protein solids.

Soluble protein extracts #1 and #2 are combined and the combined extract is adjusted to pH 7.0 by addition of 11% NaOH solution if the pH is below 7, which is followed by concentration of the protein extract in the feed tank to 10-20% solids using a ultrafiltration membrane with a molecular weight cutoff of 10,000-100,000 daltons. The protein extract is pumped through the membrane unit while the retentate is recycled back to the feed tank and the permeate is collected in another tank.

Water is then added into the feed tank and diafiltration is conducted using the ultrafiltration membrane with a molecular weight cutoff of 10,000-100,000 daltons. The original volume of protein solution in the feed tank is held constant by adding water to make up for the removed permeate. The retentate is recycled back to the feed tank. Sufficient amount of water is used in the diafiltration process until the retentate contains 90% protein or higher on a dry weight basis.

The purified protein extract from ultrafiltration and diafiltration is mixed with the washed insoluble protein solids, which is followed by pasteurization (UV or heat). The pasteurized protein slurry containing soluble and insoluble proteins is spray dried into protein concentrate containing 70% protein or higher.

Example 10

Figure 35:
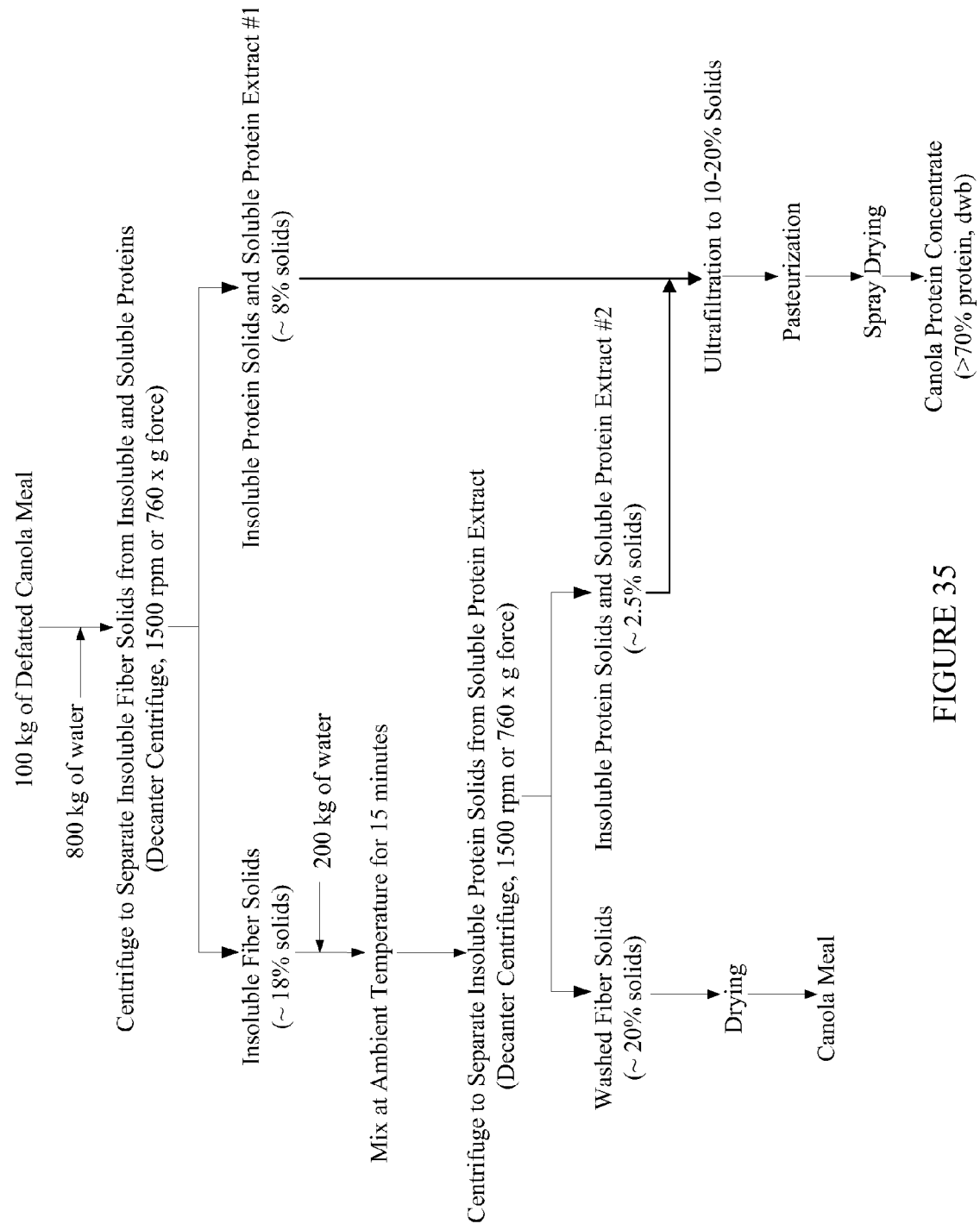
FIG. 35 is a schematic representation of a second embodiment illustrating a preparation of a protein concentrate.

Hypothetical Example of Preparation of Canola Protein Concentrate Containing Greater than 70% Protein A schematic representation for preparation of a canola protein concentrate by membrane filtration is shown in FIG. 35. 100 kg of defatted meal is mixed with 800 kg of water at a ratio of 1 to 8 (by weight) under homogeneous agitation. This is followed by centrifugation at ambient temperature using a Decanter Centrifuge at 1500 rpm bowl speed and a low pool depth to separate the insoluble fiber solids from the protein slurry #1 containing insoluble and soluble proteins. The insoluble fiber solids are mixed with 200 kg of water for 15 minutes at ambient temperature, which is followed by centrifugation using the Decanter Centrifuge at 1500 rpm bowl speed and a low pool depth to separate the washed fiber solids from the protein slurry #2 containing insoluble and soluble proteins.

Protein slurries #1 and #2 are combined and the combined slurry is adjusted to pH 7.0 by addition of 11% NaOH solution if the pH is below 7, which is followed by concentration of the protein slurry in the feed tank to about 20% solids using a microfiltration membrane of 0.1-0.2 micron and an ultrafiltration membrane with a molecular weight cutoff of 10,000-100,000 daltons. The protein slurry is pumped through the membrane unit while the retentate is recycled back to the feed tank and the permeate is collected in another tank.

The purified protein slurry from the ultrafiltration process is pasteurized by UV or heat. The pasteurized protein slurry containing soluble and insoluble proteins is spray dried into protein concentrate containing 70% protein.

Prophetic Example 11

Protein Concentrate of about 70-75% Protein Fiber Hydrolysis and Ethanol Washing The process for preparation of protein-enriched meal is the same as that of Example 1. Approximately 1 kg of protein-enriched meal is mixed with 6 kg of water in a lab Eberbach Waring Blenderunder for 5 minutes to breakdown the insoluble protein and fiber particles. The protein slurry is added to a beaker and pH of the slurry is adjusted to 5±0.2 under good agitation using a magnetic stirrer. Approximately 0.5% cellulase or cellulase complex based on the weight of starting protein enriched meal is added to the protein slurry. The slurry is heated to 55-60° C. and held at this temperature range for 4 hours. After enzymatic reaction, 8 kg of 100% (v/v) ethanol is added to the protein slurry, which is followed by mixing for 0.5 hour at 55-60° C. The protein slurry is centrifuged at 4,000 g force for 15 minutes to separate the protein solids from the sugar extract. The sugar extract is concentrated and dried to produce a dried sugar and fraction. The protein solids are dried under vacuum to produce a protein concentrate containing 70-75% protein on a dry weight basis.

Prophetic Example 12

Protein Concentrate of ≥80% Protein and Protein Isolate of ≥90% Protein

Fiber Removal by Screening and Centrifugation 1,000 kg of canola seed at 7-10% moisture is conditioned at 80±5° C. for 30±10 minutes in a stack cooker, which is followed by pressing using a DeSmet mini press. Approximately 800 kg of pressed cake and 200 kg of pressed oil are produced. The pressed cake has a PDI (protein dispersibility index) of 30-35. The pressed cake is extracted with hexane at 55-60° C. for 1 hour using a Crown counter-current extractor at a ratio of hexane to cake of 2 to 1 by weight. The extracted meal is desolventized and dried at 50° C. for 5 hours under vacuum using a Littleford® dryer to a solvent residue of less than 500 ppm. Approximately 520 kg of extracted meal is produced.

The extracted meal is milled using a disc mill at a gap of 0.02" and the milled meal is screened through a 45 US mesh screen using a Rotary Vibratory Screen. Approximately 220 kg of protein enriched meal and 300 kg of fiber enriched meal are produced.

Approximately 220 kg of protein enriched meal is mixed with 2,200 kg of water under good agitation. The protein slurry is screened through a 40 mesh US screen at ambient temperature to remove some fiber. The slurry is adjusted to a pH of 7, which is followed by wet milling through a wet mill (Szego Mill) at ambient temperature. The slurry is centrifuged using a decanter (Bird Decanter) at ambient temperature to separate the rest of fiber from the soluble and insoluble proteins at a bowl speed of 1,500 rpm. The slurry of soluble and insoluble proteins is centrifuged again at ambient temperature to separate the soluble protein solution from the insoluble protein precipitates using a disc stack centrifuge (Westfalia® Desludger).

The insoluble protein precipitates are washed with water 2 times at ambient temperature, and the washed protein precipitates are separated from the washing liquid using a disc stack centrifuge at ambient temperature. The washed protein precipitates are mixed with 2 parts of water and pH of the slurry is adjusted to pH7 at ambient temperature. The slurry of protein precipitates is spray dried using a spray dryer at an inlet temperature of 190° C. and outlet temperature of 85° C. to a dried protein concentrate of 80-85% protein on a dry weight basis.

The soluble protein solution recovered from the centrifugation operations is heated to 45-50° C. before being passed through hollow fiber ultrafiltration cartridge membranes with a molecular weight cutoff of 10,000 daltons. The hollow fiber cartridges are fitted to a Millipore® ultrafiltration unit. The retentate was recycled back to the feed tank and the permeate is discarded. The ultrafiltration process is continued until the amount of protein solution in the feed tank is equal to 25% of its initial weight. After the ultrafiltration is completed; diafiltration is conducted at 45-50° C. using the same ultrafiltration unit which is fitted with the same hollow fiber cartridges. The original volume of protein solution in the feed tank is held constant by adding water to make up for the removed permeate. The retentate is recycled back to the feed tank. The amount of water received to maintain the original volume of protein solution is 3 times the original volume of protein solution. Finally, after all the water is added to the feed tank, the purified protein solution is adjusted to pH7 before it is spray dried into a dried protein isolate containing ≥90% protein on a dry weight basis using a spray dryer. The spray drying conditions are the same as those used for the protein concentrate.

Prophetic Example 13

Protein Concentrate of ≥80% Protein and Protein Isolate of ≥90% Protein

Fiber Hydrolysis by Cellulase or Cellulase Complex

The process for preparation of protein enriched meal from canola seed is the same as that of Prophetic Example 12.

Approximately 220 kg of protein enriched meal is mixed with 2,200 kg of water under good agitation. The protein slurry is screened through a 40 mesh US screen at ambient temperature to remove some fiber, which is followed by wet milling the protein slurry through a wet mill (Szego Mill) at ambient temperature. The protein slurry is centrifuged at ambient temperature to separate the soluble protein solution from the insoluble protein and fiber solids using a disc stack centrifuge (Wesffalia® Desludger).

The insoluble solids are mixed with 3 parts of water, which is followed by pH adjustment to 5±0.2. Approximately 0.5% cellulase or cellulase complex based on the weight of starting protein enriched meal is added to the protein slurry. The slurry is heated to 55-60° C. and held at this temperature range for 4 hours. After enzymatic reaction, the insoluble protein solids are washed with water following the same process as outlined in Example 4 to produce a protein concentrate of ≥80% protein.

The process to produce protein isolate of ≥90% protein from the soluble protein solution is the same as that of Example 12.

Example 14

Preparation of Canola Protein Concentrate

Figure 40:
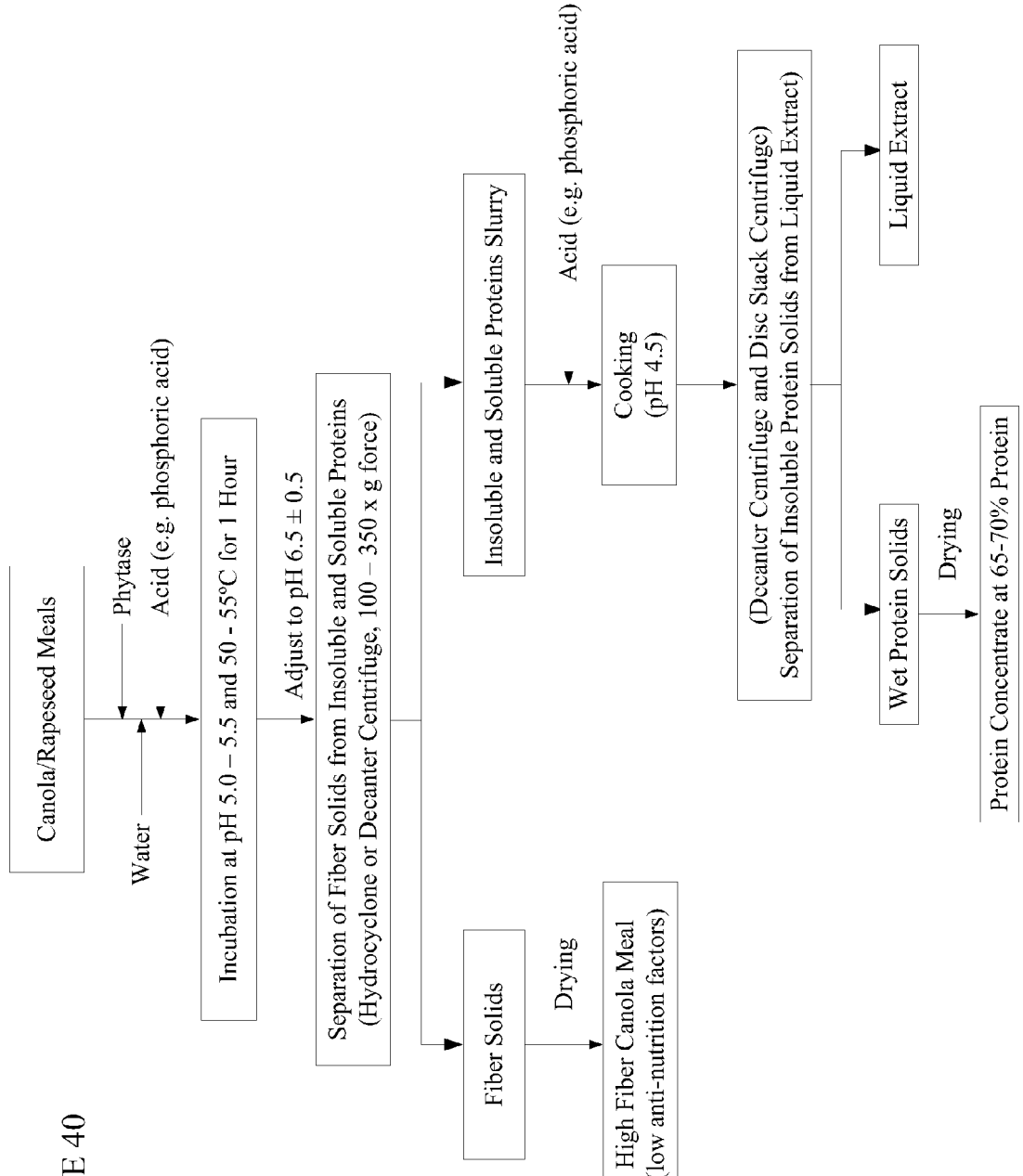
FIG. 40 is a schematic representation of a first embodiment showing the removal of fiber during the preparation of a protein concentrate from a defatted meal.
Figure 41:
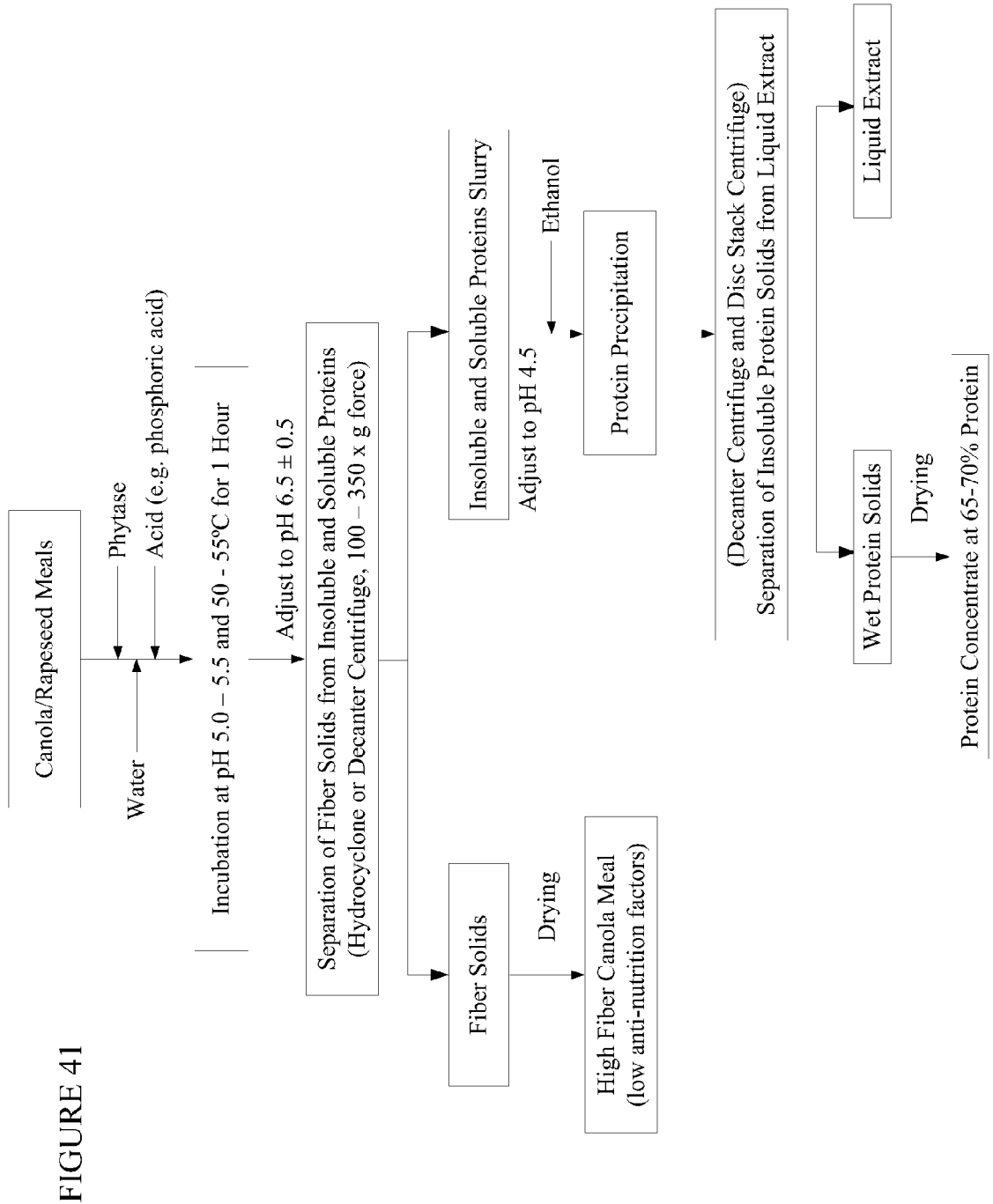
FIG. 41 is a schematic representation of a second embodiment showing the removal of fiber during the preparation of a protein concentrate from a defatted meal.
Figure 42:
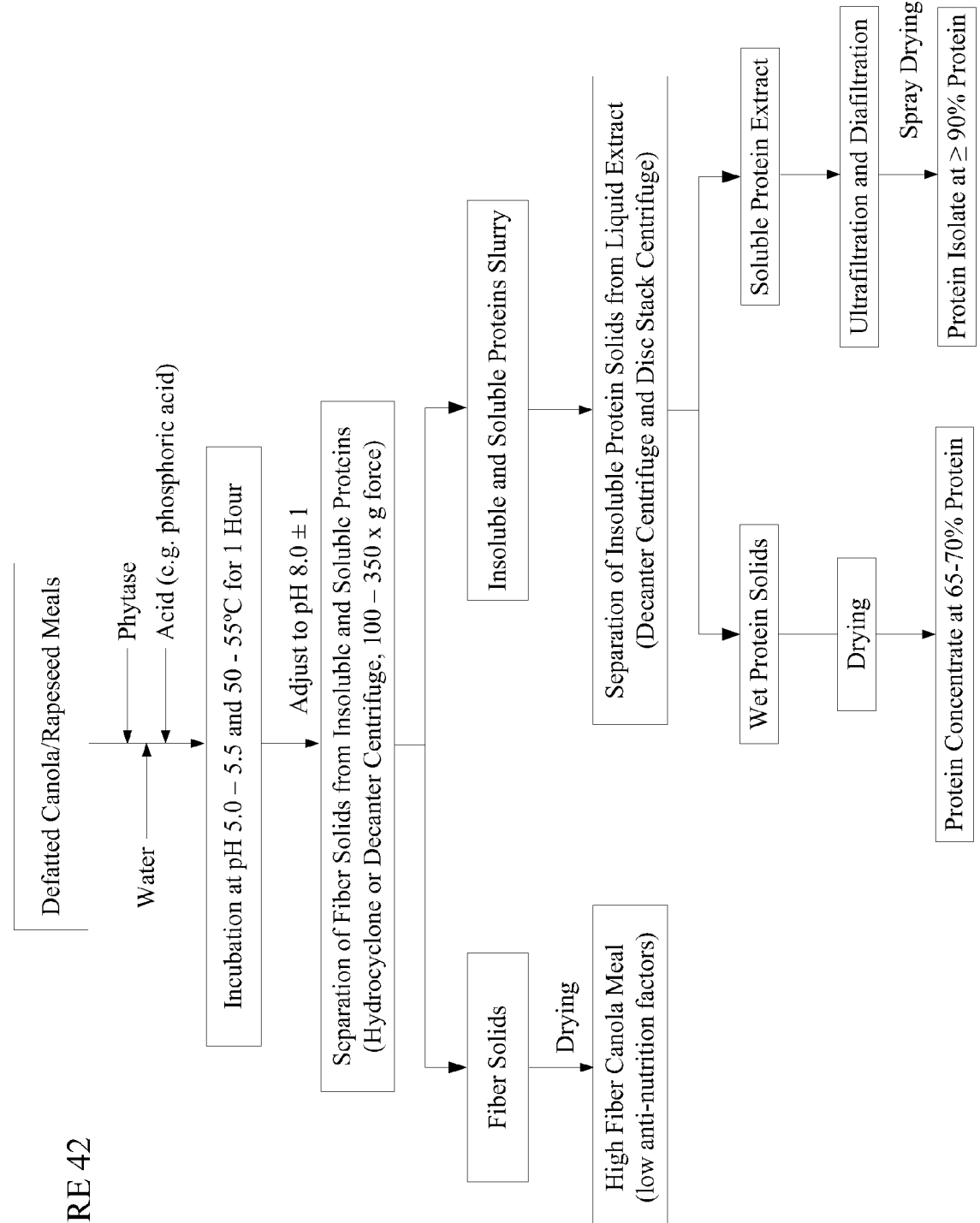
FIG. 42 is a schematic representation showing the removal of fiber during the preparation of a protein concentrate and a protein isolate from a defatted meal.

A canola protein concentrate was produced from 3,325 kg of low temperature defatted canola meal (*B. juncea*). Seven batches of processing were carried out with 500 kg of defatted meal for six batches and 325 kg of defatted meal for the last batch. For each batch of processing, defatted canola meal was mixed with tap water at a ratio of 1 to 8 by weight. The canola meal slurry was mixed at ambient temperature for 1 hour before it was pumped to an Andritz® decanter centrifuge (Model D3LVN, Andritz Separation Inc., San Leandro, Calif., USA) at ambient temperature for the separation of fiber solids from protein slurry containing soluble and insoluble proteins. A typical spin down test showed three layers, 50% top supernatant layer, 25% middle insoluble fine protein solids, and 25% insoluble coarse fiber solids. The decanter centrifuge was operated at the optimum conditions in order to have a clean separation of the bottom coarse fiber solids (25% of the total canola meal slurry) from the protein slurry containing supernatant (50% of the total canola meal slurry) and fine insoluble protein solids (25% of the total canola meal slurry). The operational conditions of the centrifuge are shown in Table 50, and procedures using low-speed centrifugation are schematically shown in FIGS. 40-42.

The protein slurry containing supernatant and fine insoluble protein solids was immediately mixed with 100% denatured ethanol at a ratio of 1 to 1 by volume by pumping the protein slurry into the ethanol in 5600 L stainless tanks. The proteins precipitated in ethanol. The majority of precipitated proteins was recovered by centrifugation using a Wesffalia® Decanter (Model CA-365) at 3,200 g (4,000 RPM). The remaining precipitated proteins in the supernatant were recovered using a Wesffalia® Disc Stack Centrifuge (Model SA-14, Germany) at 6,715 g (7,560 rpm). The recovered protein solids were mixed with 85% ethanol (v/v) at ambient temperature for 1 hour. The amount of 85% ethanol (v/v) was equivalent to 6 times of the starting weight of defatted canola meal. The washed protein solids were recovered by centrifugation using the Westfalia Decanter (Model CA-365) at 3,200 g (4,000 RPM) and ambient temperature. The washed protein solids were again mixed with 85% ethanol (v/v) equivalent to 6 times of starting weight of defatted canola meal. The second washed protein solids were also recovered by centrifugation using the Westfalia® Decanter (Model CA-365) at 3,200 g (4,000 RPM) and ambient temperature. Finally, the second washed protein solids were dried to 3.11-6.66% moisture using a Barr-Rosin Closed Circuit Ring Dryer. Approximately 760 kg of protein concentrate at 69.2-72.7% protein (dwb) was produced from 3,325 kg of defatted canola meal (as seen in Table 51). The produced protein concentrate was a free flow powder with cream white color. It contained a very low glucosinolate content of 0.2 μmole/g, a sinapine content of 0.019% and a phytate content of <0.05%.

The recovered yield of canola protein concentrate can be increased significantly by washing of the fiber solids once or twice in order to recover more soluble and insoluble proteins. Ethanol was reclaimed and recycled from the liquid streams through evaporation and distillation using a single stage falling film evaporator and a bubble sieve tray distillation system.

As shown in Table 50, the wet fiber separation process by centrifugation at 274-350 g using the Andritz® Decanter (as seen in Table 50) reduced the crude fiber content to 2.60-3.28% in the protein slurries from 6.98% in the defatted canola meal on a dry weight basis. The crude fiber content in the fiber solids was increased to 12.14-14.03% (dwb). Ethanol precipitation process increased the protein content from 52.1-54.2% (dwb) in the protein slurries to 63.8-67.4% (dwb) in the precipitated proteins. Wash of the precipitated proteins with 85% ethanol (v/v) twice further increased the protein content to 69.2-72.7% protein (dwb) in the final protein concentrates.

Example 15

Preparation of Canola Protein Isolate Using Phytase

Approximately 62.5 kg of defatted canola meal was mixed with 500 kg of water in a tank. Approximately 50 g of phytase (Natuphos® 10,000 L Phytase) at 0.08% dosage based on the starting weight of defatted canola meal was added to the canola meal slurry. The pH of canola meal slurry was at about 6.0 and temperature between 20° C.-38° C. After holding for 1.5 hours under agitation, the protein fraction was separated from the wet solids using an Alfa Laval® decanter centrifuge at maximum g force.

The wet solids were mixed with 331 kg of water in a tank at ambient temperature for 80 minutes. This was followed by centrifugation using the decanter to separate the washing extract from the washed solids.

The protein fractions were combined together and approximately 736 kg of combined protein fractions was produced. The combined protein fraction was clarified using an Alfa Laval® disc stack centrifuge to remove the remaining insoluble solids. Approximately 59 kg of wet solids and 677 kg of clarified protein extract were produced, respectively.

677 kg of clarified protein extract was concentrated at 41-47° C. from the initial 2.45% solids to 16% solids at an average flux rate of 58 liters per square meter per hour using an Alfa Laval® UF system fitted with spiral wound membrane (2×GR60PP-3838/80, 6.08 m² total surface area) with a molecular weight cut-off of 25,000 Dalton. Purify of protein extract was increased from 45% to 85% by ultrafiltration.

Phytase broke phytates through an enzymatic action, which prevented the gel formation of phytates-protein complex on the membrane. This resulted in higher average flux rate and increased the filtration efficiency.

Example 16

Preparation of Canola Protein Isolate Using Phytase During Filtration

Approximately 64 kg of defatted canola meal was mixed with 510 kg of water in a tank. The pH of canola meal slurry was at about 6.0 and temperature at 21° C. After holding for 1 hour and 50 minutes under agitation, the protein fraction was separated from wet solids using an Alfa Laval® decanter centrifuge at maximum g force.

The wet solids were mixed with 330 kg of water in a tank at ambient temperature for 1 hour. This was followed by centrifugation using the decanter to separate the washing extract from the washed solids.

The protein fractions were combined together and approximately 868 kg of combined protein fraction was produced. The combined protein fraction was clarified using an Alfa Laval® disc stack centrifuge to remove the remaining insoluble solids. Approximately 67 kg of wet solids and 801 kg of clarified protein extract were produced, respectively.

801 kg of clarified protein extract was fed to a Alfa Laval UF® system fitted with spiral wound membrane (2×GR60PP-3838/80, 6.08 m² total surface area) with a molecular weight cut-off of 25,000 Dalton. Shortly after the UF filtration was started at 40-43° C., a severe drop in flux rate was observed, from 65 liters per square meter per hour to 11 liters per square meter per hour in 23 minutes. Approximately 50 g of phytase (Natuphos® 10,000 L Phytase) at 0.08% dosage based on the starting weight of defatted canola meal was added to the clarified protein extract. The flux rate of UF filtration increased quickly from 11 liters per square meter per hour to 65 liters per square meter per hour. The clarified protein extract was concentrated at 44-50° C. from the initial 2.5% solids to 20% solids at an average flux rate of 41 liters per square meter per hour using the Alfa Laval UF system. Purify of protein extract was increased to 86% by ultrafiltration.

Discussion

Phytase broke phytates through enzymatic action, which prevented the gel formation of phytates-protein complex on the membrane surface. This resulted in higher average flux rate and increased the filtration efficiency.

Example 17

Preparation of Canola Protein Isolate Using Phytase at High pH

Approximately 55.5 kg of defatted canola meal was mixed with 444 kg of water in a tank. Approximately 50 g of phytase (Natuphos 10,000 L Phytase) at 0.09% dosage based on the starting weight of defatted canola meal was added to the canola meal slurry. The pH of canola meal slurry was adjusted from 6.0 to 7.0 by addition of 6 M NaOH. The temperature of canola meal slurry was 25° C. After holding for 1 hour and 40 minutes under agitation, the protein fraction was separated from wet solids using a Alfa Laval® decanter centrifuge at maximum g force.

The wet solids were mixed with 300 kg of water in a tank at ambient temperature for 1 hour. This was followed by centrifugation using the decanter to separate the washing extract from the washed solids.

The protein fractions were combined together and approximately 681 kg of combined protein extract was produced. The combined protein extract was clarified using an Alfa Laval disc stack centrifuge to remove the remaining insoluble solids. Approximately 77 kg of wet solids and 604 kg of clarified protein extract were produced, respectively. The pH of the clarified protein extract was adjusted to 8.0 by addition of 6M NaOH.

604 kg of clarified protein extract at pH8.0 was fed to an Alfa Laval UF system fitted with spiral wound membrane (2×GR60PP-3838/80, 6.08 m² total surface area) with a molecular weight cut-off of 25,000 Dalton. The ultrafiltration temperature was controlled at 34-48° C. Severe drop in flux rate occurred from 53 liters per square meter per hour to 26 liters per square per hour in 29 minutes. The pH of the clarified protein extract was adjusted to 6.0, but no change in the flux rate of UF filtration process was observed.

Discussion

Phytase has an optimum enzyme activity in the pH range of 3.0-6.0 and the temperature range of 30-50° C. Phytase has little enzymatic activity above a pH of 7.0-7.5. Therefore, phytase had no or little enzyme activity in this trial due to a high pH of 7.0-8.0. Phytase might also be inactivated in high pH of 8.0.

Example 18

Preparation of Hydrolyzed Protein Concentrate from Recovered Fiber Solids

Approximately 126.3 kg of insoluble fiber solids were mixed with 100 kg of water in a tank. This was followed by pH adjustment to 8.3±0.1 using 0.9 kg of 11.06% NaOH solution. Approximately 0.5 kg of a $1^{st}$ protease (Alcalase® 2.4L FG) was added to the slurry. The slurry was then heated to 60±2° C. and held at this temperature for 4 hours. The slurry was cooled down to 50±2° C. and pH adjusted to 6.5. Approximately 0.5 kg of the $2^{nd}$ protease (Flavouzyme®) was added to the slurry, which was followed by holding at 50±2° C. for 4 hours. The slurry was centrifuged using a Westfalia® Decanter at 3300×g to separate the hydrolyzed protein extract from the insoluble fiber fraction. The insoluble fiber was washed further with 120 kg of filtered tap water, which was again followed by centrifugation at 3300×g to separate the wash protein extract from the washed fiber solids using the Westfalia® Decanter. The hydrolyzed protein extract and the wash hydrolyzed protein extract were combined. The combined hydrolyzed protein extract was fed to a Millipore® Ultrafiltration Unit (Model A60, Millipore Corporation, Bedford, Mass., USA) at ambient temperature. The Ultrafiltration Unit (UF) was fitted with three hollow fiber cartridges having a molecular weight cutoff of 10,000 daltons. Each cartridge contained 5 m² of membrane surface area. The hydrolyzed protein extract was pumped through the hollow fiber cartridges at a rate of 800-1000 kg/hr. The retentate was recycled back to the feed tank and the permeate was collected in another tank. The UF unit was operated at an inlet pressure of 25 psi maximum and a retentate back pressure of 15 psi maximum. The flux rate or permeate rate was about 190-300 kg/hr throughout the ultrafiltration process. The ultrafiltration process continued until about 40 kg of retentate remained in the feed tank. Approximately 260 kg of water was added continuously into the feed tank and ultrafiltration was conducted at ambient temperature using the same UF unit fitted with the same three hollow fiber cartridges. The original volume of retentate in the feed tank was held constant by adding water to make up for the removed permeate. The retentate was recycled back to the feed tank. The ultrafiltration process continued until all 260 kg of water was added to the retentate.

Approximately 540 kg of permeate and 47.7 kg of retentate were obtained from the ultrafiltration process. The permeate was spray dried to produce hydrolyzed protein concentrate using a Komline® Sanderson pilot plant spray dryer equipped with a centrifugal atomizer with a wheel speed up to 10,000 rpm (Komline® Sanderson Ltd., Brampton, Ontario, Canada). The spray drying operation was conducted at an inlet air temperature of 185±5° C. and an outlet air temperature of 85±5° C. Approximately 3.36 kg of spray dried hydrolyzed protein concentrate containing 82% protein (dwb) was produced.

Example 19

Sedimentation Velocity Analysis of Protein Content of Canola Protein Isolate, Protein Concentrate and Protein Hydrolyzate Aliquots of each of a protein isolate, protein concentrate and a protein hydrolyzate were dissolved in 3% NaCl at a weight concentration of 10 mg of powder per mL. After sitting overnight, a small portion of each was diluted 10-fold to make a solution for sedimentation velocity analysis.

Samples of the protein isolate, protein concentrate and protein hydrolyzate were loaded into cells with 2-channel charcoal-epon centerpieces with 12 mm optical pathlength. The 3% NaCl dilution buffer was loaded into the reference channel of each cell. The loaded cells were then placed into an AN-60Ti analytical rotor, loaded into a Becker-Coulter ProteomeLab® XL-I analytical ultracentrifuge equipped with both absorbance and Rayleigh interference (refractive index) optical detection, and brought to 20° C. The rotor was then brought to 3,000 rpm and the samples were scanned (using both absorbance scans and refractive index scans) to confirm proper cell loading. The rotor was then brought to the final run speed of 55,000 rpm. Scans were recorded at this rotor speed approximately every 3.2 min for about 6.2 hours (114 total scans for each optical system for each sample), and then the scan rate was dropped to every 20 minutes for an additional 15 hours (30 additional scans). Only the refractive index scans were analyzed.

Discussion

The refractive index scans were analyzed using the c(s) method and analysis program SEDFIT (version 11.3) (see Schuck, P. (2000), Size-distribution analysis of macromolecules by sedimentation velocity ultracentrifugation and Lamm equation modeling, *Biophys. J.*, 78, 1606-1619, herein incorporated by reference). In this approach, many raw data scans are directly fitted (about 195,000 data points for each sample), to derive the distribution of sedimentation coefficients, while modeling the influence of diffusion on the data in order to enhance the resolution. The method works by assigning a diffusion coefficient to each value of sedimentation coefficient based on an assumption that all species have the same overall hydrodynamic shape (with shape defined by the frictional coefficient ratio relative to that for a sphere, $f/f_0$). The $f/f_0$ values were varied to find the best overall fir of the data for each sample. A maximum entropy regularization probability of 0.683 (1σ) was used, and both time-dependent and radially-independent noise were removed. To convert the raw sedimentation coefficients to approximate standardized values all proteins in the samples were assumed to have a partial specific volume of 0.73 mL/g. A density of 1.01919 g/mL and viscosity of 1.0503 cp at 20° C. were calculated for 3% NaCl using the program SEDNTERP (see Laue, T. M., Shah, B. D., Ridgeway, T. M., and Pelletier, S. L. (1992) In: Analytical ultracentrifugation in biochemistry and polymers and science, S. E. harding, A. J. Rowe, and J. C. Horton, eds. Royal Society of Chemistry, Cambridge, pp. 90-125, herein incorporated by reference).

Figure 43:
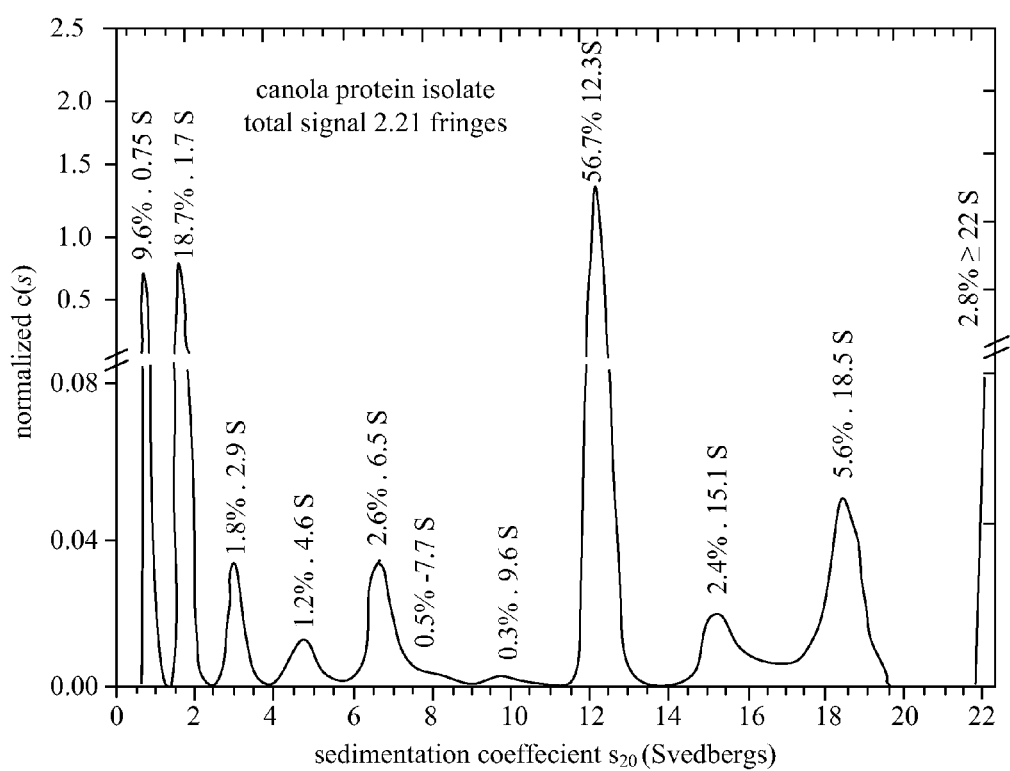
FIG. 43 is a graph showing sedimentation velocity of proteins in a protein isolate.
Figure 44:
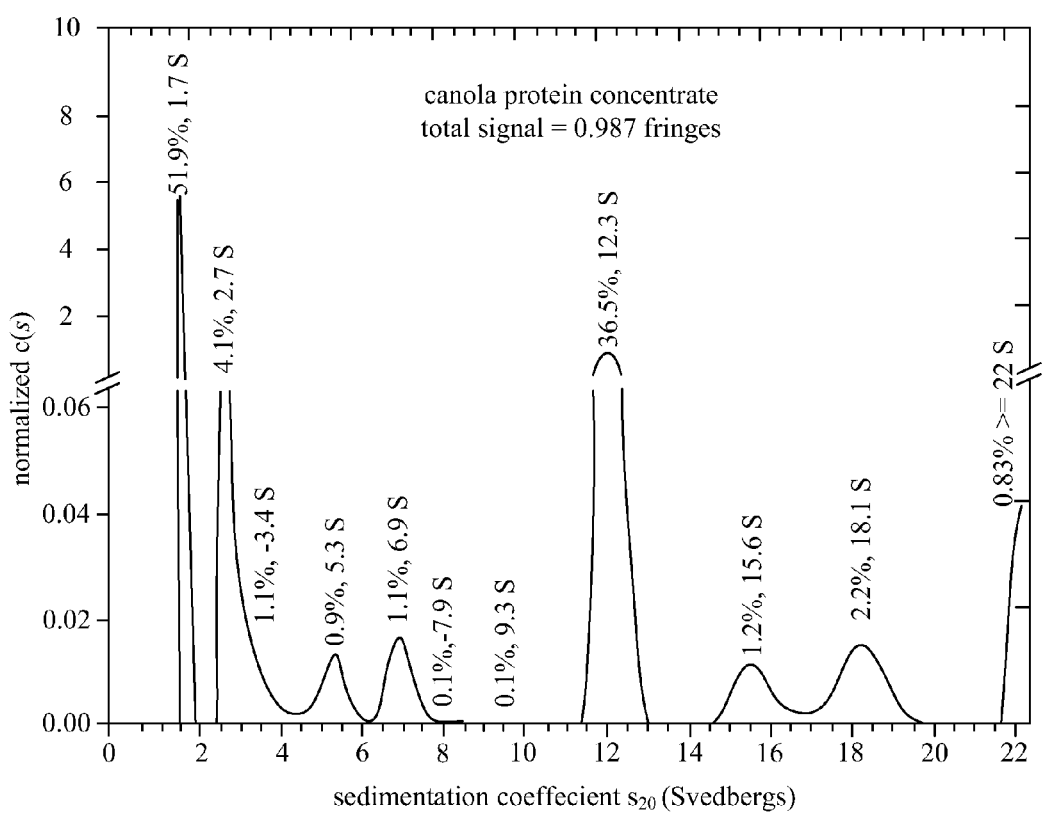
FIG. 44 is a graph showing sedimentation velocity of proteins in a protein concentrate.

The high-resolution sedimentation coefficient distributions for the canola protein isolate and canola protein concentrate samples are shown in FIGS. 43 and 44, respectively. The graphs show a vertical axis giving the concentration and the horizontal axis showing the separation on the basis of sedimentation coefficient. Each distribution has been normalized to account for any concentration differences among the samples, by setting the total area under the curve to 1.0 (100%) so the area for each peak gives the fraction of that species. The sedimentation coefficients have been approximately converted to standard conditions (adjusted for the fact that the density and viscosity of 3% NaCl are greater than those for pure water). This conversion is approximate because the information needed to make a precise buoyancy correction for each individual component is not known, and therefore a typical value is used for all components (the as-measured raw sedimentation coefficients were multiplied by 1.1108 to convert to $s_{20,w}$ values).

The protein isolate had the following percentages of proteins: 0.75S (9.6% w/w), 1.7S (16.7%), 2.9S (1.8%), 4.6S (1.2%), 6.5S (2.6%), 7.7S (0.5%), 9.6S (0.3%), 12.3S (56.7%), 15.1S (2.4%), 18.5S (5.6%) and 22S (2.8%) as shown in FIG. 43.

The protein concentrate had the following percentages of proteins: 1.7S (51.9% w/w), 2.7S (4.1%), 3.4S (1.1%), 5.3S (0.9%), 6.9S (1.1%), 7.9S (0.1%), 9.3S (0.1%), 12.3S (36.5%), 15.6 S (1.2%), 18.1S (2.2%) and 22S (0.8%) as shown in FIG. 44.

Figure 45:
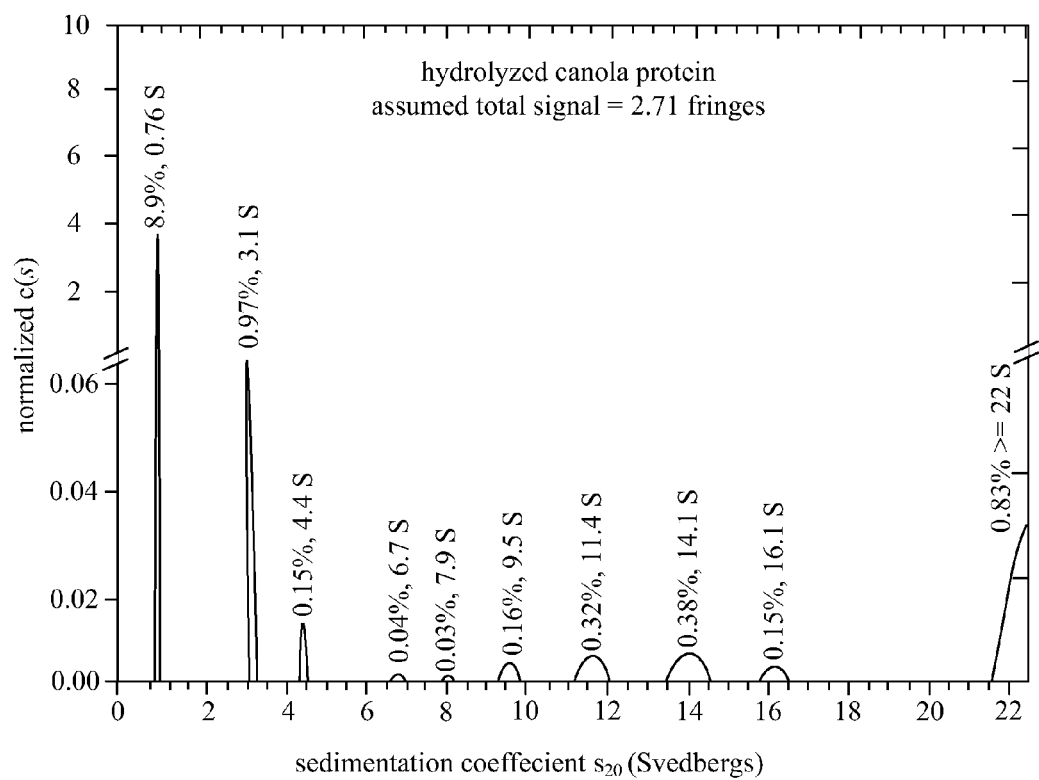
FIG. 45 is a graph showing sedimentation velocity of proteins in a hydrolyzed protein concentrate.

The hydrolyzed protein concentrate had the following percentages of proteins: 0.78S (8.9% w/w), 3.1S (0.97%), 4.4S (0.15%), 6.7S (0.04%), 7.9S (0.03%), 9.5S (0.16%), 11.4S (0.32%), 14.1S (0.38%) and 16.1S (0.15%) as shown in FIG. 45.

The size distribution for the canola protein isolate is shown in FIG. 44, possessing a total of 92.8% protein on a dry weight basis. The main component (largest fraction weight) is a species at 12.3S which is 56.7% of the total, which corresponds to a 12S protein. The two next most abundant species are at 1.7S (16.7%) (corresponding to "2S" protein) and 0.75S (9.6%) (which could also correspond to "2S" protein). Five additional minor peaks or shoulders occur between those species and the main 12.3S peak, and three other peaks sedimenting faster than the main peak. There is also a peak at 22.2S, it is possible that some or all of this 2.8% is actually sedimenting faster than 22.2S. It is also possible that the isolate sample contained some very large aggregates or incompletely-dissolved components that pelleted during the rotor acceleration to 55,000 rpm and therefore were not detected.

The results for the canola protein concentrate sample are shown in FIG. 44, possessing a total of 71.2% protein on a dry weight basis. The protein concentration (total signal) of this sample is more than 2-fold lower than that of the protein isolate, presumably due to loss of insoluble material. In this case the principal component is the peak at 1.7S (corresponding to a "2S" protein), which is 51.9% of the total, with the 12S protein still a major component (36.5%). This sample contains little of a 7S component. It is important to note that equivalent peaks will not necessarily appear at exactly the same sedimentation coefficient. With this method it is normal for the positions of minor peaks to shift somewhat from one sample to another—the sedimentation coefficients for species at levels of a few percent or less cannot be determined with high precision (there is noise on the x-axis).

The results for the hydrolyzed canola protein sample are shown in FIG. 45, possessing a total of 82% protein on a dry weight basis. The normalization to give percentages of the total was handled differently for this sample, as it was not possible to measure the total signal for this sample because some of the peptide fragments are so small that even after over 21 hr at 55,000 rpm they have not sedimented sufficiently to deplete the concentration to zero at the inner regions of the cell. Therefore the total signal was estimated based on the weight concentration (1 mg of powder per mL), a peptide content for the powder of 82% by weight, and the nominal detector sensitivity of 3.3±0.1 fringes per (mg/mL). The vertical scaling in FIG. 43 is identical to that for FIG. 44. Therefore in FIG. 44 the area under each peak measures the fraction of that protein species remaining after hydrolysis (fraction of the total, not fraction of that individual species), and the total area under the curve is less than 100%. The actual total area is 12.0% (that is, peptides or proteins that are still large enough to sediment significantly represent 12.0% of the total expected signal). Note that the peak at 0.78S represents nearly three-fourths of that total of 12.0%, and this peak could represent a fragment of one of the larger proteins. Because the areas for many of the other peaks in this sample are so small the ones below 1% are listed to the nearest 0.01% to limit the round-off error. The peak at 1.7 S was not detected in this sample. The peak at 11.4 S (0.32%) may represent a partially-digested (clipped) form of the 12.3 S species; whether or not that is correct, it is clear that species at 11-13 S are at least 100-fold less abundant than in FIGS. 43 and 44.

Example 21

Preparation of Ethanol Defatted Meal from Canola Press Cake (*B. juncea*)

Approximately 5 kg of press cake was extracted with 16 L of hot SDAG 13 denatured ethanol at close to ethanol boiling point of about 78° C. for 5 hours using a pilot plant Soxhlet system. Hot ethanol close to its boiling point of 78° C. percolated through canola press cake in a large thimble and the miscella containing ethanol and dissolved crude oil was collected in a round bottom flask that was heated by steam. Ethanol vapor passed up the side arm of the extraction tube into the condenser where it was condensed. The condensed ethanol dripped back into the thimble containing press cake. Hot ethanol again percolated through the press cake. The process was repeated 5 times until majority of oil in the press cake was extracted by the hot ethanol.

The extracted oil was recovered by evaporation and desolventization to remove the ethanol from the miscella under vacuum at 60° C. After ethanol removal, phase separation occurred and oil was separated from the water layer containing extracted sugars.

The ethanol extracted meal was desolventized in a laboratory fume hood for three days at room temperature. Multiple batches of extraction were conducted to generate 36.9 kg of ethanol defatted canola meal. The desolventized meal was milled using a pilot plant hammer mill fitted with a ⅛" round hole screen. Approximately 35.46 kg of milled defatted canola meal was collected and used for the pilot plant trial.

Example 22

Preparation of Ethanol Defatted Meal from Canola Seed (*B. napus*)

Approximately 40 kg of regular canola seed (*B. napus*) containing 6.8% moisture was heated in a microwave oven for 2 minutes (heated to 85-95° C.). The canola seed was then covered with an aluminum foil and heated at 95° C. in a forced air oven for 30 minutes.

After the heat treatment, the canola seed was flaked using a lab flaking mill. The flaked and heat treated seed was pressed using a Gusta Laboratory Screw Press. The press cake was extracted with hot ethanol using a pilot plant Soxhlet extractor. For each batch of extraction, approximately 5 kg of press cake was extracted with 15 liters of SDAG 13 denatured ethanol for 5 hours at a temperature close to ethanol boiling point of 78° C.

The ethanol defatted canola meal was desolventized in a laboratory fume hood for three days at room temperature. Approximately 16.96 kg of defatted canola meal was obtained after desolventization and drying. The defatted and desolventized meal was milled using the pilot plant hammer mill fitted with the ⅛" round hole screen. Approximately 16.60 kg of milled defatted canola meal was collected and used for the pilot plant trial.

Example 23

Preparation of Protein Concentrate from Ethanol-Defatted Canola Meal (*B. juncea*) without Protease A control to prepare protein concentrate without the use of protease for protein hydrolysis is performed. Approximately 100 g of ethanol defatted canola meal (*B. juncea*) was mixed with 800 g of water at ambient temperature. The canola meal slurry had a pH 5.94, which was in the acceptable pH range for phytate hydrolysis. The canola meal slurry was heated to 52±2° C. and 0.3% phytase (Natuphos. powder form, 10,000 FTU/g) based on the weight of canola meal was added to the slurry. Hydrolysis of phytates was carried out at 52±2° C. for 1 hour. After hydrolysis of phytates, the pH of canola meal slurry was adjusted to 7.0±0.2 by slow addition of 10% NaOH solution.

After pH adjustment to 7.0±0.2, the canola meal slurry was centrifuged at 4,000 rpm for 10 minutes using a lab centrifuge. Three layers defined as the top layer of liquid extract, the middle layer of insoluble protein solids and the bottom layer of insoluble fiber solids were obtained in the centrifuge bottles. The larger fiber particles with higher density settled faster than the smaller insoluble protein particles with lower density. Therefore, the larger fiber particles settled to the bottom of the bottles at first. The smaller insoluble protein particles with lower density settled on the top of the fiber solids. The liquid extract containing soluble proteins was the top supernatant layer. The bottom fiber solids were manually separated from the middle layer of insoluble protein solids and the top layer of soluble protein extract. The fiber solids were mixed with water at a ratio of 1 to 2.5 by weight at ambient temperature, which was followed by centrifugation at 4000 rpm for 10 minutes. The bottom fiber layer was again manually separated from the middle insoluble protein and the top protein extract layers. This water washing and fiber separation process was repeated three times. All the middle layers of insoluble protein solids and the top layers of soluble protein extract were combined together. The protein slurry was adjusted to pH 4.5 by addition of 50% phosphoric acid. This was followed by centrifugation at 4,000 rpm to separate the precipitated protein solids from the supernatant. Approximately 167 g of precipitated protein solids was produced. The precipitated protein solids were mixed with 167 g of water. pH of the protein slurry was adjusted to 7.0 by addition of 10% NaOH solution. This was followed by freeze drying into 23 g of protein concentrate.

Example 24

Figure 46:
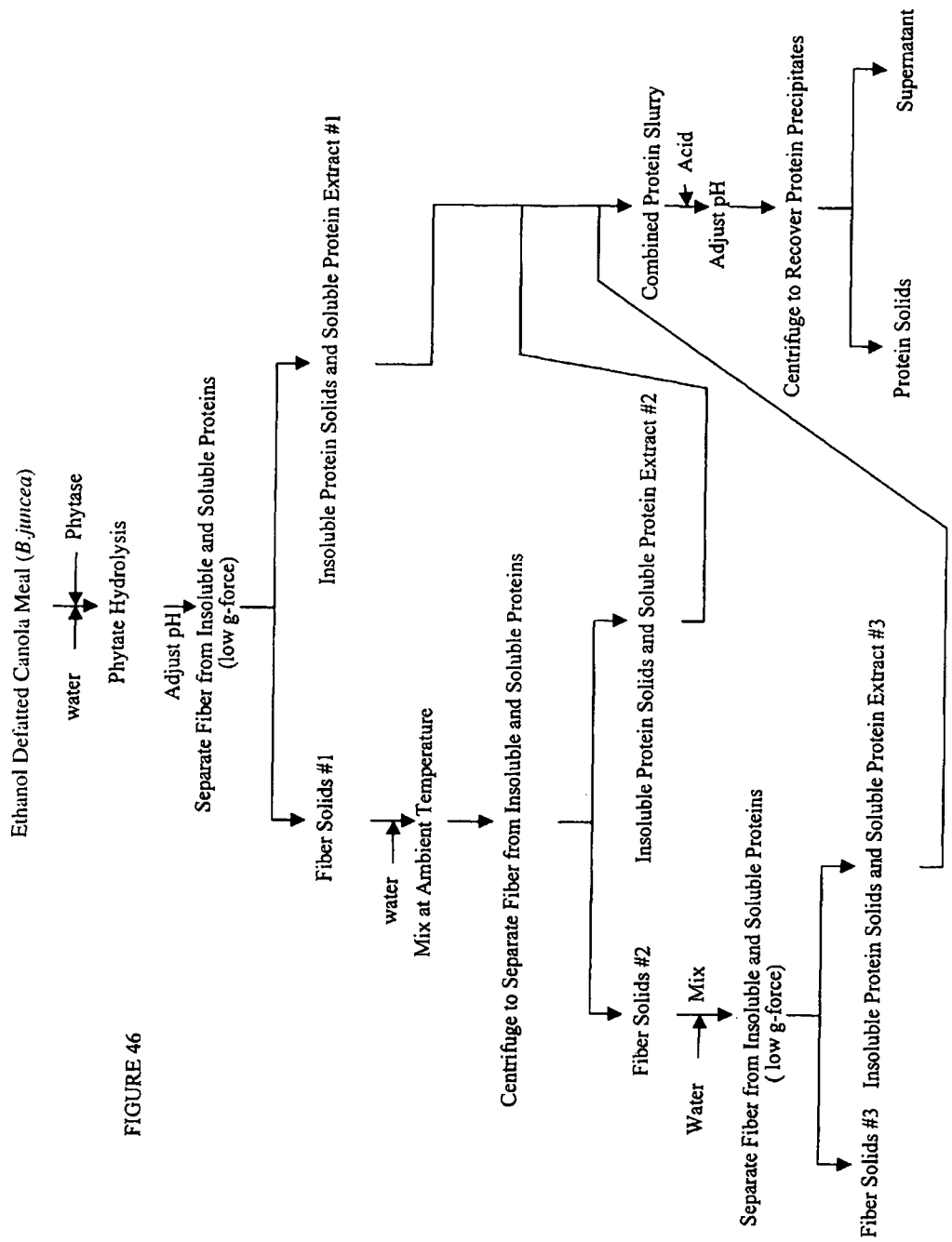
FIGS. 46 and 47 are schematic representations illustrating a preparation of a protein concentrate from a defatted meal using a protease.
Figure 47:
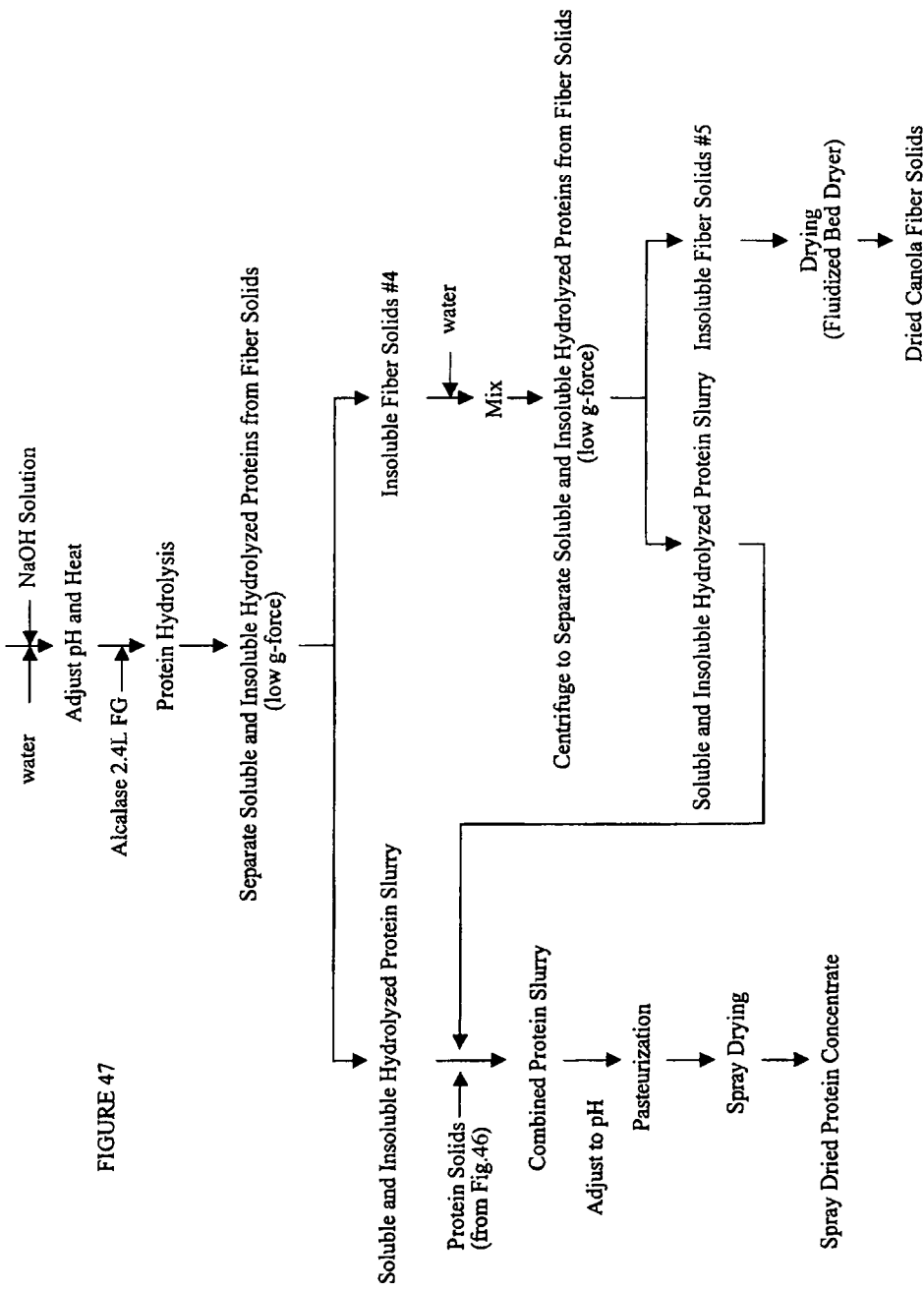

Preparation of Protein Concentrate from Ethanol-Defatted Canola Meal (*B. juncea*) Using 0.5% Alcalase A schematic flowchart for production of protein concentrate from ethanol defatted canola meal is shown in FIGS. 46 and 47. Approximately 35.46 kg of defatted canola meal was mixed with 280 kg of tap water at a ratio of 1 to 8 by weight under good agitation. The canola meal slurry had a pH 6.03, which was in the acceptable pH range for phytate hydrolysis. The canola meal slurry was heated to 52±2° C. and 0.11 kg of phytase (Natuphos. powder form, 10,000 FTU/g) was added to the canola meal slurry. Hydrolysis of phytates was carried out at 52±2° C. for 1 hour.

After hydrolysis of phytates, the pH of canola meal slurry was adjusted to 7.0±0.1 by slow addition of 1.134 kg of 12.68% NaOH solution. This was followed by centrifugation using a Bird Decanter Centrifuge (Bird 6" Continuous Bowl Centrifuge, Bird Machine Company of Canada, Saskatoon, Saskatchewan) at 1,500 rpm bowl speed (~175-180×g force) and a low pool depth. A spin down of the canola meal slurry in a centrifuge tube using a bench top centrifuge showed three distinct layers: liquid extract as the top layer, insoluble protein cake of fine protein particles as the middle layer and the coarse fiber solids as the bottom layer.

The protein slurry was pumped through the Bird Decanter at ambient temperature and a feed rate of 150-200 kg/h and it was operated at a bowl speed of 1,500 rpm and a low pool depth to separate the coarse fiber solids from the soluble and insoluble protein fractions. Approximately 118 kg of fiber solids (fiber solids #1) and 201 kg of protein slurry containing soluble and insoluble proteins were produced, respectively. The 118 kg of fiber solids was then mixed with 177 kg of water in a tank for 10 minutes, which was followed by centrifugation at ambient temperature using the Bird Decanter at a bowl speed of 1,500 rpm (175-180×g force) and a feed rate of 150-200 kg/hr. Approximately 116 kg of the $1^{st}$ washed fiber solids (fiber solids #2) and 179 kg of protein slurry containing soluble and insoluble proteins were produced. The 116 kg of fiber solids was again mixed with 175 kg of water in a tank for 10 minutes, which was followed by centrifugation at ambient temperature using the Bird Decanter at a bowl speed of 1,500 rpm (175-180×g force) and a feed rate of 150-200 kg/hr. Approximately 111 kg of the $2^{nd}$ washed fiber solids (fiber solids #3) and 180 kg of protein slurry containing soluble and insoluble proteins were produced.

Protein slurries containing soluble and insoluble proteins from the above three centrifugation steps were combined and approximately 560 kg of combined protein slurry was obtained. pH of the combined protein slurry was adjusted to 4.5±0.1 by addition of 4.5 kg of 25% phosphoric acid. This was followed by centrifugation using a Westfalia Decanter (Model CA 225-010, Centrico Inc., Northvale, N.J., USA) at ambient temperature and a bowl speed of 5,200 rpm (3,300 g force) to recover the precipitated protein solids. Approximately 521 kg of supernatant and 33 kg of insoluble protein solids were produced.

The 111 kg of the fiber solids #3 was mixed with 167 kg of water in a tank (FIG. 47). This was followed by pH adjustment to 8.3±0.1 using 0.2 kg of 12.68% NaOH solution. The fiber slurry was then heated to 60±2° C. and approximately 0.177 kg of Alcalase 2.4L FG (0.5% protease based on the starting weight of canola meal) was added to the slurry. The slurry was held at 60±2° C. for 2 hours. After partial protein hydrolysis, the slurry was centrifuged using the Bird Decanter Centrifuge at 1500 rpm bowl speed (~175-180×g force) and a low pool depth to separate the coarse fiber solids from the soluble and insoluble hydrolyzed protein fractions. A spin down of the hydrolyzed protein slurry in a centrifuge tube using a bench top centrifuge, showed three distinct layers: soluble hydrolyzed protein extract as the top layer, insoluble protein solids as the middle layer and the coarse fiber solids as the bottom layer. The objective was to separate the top and middle layers (the soluble hydrolyzed protein extract and the insoluble protein solids) from the bottom layer (coarse fiber solids). Approximately 87 kg of fiber solids and 191 kg of hydrolyzed protein slurry containing soluble and insoluble hydrolyzed proteins were produced, respectively. The 87 kg of fiber solids was then mixed with 130 kg of water in a tank for 10 minutes, which was followed by centrifugation at ambient temperature using the Bird Decanter at a bowl speed of 1,500 rpm (175-180×g force) and a feed rate of 150-200 kg/hr. Approximately 67 kg of the washed fiber solids and 150 kg of hydrolyzed protein slurry containing soluble and insoluble hydrolyzed proteins were produced.

The hydrolyzed protein slurries containing soluble and insoluble hydrolyzed proteins from the above two centrifugation steps were combined. The 33 kg of precipitated and unhydrolyzed protein solids was added to the combined protein slurry containing soluble and insoluble hydrolyzed proteins under good agitation. pH of the combined protein slurry was adjusted to 7.0±0.1 by addition of 1.82 kg of 12.68% NaOH solution. This was followed by pasteurization at 75±2° C. for 2 minutes using a shell and tube heat exchanger. The pasteurized protein slurry was then spray dried into protein concentrate using a Komline Sanderson pilot plant spray dryer equipped with a centrifugal atomizer with a wheel speed up to 10,000 rpm (Komline Sanderson Ltd., Brampton, Ontario, Canada). The spray drying operation was conducted at an inlet air temperature of 185±5° C. and an outlet air temperature of 75±2° C. Approximately 5 kg of spray dried protein concentrate containing 67% protein (dwb) was produced. The protein concentrate was a mix a mixture of unhydrolyzed, hydrolyzed and partially hydrolyzed proteins and did not have a bitter taste.

The 67 kg of the final washed fiber solids generated from the protein hydrolysis and the low G force fiber separation process was dried at 70° C. using a fluidized bed dryer. Approximately 9.7 kg of dried fiber solids was produced.

As shown in Table 52, a protein concentrate containing 67.2% protein (dwb) was produced from *juncea* press cake. This protein concentrate does not have a bitter taste. The protein concentrate is a free flowing powder. It has a low fiber content of 5.25% (dwb). The results of glucosinolates in *Juncea* press cake, ethanol defatted *Juncea* meal, *Juncea* protein concentrate and *Juncea* fiber solids are shown in Table 53. The content of total aliphatic glucosinomates in *Juncea* press cake and ethanol defatted *Juncea* meal is high and at similar level. Wet separation processing reduced the total aliphatic glucosinolates dramatically from 12.87-12.94 μmoles/g in *Juncea* press cake and ethanol defatted *Juncea* meal to 0.68 μmole/g in *Juncea* protein concentrate and 0.11 μmole/g in *Juncea* fiber solids.

Example 25

Figure 48:
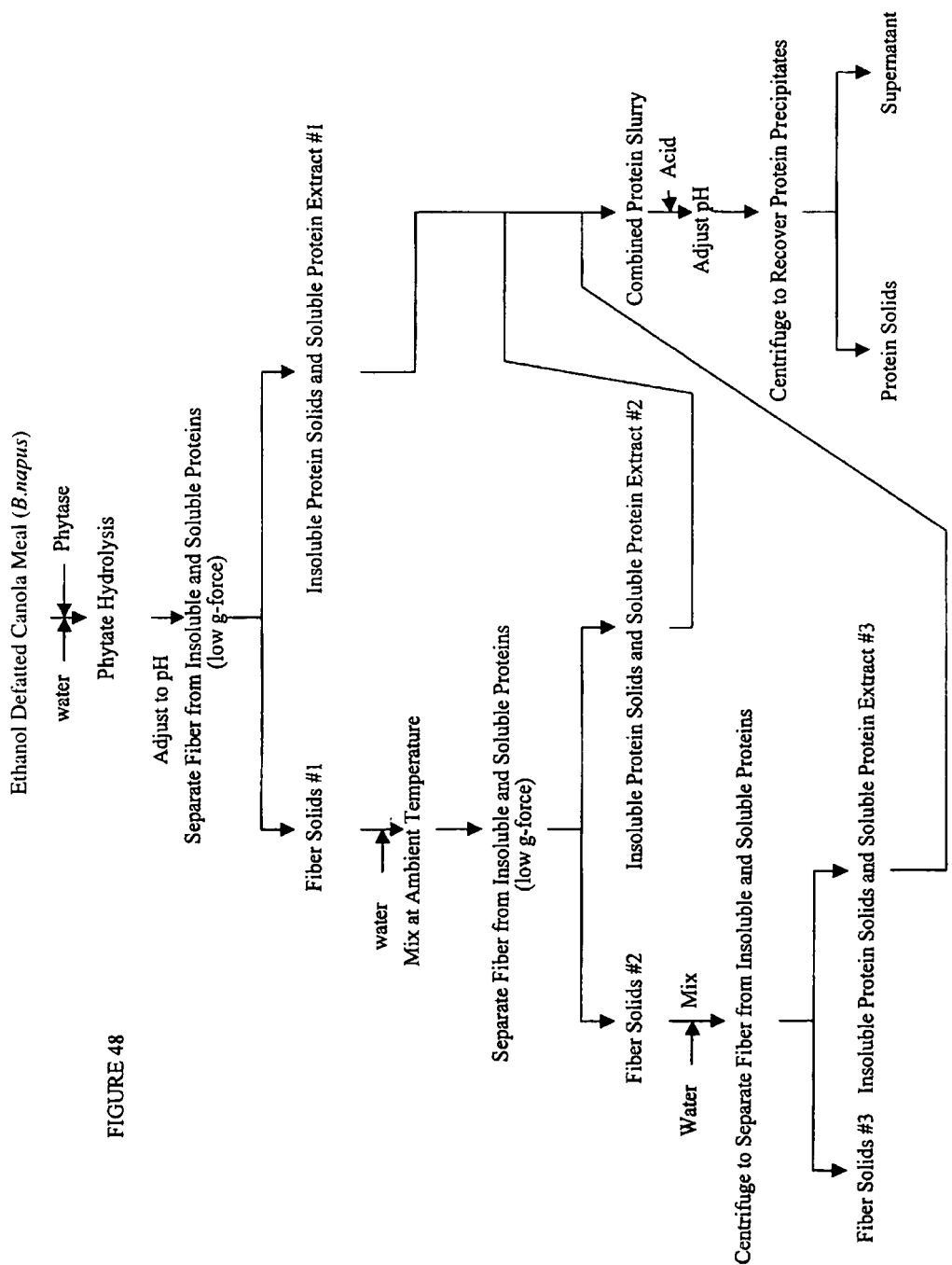
FIGS. 48 and 49 are schematic representations illustrating a preparation of a protein concentrate from a defatted meal using a protease.
Figure 49:
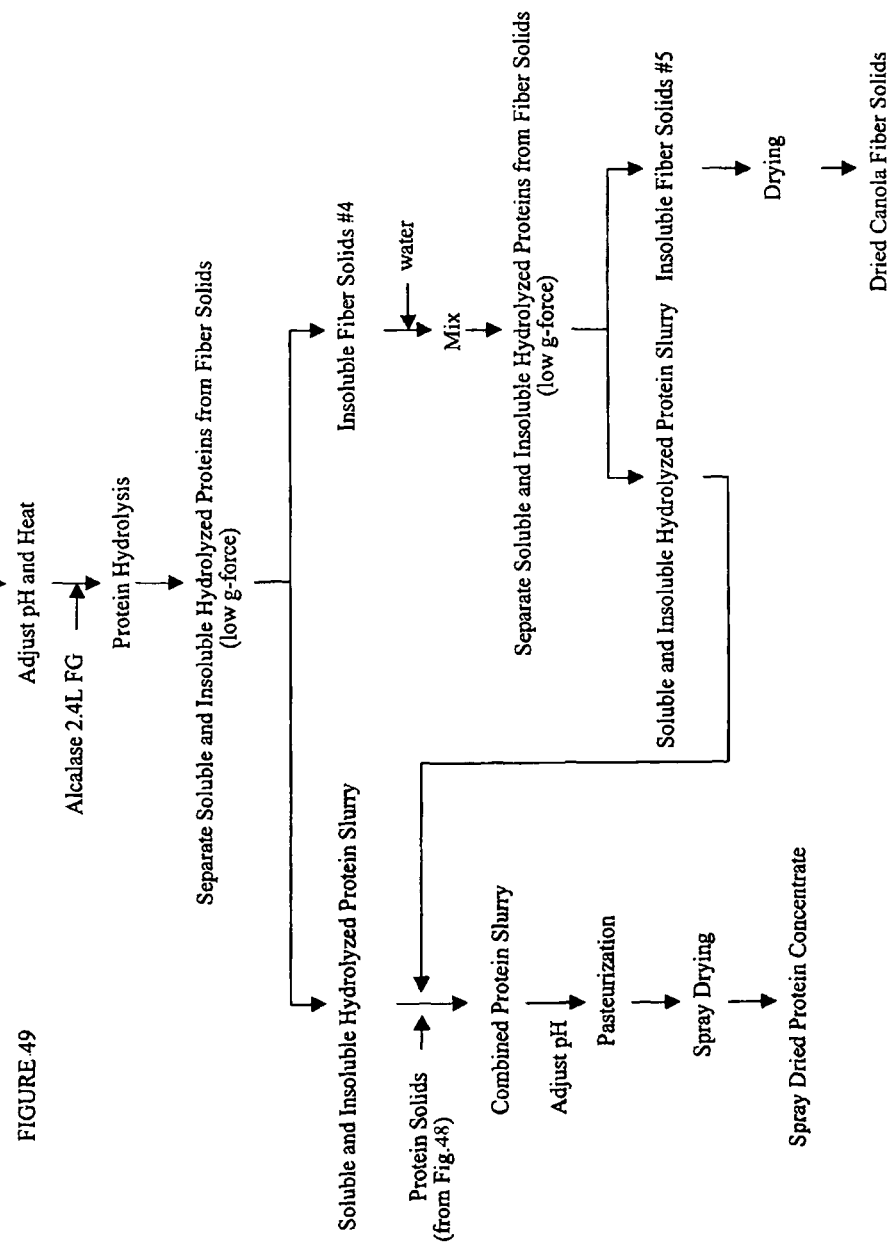

Preparation of Protein Concentrate from Ethanol-Defatted Canola Meal (*B. napus*) Using 0.5% Alcalase A schematic flowchart for production of protein concentrate from ethanol defatted canola meal (*B. napus*) is shown in FIGS. 48 and 49. Approximately 16.6 kg of defatted canola meal was mixed with 133 kg of tap water at a ratio of 1 to 8 by weight under good agitation. The canola meal slurry had a pH 5.79, which was in the acceptable pH range for phytate hydrolysis. The canola meal slurry was heated to 52±2° C. and 0.05 kg of phytase (Natuphos. powder form, 10,000 FTU/g) was added into the canola meal slurry. Hydrolysis of phytates was carried out at 52±2° C. for 1 hour.

After hydrolysis of phytates, the pH of canola meal slurry was adjusted to 7.0±0.1 by slow addition of 0.64 kg of 12.68% NaOH solution. This was followed by centrifugation using a Bird Decanter Centrifuge (Bird 6" Continuous Bowl Centrifuge, Bird Machine Company of Canada, Saskatoon, Saskatchewan) at 1500 rpm bowl speed (~175-180×g force) and a low pool depth. The Bird Decanter is of variable speed design and can be operated at a bowl speed of 1,000-5,000 rpm (100-2130×g force) and a pool depth of 5 to 19 mm. A spin down of the canola meal slurry in a centrifuge tube using a bench top centrifuge showed three distinct layers: liquid extract as the top layer, insoluble protein solids as the middle layer and the coarse fiber solids as the bottom layer. The objective was to separate the top and middle layers (the soluble protein extract and the insoluble protein solids) from the bottom layer (coarse fiber solids). The bird decanter was operated at a low pool depth and a bowl speed of 1,000, 1,500, 2,000, 2,500 and 3,000 rpm and the separation efficiency was evaluated by spin down tests of the feed slurry, the fiber fraction and the protein slurry using the bench top centrifuge. It was observed that the best separation efficiency of the coarse fiber solids from the insoluble fine protein solids and the soluble protein extract was obtained at a bowl speed of 1,500 rpm (~175-180×g force) and a low pool depth.

The protein slurry was pumped through the Bird Decanter at ambient temperature and a feed rate of 150-200 kg/h and it was operated at a bowl speed of 1,500 rpm and a low pool depth to separate the coarse fiber solids from the soluble and insoluble protein fractions. Approximately 45 kg of fiber solids (fiber solids #1) and 105 kg of protein slurry containing soluble and insoluble proteins were produced, respectively. The 45 kg of fiber solids was then mixed with 68 kg of water in a tank for 10 minutes, which was followed by centrifugation at ambient temperature using the Bird Decanter at a bowl speed of 1,500 rpm (175-180×g force) and a feed rate of 150-200 kg/hr. Approximately 46 kg of the $1^{st}$ washed fiber solids (fiber solids #2) and 67 kg of protein slurry containing soluble and insoluble proteins were produced. The 46 kg of fiber solids was again mixed with 68 kg of water in a tank for 10 minutes, which was followed by centrifugation at ambient temperature using the Bird Decanter at a bowl speed of 1,500 rpm (175-180×g force) and a feed rate of 150-200 kg/hr. Approximately 29 kg of the $2^{nd}$ washed fiber solids (fiber solids #3) and 85 kg of protein slurry containing soluble and insoluble proteins were produced.

Protein slurries containing soluble and insoluble proteins from the above three centrifugation steps were combined and approximately 257 kg of combined protein slurry was obtained. pH of the combined protein slurry was adjusted to 4.5±0.1 by addition of 4.3 kg of 25% phosphoric acid. This was followed by centrifugation using a Westfalia Decanter (Model CA 225-010, Centrico Inc., Northvale, N.J., USA) at ambient temperature and a bowl speed of 5,200 rpm (3,300 g force) to recover the precipitated protein solids. Approximately 217 kg of supernatant and 39.8 kg of insoluble protein solids were produced.

The 29 kg of fiber solids #3 was mixed with 43 kg of water in a tank. This was followed by pH adjustment to 8.3±0.1 using 0.06 kg of 12.68% NaOH solution. The fiber slurry was then heated to 60±2° C. and approximately 0.083 kg of Alcalase 2.4L FG (0.5% protease based on the weight of starting canola meal) was added to the slurry. The slurry was held at 60±2° C. for 2 hours. After partial protein hydrolysis, the slurry was centrifuged using the Bird Decanter at 1500 rpm bowl speed (~175-180×g force) and a low pool depth to separate the coarse fiber solids from the soluble and insoluble hydrolyzed protein fractions. A spin down of the hydrolyzed slurry in a centrifuge tube using a bench top centrifuge, showed three distinct layers: soluble hydrolyzed protein extract as the top layer, insoluble protein solids as the middle layer and the coarse fiber solids as the bottom layer. The objective was to separate the top and middle layers (the soluble hydrolyzed protein extract and the insoluble protein solids) from the bottom layer (coarse fiber solids). Approximately 20 kg of fiber solids and 52 kg of hydrolyzed protein slurry containing soluble and insoluble hydrolyzed proteins were produced, respectively. The 20 kg of fiber solids was then mixed with 30 kg of water in a tank for 10 minutes, which was followed by centrifugation at ambient temperature using the Bird Decanter at a bowl speed of 1,500 rpm (175-180×g force) and a feed rate of 150-200 kg/hr. Approximately 18.8 kg of the washed fiber solids and 31.2 kg of the hydrolyzed protein slurry containing soluble and insoluble proteins were produced.

The hydrolyzed protein slurries containing soluble and insoluble hydrolyzed proteins from the above two centrifugation steps were combined. The 39.8 kg of precipitated and unhydrolyzed protein solids was added to the combined protein slurry containing soluble and insoluble hydrolyzed proteins under good agitation. pH of the combined protein slurry was adjusted to 7.0±0.1 by addition of 0.72 kg of 12.68% NaOH solution. This was followed by pasteurization at 75±2° C. for 2 minutes using a shell and tube heat exchanger. The pasteurized protein slurry was then spray dried into protein concentrate using a Komline Sanderson pilot plant spray dryer equipped with a centrifugal atomizer with a wheel speed up to 10,000 rpm (Komline Sanderson Ltd., Brampton, Ontario, Canada). The spray drying operation was conducted at an inlet air temperature of 185±5° C. and an outlet air temperature of 75±2° C. Approximately 3 kg of spray dried protein concentrate containing 62% protein (dwb) was produced. The protein concentrate was a mix a mixture of unhydrolyzed, hydrolyzed and partially hydrolyzed proteins and did not have a bitter taste.

The 18.8 kg of the final washed fiber solids generated from the protein hydrolysis and the low G force fiber separation process was dried at 70° C. using a fluidized bed dryer. Approximately 3.6 kg of dried fiber solids was produced.

As shown in Table 54, a protein concentrate containing 62% protein (dwb) was produced from canola seed (*B. napus*). This protein concentrate does not have a bitter taste. The protein concentrate is a free flowing powder. It has a fiber content of 6.69% (dwb). The results of glucosinolates in canola seed (*B. napus*), ethanol defatted *Napus* meal, *Napus* protein concentrate and *Napus* fiber solids are shown in Table 55. The content of total aliphatic glucosinomates in canola seed (*B. napus*) and ethanol defatted *Napus* meal is high and at similar level on an oil free basis. Wet separation processing reduced the total aliphatic glucosinolates dramatically from 6.7 μmoles/g in ethanol defatted *Napus* meal to 0.31 μmole/g in *Napus* protein concentrate and <0.05 μmole/g in *Napus* fiber solids.

The results of amino acid profile for ethanol defatted *Juncea* meal, ethanol defatted *Napus* meal, *Juncea* protein concentrate and *Napus* protein concentrate on a dry weight basis are shown in Table 56.

The comparison of amino acid profiles for *Juncea* protein concentrates, *Napus* protein concentrate, soy and pea protein isolates is shown in Table 56. From the amino acid profiles as shown in Table 57, canola protein compares favorably to that of soy protein or pea protein. Canola protein is of high nutritional quality and capable of providing adequate amounts of all essential amino acids. Canola protein contains much higher sulphur containing amino acids such as methionine and cystine than soy and pea proteins. Canola protein contains 81-83% higher methionine than soy protein and 108-110% higher methionine than pea protein.

Example 26

Preparation of Protein Concentrate from Ethanol-Defatted Canola Meal (*B. juncea*) Using 0.1% Alcalase Approximately 150 g of ethanol defatted canola meal (*B. juncea*) was mixed with 1,200 g of water at ambient temperature. The canola meal slurry had a pH 5.94, which was in the acceptable pH range for phytate hydrolysis. The canola meal slurry was heated to 52±2° C. and 0.3% phytase (Natuphos. powder form, 10,000 FTU/g) based on the weight of canola meal was added into the slurry. Hydrolysis of phytates was carried out at 52±2° C. for 1 hour. After hydrolysis of phytates, the pH of canola meal slurry was adjusted to 7.0±0.1 by slow addition of 10% NaOH solution.

After pH adjustment to 7.0±0.1, the canola meal slurry was centrifuged at 4,000 rpm for 10 minutes using a lab centrifuge. Three layers defined as the top layer of liquid extract, the middle layer of insoluble protein solids and the bottom layer of insoluble fiber solids were obtained in the centrifuge bottles. The larger fiber particles with higher density settled faster than the smaller insoluble protein particles with lower density. Therefore, the larger fiber particles settled to the bottom of the bottles at first. The smaller insoluble protein particles with lower density settled on the top of the fiber solids. The liquid extract containing soluble proteins was the top layer. The bottom fiber solids were manually separated from the middle layer of insoluble protein solids and the top layer of soluble protein extract. The fiber solids were mixed with water at a ratio of 1 to 1 by weight at ambient temperature, which was followed by centrifugation at 4,000 rpm for 10 minutes. The bottom fiber solids were again manually separated from the middle layer of insoluble protein solids and the top layer of soluble protein extract. This water washing and fiber separation process was repeated three times. Approximately 329 g of the final washed fiber solids was obtained. All the middle layers of insoluble protein solids and the top layers of soluble protein extract were combined together and approximately 2,994 g of protein slurry was obtained. The protein slurry was adjusted to pH 4.5 by addition of 50% phosphoric acid. This was followed by centrifugation at 4,000 rpm to separate the precipitated protein solids from the supernatant. The precipitated protein solids were mixed with water at a ratio of 1 to 2 by weight, which was followed by centrifugation at 4,000 rpm for 10 minutes to separate the washed protein solids from the washing extract.

The 329 g of the washed fiber solids was mixed with water at a ratio of 1 to 1.5 by weight. pH of the slurry was adjusted 8.3±0.1 by addition of 10% NaOH solution. The fiber slurry was heated to 60±2° C. 0.1 g of Alcalase (0.1% dosage based on the weight of canola meal) was added to the slurry and protein hydrolysis was carried out at 60±2° C. for 2 hours. After protein hydrolysis, the slurry was centrifuged at 4,000 rpm for 10 minutes using the lab centrifuge. Three layers defined as the top layer of hydrolyzed protein extract, the middle layer of insoluble protein solids and the bottom layer of insoluble fiber solids were obtained in the centrifuge bottles. The fiber solids were manually separated from the soluble hydrolyzed protein extract and the insoluble protein solids. The insoluble fiber solids were mixed with water at a ratio of 1 to 1 by weight. This was followed by centrifugation at 4,000 rpm for 10 minutes using the lab centrifuge. The washed fiber solids were again separated from the top layer of hydrolyzed protein extract and the middle layer of insoluble protein solids. Approximately 200 g of washed fiber solids was obtained. All the top layers of hydrolyzed protein extract and the middle layers of insoluble protein solids were combined together. Approximately 1,426 g of hydrolyzed protein slurry containing soluble hydrolyzed protein extract and insoluble protein solids were obtained.

The hydrolyzed protein slurry was mixed with the washed and unhydrolyzed protein precipitates and pH of the mixture was adjusted to pH7.0 before freeze drying into 75 g of protein concentrate. The protein concentrate was a mix a mixture of unhydrolyzed, hydrolyzed and partially hydrolyzed proteins and did not have a bitter taste.

Example 27

Preparation of Protein Concentrate from Ethanol-Defatted Canola Meal (*B. juncea*) Using 0.5% Alcalase Approximately 100 g of ethanol defatted canola meal (*B. juncea*) was mixed with 800 g of water at ambient temperature. The canola meal slurry had a pH 5.92, which was in the acceptable pH range for phytate hydrolysis. The canola meal slurry was heated to 52±2° C. and 0.3% phytase (Natuphos. powder form, 10,000 FTU/g) based on the weight of canola meal was added to the slurry. Hydrolysis of phytates was carried out at 52±2° C. for 1 hour. After hydrolysis of phytates, the pH of canola meal slurry was adjusted to 7.0±0.1 by slow addition of 10% NaOH solution.

After pH adjustment to 7.0±0.1, the canola meal slurry was centrifuged at 4,000 rpm for 10 minutes using a lab centrifuge. Three layers defined as the top liquid layer, the middle layer of insoluble protein solids and the bottom layer of insoluble fiber solids were obtained in the centrifuge bottles. The larger fiber particles with higher density settled faster than the smaller insoluble protein particles with lower density. Therefore, the larger fiber particles settled to the bottom of the bottles at first. The smaller insoluble protein particles with lower density settled on the top of the fiber solids. The liquid extract containing soluble proteins was the top layer. The bottom fiber solids were manually separated from the middle layer of insoluble protein solids and the top layer of liquid extract. The fiber solids were mixed with water at a ratio of 1 to 1 by weight at ambient temperature, which was followed by centrifugation at 4,000 rpm for 10 minutes. The bottom fiber solids were again manually separated from the middle layer of insoluble protein solids and the top layer of protein extract. This water washing and fiber separation process was repeated three times. Approximately 267 g of the final washed fiber solids was obtained. All the middle layers of insoluble protein solids and the top layer of soluble protein extract were combined together and approximately 1,343 g of protein slurry was obtained. The protein slurry was adjusted to pH 4.5 by addition of 50% phosphoric acid. This was followed by centrifugation at 4,000 rpm to separate the precipitated protein solids (116 g) from the supernatant (1227 g). The precipitated protein solids were mixed with water at a ratio of 1 to 2 by weight, which was followed by centrifugation at 4,000 rpm for 10 minutes to separate the washed protein solids from the washing extract.

The 267 g of the washed fiber solids was mixed with water at a ratio of 1 to 1.5 by weight. pH of the slurry was adjusted 8.3±0.1 by addition of 10% NaOH solution. The fiber slurry was heated to 60±2° C. 0.5 g of Alcalase (0.5% dosage based on the weight of canola meal) was added to the slurry and protein hydrolysis was carried out at 60±2° C. for 2 hours. After protein hydrolysis, the slurry was centrifuged at 4,000 rpm for 10 minutes using the lab centrifuge. Three layers defined as the top layer of hydrolyzed protein extract, the middle layer of insoluble protein solids and the bottom layer of insoluble fiber solids were obtained in the centrifuge bottles. The fiber solids were manually separated from the hydrolyzed protein extract and the insoluble protein solids. The insoluble fiber solids were mixed with water at a ratio of 1 to 1 by weight. This was followed by centrifugation at 4,000 rpm for 10 minutes using the lab centrifuge. The washed fiber solids were again separated from the top layer of hydrolyzed protein extract and the middle layer of insoluble protein solids. Approximately 158 g of washed fiber solids was obtained. All the top layers of hydrolyzed protein extract and the middle layers of insoluble protein solids were combined together as the hydrolyzed protein slurry.

The hydrolyzed protein slurry was mixed with the washed and unhydrolyzed protein precipitates and pH of the mixture was adjusted to pH7.0 before freeze drying into 68 g of dried protein concentrate. The protein concentrate was a mix a mixture of unhydrolyzed, hydrolyzed and partially hydrolyzed proteins and did not have a bitter taste.

Example 28

Preparation of Protein Concentrate from Ethanol-Defatted Canola Meal (*B. napus*) Using 0.5% Protamex Approximately 100 g of ethanol canola meal (*B. juncea*) was mixed with 800 g of water at ambient temperature. The canola meal slurry had a pH 5.72, which was in the acceptable pH range for phytate hydrolysis. The canola meal slurry was heated to 52±2° C. and 0.3% phytase (Natuphos. powder form, 10,000 FTU/g) based on the weight of canola meal was added to the slurry. Hydrolysis of phytates was carried out at 52±2° C. for 1 hour. After hydrolysis of phytates, the pH of canola meal slurry was adjusted to 7.0±0.2 by slow addition of 10% NaOH solution.

After pH adjustment to 7.0±0.1, the canola meal slurry was centrifuged at 4,000 rpm for 10 minutes using a lab centrifuge. Three layers defined as the top layer of liquid extract, the middle layer of insoluble protein solids and the bottom layer of insoluble fiber solids were obtained in the centrifuge bottles. The larger fiber particles with higher density settled faster than the smaller insoluble protein particles with lower density. Therefore, the larger fiber particles settled to the bottom of the bottles at first. The smaller insoluble protein particles with lower density settled on the top of the fiber solids. The liquid extract containing soluble proteins was the top supernatant layer. The bottom fiber solids were manually separated from the middle layer of insoluble protein solids and the top layer of soluble protein extract. The fiber solids were mixed with water at a ratio of 1 to 1 by weight at ambient temperature, which was followed by centrifugation at 4000 rpm for 10 minutes. The bottom fiber layer was again manually separated from the middle insoluble protein and the top protein extract layers. This water washing and fiber separation process was repeated three times. All the middle layers of insoluble protein solids and the top layers of soluble protein extract were combined together and approximately 1,329 g of protein slurry was obtained. The protein slurry was adjusted to pH 4.5 by addition of 50% phosphoric acid. This was followed by centrifugation at 4,000 rpm to separate the precipitated protein solids from the supernatant. The precipitated protein solids were mixed with water at a ratio of 1 to 2 by weight, which was followed by centrifugation at 4,000 rpm for 10 minutes to separate the washed protein solids (95 g) from the washing extract. Approximately 1,481 g of soluble sugar extract was generated.

The washed fiber solids were mixed with water at a ratio of 1 to 1.5 by weight. pH of the slurry was adjusted to 6.0±0.1 by addition of 10% NaOH solution. The fiber slurry was heated to 42±2° C. 0.5 g of Protamex (0.5% dosage based on the weight of meal) was added to the slurry and protein hydrolysis was carried out at 42±2° C. for 2 hours. After protein hydrolysis, the slurry was centrifuged at 4,000 rpm for 10 minutes using the lab centrifuge. Three layers defined as the top layer of soluble hydrolyzed protein extract, the middle layer of insoluble protein solids and the bottom layer of insoluble fiber solids were obtained in the centrifuge bottles. The fiber solids were manually separated from the hydrolyzed protein extract and the insoluble protein solids. The insoluble fiber solids were mixed with water at a ratio of 1 to 1 by weight. This was followed by centrifugation at 4,000 rpm for 10 minutes using the lab centrifuge. The washed fiber solids were again separated from the top layer of hydrolyzed protein extract and the middle layer of insoluble protein solids. Approximately 155 g of washed fiber solids was obtained. All the top layers of hydrolyzed protein extract and the middle layers of insoluble protein solids were combined together. Approximately 1,004 g of hydrolyzed protein slurry containing soluble hydrolyzed protein extract and insoluble protein solids were obtained.

The hydrolyzed protein slurry (1,004 g) was mixed with the washed and unhydrolyzed protein precipitates (95 g) and pH of the mixture was adjusted pH7.0 before freeze drying into 52 g of dried protein concentrate. The protein concentrate was a mix a mixture of unhydrolyzed, hydrolyzed and partially hydrolyzed proteins and did not have a bitter taste.

The results of proximate analysis for ethanol defatted canola meal (B. juncea) and protein concentrate are shown in Table 58. As shown in Table 58, protein concentrate containing 67.6% protein (dwb) and 69.6% protein (dwb) were produced from ethanol defatted Juncea meal using 0.1% and 0.5% Alcalase, respectively. Protein concentrate containing 66.7% protein was produced without the use of protease. Protein concentrate containing 66.0% protein was produced with the use of 0.5% Protamex. Protein concentrates have fiber content of 6.53-8.26% (dwb). Protein hydrolysis with the use of protease helps to reduce the protein content and to increase the fiber content in the fiber solids and thus helps to improve the protein recovery yield.

The yield of protein concentrates based on the starting weight of the ethanol defatted canola meal (B. juncea) is shown in Table 59. The use of protease improves the yield of protein concentrate from 23% to 38-68% for ethanol defatted canola meal (B. juncea). The improvement of protein concentrate yield by protein hydrolysis with the use of protease resulted from two factors: (1) solubiliztion of insoluble proteins in the fiber solids by protease and (2) help to release of insoluble protein particles through the enzymatic hydrolysis so that the fiber particles could be effectively separated from the insoluble proteins by a low G centrifugal separation force.

Figure 50:
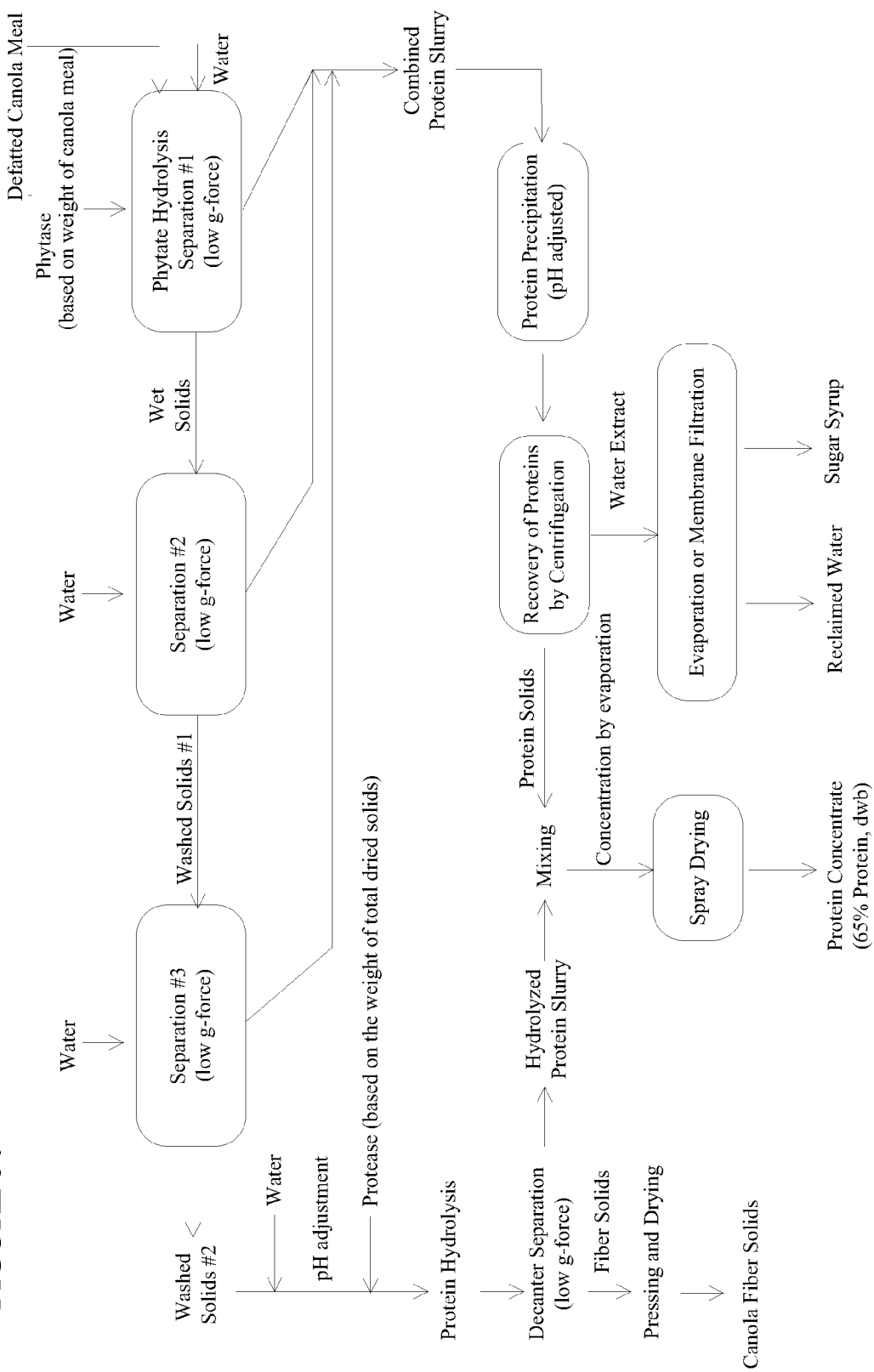
FIG. 50 is a schematic representation illustrating a preparation of a protein concentrate using a concurrent process.
Figure 51:
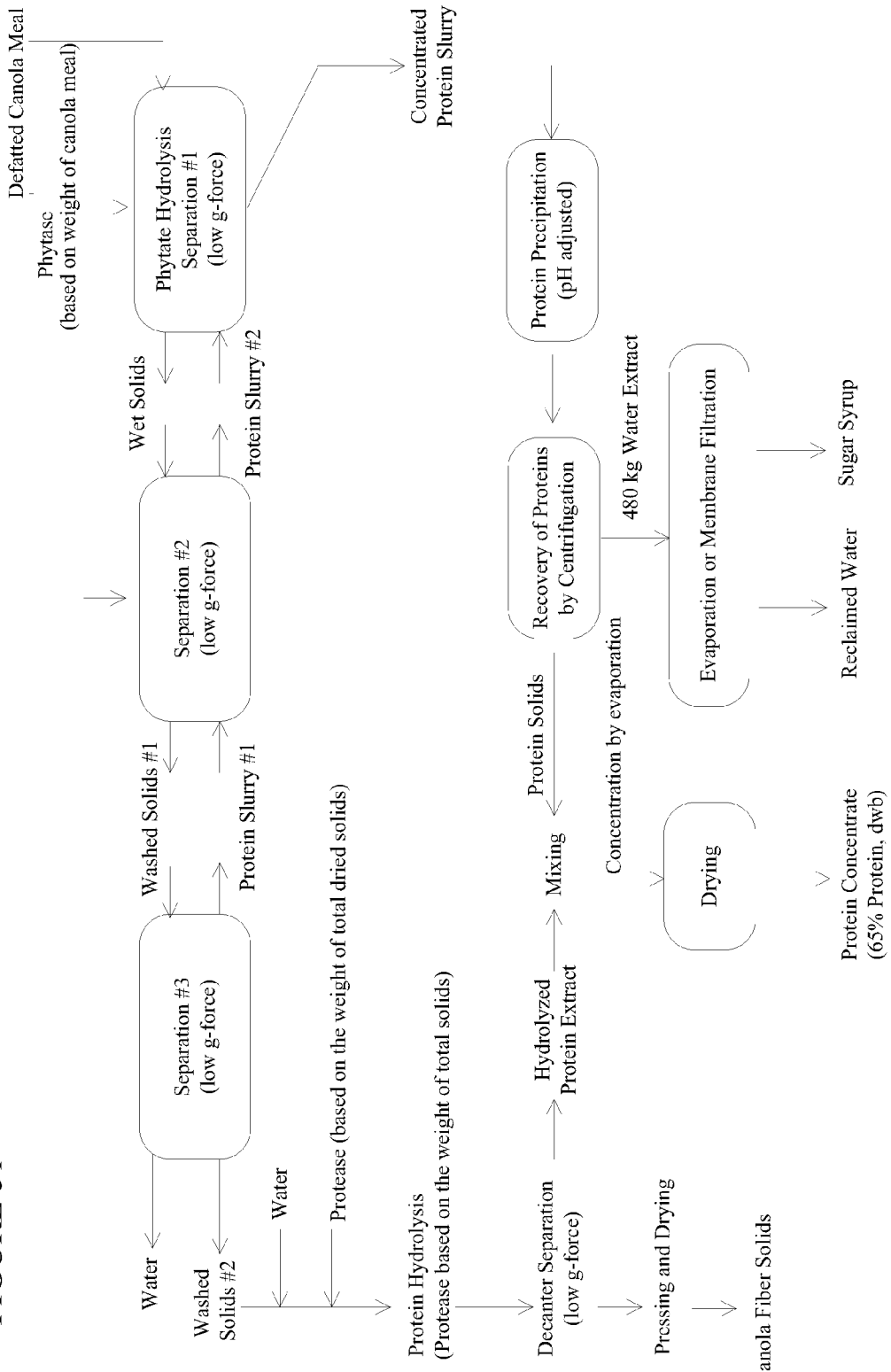
FIG. 51 is a schematic representation illustrating a preparation of a protein concentrate using a counter-current process.

As shown in FIGS. 50 and 51, the processes of the present disclosure are, in one embodiment, performed using a concurrent process (FIG. 50), or in another embodiment, a counter-current process (FIG. 51). In the counter-current process, there is substantial savings of water and energy as well as much better production throughput because the volume of the process streams is greatly reduced. For example, with a three stage counter-current process, the volume of the process streams can be reduced by 35-50%. This greatly reduces the amount of water used in the process. The volume of process streams is also greatly reduced leading to higher production throughput, short processing time and better processing efficiency. In addition, the amount of water to be removed from the production process is also greatly reduced resulting in energy savings.

Example 29

Preparation of Protein Isolate from Canola Seed

Six batches of canola protein isolate were produced from low temperature defatted canola meal (B. juncea). For a typical batch of production for canola protein isolate, approximately 409 kg-421 kg of defatted canola meal was mixed with 3,265 kg-3,372 kg of water at a ratio of 1 to 8 (defatted canola meal to water by weight) at 52±2° C. under good agitation. The canola meal slurry had an initial pH of 5.49-5.54. 1.85 kg of phytase (Natuphos. powder form, 10,000 FTU/g) was added to the canola meal slurry, which was followed by addition of 0.8 kg of Nisin to control microbial growth. The canola meal slurry was held at 52±2° C. for 1 hour for phytate hydrolysis.

After hydrolysis of phytates, the pH of canola meal slurry was adjusted to 6.92-6.94 by slow addition of 45.9 kg of 10% NaOH solution. This was followed by centrifugation to separate the soluble protein extract from the insoluble solids using a Westfalia Decanter Centrifuge at a feed rate of about 800 L/hr. The decanter centrifuge was operated to minimize the insoluble solid residues in the soluble protein extract. Typically, the insoluble solid residues in the soluble protein extract were controlled at a level of less than 0.1 ml of insoluble solids in 15 ml of the soluble protein extract in a spin down test. A Westfalia Disc Stack centrifuge was used to remove the remaining residues of the insoluble solids in the soluble protein extract for some batches of operation prior to ultrafiltration.

The soluble protein extract was kept as cold as possible (8-15° C.) in a tank with cold water circulated through its jacket. The soluble protein extract was concentrated to one tenth of its original volume using an ultrafiltration unit (UF) fitted with 10,000 dalton molecular weight cut-off polyethersulfone membranes. During the ultrafiltration, the retentate was recycled back to the feed tank while the permeate was collected in a separate tank. The ultrafiltration process stopped when the retentate volume was reduced to 1/10 of the original volume of the soluble protein extract.

Water containing 25 ppm of nisin was added to the feed tank and diafiltration was conducted using the same UF unit fitted with the same polyethersulfone membranes. The original volume of the concentrated protein extract in the feed tank was held constant while water was added to the feed tank to make up for the removed permeate. The retentate was recycled back to the feed tank. The diafiltration process stopped when the amount of water added equalled to 4 times of the original volume of the concentrated protein extract from the UF operation.

The purified protein extract generated from the ultrafiltration and diafiltration process was spray dried using a spray dryer. The purified protein extract was fed to the spray dryer by pumping at a feed rate of 90-110 kg per hour. The spray drying operation was conducted at an inlet air temperature of 165-170° C. and an outlet air temperature of 70-80° C. Approximately 15-25 kg of spray dried protein isolate containing 90-95% protein (dwb) was produced per batch of operation. The molecular weight distribution of the proteins in the canola protein isolate is shown in Table 60.

TABLE 1

Heat Treatment Conditions

| Heat Treatment | Temperature (° C.) | Residence Time |
|---|---|---|
| 1 | 75 | 15 seconds |
| 2 | 80 | 15 seconds |
| 3 | 85 | 15 seconds |
| 4 | 85 | 15 seconds |
| 5 | 85 | 15 seconds |
| 6 | 90 | 15 seconds |
| Control | 95 | 30 minutes |

TABLE 2

Heat Treatment Conditions

| Heat Treatment | Temperature (° C.) | Time (second.) |
|---|---|---|
| 1 | 100 | 15 |
| 2 | 105 | 15 |
| 3 | 110 | 15 |
| 4 | 120 | 15 |
| 5 | 130 | 15 |

TABLE 3

Evaluation of Heat Treatments on Quality of Defatted Canola Meal (*B. juncea*)

| Heat Treatment Conditions | Moisture of Defatted Meal (%) | PDI of Defatted Meal | Protein of Defatted Meal (%, as is) | Oil of Defatted Meal (%, as is) |
|---|---|---|---|---|
| 75° C. for 15 Seconds. | 7.81 | 34.43 | 41.3 | 2.08 |
| 80° C. for 15 Seconds. | 7.30 | 34.17 | 43.2 | 1.54 |
| 85° C. for 15 Seconds | 11.56 | 31.55 | 41.3 | 4.03 |
| 90° C. for 15 Seconds | 7.54 | 31.98 | 43.0 | 1.29 |
| 95° C. for 15 Seconds | 7.82 | 31.97 | 41.9 | 1.47 |
| 100° C. for 15 Seconds | 7.50 | 30.33 | 40.2 | 1.74 |
| 105° C. for 15 Seconds | 7.79 | 29.32 | 39.0 | 1.99 |
| 110° C. for 15 Seconds | 7.67 | 27.82 | 37.7 | 1.64 |
| 120° C. for 15 Seconds | 7.11 | 23.10 | 33.7 | 1.58 |
| 130° C. for 15 Seconds | 7.19 | 18.20 | 28.6 | 1.66 |
| No Heat Treatment | 10.37 | 31.92 | 39.2 | 5.31 |
| Heat Treatment at 95° C. for 0.5 Hr. | 8.03 | 32.22 | 42.6 | 2.78 |

TABLE 4

Evaluation of Heat Treatment on the Sulphur Content of Pressed and Extracted Canola Oils (*B. juncea*)

| Heat Treatment Conditions | Sulphur in Pressed Oil (ppm) | Sulphur in butane/R134a Extracted Oil (ppm) | Sulphur in Methyl Pentane Extracted Oil (ppm) |
|---|---|---|---|
| 75° C. for 15 Seconds. | 21.5 | 99.3 | 222 |
| 80° C. for 15 Seconds. | 9.77 | 101 | 175 |
| 85° C. for 15 Seconds | 9.82 | 562 | 111 |
| 90° C. for 15 Seconds | 9.67 | 86.4 | 55.3 |
| 95° C. for 15 Seconds | 8.71 | 75.8 | 34.5 |
| 100° C. for 15 Seconds | 8.65 | 71.4 | not determined |
| 105° C. for 15 Seconds | 7.13 | 61.8 | not determined |
| 110° C. for 15 Seconds | 8.94 | 55.8 | not determined |
| 120° C. for 15 Seconds | 8.77 | 48.7 | not determined |
| 130° C. for 15 Seconds | 9.82 | 19.9 | not determined |
| No Heat Treatment | 46.9 | 303 | 205 |
| Heat Treatment at 95° C. for 0.5 Hr. | 41.8 | 254 | 98.3 |

TABLE 5

Evaluation of Heat Treatment on the FFA Content of Pressed and Extracted Canola Oils (*B. juncea*)

| Heat Treatment Conditions | FFA in Pressed Oil (%) | FFA in butane/R134a Extracted Oil (%) | FFA in Methyl Pentane Extracted Oil (%) |
|---|---|---|---|
| 75° C. for 15 Seconds. | 1.67 | 2.48 | 2.70 |
| 80° C. for 15 Seconds. | 1.70 | 2.35 | 2.40 |
| 85° C. for 15 Seconds | 1.67 | 2.61 | 2.48 |
| 90° C. for 15 Seconds | 1.65 | 2.06 | 2.39 |
| 95° C. for 15 Seconds | 1.60 | 2.22 | 2.38 |
| 100° C. for 15 Seconds | 1.26 | 2.07 | not determined |
| 105° C. for 15 Seconds | 1.38 | 2.12 | not determined |
| 110° C. for 15 Seconds | 1.23 | 2.13 | not determined |
| 120° C. for 15 Seconds | 1.37 | 1.94 | not determined |
| 130° C. for 15 Seconds | 1.33 | 2.15 | not determined |
| No Heat Treatment | 1.67 | 2.47 | 2.72 |
| Heat Treatment at 95° C. for 0.5 Hr. | 1.67 | 2.63 | 2.78 |

TABLE 6

Evaluation of Heat Treatment on the Phosphorus Content of Pressed and Extracted Canola Oils (*B. juncea*)

| Heat Treatment Conditions | Phosphorus in Pressed Oil (ppm) | Phosphorus in butane/R134a Extracted Oil ppm) | Phosphorus in Methyl Pentane Extracted Oil (ppm) |
|---|---|---|---|
| 75° C. for 15 Seconds. | not determined | 2.93 | 1020 |
| 80° C. for 15 Seconds. | not determined | 2.65 | 899 |
| 85° C. for 15 Seconds | not determined | 8.43 | 975 |
| 90° C. for 15 Seconds | not determined | 2.72 | 735 |
| 95° C. for 15 Seconds | not determined | 22.8 | 805 |
| 100° C. for 15 Seconds | 36.2 | not determined | not determined |
| 105° C. for 15 Seconds | 26.3 | not determined | not determined |
| 110° C. for 15 Seconds | 31.8 | not determined | not determined |
| 120° C. for 15 Seconds | 117 | not determined | not determined |
| 130° C. for 15 Seconds | 30.3 | not determined | not determined |

TABLE 6-continued

Evaluation of Heat Treatment on the Phosphorus Content of Pressed and Extracted Canola Oils (*B. juncea*)

| Heat Treatment Conditions | Phosphorus in Pressed Oil (ppm) | Phosphorus in butane/R134a Extracted Oil ppm | Phosphorus in Methyl Pentane Extracted Oil (ppm) |
|---|---|---|---|
| Seconds | | | |
| No Heat Treatment | not determined | 4.25 | 962 |
| Heat Treatment at 95° C. for 0.5 Hr. | not determined | not determined | 875 |

TABLE 7

Analytical Results of Pressed Canola Cakes (*B. juncea*)

| Sample | Moisture of Press Cake (%) | Oil Content of Press Cake (%) |
|---|---|---|
| 75° C. for 15 Seconds. | 11.4 | 26.2 |
| 80° C. for 15 Seconds. | 10.4 | 27.6 |
| 85° C. for 15 Seconds | 10.2 | 24.4 |
| 90° C. for 15 Seconds | 9.00 | 27.9 |
| 95° C. for 15 Seconds | 9.46 | 26.9 |
| 100° C. for 15 Seconds | 8.20 | 28.0 |
| 105° C. for 15 Seconds | 7.60 | 22.7 |
| 110° C. for 15 Seconds | 9.01 | 23.5 |
| 120° C. for 15 Seconds | 8.60 | 37.7 |
| 130° C. for 15 Seconds | 6.15 | 22.1 |
| No Heat Treatment | 12.0 | 26.4 |
| Heat Treatment at 95° C. for 0.5 Hr. | 12.1 | 24.6 |

TABLE 8

Analysis of Defatted Meal, Protein-Enriched Meal and 65% Protein Concentrate

| Sample | Moisture (%) | Protein (%, dwb) | Ash (%, dwb) | Crude Fiber (%, dwb) | Oil (% dwb) | Carbohydrates (%, dwb) |
|---|---|---|---|---|---|---|
| Canola Seed (*b. juncea*) | 6.25 | 27.24 | 4.1 | 4.52 | 42.27 | 21.87 |
| Pressed Cake | 8.2 | 33.66 | 5.23 | 5.2 | 30.5 | 25.41 |
| Defatted Meal | 7.5 | 43.36 | 7.29 | 6.99 | 1.88 | 40.38 |
| Protein Enriched Meal | 6.76 | 52.44 | 7.47 | 4.37 | 1.56 | 34.16 |
| Fiber Enrich Meal | 7.47 | 43.01 | 6.94 | 9.83 | 2.44 | 37.78 |
| Protein Concentrate | 4.55 | 64.74 | 8.23 | 5.77 | 0.55 | 20.71 |
| Dried Sugar Fraction | 6.43 | 12.40 | 5.75 | 0.17 | 1.93 | 79.75 |

TABLE 9

Water Addition and Seed Weight for Each Batch of Moisture Adjustment and Mixing

| Batch | Weight of Canola Seed (kg) | Amount of Water Added (kg) | Mixing Time (Min.) |
|---|---|---|---|
| 1 | 220.5 | 4.41 | 5 |
| 2 | 221.0 | 4.42 | 5 |
| 3 | 221.0 | 4.42 | 5 |
| 4 | 222.0 | 4.44 | 5 |
| 5 | 223.5 | 4.47 | 5 |
| 6 | 225.0 | 4.50 | 5 |
| 7 | 221.0 | 4.42 | 5 |
| 8 | 225.0 | 4.50 | 5 |
| 9 | 211.0 | 4.22 | 5 |
| 10 | 224.5 | 4.49 | 5 |
| 11 | 222.0 | 4.44 | 5 |
| 12 | 220.5 | 4.41 | 5 |
| 13 | 214.0 | 4.28 | 5 |
| 14 | 47.5 | 0.95 | 5 |
| Total | 2918.5 | 53.96 | |

TABLE 10

Mass Balance of Flaking and Pressing Trials

| Sample | Canola Seed (kg) | Flaked Seed (kg) | Press Cake (kg) | Press Oil (kg) | Ratio of Cake/Seed |
|---|---|---|---|---|---|
| Sample 1a | 300.5 | NA | 181.6 | 73.1 | 60.43 |
| Sample 1b | 2,676 | 2,676 | 1,566 | 872 | 58.52 |

TABLE 11

Results of Proximate Analysis for Canola Seed and Press Cakes

| | Canola Seed (moisture adjusted) | Sample 1a | Sample 1b |
|---|---|---|---|
| Moisture (%) | 8.12 | 7.62 | 10.33 |
| Protein (%, dwb[a]) | 27.00 | 34.86 | 42.04 |
| Crude Oil (%, dwb[a]) | 44.39 | 32.37 | 12.58 |
| Crude Fiber (%, dwb[a]) | 4.75 | 5.3 | 7.00 |
| Ash (%, dwb[a]) | 4.56 | 4.87 | 7.02 |

[a]dwb = dry weight basis

TABLE 12

The Results of Screening Trials for Lab and Milled Canola Meals

| Screening Trial Milled Canola Meal | Sample 1e (%, w/w) | Sample 1f (%, w/w) |
|---|---|---|
| 1 | 57.23 | 42.76 |
| 2 | 47.05 | 52.94 |
| 3 | 42.33 | 57.66 |
| 4 | 49.49 | 50.51 |
| 5 | 49.29 | 50.71 |
| 6 | 43.96 | 56.04 |
| 7 | 46.89 | 53.11 |
| 8 | 47.16 | 52.84 |
| Average | 47.93 | 52.07 |
| Milling and Screening - Sample 2b | 42.85 | 57.15 |
| Milling and Screening - Sample 3b | 40.31 | 59.69 |
| Screening Trial - Sample 1 | 37.14 | 62.86 |

TABLE 13

Processing Conditions for Samples 1-3 of Press Cakes, Extracted Meals, Fiber Enriched Meals and Protein Concentrates

| | Sample 1 | Sample 2 | Sample 3 |
|---|---|---|---|
| Canola Seed | B. juncea | B. juncea | B. juncea |
| Flaking | Yes | No | No |
| Temperature of Heat Treatment in Cooker | 75-96° C. | N/A | N/A |
| Residence Time in Cooker | 20 minutes | 30 minutes | 30 minutes |
| Press Cake Temperature | 68-79° C. | NA | NA |
| Extraction of Press Cake | Butane/R134a | Butane/R134a | Butane/R134a |
| Temperature for Milling and Screening of Defatted Meals | Room Temperature (23° C.) | Room Temperature (23° C.) | Room Temperature (23° C.) |
| Extraction of Protein Enriched Meals | Room Temperature (23° C.) 80% (v/v) ethanol Three Extractions (ratio of 1 to 6 by weight of meal to ethanol) | Room Temperature (23° C.) 80% (v/v) ethanol Three Extractions (ratio of 1 to 6 by weight of meal to ethanol) | Room Temperature (23° C.) 80% (v/v) ethanol Three Extractions (ratio of 1 to 6 by weight of meal to ethanol) |
| Temperature and Residence Time for Desolventization and Drying of Protein Concentrates | 54 ± 3° C. for 18 hours in a Vacuum Dryer | Room Temperature (23° C.) in a Fume Hood for 3 days 50° C. in a Vacuum Dryer for 15 Hours | Room Temperature (23° C.) in a Fume Hood for 3 days 50° C. in a Vacuum Dryer for 15 Hours |
| Milling and Screening | Room Temperature (23° C.) | Room Temperature (23° C.) | Room Temperature (23° C.) |

TABLE 14

Moisture and Oil Contents of Samples 1a-d

| Sample | Mass of Run | Moisture Content (%) | Crude Oil Content (%, dwb[a]) |
|---|---|---|---|
| Sample 1a | 1 kg | 9.32 | 26.81 |
| Sample 1c | 1 kg | 6.13 | 8.75 |
| Sample 1b | 1 kg | 8.58 | 15.12 |
| Sample 1d | 1 kg | 5.81 | 1.94 |
| Sample 1b | 9 kg | 8.00 | 27.83 |
| Sample 1d | 9 kg | 5.38 | 12.73 |

[a]dwb = dry weight basis

TABLE 15

Moisture and Oil Contents of Press Cake from Flaking Trial (Sample 1b)

| Sample | Mass of Run | Moisture Content (%) | Crude Oil Content (%, dwb[a]) |
|---|---|---|---|
| Sample 1b | 8.9 kg | 7.73 | 13.94 |
| Sample 1b | 8.9 kg | 7.25 | 14.00 |
| Sample 1b | 8.9 kg | 7.38 | 15.03 |
| Sample 1b | 8.9 kg | 7.22 | 17.68 |
| Sample 1b | 8.9 kg | 6.90 | 22.90 |
| Sample 1b | 8.9 kg | 7.05 | 19.68 |
| Sample 1b | 8.9 kg | 7.30 | 19.77 |
| Sample 1b | 8.9 kg | 7.70 | 19.92 |
| Sample 1b | 8.9 kg | 7.85 | 19.01 |
| Sample 1b | 8.9 kg | 8.02 | 14.68 |
| Flaked Juncea Press Cake Composite (Multiple Runs) | NA | 9.13 | 13.76 |
| Flaked Juncea Press Cake Composite (Multiple Runs) | NA | 9.04 | 13.52 |
| Sample 1b | 9 kg | 8.42 | 13.03 |
| Sample 1b | 9 kg | 8.26 | 13.04 |
| Sample 1b | 9 kg | 6.63 | 13.33 |
| Sample 1b | 8.9 kg | 8.32 | 13.46 |
| Sample 1b | 8.9 kg | 8.36 | 13.65 |
| Sample 1b | 8.9 kg | 8.35 | 13.73 |
| Sample 1b | 8.9 kg | 8.57 | 12.96 |
| Sample 1b | 8.9 kg | 8.58 | 12.92 |
| Sample 1b | 8.9 kg | 8.40 | 12.72 |
| Sample 1b | 8.9 kg | 8.00 | 13.06 |
| Sample 1b | 8.9 kg | 7.14 | 17.21 |
| Sample 1b | 8.9 kg | 7.29 | 16.80 |
| Sample 1b | 8.9 kg | 7.20 | 14.26 |
| Flaked Juncea Press Cake Composite | NA | 7.97 | 13.22 |

TABLE 15-continued

Moisture and Oil Contents of Press Cake from Flaking Trial (Sample 1b)

| Sample | Mass of Run | Moisture Content (%) | Crude Oil Content (%, dwb[a]) |
|---|---|---|---|
| Flaked Juncea Press Cake Composite (Multiple Runs) | NA | 8.49 | 14.38 |
| Flaked Juncea Press Cake Composite (Multiple Runs) | NA | 8.09 | 14.07 |
| Flaked Juncea Press Cake Composite (Multiple Runs) | NA | 7.41 | 16.64 |
| Flaked Juncea Press Cake Composite (Multiple Runs) | NA | 7.95 | 14.92 |
| Flaked Juncea Press Cake Composite (Multiple Runs) | NA | 8.33 | 15.86 |
| Flaked Juncea Press Cake Composite (Multiple Runs) | NA | 7.1 | 14.90 |
| Flaked Juncea Press Cake Composite (Multiple Runs) | NA | 7.68 | 13.91 |
| Flaked Juncea Press Cake Composite (Multiple Runs) | NA | 8.47 | 14.18 |

[a]dwb = dry weight basis

TABLE 16

Moisture and Oil Contents of Sample 1d

| Sample | Mass of Run | Moisture Content (%) | Crude Oil Content (%, dwb[a]) |
|---|---|---|---|
| Sample 1d | 8.9 kg | 4.81 | 1.70 |
| Sample 1d | 8.9 kg | 4.14 | 1.76 |
| Sample 1d | 8.9 kg | 6.53 | 2.3 |
| Sample 1d | 8.9 kg | 6.44 | 2.45 |
| Sample 1d | 8.9 kg | 6.54 | 2.63 |
| Sample 1d | 8.9 kg | 6.18 | 1.89 |
| Sample 1d | 8.9 kg | 5.80 | 2.49 |
| Sample 1d | 8.9 kg | 6.33 | 2.93 |
| Sample 1d | 8.9 kg | 6.10 | 2.85 |
| Sample 1d | 8.9 kg | 6.02 | 2.14 |
| Sample 1d | 8.9 kg | 5.61 | 2.26 |
| Flaked Juncea Extracted Meal Composite (Multiple Runs) | — | 8.70 | 2.36 |
| Flaked Juncea Extracted Meal Composite (Multiple Runs) | — | 8.27 | 2.30 |
| Flaked Juncea Extracted Meal Composite (Multiple Runs) | 9 kg | 8.20 | 2.68 |
| Flaked Juncea Extracted Meal Composite (Multiple Runs) | 9 kg | 8.38 | 2.13 |
| Flaked Juncea Extracted Meal Composite (Multiple Runs) | 9 kg | 7.13 | 2.27 |
| Flaked Juncea Extracted Meal Composite (Multiple Runs) | 9 kg | 7.74 | 2.03 |
| Sample 1d | 9 kg | 6.44 | 2.63 |
| Sample 1d | 9 kg | 6.28 | 2.50 |
| Sample 1d | 9 kg | 6.54 | 3.13 |
| Flaked Juncea Extracted Meal Composite (Multiple Runs) | — | 7.40 | 2.79 |
| Flaked Juncea Extracted Meal Composite (Multiple Runs) | — | 7.79 | 2.51 |
| Flaked Juncea Extracted Meal Composite (Multiple Runs) | — | 8.18 | 2.47 |
| Flaked Juncea Extracted Meal Composite (Multiple Runs) | — | 6.46 | 2.44 |
| Flaked Juncea Extracted Meal Composite (Multiple Runs) | — | 6.84 | 2.78 |
| Flaked Juncea Extracted Meal Composite (Multiple Runs) | — | 8.03 | 1.87 |
| Flaked Juncea Extracted Meal Composite (Multiple Runs) | — | 6.70 | 2.70 |
| Flaked Juncea Extracted Meal Composite (Multiple Runs) | — | 6.39 | 1.79 |
| Flaked Juncea Extracted Meal Composite (Multiple Runs) | — | 7.06 | 2.02 |

[a]dwb = dry weight basis

TABLE 17

Results of Proximate Analysis for Juncea Seed and Samples 1b, 1d-g, 2a-d and 3a-d

| Sample | Moisture (%) | Protein (%, dwb[a]) | Crude Oil (%, dwb[a]) | Ash (%, dwb[a]) | Crude Fiber (%, dwb[a]) | PDI |
|---|---|---|---|---|---|---|
| Canola Seed (B. juncea) | 8.12 | 27.00 | 44.39 | 4.56 | 4.75 | 25.64 |
| Sample 1b | 10.33 | 42.04 | 12.58 | 7.02 | 7.00 | 28.78 |
| Sample 1d | 6.86 | 47.02 | 1.38 | 8.12 | 7.75 | 33.35 |
| Sample 2a | 6.56 | 49.98 | 0.92 | 7.12 | 7.63 | 33.04 |
| Sample 3a | 6.99 | 47.31 | 2.29 | 6.61 | 7.60 | 28.42 |
| Sample 1f | 6.18 | 46.10 | 2.48 | 6.86 | 8.28 | 31.91 |
| Sample 2c | 6.60 | 46.25 | 1.48 | 6.90 | 9.79 | 29.41 |
| Sample 3c | 6.73 | 44.39 | 3.18 | 6.45 | 8.60 | 29.33 |
| Sample 1e | 6.90 | 53.92 | 1.49 | 7.07 | 5.03 | — |
| Sample 2b | 6.16 | 54.77 | 0.51 | 7.06 | 5.49 | — |
| Sample 3b | 6.50 | 52.62 | 1.37 | 6.67 | 4.82 | — |

TABLE 17-continued

Results of Proximate Analysis for *Juncea* Seed and Samples 1b, 1d-g, 2a-d and 3a-d

| Sample | Moisture (%) | Protein (%, dwb[a]) | Crude Oil (%, dwb[a]) | Ash (%, dwb[a]) | Crude Fiber (%, dwb[a]) | PDI |
|---|---|---|---|---|---|---|
| Sample 1g | 5.51 | 65.80 | 0.41 | 8.03 | 7.16 | — |
| Sample 2d | 5.52 | 68.69 | 0.02 | 8.1 | 7.11 | — |
| Sample 3d | 5.32 | 69.60 | 0.31 | 7.68 | 6.37 | — |

[a]dwb = dry weight basis

TABLE 18

Yields of Protein Concentrates

| Sample | Weight of Protein Enriched Meal (kg) | Weight of Protein Concentrate (kg) | Yield of Protein Concentrate (%) |
|---|---|---|---|
| 1g | 412 (Sample 1e) | 248.3 | 60.27 |
| 2d | 1.5 (Sample 2b) | 1.1 | 73.33 |
| 3d | 3.9 (Sample 3b) | 2.38 | 61.03 |

TABLE 19

Analytical Results of Sample 2d

| Moisture | 4.86% (as is) |
|---|---|
| Gross Fat | 0.28% (as is) |
| Gross Protein | 65.0% (as is) |
| Gross Ash | 7.00% (as is) |
| Gross Fiber | 6.30% (as is) |
| Carbohydrate | 16.56% (as is) |
| Starch | 0.56% (as is) |
| Total Glucosinolate | 0.500 µmole/g |
| Phytic Acid | 732 (mg/kg) |
| Phytic Bounded Phosphorus | 206 (mg/kg) |

TABLE 20

Amino Acid Profile (Acid Hydrolysis) of Sample 2d

| Alanine | 3.18 (g/100 g) |
|---|---|
| Arginine | 4.89 (g/100 g) |
| Aspartic Acid | 5.74 (g/100 g) |
| Glutamic Acid | 10.6 (g/100 g) |
| Glycine | 3.67 (g/100 g) |
| Histidine | 1.82 (g/100 g) |
| Isoleucine | 2.84 (g/100 g) |
| Leucine | 5.23 (g/100 g) |
| Lysine | 3.28 (g/100 g) |
| Phenylalanine | 2.87 (g/100 g) |
| Proline | 3.30 (g/100 g) |
| Serine | 3.06 (g/100 g) |
| Threonine | 3.10 (g/100 g) |
| Tyrosine | 2.35 (g/100 g) |
| Valine | 3.46 (g/100 g) |
| Tryptophan | 0.927 (g/100 g) |
| Cystein + Cystine | 1.02 (g/100 g) |
| Methionine | 1.23 (g/100 g) |

TABLE 21

Glucosinolate Profile of Samples 1g, 2d and 3d on a Dry Weight Basis

|  | Sample 1g | Sample 2d | Sample 3d |
|---|---|---|---|
| Total Glucosinolates (µmole/g) | 3.81 | 6.85 | 0.46 |
| allyl | — | 0.06 | — |
| 3-butenyl | 1.41 | 2.36 | 0.20 |
| 4-pentenyl | 0.06 | 0.11 | — |
| 2-OH-3-butenyl | — | 0.13 | — |
| 2-OH-4-pentenyl | — | — | — |
| CH3-thiopentenyl | — | — | — |
| phenylethyl | — | — | — |
| CH3-thiopentenyl | — | — | — |
| 3-CH3-indolyl | — | — | — |
| 4-OH-3-CH3-indolyl | 2.34 | 4.18 | 0.26 |
| Total Aliphatic Glucosinolates | 1.52 | 2.59 | 0.22 |

TABLE 22

Glucosinolate Profile of 1d, 2a and 3a on a Dry Weight Basis

|  | Sample 1d | Sample 2a | Sample 3a |
|---|---|---|---|
| Total Glucosinolates (µmole/g) | 20.93 | 20.87 | 18.60 |
| allyl | 0.27 | 0.29 | 0.26 |
| 3-butenyl | 14.26 | 14.23 | 12.70 |
| 4-pentenyl | 0.84 | 0.83 | 0.72 |
| 2-OH-3-butenyl | 0.88 | 0.90 | 0.76 |
| 2-OH-4-pentenyl | — | — | — |
| CH3-thiopentenyl | 0.03 | 0.09 | — |
| phenylethyl | 0.18 | 0.19 | 0.14 |
| CH3-thiopentenyl | 0.05 | 0.05 | — |
| 3-CH3-indolyl | 0.11 | 0.11 | 0.13 |
| 4-OH-3-CH3-indolyl | 2.29 | 4.18 | 3.89 |
| Total Aliphatic Glucosinolates | 15.97 | 15.96 | 14.18 |

TABLE 23

Sinapine and Phytate Contents in Samples 1g, 2d and 3d and Samples 1d, 2a and 3a on an As Is Basis

|  | Sample 1g | Sample 2d | Sample 3d |
|---|---|---|---|
| Sinapine (phenyl propanoid) % (as is) | 0.006 | 0.003 | 0.007 |
| Total Phytic Acid % (as is) | 3.18 | 2.71 ± 0.029 | 3.35 ± 0.039 |

|  | Sample 1d | Sample 2a | Sample 3a |
|---|---|---|---|
| Sinapine (phenyl propanoid) % (as is) | 0.122 | 0.239 | 0.104 |
| Total Phytic Acid % (as is) | 2.53 ± 0.10 | 2.56 ± 0.15 | 2.59 ± 0.13 |

TABLE 24

Solvent Residues in 1, 2a and 2c Before Vacuum Drying

| Sample | Solvent Residues |
|---|---|
| 1 | Butane: 160 ppm and R134a: 435.2 ppm |
| 2a | Butane: 194 ppm and R134a: 1414.3 ppm |
| 2c | Butane: 178 ppm and |

TABLE 24-continued

Solvent Residues in 1, 2a and 2c Before Vacuum Drying

| Sample | Solvent Residues |
|---|---|
| | R134a: 1049.3 ppm |

TABLE 25

Solvent Residues in Samples 1-3 after Desolventization and Drying in a Vacuum Dryer at 50° C. for 15 Hours.

| | Sample 1 | Sample 2 | Sample 3 |
|---|---|---|---|
| Sample 1d, 2a and 3a | Butane: <10 ppm<br>R134a: <10 ppm | Butane: 16.8 ppm<br>R134a: 41.5 ppm | Butane: 11 ppm<br>R134a: <10 ppm |
| Sample 1f, 2c and 3c | Butane: <10 ppm<br>R134a: <10 ppm | Butane: 15 ppm<br>R134a: 41.7 ppm | Butane: <10 ppm<br>R134a: <10 ppm |
| Sample 1g, 2d and 3d | Ethanol: 32.8 ppm<br>Ethyl Acetate: <1.0 ppm<br>Butane: <10 ppm<br>R134a: <10 ppm | Ethanol: NA<br>Ethyl Acetate: <1.0 ppm<br>Butane: <10 ppm<br>R134a: <10 ppm | Ethanol: 6.6 ppm<br>Ethyl Acetate: <1.0 ppm<br>Butane: <10 ppm<br>R134a: <10 ppm |

TABLE 26

Results of the Proximate Analysis for Canola Seed, Canola Seed Press Cake, Defatted Meal, Protein Enriched Meal, Fiber Enriched Meal, Canola Protein Concentrate, Hydrolyzed Canola Protein Concentrate and Canola Protein Isolate.

| Sample | Moisture (%) | Protein (%, dwb$^a$) | Ash (%, dwb$^a$) | Oil (%, dwb$^a$) | Crude Fiber (%, dwb$^a$) |
|---|---|---|---|---|---|
| Canola Seed | 8.12 | 27.0 | 4.56 | 44.39 | 4.75 |
| Canola Seed Press cake | 10.33 | 42.0 | 7.02 | 12.58 | 7.00 |
| Defatted Meal | 6.86 | 47.0 | 8.12 | 1.38 | 7.75 |
| Protein Enriched Meal | 6.71 | 52.0 | 8.34 | 0.84 | 5.53 |
| Fiber Enriched Meal | 6.91 | 43.6 | 7.88 | 1.29 | 9.00 |
| Protein Concentrate | 6.14 | 70.6 | 10.5 | 0.11 | 4.88 |
| Hydrolyzed Protein Concentrate | 6.44 | 88.8 | 5.98 | 0.24 | 0.00 |
| Protein Isolate | 3.90 | 92.8 | 3.54 | 0.04 | 0.00 |

$^a$ dwb = dry weight basis

TABLE 27

Results of Proximate Analysis on Samples for Production of Protein Concentrate Having About 70% Protein

| Sample | Solids (%) | Moisture (%) | Protein (%, dwb) | Ash (%, dwb) | Oil (%, dwb) | Crude Fiber (%, dwb) |
|---|---|---|---|---|---|---|
| Bird Decanter - Canola fiber 1$^{st}$ pass | 15.42 | 4.19 | 47.5 | 8.42 | 0.66 | 10.2 |
| Bird Decanter - Washed Canola fiber 2$^{nd}$ pass | 15.33 | 4.81 | 45.4 | | 0.69 | 12.7 |
| Bird Decanter - Protein slurry after fiber removal | 8.26 | 10.3 | 52.4 | 10.16 | 0.06 | 3.20 |
| Bird Decanter - Protein slurry after fiber removal 2$^{nd}$ pass | 4.80 | 7.37 | 49.6 | 9.61 | 0.42 | 6.52 |
| Westfalia decanter - Protein solids #1 | 19.54 | 7.35 | 52.6 | 10.81 | 0.21 | 6.89 |
| Westfalia decanter - Protein Extract #1 | 3.75 | — | — | 7.29 | — | — |
| Westfalia decanter - Protein solids #2 | 15.74 | 6.59 | 48.4 | 11.49 | 0.14 | 9.92 |
| Westfalia decanter - Protein extract #2 | 1.65 | — | — | — | — | — |
| Disc stack centrifuge - Protein solids | 15.72 | — | — | — | — | — |
| Disc stack centrifuge - Clarified protein extract | 2.61 | — | — | — | — | — |
| Permeate - Ultrafiltration | 1.14 | — | — | — | — | — |
| Permeate - Diafiltration | 0.19 | — | — | — | — | — |
| Protein retentate - Ultrafiltration (UF) | 13.17 | 6.90 | 90.4 | 2.14 | 0.12 | 0.00 |
| Protein retentate - Diafiltration (DF) | 3.40 | 1.34 | 92.4 | 2.65 | 0.01 | 0.03 |
| Protein isolate solution - UF and DF | 5.50 | — | — | — | — | — |
| Westfalia decanter - hydrolyzed protein extract 1 | 2.27 | — | 75.0 | — | — | — |
| Westfalia decanter - canola fiber solids #1 | 12.98 | 5.89 | 27.8 | 18.1 | 2.53 | 14.5 |
| Westfalia decanter - hydrolyzed protein extract 2 | 1.12 | — | 58.5 | — | — | — |
| Westfalia decanter - canola fiber solids - 2$^{nd}$ centrifuge | 11.74 | 5.84 | 19.6 | 18.8 | 2.28 | 21.4 |

TABLE 28

Amino Acid Profiles of Protein Concentrate, Hydrolyzed Protein Concentrate and Protein Isolate on a Dry Weight Basis

| Amino Acid | Protein Concentrate | Hydrolyzed Protein Concentrate | Protein Isolate |
|---|---|---|---|
| Aspartic Acid (%, dwb$^a$) | 4.84 | 7.05 | 7.91 |
| Glutamic Acid (%, dwb$^a$) | 12.25 | 15.71 | 17.48 |
| Serine (%, dwb$^a$) | 3.61 | 4.63 | 4.45 |
| Glycine (%, dwb$^a$) | 3.82 | 4.58 | 5.13 |
| Histidine (%, dwb$^a$) | 1.71 | 2.20 | 2.19 |
| Arginine (%, dwb$^a$) | 5.79 | 7.41 | 6.92 |
| Threonine (%, dwb$^a$) | 3.18 | 4.35 | 3.74 |
| Alanine (%, dwb$^a$) | 3.48 | 4.90 | 4.56 |
| Proline (%, dwb$^a$) | 4.07 | 5.70 | 5.22 |
| Tyrosine (%, dwb$^a$) | 2.77 | 5.10 | 3.28 |
| Valine (%, dwb$^a$) | 3.79 | 4.77 | 4.95 |
| Methionine (%, dwb$^a$) | 1.40 | 1.75 | 2.02 |
| Cystine (%, dwb$^a$) | 1.17 | 1.46 | 1.55 |
| Isoleucine (%, dwb$^a$) | 3.18 | 4.75 | 4.06 |
| Leucine (%, dwb$^a$) | 5.76 | 6.38 | 7.36 |
| Phenylalanine (%, dwb) | 3.34 | 3.62 | 4.23 |
| Lysine (%, dwb$^a$) | 3.77 | 5.55 | 4.10 |
| Tryptophan (%, dwb$^a$) | 1.02 | 1.09 | 1.38 |

TABLE 28-continued

Amino Acid Profiles of Protein Concentrate, Hydrolyzed Protein Concentrate and Protein Isolate on a Dry Weight Basis

| Amino Acid | Protein Concentrate | Hydrolyzed Protein Concentrate | Protein Isolate |
|---|---|---|---|
| Total Amino Acid (%, dwb[a]) | 68.95 | 91.00 | 90.53 |

[a]dwb = dry weight basis

TABLE 29

Amino Acid Profiles of Canola Protein Concentrate, Hydrolyzed Canola Protein Concentrate, Canola Protein Isolate, Soy Protein Isolate and Pea Protein Isolate on a Normalized Basis of Pure Protein

| Amino Acid | Canola Protein Concentrate | Hydrolyzed Canola Protein Concentrate | Canola Protein Isolate | Soy Protein Isolate | Pea Protein Isolate |
|---|---|---|---|---|---|
| Aspartic Acid (%) | 7.02 | 7.75 | 8.74 | 11.5 | 11.78 |
| Glutamic Acid (%) | 17.77 | 17.26 | 19.31 | 19.0 | 19.13 |
| Serine (%) | 5.24 | 5.09 | 4.92 | 5.2 | 5.28 |
| Glycine (%) | 5.54 | 5.03 | 5.67 | 4.1 | 3.86 |
| Histidine[a] (%) | 2.48 | 2.42 | 2.42 | 2.6 | 2.55 |
| Arginine (%) | 8.40 | 8.14 | 7.64 | 7.5 | 8.58 |
| Threonine[a] (%) | 4.61 | 4.78 | 4.13 | 3.8 | 3.68 |
| Alanine (%) | 5.05 | 5.39 | 5.04 | 4.2 | 4.15 |
| Proline (%) | 5.90 | 6.26 | 5.77 | 5.1 | 4.15 |
| Tyrosine (%) | 4.02 | 5.60 | 3.62 | 3.8 | 3.68 |
| Valine[a] (%) | 5.50 | 5.24 | 5.47 | 5.0 | 4.90 |
| Methionine[a] (%) | 2.03 | 1.92 | 2.23 | 1.3 | 1.13 |
| Cystine (%) | 1.70 | 1.60 | 1.71 | 1.3 | 1.04 |
| Isoleucine[a] (%) | 4.61 | 5.22 | 4.49 | 4.8 | 4.43 |
| Leucine[a] (%) | 8.35 | 7.01 | 8.13 | 8.1 | 8.20 |
| Phenylalanine[a] (%) | 4.84 | 3.98 | 4.67 | 5.2 | 5.29 |
| Lysine[a] (%) | 5.47 | 6.10 | 4.53 | 6.2 | 7.26 |
| Tryptophan[a] (%) | 1.49 | 1.20 | 1.52 | 1.3 | 0.94 |
| Total Amino Acid (%) | 100 | 100 | 100 | 100 | 100 |

[a]Nine essential amino acids.

TABLE 30

Essential Amino Acid Profiles of Canola Protein Concentrate, Hydrolyzed Canola Protein Concentrate, Canola Protein Isolate, Soy Protein Isolate and Pea Protein Isolate and Their Functions on Human Nutrition

| Amino Acid | Canola Protein Concentrate | Hydrolyzed Canola Protein Concentrate | Canola Protein Isolate | Soy Protein Isolate | Pea Protein Isolate | Specific Benefit and Impact on Human Nutrition |
|---|---|---|---|---|---|---|
| Histidine (%) | 2.48 | 2.42 | 2.42 | 2.6 | 2.55 | — |
| Threonine (%) | 4.61 | 4.78 | 4.13 | 3.8 | 3.68 | Brain Activity |
| Valine[a] (%) | 5.50 | 5.24 | 5.47 | 5.0 | 4.90 | Muscle Mass |
| Methionine (%) | 2.03 | 1.92 | 2.23 | 1.3 | 1.13 | Muscle Building, Antioxidant and Development of Appendages |
| Isoleucine (%) | 4.61 | 5.22 | 4.49 | 4.8 | 4.43 | Muscle Mass |
| Leucine (%) | 8.35 | 7.01 | 8.13 | 8.1 | 8.20 | Muscle Mass |
| Phenylalanine (%) | 4.84 | 3.98 | 4.67 | 5.2 | 5.29 | — |
| Lysine (%) | 5.47 | 6.10 | 4.53 | 6.2 | 7.26 | Growth |
| Tryptophan (%) | 1.49 | 1.20 | 1.52 | 1.3 | 0.94 | Sleep Aid and Anti-depression |

TABLE 31

Functional Properties of Canola Protein Isolate as Compared to Soy and Pea Protein Isolates

| Sample | Concentration of Protein Isolate (%, w/w) | Emulsifying Capacity at pH 7 (%) | Emulsion Stability at pH 7 (%) | Foaming Capacity at pH 7 (%) | Foam Stability at pH 7 (%) |
|---|---|---|---|---|---|
| Canola Protein Isolate | 0.5 | 58 | 55 | 352 | 18.5 |
|  | 1.0 | 66 | 60 | 389 | 26 |
| Soy Protein Isolate | 0.5 | 59 | 57 | 108 | 4.9 |
|  | 1.0 | 64 | 60 | 478 | 21 |
| Pea Protein | 0.5 | 57 | 52 | 24.4 | 7 |
|  | 1.0 | 62 | 58 | 202 | 7 |

TABLE 31-continued

Functional Properties of Canola Protein Isolate as Compared to Soy and Pea Protein Isolates

| Sample | Concentration of Protein Isolate (%, w/w) | Emulsifying Capacity at pH 7 (%) | Emulsion Stability at pH 7 (%) | Foaming Capacity at pH 7 (%) | Foam Stability at pH 7 (%) |
|---|---|---|---|---|---|
| Isolate | | | | | |

TABLE 32

Functional Properties of Canola Protein Isolate

| Functional Property | Results and Comments |
|---|---|
| Emulsifying Capacity | Emulsifying capacity of 0.5% canola protein isolate solution was high, comparable to that of 5% native egg yolk. |

| Oil Content of Emulsion | Emulsion of Canola Protein Isolate |
|---|---|
| 50.0 | Stable |
| 60.0 | Stable |
| 70.0 | Stable |
| 72.5 | Stable |
| 75.0 | Stable |
| 77.5 | Instable |

Figure 36:
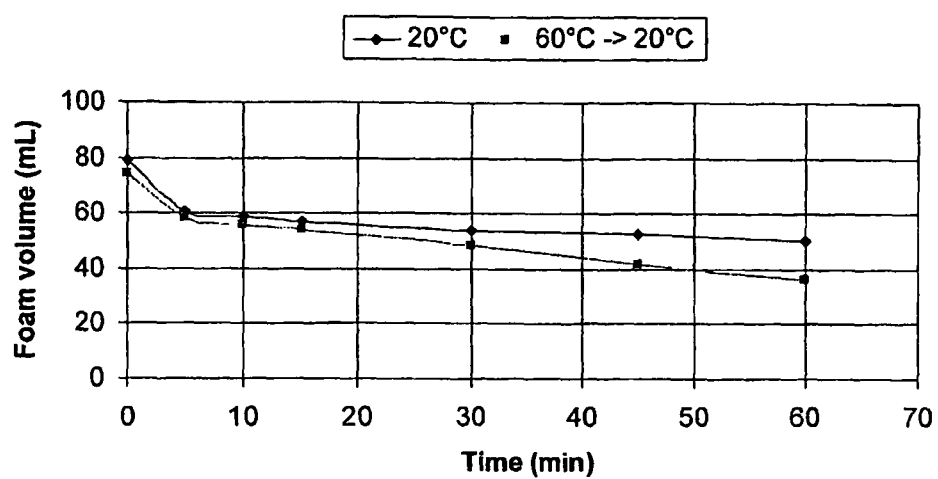
FIG. 36 is a graph showing the foam volume of a protein isolate produced in accordance with a process of the present disclosure.

| Foaming and Foam Stability | Foaming properties of canola protein isolate were superior in comparison to whey protein isolate as shown in FIG. 36. |
|---|---|

| Time (min) | Foam Volume (mL) Whipping at 20° C. for 1 minute | Foam Volume (mL) Heated at 60° for 15 minutes and then cooled to 20° C., finally whipping at 20° C. for 1 minute |
|---|---|---|
| 0 | 80 | 75 |
| 5 | 61 | 59 |
| 10 | 60 | 58 |
| 15 | 58 | 56 |
| 30 | 53 | 50 |
| 45 | 52 | 42 |
| 60 | 50 | 38 |

Figure 37:
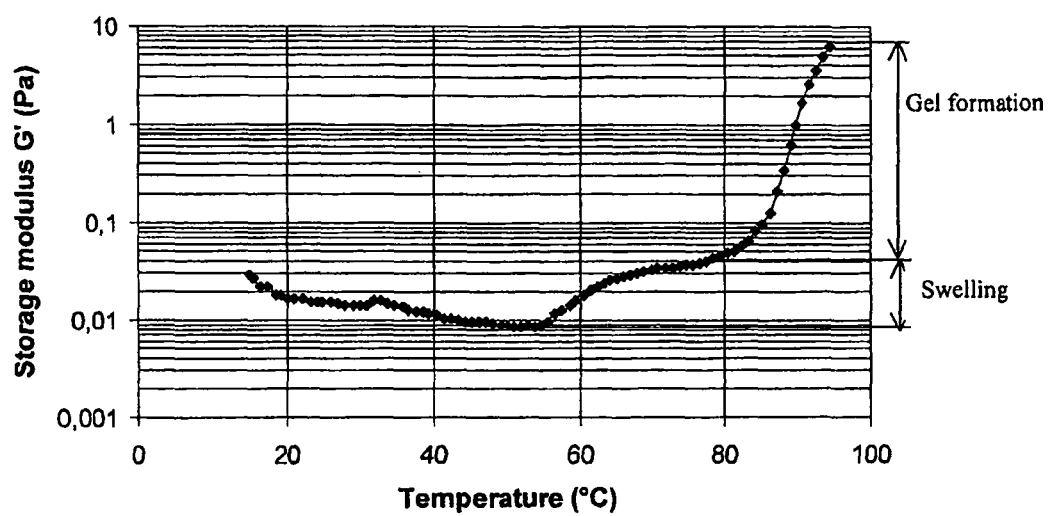
FIG. 37 is a graph showing the gel forming temperature of a protein isolate produced in accordance with a process of the present disclosure.
Figure 38:
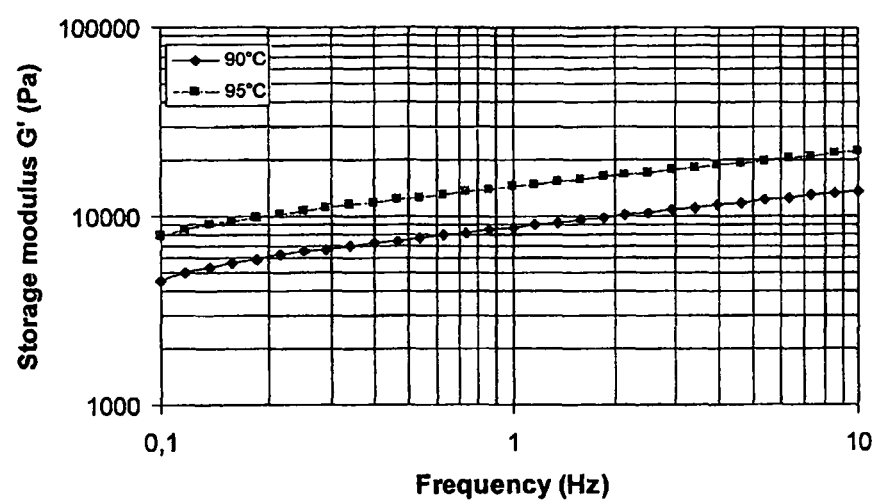
FIG. 38 is a graph showing the oscillation tests of gels of a protein isolate produced in accordance with a process of the present disclosure.
Figure 39:
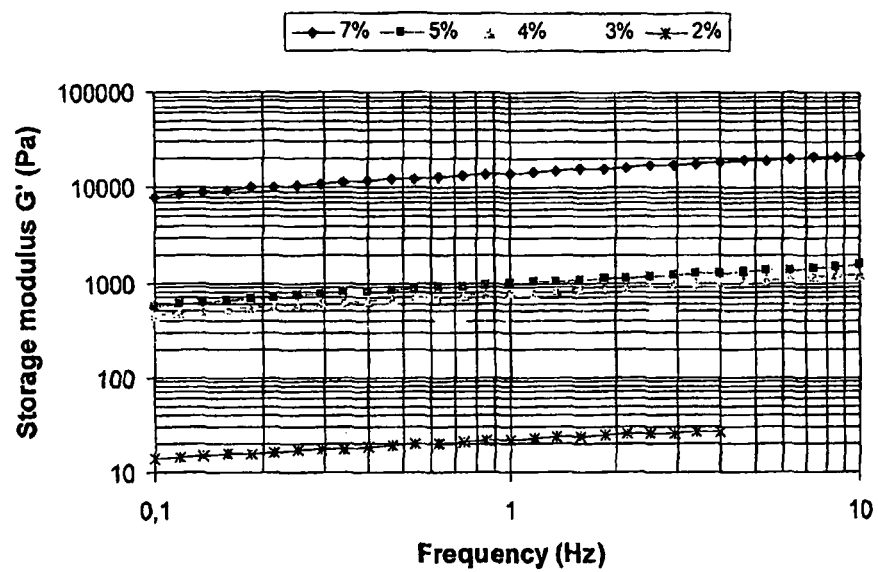
FIG. 39 is a graph showing the oscillation test of gels of different concentrations of a protein isolate produced in accordance with a process of the present disclosure.

| Gel Formation and Gel Strength | Canola protein isolate required higher temperature for gel formation in comparison to whey protein isolate, as shown in FIGS. 37 and 38. Gel firmness of canola protein isolate was comparable to that of whey protein isolate and soy protein isolate gels at 5% protein content. For canola protein isolate, gels with 7% protein content were strong, gels with 3-5% content possessed a medium scaled strength, and gels with 2% protein content were very weak, as shown in FIG. 39. |
|---|---|
| Water Immobilization | Water immobilization of canola protein isolate gels was slightly lower than that of whey protein isolate gels. |

TABLE 33

Results of Solubility Tests on Canola, Pea and Soy Protein Isolate

| Test Method | Solubility |
|---|---|
| | Borate-phosphate buffer (12.20 g/L of $NaH_2PO_4 \cdot H_2O$ and 8.91 g/L of $Na_2B_4O_7 \cdot 10H_2O$) 1% concentration pH 6.7 |

TABLE 33-continued

Results of Solubility Tests on Canola, Pea and Soy Protein Isolate

| | Solubility |
|---|---|
| | 39° C. 1 hour |
| Solubility of Canola Protein Isolate (%, w/w) (Obtained from Example 5(b)) | 99.81 |
| Solubility of Pea Protein Isolate (%, w/w) | 18.85 |
| Solubility of Soy Protein Isolate (%, w/w) | 25.21 |

TABLE 34

Anti-nutritional Factors of Canola Protein Isolate

| Anti-nutritional Factors | Content |
|---|---|
| Total Glucosinolate | 0.200 µmol/g |
| Erucic Acid | 0.1% of total fat (1.7% total fat) |
| Phytic Acid | <0.05% |
| Phytic Bounded Phosphorus | <0.01% |
| Allyl Isothiocyanate | <0.02% |

TABLE 35

Glucosinolates in *Juncea* Seed, Press Cake, BioExx Extracted Meal, Protein Enriched meal, Fiber Enriched Meal, Protein Concentrate, Hydrolyzed Protein Concentrate, and Protein Isolate

| Glucosinolates | *Juncea* Seed | Press Cake | BioExx Extracted Meal | Protein Enriched Meal |
|---|---|---|---|---|
| Allyl (µmoles/g) | 0.12 | 0.21 | 0.25 | 0.26 |
| 3-butenyl (µmoles/g) | 6.69 | 10.34 | 12.23 | 14.71 |
| 4-pentenyl (µmoles/g) | 0.46 | 0.72 | 0.85 | 0.99 |
| 2-OH-3-butenyl (µmoles/g) | 0.76 | 1.18 | 1.40 | 1.58 |
| CH3-thiobutenyl (µmoles/g) | 0 | 0.05 | 0.05 | 0.05 |
| Phenylethyl (µmoles/g) | 0.17 | 0.27 | 0.32 | 0.37 |
| 3-CH3-indolyl (µmoles/g) | 0.48 | 0.81 | 0.91 | 1.01 |
| 4-OH-3-CH3-indolyl (µmoles/g) | 2.11 | 2.95 | 3.56 | 4.20 |
| Total Aliphatics (µmoles/g) | 7.92 | 12.26 | 14.51 | 17.31 |

| Glucosinolates | Fiber Enriched Meal | Canola Protein Concentrate | Hydrolyzed Protein Concentrate | Canola Protein Isolate |
|---|---|---|---|---|
| Allyl (µmoles/g) | 0.21 | 0 | 0 | 0 |
| 3-butenyl (µmoles/g) | 12.64 | 0.11 | 0.23 | 0.17-0.41 |
| 4-pentenyl (µmoles/g) | 0.86 | 0 | 0 | 0 |
| 2-OH-3-butenyl (µmoles/g) | 1.53 | 0 | 0 | 0 |
| CH3-thiobutenyl (µmoles/g) | 0 | 0 | 0 | 0 |
| Phenylethyl (µmoles/g) | 0.33 | 0 | 0 | 0 |

TABLE 35-continued

Glucosinolates in *Juncea* Seed, Press Cake, BioExx Extracted Meal, Protein Enriched meal, Fiber Enriched Meal, Protein Concentrate, Hydrolyzed Protein Concentrate, and Protein Isolate

| | | | | |
|---|---|---|---|---|
| 3-CH3-indolyl (µmoles/g) | 0.91 | 0 | 0 | 0 |
| 4-OH-3-CH3-indolyl (µmoles/g) | 3.26 | 0 | 0 | 0 |
| Total Aliphatics (µmoles/g) | 15.05 | 0.11 | 0.23 | 0.17-0.41 |

TABLE 36

Results of Proximate Analysis for Defatted *Juncea* Meal, Protein Enriched Meal, Fiber Enriched Meal, Protein Concentrate and Hydrolyzed Canola Protein Concentrate

| Sample | Moisture (%) | Protein (%, dwb[a]) | Ash (%, dwb[a]) | Oil (%, dwb[a]) | Crude Fiber (%, dwb[a]) |
|---|---|---|---|---|---|
| Defatted *Juncea* Meal | 6.43 | 48.0 | 7.50 | 2.15 | 7.75 |
| Protein Enriched Meal | 5.92 | 51.5 | 7.71 | 1.23 | 5.48 |
| Fiber Enriched Meal | 6.12 | 45.0 | 7.42 | 2.33 | 8.86 |
| Protein Concentrate | 7.83 | 68.2 | 8.56 | 0.10 | 5.71 |
| Hydrolyzed Protein Concentrate | 8.69 | 82.0 | 5.84 | 0.11 | 0.12 |

[a] dwb = dry weight basis

TABLE 37

Results of Proximate Analysis of Ethanol Washed Protein Solids

| Sample | Solids (%) | Protein (%, dwb[a]) | Ash (%, dwb[a]) | Oil (%, dwb[a]) | Crude Fiber (%, dwb[a]) |
|---|---|---|---|---|---|
| Ethanol Washed Protein Solids #1 | 14.07 | 61.4 | 8.26 | 0.74 | 5.53 |
| Ethanol Washed Protein Solids #2 | 19.22 | 66.3 | 8.43 | 0.53 | 5.81 |
| Ethanol Washed Protein Solids #3 | 19.39 | 67.8 | 8.38 | 0.41 | 5.97 |
| Protein Concentrate | 92.17 | 68.2 | 8.56 | 0.10 | 5.71 |

[a] dwb = dry weight basis

TABLE 38

Protein Recovery Yield Through Protein Hydrolysis and Membrane Purification

| Sample | Weight (kg) | Solid Content (%) | Protein (%, dwb) | Protein Weight (kg, dwb) |
|---|---|---|---|---|
| Insoluble Fiber Solids | 126.3 | 13.91 | 46.0 | 8.08 |
| Soluble Hydrolyzed Protein Extract | 328 | 2.59 | 84.0 | 7.14 |
| Hydrolyzed Protein Retentate from UF | 47.7 | 1.36 | 39.8 | 0.26 |
| Hydrolyzed Protein Permeate | 540 | — | — | 6.88 |

TABLE 39

Results of Absorbance and Transmittance for Hydrolyzed Canola Protein concentrate, Soy and Pea Protein Isolate Solutions at 720 nm Wavelength

| Sample | Absorbance | Transmittance | Percent Transmittance |
|---|---|---|---|
| 1% Hydrolyzed Protein Concentrate Solution | 0.014 | 0.97 | 97 |
| 3% Hydrolyzed Protein Concentrate Solution | 0.053 | 0.89 | 89 |
| 5% Hydrolyzed Protein Concentrate Solution | 0.063 | 0.87 | 87 |
| 1% Soy Protein Isolate Solution | >3.8 | <0.00016 | <0.016 |
| 1% Pea Protein Isolate Solution | >3.8 | <0.00016 | <0.016 |

TABLE 40

Mass Balance Data for Crushing and Extraction of Regular and *Juncea* Canola Seeds

| 10 kg of Regular Canola Seed (*B. napus*) | 499 kg of *Juncea* Seed (*B. juncea*) |
|---|---|
| 6.32 kg of Press Cake | 278.9 kg of Press Cake |
| 3.26 kg of Press Oil | 138.1 kg of Press Oil |
| 5.02 kg of Defatted Meal | 8.23 kg of Defatted Meal from 10 kg of Press Cake |
| 1.76 kg of Protein Enriched Meal from 4.01 kg of Defatted Meal | 1.53 kg of Protein Enriched Meal from 3.52 kg of Defatted Meal |
| 2.24 kg of Fiber Enriched Meal from 4.01 kg of Defatted Meal | 1.84 kg of Fiber Enriched Meal from 3.52 kg of Defatted Meal |

TABLE 41

Mass Balance Data for the Wet Fiber Separation to Remove Fiber and Prepare Canola Protein Concentrates

| Regular Canola Protein Slurry (*B. napus*) | *Juncea* Protein Slurry (*B. juncea*) |
|---|---|
| 0.75 kg of Protein Enriched Meal | 1 kg of Protein Enriched Meal |
| 6 kg of Water | 8 kg of Water |
| 1.708 kg of Total Insoluble Wet Solids | 2.282 kg of Total Insoluble Wet Solids |
| 0.347 kg of Wet Fiber Solids | 0.431 kg of Wet Fiber Solids |
| 19.13 kg of Sugar Extract | 27.32 kg of Sugar Extract |
| 0.418 kg of Dried Protein Concentrate | 0.544 kg of Dried Protein Concentrate |

TABLE 42

Results of Proximate Analysis for Regular and *Juncea* Defatted Meals, and Protein and Fiber Enriched Meals

| Sample | Moisture (%) | Protein (%, dwb[a]) | Crude Oil (%, dwb[a]) | Ash (%, dwb[a]) | Crude Fiber (%, dwb[a]) |
|---|---|---|---|---|---|
| Defatted Regular Canola Meal | 7.11 | 46.8 | 1.04 | 7.35 | 9.90 |
| Defatted *Juncea* Meal | 7.18 | 48.7 | 0.87 | 7.48 | 7.44 |
| Protein Enriched Regular Canola Meal | 6.77 | 51.5 | 0.51 | 7.52 | 7.09 |
| Protein Enriched *Juncea* Meal | 6.54 | 52.8 | 0.34 | 7.55 | 5.36 |
| Fiber Enriched Regular Canola Meal | 7.03 | 43.9 | 1.61 | 7.09 | 13.3 |
| Fiber Enriched *Juncea* Meal | 6.73 | 45.6 | 1.06 | 7.12 | 9.71 |

[a] dwb = dry weight basis

TABLE 43

Results of Proximate Analysis for Regular and *Juncea* Protein Concentrates and Fiber Fraction from Wet Separation Process

| Sample | Moisture (%) | Protein (%, dwb[a]) | Crude Oil (%, dwb[a]) | Ash (%, dwb[a]) | Crude Fiber (%, dwb[a]) |
|---|---|---|---|---|---|
| Regular Canola Protein Concentrate | 5.26 | 66.9 | 0.21 | 7.83 | 7.30 |
| *Juncea* Canola Protein Concentrate | 3.90 | 71.2 | 0.13 | 7.99 | 5.96 |
| Regular Canola Fiber Fraction | 6.74 | 36.3 | 1.52 | 5.83 | 21.6 |
| *Juncea* Fiber Fraction | 5.68 | 48.2 | 1.41 | 7.91 | 11.49 |

[a] dwb = dry weight basis

TABLE 44

Amino Acid Profiles of Canola Protein Concentrates and Methyl Pentane Defatted Regular Canola and *Juncea* Meals on a Normalized Basis of Pure Protein.

| Amino Acid | Defatted Regular Canola Meal (*B. napus*) | Defatted *Juncea* Meal (*B. juncea*) | Regular Canola Protein Concentrate | *Juncea* Protein Concentrate |
|---|---|---|---|---|
| Aspartic Acid (%) | 6.86 | 7.55 | 6.75 | 7.17 |
| Glutamic Acid (%) | 18.93 | 19.00 | 19.27 | 18.78 |
| Serine (%) | 5.03 | 5.15 | 4.95 | 4.95 |
| Glycine (%) | 5.45 | 5.48 | 5.40 | 5.41 |
| Histidine[a] (%) | 2.77 | 2.21 | 2.39 | 2.39 |
| Arginine (%) | 7.78 | 7.71 | 7.29 | 8.22 |
| Threonine[a] (%) | 3.86 | 4.24 | 3.89 | 4.10 |
| Alanine (%) | 4.90 | 5.00 | 4.81 | 4.88 |
| Proline (%) | 7.15 | 6.47 | 6.80 | 6.27 |
| Tyrosine (%) | 3.62 | 3.66 | 3.79 | 3.96 |
| Valine[a] (%) | 5.45 | 5.30 | 5.28 | 5.22 |
| Methionine[a] (%) | 2.24 | 2.04 | 2.34 | 2.11 |
| Cystine (%) | 2.64 | 2.32 | 2.30 | 2.11 |
| Isoleucine[a] (%) | 3.88 | 4.18 | 3.96 | 4.08 |
| Leucine[a] (%) | 7.34 | 7.66 | 7.68 | 7.91 |
| Phenylalanine[a] (%) | 4.25 | 4.50 | 4.55 | 4.65 |
| Lysine[a] (%) | 6.73 | 6.26 | 6.96 | 6.27 |
| Tryptophan[a] (%) | 1.05 | 1.41 | 1.45 | 1.54 |
| Total Amino Acid (%) | 100 | 100 | 100 | 100 |

[a] Nine essential amino acids.

TABLE 45

Results of Solubility Test on Defatted Canola Meals, Protein Concentrates, and Commercial Samples of Soy and Pea Protein Isolates

| Test Method | Borate-phosphate buffer (12.20 g/L of $NaH_2PO_4 \cdot H_2O$ and 8.91 g/L of $Na_2B_4O_7 \cdot 10H_2O$), 1% concentration, pH 6.7, 39° C., 1 hour |
|---|---|
| Protein Solubility of Defatted Regular Canola Meal (*B. napus*) (%, w/w) | 31.48 |
| Protein Solubility of Defatted *Juncea* Meal (*B. juncea*) (%, w/w) | 30.36 |
| Protein Solubility of Regular Canola Protein Concentrate (%, w/w) | 36.76 |
| Protein Solubility of *Juncea* Protein Concentrate (%, w/w) | 32.27 |
| Protein Solubility of Commercial Soy Protein Isolate (%, w/w) | 22.90 |
| Protein Solubility of Commercial Pea Protein Isolate (%, w/w) | 15.93 |

TABLE 46

Results of Anti-nutritional Factors.

| Sample | Sinapine (%) | Betain (%) | Choline (%) | Phytate (IP5 & IP6) (%, as is) |
|---|---|---|---|---|
| Defatted Regular Canola Meal (*B. napus*) | 0.188 | 0.592 | 0.252 | 3.35 |
| Defatted *Juncea* Meal (*B. juncea*) | 0.784 | 0.385 | 0.214 | 3.24 |
| Regular Canola Protein Concentrate | 0.073 | 0.003 | 0.003 | 4.46 |
| *Juncea* Protein Concentrate | 0.050 | 0.001 | 0.004 | 4.67 |
| *Juncea* Protein Isolate | 0.105 | 0.004 | 0.051 | 1.01 |
| Soy Protein Isolate | 0.063 | 0.002 | 0.047 | 2.14 |
| Pea Protein Isolate | 0.058 | 0.004 | 0.010 | 2.43 |

TABLE 47

Results of Proximate Analysis for Defatted *Juncea* Meal and Protein Concentrate

| Sample | Moisture (%) | Protein (%, dwb[a]) | Ash (%, dwb[a]) | Oil (%, dwb[a]) | Crude Fiber (%, dwb[a]) |
|---|---|---|---|---|---|
| Defatted *Juncea* Meal | 6.43 | 48.0 | 7.50 | 2.15 | 7.75 |
| Canola Protein Concentrate | 5.02 | 73.3 | 9.44 | 0.51 | 3.78 |

[a] dwb = dry weight basis

TABLE 48

Results of Proximate Analysis for Canola Protein Slurries Containing Soluble and Insoluble Proteins, Canola Fiber Solids, Washed Canola Fiber Solids and Insoluble Protein Solids

| Sample | Solids (%) | Protein (%, dwb[a]) | Ash (%, dwb[a]) | Oil (%, dwb[a]) | Crude Fiber (%, dwb[a]) |
|---|---|---|---|---|---|
| Insoluble Protein Solids | 6.31 | 52.6 | 8.84 | 0.61 | 1.38 |

TABLE 48-continued

Results of Proximate Analysis for Canola Protein Slurries Containing Soluble and Insoluble Proteins, Canola Fiber Solids, Washed Canola Fiber Solids and Insoluble Protein Solids

| Sample | Solids (%) | Protein (%, dwb [a]) | Ash (%, dwb [a]) | Oil (%, dwb [a]) | Crude Fiber (%, dwb [a]) |
|---|---|---|---|---|---|
| and Soluble Protein Extract #1A | | | | | |
| Insoluble Protein Solids and Soluble Protein Extract #2A | 8.81 | 55.4 | 9.06 | 0.29 | 3.32 |
| Insoluble Protein Solids and Soluble Protein Extract #3A | 9.87 | 55.0 | 8.91 | 0.39 | 1.94 |
| Insoluble Protein Solids and Soluble Protein Extract #4A | 9.63 | 55.5 | 8.71 | 0.39 | 1.44 |
| Insoluble Protein Solids and Soluble Protein Extract #5A | 12.46 | 54.4 | 7.1 | 0.38 | 1.93 |
| Insoluble Protein Solids and Soluble Protein Extract #6A | 12.04 | 57.6 | 8.86 | 1.01 | 1.60 |
| Insoluble Fiber Solids #1A | 16.65 | 44.9 | 6.97 | 2.85 | 9.58 |
| Insoluble Fiber Solids #2A | 19.02 | 45.1 | 7.35 | 3.22 | 10.23 |
| Insoluble Fiber Solids #3A | 17.54 | 46.6 | 7.79 | 2.34 | 8.04 |
| Insoluble Fiber Solids #4A | 20.46 | 43.4 | 7.10 | 3.17 | 10.64 |
| Insoluble Fiber Solids #5A | 20.32 | 44.4 | 7.46 | 2.29 | 9.17 |
| Insoluble Fiber Solids #6A | 20.04 | 44.8 | 7.38 | 3.22 | 10.16 |
| Insoluble Protein Solids and Soluble Protein Extract #1B | 1.90 | 49.1 | 12.05 | 0.45 | 0.48 |
| Insoluble Protein Solids and Soluble Protein Extract #2B | 6.12 | 52.9 | 9.14 | 0.46 | 2.00 |
| Insoluble Protein Solids and Soluble Protein Extract #3B | 5.32 | 55.5 | 10.64 | 0.68 | 2.72 |
| Insoluble Protein Solids and Soluble Protein Extract #4B | 6.56 | 50.8 | 9.15 | 0.49 | 1.75 |
| Insoluble Protein Solids and Soluble Protein Extract #5B | 3.94 | 51.2 | 10.0 | 0.19 | 0.19 |
| Insoluble Protein Solids and Soluble Protein Extract #6B | 5.60 | 56.8 | 10.05 | 1.53 | 1.35 |
| Washed Fiber Solids #1B | 17.28 | 43.1 | 5.45 | 3.08 | 14.23 |
| Washed Fiber Solids #2B | 18.34 | 43.0 | 6.01 | 3.52 | 12.93 |
| Washed Fiber Solids #3B | 17.92 | 43.8 | 6.33 | 3.69 | 13.19 |
| Washed Fiber Solids #4B | 18.23 | 41.6 | 6.46 | 3.39 | 14.09 |
| Washed Fiber Solids #5B | 20.71 | 40.9 | 6.20 | 4.26 | 13.97 |
| Washed Fiber Solids #6B | 17.68 | 41.0 | 6.26 | 3.90 | 10.6 |
| Soluble and Insoluble Protein Slurry #1C | 4.34 | 53.4 | 10.0 | 0.60 | 1.57 |
| Soluble and Insoluble Protein Slurry #2C | 6.83 | 53.2 | 9.66 | 0.43 | 2.20 |
| Soluble and Insoluble Protein Slurry #3C | 5.89 | 53.6 | 9.20 | 0.30 | 9.00 |
| Soluble and Insoluble Protein Slurry #4C | 7.97 | 53.4 | 8.98 | 0.29 | 1.17 |
| Soluble and Insoluble Protein Slurry #5C | 9.03 | 53.9 | 8.83 | 0.77 | 2.02 |
| Insoluble Protein Solids #1C | 10.57 | 44.2 | 6.20 | 2.52 | 12.74 |
| Insoluble Protein Solids #2C | 8.49 | 48.2 | 7.56 | 1.63 | 7.08 |
| Insoluble Protein Solids #3C | 8.41 | 49.1 | 7.51 | 1.72 | 6.80 |
| Insoluble Protein Solids #4C | 15.27 | 43.8 | 7.53 | 2.86 | 10.79 |
| Insoluble Protein Solids #5C | 11.39 | 50.0 | 7.65 | 2.19 | 4.98 |

[a] dwb = dry weight basis

TABLE 49

Results of Proximate Analysis for Ethanol Precipitated and Washed Protein Solids

| Sample | Solids (%) | Protein (%, dwb [a]) | Ash (%, dwb [a]) | Oil (%, dwb [a]) | Crude Fiber (%, dwb [a]) |
|---|---|---|---|---|---|
| Ethanol Precipitated Protein Solids #1 | 29.66 | 69.3 | 8.90 | 0.76 | 4.76 |
| Ethanol Washed Protein Solids #2 | 30.67 | 70.6 | 9.17 | 0.60 | 4.10 |
| Ethanol Washed Protein Solids #3 | 47.53 | 73.3 | 9.44 | 0.51 | 3.78 |

[a] dwb = dry weight basis

TABLE 50

Conditions of Andritz Decanter Centrifuge for Fiber Separation

| Batch | Bowl Speep (RPM) | G Force (g) | Differential Speed (RPM) | Bowl Torque (%) | Scroll Torque (%) |
|---|---|---|---|---|---|
| 1 | 1,235 | 274 | 10 | 34 | 7 |
| 2 | 1,226 | 274 | 14 | 34 | 10 |
| 3 | 1,350 | 350 | 14 | 34 | 11 |
| 4 | 1,350 | 350 | 14 | 34 | 11 |
| 5 | 1,350 | 350 | 14 | 34 | 11 |
| 6 | 1,350 | 350 | 14 | 34 | 11 |
| 7 | 1,350 | 350 | 14 | 34 | 11 |

TABLE 51

Results of Proximate Analysis for Production of Protein Concentrate from Defatted Canola Meal

| Sample | % Solids | % Protein (dwb) | % Ash (dwb) | % Oil (dwb) | % Crude Fiber (dwb) |
|---|---|---|---|---|---|
| Defatted Canola Meal | 93.16 | 48.6 | 7.47 | 2.45 | 6.98 |
| Fiber Solids - batch 1 | 18.42 | 41.6 | 6.28 | 3.78 | 12.68 |
| Fiber Solids - Batch 2 | 18.06 | 41.2 | 6.28 | 3.57 | 12.80 |
| Fiber Solids - Batch 3 | 18.88 | 41.2 | 6.19 | 3.79 | 12.14 |
| Fiber Solids - Batch 4 | 19.42 | 41.1 | 6.16 | 3.65 | 13.53 |

TABLE 51-continued

Results of Proximate Analysis for Production of
Protein Concentrate from Defatted Canola Meal

| Sample | % Solids | % Protein (dwb) | % Ash (dwb) | % Oil (dwb) | % Crude Fiber (dwb) |
|---|---|---|---|---|---|
| Fiber Solids - Batch 5 | 19.88 | 41.0 | 6.25 | 4.06 | 14.03 |
| Fiber Solids - Batch 6 | 19.25 | 41.1 | 6.19 | 3.13 | 13.58 |
| Fiber Solids - Batch 7 | 18.84 | 41.0 | 6.13 | 3.14 | 13.30 |
| Protein Slurry - Batch 1 | 7.01 | 52.1 | 8.45 | 0.80 | 2.60 |
| Protein Slurry - Batch 2 | 7.34 | 53.9 | 9.30 | 0.91 | 2.95 |
| Protein Slurry - Batch 3 | 7.31 | 54.2 | 8.70 | 0.81 | 2.83 |
| Protein Slurry - Batch 4 | 7.25 | 53.4 | 8.68 | 1.09 | 3.21 |
| Protein Slurry - Batch 5 | 7.34 | 53.1 | 8.56 | 1.16 | 3.01 |
| Protein Slurry - Batch 6 | 7.22 | 52.8 | 8.50 | 1.48 | 3.28 |
| Protein Slurry - Batch 7 | 6.24 | 52.9 | 8.62 | 1.44 | 2.83 |
| Precipitated Proteins - Batch 1 | 16.56 | 65.9 | 8.27 | 0.76 | 4.54 |
| Precipitated Proteins - Batch 2 | 4.71 | 63.9 | 8.35 | 0.76 | 4.98 |
| Precipitated Proteins - Batch 3 | 18.74 | 63.9 | 8.27 | 0.81 | 5.22 |
| Precipitated Proteins - Batch 4 | 4.38 | 63.8 | 8.63 | 1.14 | 4.13 |
| Precipitated Proteins - Batch 5 | 4.08 | 65.3 | 8.79 | 1.21 | 4.26 |
| Precipitated Proteins - Batch 6 | 16.92 | 64.9 | 8.31 | 0.89 | 4.90 |
| Precipitated Proteins - Batch 7 | 4.52 | 67.4 | 8.81 | 0.72 | 4.06 |
| Dried Protein Concentrate - Batch 1 | 95.15 | 69.2 | 8.03 | 0.29 | 6.33 |
| Dried Protein Concentrate - Batch 2 | 94.67 | 71.6 | 9.76 | 0.46 | 5.26 |
| Dried Protein Concentrate - Batch 3 | 93.69 | 71.7 | 9.10 | 0.48 | 4.81 |
| Dried Protein Concentrate - Batch 4 | 93.34 | 72.0 | 8.97 | 0.79 | 4.83 |
| Dried Protein Concentrate - Batch 5 | 95.74 | 72.1 | 8.98 | 0.78 | 4.64 |
| Dried Protein Concentrate - Batch 6 | 96.89 | 70.3 | 8.65 | 0.74 | 4.88 |
| Dried Protein Concentrate - Batch 7 | 94.32 | 72.7 | 9.13 | 0.64 | 4.31 |

TABLE 52

Results of Proximate Analysis for Canola Press cake (*B. juncea*), Defatted Canola Meal (*B. juncea*), Protein Concentrate and Dried Canola Fiber Solids.

| Sample | Moisture (%) | Protein (%, dwb [a]) | Ash (%, dwb [a]) | Oil (%, dwb [a]) | Crude Fiber (%, dwb [a]) |
|---|---|---|---|---|---|
| Canola Press Cake (*B. juncea*) | 5.13 | 41.4 | 6.61 | 21.5 | 10.2 |
| Defatted Canola Meal (*B. juncea*) | 7.73 | 52.2 | 7.98 | 1.46 | 8.02 |
| Protein Concentrate | 4.58 | 67.2 | 9.12 | 0.15 | 5.25 |
| Dried Fiber Solids | 3.77 | 34.6 | 4.48 | 3.82 | 20.5 |

[a] dwb = dry weight basis

TABLE 53

Glucosinolates in *Juncea* Press Cake. *Juncea* Defatted Meal, *Juncea* Protein Concentrate and *Juncea* Fiber Solids.

| Glucosinolates | Juncea Press Cake | Juncea Defatted Meal | Juncea Protein Concentrate | Juncea Fiber Solids |
|---|---|---|---|---|
| Allyl (μmoles/g) | 0.19 | 0.20 | 0 | 0 |
| 3-butenyl (μmoles/g) | 11.26 | 11.24 | 0.61 | 0.11 |
| 4-pentenyl (μmoles/g) | 0.46 | 0.46 | 0 | 0 |
| 2-OH-3-butenyl (μmoles/g) | 1.14 | 1.22 | 0.06 | 0 |
| Phenylethyl (μmoles/g) | 0.19 | 0.19 | 0 | 0 |
| 3-CH3-indolyl (μmoles/g) | 0.11 | 0.13 | 0 | 0 |
| 4-OH-3-CH3-indolyl (μmoles/g) | 1.39 | 1.98 | 0.24 | 0 |
| Total Aliphatics (μmoles/g) | 12.87 | 12.94 | 0.68 | 0.11 |

TABLE 54

Results of Proximate Analysis for Canola Seed (*B. napus*), Canola Press Cake (*B. napus*), Defatted Canola Meal (*B. napus*), Protein Concentrate and Dried Canola Fiber Solids.

| Sample | Moisture (%) | Protein (%, dwb [a]) | Ash (%, dwb [a]) | Oil (%, dwb [a]) | Crude Fiber (%, dwb [a]) |
|---|---|---|---|---|---|
| Canola Seed (*B. napus*) (Clearfield Non-GMO) | 6.68 | 23.1 | 3.95 | 48.9 | 6.68 |
| Canola Press Cake (*B. napus*) | 6.84 | 34.7 | 5.84 | 12.7 | 12.1 |
| Defatted Canola Meal | 6.83 | 49.1 | 7.83 | 2.34 | 13.5 |

TABLE 54-continued

Results of Proximate Analysis for Canola Seed (*B. napus*), Canola Press Cake (*B. napus*), Defatted Canola Meal (*B. napus*), Protein Concentrate and Dried Canola Fiber Solids.

| Sample | Moisture (%) | Protein (%, dwb[a]) | Ash (%, dwb[a]) | Oil (%, dwb[a]) | Crude Fiber (%, dwb[a]) |
|---|---|---|---|---|---|
| (*B. napus*) | | | | | |
| Protein Concentrate | 3.13 | 61.9 | 8.17 | 0.67 | 6.69 |
| Dried Fiber Solids | 6.05 | 24.5 | 3.02 | 4.10 | 33.7 |

[a] dwb = dry weight basis

TABLE 55

Glucosinolates in Canola Seed (*B. napus*), *Napus* Defatted Meal, *Napus* Protein Concentrate and *Napus* Fiber Solids.

| Glucosinolates | *Napus* Seed (Clearfield Canola Seed) | *Napus* Defatted Meal | *Napus* Protein Concentrate | *Napus* Fiber Solids |
|---|---|---|---|---|
| 3-butenyl (μmoles/g) | 1.18 | 2.02 | 0.12 | 0 |
| 4-pentenyl (μmoles/g) | 0.17 | 0.28 | 0 | 0 |
| 2-OH-3-butenyl (μmoles/g) | 2.38 | 4.32 | 0.18 | 0 |
| 2-OH-4-pentenyl (μmoles/g) | 0.06 | 0.09 | 0 | 0 |
| CH3-thiobutenyl (μmoles/g) | 0.07 | 0.12 | 0 | 0 |
| Phenylethyl (μmoles/g) | 0.12 | 0.20 | 0 | 0 |
| CH3-thiopentenyl (μmoles/g) | 0.06 | 0.10 | 0 | 0 |
| 3-CH3-indolyl (μmoles/g) | 0.33 | 0.63 | 0 | 0 |
| 4-OH-3-CH3-indolyl (μmoles/g) | 3.49 | 7.92 | 0 | 0 |
| Total Aliphatics (μmoles/g) | 3.79 | 6.70 | 0.31 | <0.05 |

TABLE 56

Amino Acid Profiles of Ethanol Defatted *Juncea* Meal, Ethanol defatted *Napus* Meal, *Juncea* Protein Concentrate and *Napus* Protein Concentrate on a Dry Weight Basis.

| Amino Acid | Defatted *Juncea* Meal (%, dwb[a]) | Defatted *Napus* Meal (%, dwb[a]) | *Juncea* Protein Concentrate (%, dwb[a]) | *Napus* Protein Concentrate (%, dwb[a]) |
|---|---|---|---|---|
| Aspartic Acid | 4.31 | 3.59 | 5.98 | 5.39 |
| Glutamic Acid | 8.67 | 8.22 | 10.69 | 10.07 |
| Serine | 2.53 | 2.31 | 3.54 | 3.32 |
| Glycine | 2.67 | 2.38 | 3.62 | 3.22 |
| Histidine | 1.51 | 1.40 | 2.00 | 1.70 |
| Arginine | 3.58 | 2.92 | 3.78 | 3.69 |
| Threonine | 2.07 | 1.77 | 2.91 | 2.79 |
| Alanine | 2.28 | 2.01 | 3.25 | 2.91 |
| Proline | 2.99 | 2.88 | 3.58 | 3.45 |
| Tyrosine | 1.73 | 1.59 | 2.57 | 2.29 |
| Valine | 2.56 | 2.36 | 3.55 | 3.31 |
| Methionine | 1.04 | 0.91 | 1.52 | 1.41 |
| Cystine | 1.17 | 1.12 | 1.15 | 1.19 |
| Isoleucine | 2.09 | 1.85 | 2.91 | 2.66 |
| Leucine | 3.82 | 3.40 | 5.44 | 5.06 |
| Phenylalanine | 2.23 | 2.01 | 3.09 | 2.92 |
| Lysine | 2.86 | 2.96 | 3.39 | 3.51 |
| Tryptophan | 0.77 | 0.73 | 1.03 | 1.00 |
| Total Amino Acids | 48.88 | 44.41 | 64.0 | 59.89 |

[a] dwb = dry weight basis

TABLE 57

Amino Acid Profiles of *Juncea* Protein Concentrate, *Napus* Protein Concentrate, Soy and Pea Protein Isolates on a Normalized Basis of Pure Protein.

| Amino Acid | *Juncea* Protein Concentrate | *Napus* Protein Concentrate | Soy Protein Isolate | Pea Protein Isolate |
|---|---|---|---|---|
| Aspartic Acid (%) | 9.34 | 9.00 | 11.5 | 11.78 |
| Glutamic Acid (%) | 16.70 | 16.81 | 19.0 | 19.13 |
| Serine (%) | 5.53 | 5.54 | 5.2 | 5.28 |
| Glycine (%) | 5.66 | 5.38 | 4.1 | 3.86 |
| Histidine[a] (%) | 3.13 | 2.84 | 2.6 | 2.55 |
| Arginine (%) | 5.91 | 6.16 | 7.5 | 8.58 |
| Threonine[a] (%) | 4.55 | 4.66 | 3.8 | 3.68 |
| Alanine (%) | 5.08 | 4.86 | 4.2 | 4.15 |
| Proline (%) | 5.59 | 5.76 | 5.1 | 4.15 |
| Tyrosine (%) | 4.02 | 3.82 | 3.8 | 3.68 |
| Valine[a] (%) | 5.55 | 5.53 | 5.0 | 4.90 |
| Methionine[a] (%) | 2.38 | 2.35 | 1.3 | 1.13 |
| Cystine (%) | 1.80 | 1.99 | 1.3 | 1.04 |
| Isoleucine[a] (%) | 4.55 | 4.44 | 4.8 | 4.43 |
| Leucine[a] (%) | 8.50 | 8.45 | 8.1 | 8.20 |
| Phenylalanine[a] (%) | 4.83 | 4.88 | 5.2 | 5.29 |
| Lysine[a] (%) | 5.30 | 5.86 | 6.2 | 7.26 |
| Tryptophan[a] (%) | 1.61 | 1.67 | 1.3 | 0.94 |
| Total Amino Acid (%) | 100 | 100 | 100 | 100 |

[a] Nine essential amino acids.

TABLE 58

Results of Proximate Analysis for Ethanol Defatted Canola Meal (*B. juncea*) and Protein Concentrate.

| Sample | Moisture (%) | Protein (%, dwb[a]) | Ash (%, dwb[a]) | Oil (%, dwb[a]) | Crude Fiber (%, dwb[a]) |
|---|---|---|---|---|---|
| Ethanol Defatted Canola Meal (*B. juncea*) | 8.33 | 52.9 | 8.41 | 1.13 | 9.16 |
| Protein Concentrate at 0% Protease | 6.37 | 66.7 | 5.23 | 0.55 | 8.26 |
| Protein Concentrate at 0.1% Alcalase | 4.49 | 67.6 | 6.82 | 0.38 | 6.81 |
| Protein Concentrate at 0.5% Alcalase | 6.64 | 69.6 | 6.74 | 0.31 | 6.53 |
| Protein Concentrate at 0.5% Protamex | 6.62 | 66.0 | 8.12 | 0.32 | 8.10 |
| Fiber Solids at 0% Protease | 9.67 | 54.5 | 6.49 | 1.40 | 14.1 |
| Fiber Solids at 0.1% Alcalase | 3.72 | 39.0 | 5.19 | 2.83 | 27.5 |
| Fiber Solids at 0.5% Alcalase | 7.47 | 34.1 | 4.78 | 3.35 | 22.9 |
| Fiber Solids at 0.5% Protamex | 0.66 | 37.9 | 4.75 | 2.86 | 27.1 |

[a] dwb = dry weight basis

TABLE 59

Yield of Protein Concentrates With and Without the Use of Protease.

| Lab Trials | Yield of Protein Concentrate from Defatted Canola Meal (B. juncea) (%, w/w) |
|---|---|
| Protein Concentrate at 0% Protease | 23 |
| Protein Concentrate at 0.1% Alcalase | 38 |
| Protein Concentrate at 0.5% Alcalase | 68 |
| Protein Concentrate at 0.5% Protamex | 52 |

TABLE 60

Molecular Weight Distribution of Canola Protein Isolate

| Samples of Canola Protein Isolate | 250 KDa | 50 KDa | 30 Kda | 12 KDa | 6 KDa | <5 Kda | Total |
|---|---|---|---|---|---|---|---|
| 1 | 60% | 5% | 4% | 15% | 15% | 1% | 100% |
| 2 | 60% | 5% | 4% | 15% | 15% | 1% | 100% |
| 3 | 60% | 5% | 4% | 15% | 15% | 1% | 100% |
| 4 | 60% | 5% | 4% | 15% | 15% | 1% | 100% |
| 5 | 60% | 5% | 4% | 15% | 15% | 1% | 100% |
| 6 | 60% | 5% | 4% | 15% | 15% | 1% | 100% |

The invention claimed is:

1. A protein isolate having a protein content of at least 90% protein comprising:
   (i) a first class of proteins having a molecular weight between 225 and 275 kDa, the first class of proteins comprising between 50-70%;
   (ii) a second class of proteins having a molecular weight between 40 and 60 kDa, the second class of proteins comprising between 3-8%;
   (iii) a third class of proteins having a molecular weight between 20 and 40 kDa, the third class of proteins comprising between 2-6%;
   (iv) a fourth class of proteins having a molecular weight between 7 and 15 kDa, the fourth class of proteins comprising between 10-20%;
   (v) a fifth class of proteins having a molecular weight between 3 and 10 kDa, the fifth class of proteins comprising between 10-20%; and
   (vi) a sixth class of proteins having a molecular weight of less than about 5 kDa and comprising less than about 1% of the protein isolate.

2. A process for the production of a protein concentrate from a seed meal, said seed meal selected from the group consisting of canola seed meal and rapeseed meal, comprising:
   i) mixing the seed meal with a solvent consisting essentially of water, ethanol or a mixture thereof to form a seed meal solvent mixture;
   ii) adjusting the pH of the mixture to solubilize proteins in the mixture;
   iii) subjecting the mixture to a g-force sufficient to separate the mixture to form
      a) a fiber fraction which may include protein, and
      b) a protein fraction comprising
         (i) insoluble protein, and
         (ii) soluble protein;
   iv) separating the fiber fraction from the protein fraction and mixing the fiber fraction with the solvent to form a fiber mixture;
   v) treating the fiber mixture with a protease at a temperature and a pH suitable for protease activity;
   vi) subjecting the treated fiber mixture of step v) to a g-force sufficient to separate the treated fiber mixture to form:
      a) a second fiber fraction, and
      b) a hydrolyzed protein fraction, comprising
         (i) an insoluble protein fraction comprising partially hydrolyzed and un-hydrolyzed protein, and
         (ii) soluble hydrolyzed protein;
   vii) adjusting the pH of the protein fraction from step iii) (b) to a pH suitable to precipitate insoluble proteins;
   viii) separating the precipitated insoluble proteins from the protein fraction; and
   ix) combining the precipitated insoluble proteins from the protein fraction of step viii) and the insoluble protein fraction from the hydrolyzed protein fraction of step vi) to form the protein concentrate.

3. The process according to claim 2, wherein the process further comprises mixing the fiber fraction with the solvent and repeating step iii) once, twice or three times.

4. The process according to claim 2, wherein the process further comprises mixing the second fiber fraction with the solvent and repeating step vi) once, twice or three times.

5. The process according to claim 2, wherein the ratio of the seed meal to the solvent is 1:3 to 1:30 (w/w).

6. The process according to claim 2, wherein the temperature suitable for protease activity is between 30° and 70° C. and the pH suitable for protease activity is between 5.0 and 9.0.

7. The process according to claim 2, wherein the g-force is between 100 g and 500 g.

8. The process according to claim 7, wherein the g-force is between 150 g and 400 g.

9. The process according to claim 8, wherein the g-force is between 170 g and 350 g.

10. The process according to claim 2, wherein any of the separating steps comprises using a centrifuge or a hydrocyclone.

11. The process according to claim 2, wherein the pH suitable to precipitate the proteins in the protein fraction is between 4.0 and 6.0.

12. The process according to claim 2, further comprising the step of drying the protein concentrate to a moisture of between 4% and 8% (w/w).

13. The process according to claim 2, wherein the hydrolyzed protein comprises peptides and free amino acids.

14. The process according to claim 2, wherein the process is conducted as a counter-current process.

15. A process for the production of a protein concentrate from a seed meal, said seed meal selected from the group consisting of canola seed meal and rapeseed meal comprising:
   i) mixing the seed meal with a solvent consisting essentially of water, ethanol or a mixture thereof to form a mixture;
   ii) adjusting the pH of the mixture to solubilize proteins in the mixture;
   iii) subjecting the mixture to a g-force sufficient to separate the mixture to form
      a) a fiber fraction which may include protein, and
      b) a protein fraction comprising
         (i) insoluble protein, and
         (ii) soluble protein;

iv) separating the fiber fraction from the protein fraction and mixing the fiber fraction with the solvent to form a fiber mixture;
v) treating the fiber mixture with a protease at a temperature and a pH suitable for protease activity;
vi) subjecting the fiber mixture to a g-force sufficient to separate the fiber mixture to form:
   a) a second fiber fraction, and
   b) a hydrolyzed protein fraction, comprising
      (i) insoluble protein comprising partially hydrolyzed and unhydrolyzed protein, and
      (ii) soluble hydrolyzed protein;
vii) mixing the protein fraction from step iii) (b) with a solvent to precipitate insoluble proteins;
ix) separating the precipitated insoluble proteins from the soluble protein in the protein fraction; and
x) combining the precipitated insoluble proteins from step ix) and the partially hydrolyzed and unhydrolyzed protein fraction from step vi) to form the protein concentrate.

16. The process according to claim 15, wherein the process further comprises mixing the fiber fraction with the solvent and repeating step iii) once, twice or three times.

17. The process according to claim 15, wherein the process further comprises mixing the second fiber fraction with the solvent and repeating step vi) once, twice or three times.

18. The process according to claim 15, wherein the ratio of the seed meal to the solvent is 1:3 to 1:30 (w/w).

19. The process according to claim 15, wherein the temperature suitable for protease activity is between 30° and 70° C. and the pH suitable for protease activity is between 5.0 and 9.0.

20. The process according to claim 15, wherein the g-force is between 100 g and 500 g.

21. The process according to claim 20, wherein the g-force is between 150 g and 400 g.

22. The process according to claim 21, wherein the g-force is between 170 g and 350 g.

23. The process according to claim 15, wherein any of the separating steps comprises using a centrifuge or a hydrocyclone.

24. The process according to claim 15, further comprising the step of drying the protein concentrate to a moisture of between 4% and 8% (w/w).

25. The process according to claim 15, wherein the hydrolyzed protein comprises peptides and amino acids.

26. The process according to claim 15, wherein the process is conducted as a counter-current process.

27. A process for the production of a protein isolate from a seed meal, said seed meal selected from the group consisting of canola seed meal and rapeseed meal comprising:
   i) mixing the oilseed seed meal with a solvent consisting essentially of water, ethanol or a mixture thereof to form a mixture;
   ii) adjusting the pH of the mixture to solubilize proteins in the mixture;
   iii) subjecting the mixture to a g-force sufficient to separate the mixture to form
      a) a fiber fraction, and
      b) a protein fraction comprising
         (i) insoluble protein, and
         (ii) soluble protein;
   iv) separating the insoluble protein from the soluble protein to recover therefrom an insoluble protein concentrate and a soluble protein extract; and
   v) subjecting the soluble protein extract to membrane filtration to recover therefrom the protein isolate.

28. The process according to claim 27, wherein the process further comprises mixing the fiber fraction with the solvent and subjecting the fiber-solvent mixture to a g-force sufficient to separate the fiber mixture to form:
   a) a second fiber fraction, and
   b) protein fraction, comprising
      (i) insoluble protein, and
      (ii) soluble protein;
   mixing and separating being repeated once, twice or three times.

29. The process according to claim 27, the ratio of the seed meal to the first blending solvent is 1:3 to 1:30 (w/w).

30. The process according to claim 27, wherein the g-force is between 100 g and 500 g.

31. The process according to claim 30, wherein the g-force is between 150 g and 350 g.

32. The process according to claim 31, wherein the g-force is between 170 g and 350 g.

33. The process according to claim 27, wherein any of the separating steps comprises using a centrifuge or a hydrocyclone.

34. The process according to claim 27, further comprising the step of drying the protein isolate to a moisture of between 4% and 8% (w/w).

35. The process according to claim 27, wherein the protein isolate is at least partially-hydrolyzed to produce peptides and free amino acids.

36. The process according to claim 35, wherein the protein isolate also comprises peptides and amino acids.

37. The process according to claim 27, wherein the process is conducted as a counter-current process.

38. The process of claim 2 for the production of a protein concentrate from a seed meal, further comprising treating the seed meal solvent mixture with phytase at a temperature and a pH suitable for phytase activity.

39. The process according to claim 38, wherein the temperature suitable for phytase activity is between 20° and 60° C. and the pH suitable for phytase activity is between 2.0 and 7.0.

40. The process of claim 15 for the production of a protein concentrate from a seed meal, further comprising treating the seed meal solvent mixture with phytase at a temperature and a pH suitable for phytase activity.

41. The process according to claim 40, wherein the temperature suitable for phytase activity is between 20° and 60° C. and the pH suitable for phytase activity is between 2.0 and 7.0.

42. The process of claim 27 for the production of a protein isolate from a seed meal, further comprising treating the seed meal solvent mixture with phytase at a temperature and a pH suitable for phytase activity.

43. The process according to claim 42, wherein the temperature suitable for phytase activity is between 20° and 60° C. and the pH suitable for phytase activity is between 2.0 and 7.0.

* * * * *